United States Patent
Yan et al.

(10) Patent No.: US 11,130,808 B2
(45) Date of Patent: Sep. 28, 2021

(54) MIXTURES OF ANTIBODIES

(71) Applicant: Qilu Puget Sound Biotherapeutics Corporation, Bothell, WA (US)

(72) Inventors: Wei Yan, Samamish, WA (US); Zhi Liu, Shoreline, WA (US); Martin J. Pentony, Bedford, MA (US)

(73) Assignee: QILU PUGET SOUND BIOTHERAPEUTICS CORPORATION, Bothell, WA (US)

( * ) Notice: Subject to any disclaimer, the term of this patent is extended or adjusted under 35 U.S.C. 154(b) by 297 days.

(21) Appl. No.: 16/303,611

(22) PCT Filed: May 5, 2017

(86) PCT No.: PCT/US2017/030676
§ 371 (c)(1),
(2) Date: Nov. 20, 2018

(87) PCT Pub. No.: WO2017/205014
PCT Pub. Date: Nov. 30, 2017

(65) Prior Publication Data
US 2019/0248899 A1 Aug. 15, 2019

Related U.S. Application Data

(60) Provisional application No. 62/432,167, filed on May 26, 2016.

(51) Int. Cl.
| | |
|---|---|
| *C07K 16/28* | (2006.01) |
| *A61K 39/00* | (2006.01) |
| *C07K 16/32* | (2006.01) |
| *A61P 35/00* | (2006.01) |
| *A61K 9/00* | (2006.01) |

(52) U.S. Cl.
CPC ........ *C07K 16/2818* (2013.01); *A61K 9/0019* (2013.01); *A61P 35/00* (2018.01); *C07K 16/2887* (2013.01); *C07K 16/2896* (2013.01); *C07K 16/32* (2013.01); *A61K 2039/507* (2013.01); *C07K 2317/10* (2013.01); *C07K 2317/14* (2013.01); *C07K 2317/21* (2013.01); *C07K 2317/24* (2013.01); *C07K 2317/31* (2013.01); *C07K 2317/40* (2013.01); *C07K 2317/51* (2013.01); *C07K 2317/515* (2013.01); *C07K 2317/522* (2013.01); *C07K 2317/55* (2013.01); *C07K 2317/56* (2013.01); *C07K 2317/73* (2013.01); *C07K 2317/732* (2013.01); *C07K 2317/734* (2013.01); *C07K 2317/76* (2013.01); *C07K 2317/92* (2013.01); *C07K 2317/94* (2013.01)

(58) Field of Classification Search
CPC ......... A61K 2039/507; C07K 2317/51; C07K 2317/515; C07K 2317/522; C07K 16/00–468
See application file for complete search history.

(56) References Cited

U.S. PATENT DOCUMENTS

| | | | |
|---|---|---|---|
| 7,932,360 B2 | 4/2011 | Van Berkel et al. | |
| 8,592,562 B2 | 11/2013 | Kannan et al. | |
| 8,679,785 B2 | 3/2014 | Carter et al. | |
| 2008/0269466 A1 | 10/2008 | Humphreys | |
| 2009/0182127 A1 | 7/2009 | Kjaergaard et al. | |
| 2012/0020952 A1 | 1/2012 | Parren et al. | |
| 2013/0177555 A1 | 7/2013 | Wilkinson et al. | |
| 2013/0336973 A1 | 12/2013 | Spreter Von Kreudenstein et al. | |
| 2013/0345406 A1 | 12/2013 | Van De Winkel et al. | |
| 2014/0010814 A1 | 1/2014 | Benhar et al. | |
| 2014/0112926 A1 | 4/2014 | Liu et al. | |
| 2014/0154254 A1 | 6/2014 | Kannan et al. | |
| 2014/0303356 A1 | 10/2014 | Gramer et al. | |
| 2015/0274807 A1 | 10/2015 | Xu et al. | |
| 2015/0291703 A1* | 10/2015 | Enami ................ C07K 16/2887 424/136.1 |
| 2015/0307628 A1 | 10/2015 | Kim et al. | |
| 2015/0376282 A1 | 12/2015 | Labrijn et al. | |
| 2016/0152726 A1 | 6/2016 | Kim | |
| 2019/0276542 A1* | 9/2019 | Liu ........................ C07K 16/30 |

FOREIGN PATENT DOCUMENTS

| | | |
|---|---|---|
| EP | 2889313 A1 | 7/2015 |
| WO | 2004061104 A2 | 7/2004 |
| WO | 2008104183 A2 | 9/2008 |
| WO | 2009089004 A1 | 7/2009 |
| WO | 2010084197 A1 | 7/2010 |
| WO | 2011109726 A2 | 9/2011 |

(Continued)

OTHER PUBLICATIONS

Examination Report dated May 7, 2020 for related EP Patent Application No. 17723832.6, in 14 pages.
Kannan Gunasekaran et al. "Enhancing antibody Fc heterodimer formation through electrostatic steering effects: applications to bispecific molecules and monovalent IgG (manuscript)." JBC Papers in Press. Apr. 16, 2010. pp. 1-20. Retrieved from the internet on Mar. 15, 2019. URL: http://www.jbc.org/content/early/2010/04/16/jbc.M110.117382.full.pdf.
Notification of Transmittal of the International Search Report and the Written Opinion of the International Searching Authority, or Declaration for International Patent Application No. PCT/US2017/030676 dated Oct. 2, 2017, 1 page.

(Continued)

*Primary Examiner* — Jessica H Roark
(74) *Attorney, Agent, or Firm* — Procopio, Cory, Hargreaves & Savitch LLP

(57) ABSTRACT

Described herein are antibodies and mixtures of antibodies optionally produced by a host cell line, nucleic acids encoding the antibodies and mixtures of antibodies, host cells containing such nucleic acids, and methods of treatment using the antibodies, mixtures of antibodies, or nucleic acids encoding the antibodies or mixtures of antibodies. Also described are methods of producing mixtures of antibodies in host cells.

21 Claims, 27 Drawing Sheets

Specification includes a Sequence Listing.

(56) References Cited

FOREIGN PATENT DOCUMENTS

| WO | 2012125495 A2 | 9/2012 |
| WO | 2013/096291 A2 | 6/2013 |
| WO | 2013/157953 A1 | 10/2013 |
| WO | 2014015804 A1 | 1/2014 |
| WO | 2014082179 A1 | 6/2014 |
| WO | 2014150973 A1 | 9/2014 |
| WO | 2015017548 A2 | 2/2015 |
| WO | 2015089080 A2 | 6/2015 |
| WO | 2015/173756 A2 | 11/2015 |
| WO | 2018/089293 A2 | 5/2018 |

OTHER PUBLICATIONS

International Search Report for International Patent Application No. PCT/US2017/030676 completed on Jul. 27, 2017 and dated Oct. 2, 2017, 12 pages.

The Written Opinion of the International Searching Authority for International Patent Application No. PCT/US2017/030676, dated Oct. 2, 2017, 14 pages.

Boutros et al., Safety Profiles of Anti-CTLA-4 and Anti-PD-1 Antibodies Alone and in Combination, 2016, Nat. Rev. Clin. Oncol. 13: 473-486.

Buchbinder and Desai, CTLA-4 and PD-1 Pathways Similarities, Differences, and Implications of Their Inhibition, 2016, Am. J. Clin. Oncol. 39(1): 98-106.

Davies et al., A Mixture of Functionally Oligoclonal Humanized Monoclonal Antibodies That Neutralize Clostridium Difficile TcdA and TcdB with High Levels of In Vitro Potency Shows In Vivo Protection in a Hamster Infection Model, 2013, Clin. Vaccine Immunol. 20(3): 377-390.

De Kruif et al., Generation of Stable Cell Clones Expressing Mixtures of Human Antibodies, 2010, Biotechnology and Bioengineering, 106(5): 741-750.

Dodev et al., A tool kit for rapid cloning and expression of recombinant antibodies, 2014, Scientific Reports, 4(1): 10 pages.

Iida et al., Sym004, a Novel EGFR Antibody Mixture, Can Overcome Acquired Resistance to Cetuximab, Oct. 2013, Neoplasia, 15(10): 1196-1206.

Klein et al., Progress in overcoming the chain association issue in bispecific heterodimeric IgG antibodies, 2012, mAbs, 4(6): 653-663.

Larkin et al., Combined Nivolumab and Ipilimumab or Monotherapy in Untreated Melanoma, 2015, The New England Journal of Medicine, 373(1): 23-34.

Leung et al., Combining lapatinib and pertuzumab to overcome lapatinib resistance due to NRG1-mediated signaling in HER2-amplified breast cancer, 2015, Oncotarget, 6(8): 5678-5694.

Lewis et al., Generation of bispecific IgG antibodies by structure-based design of an orthogonal Fab interface, 2014, Nature Biotechnology, 32: 191-198.

Li et al., Cell culture processes for monoclonal antibody production, 2010, MARS, 2(5): 466-479.

Liu et al., A Novel Antibody Engineering Strategy for Making Monovalent Bispecific Heterodimeric IgG Antibodies by Electrostatic Steering Mechanism, 2015, The Journal of Biological Chemistry 290(12): 7535-7562.

Lindzen et al., Tailored cancer immunotherapy using combinations of chemotherapy and a mixture of antibodies against EGF-receptor ligands, 2010, 107(28): 12559-12563.

Logtenberg, Antibody cocktails: next-generation biopharmaceuticals with improved potency, 2007, Trends in Biotechnology, Elsevier Publications, Cambridge, GB, 25(9): 390-394.

Mazor et al., Improving target cell specificity using a novel monovalent bispecific IgG design, 2015, mAbs, 7(2): 377-389.

Nielsen et al., Single-Batch Production of Recombinant Human Polyclonal Antibodies, 2010, Mol. Biotechnol. 45: 257-266.

Rasmussen et al., Recombinant Antibody Mixtures: Production Strategies and Cost Considerations, 2012, Archives of Biochemistry and Biophysics, 526(2): 139-145.

Rasmussen et al., Manufacture of recombinant polyclonal antibodies, 2007, Biotechnol Lett, 29: 845-852.

Reiter et al., Engineering antibody Fv fragments for cancer detection and therapy: Disulfide-stabilized Fv fragments, 1996, Nature Biotechnology 14: 1239-1245.

Robak, The emerging therapeutic role of antibody mixtures, 2013, Expert Opinion, Bio. Ther. 13(7): 953-958. doi: 101517/14712598. 2013.99133. Epub May 7, 2013.

Scheuer et al., Strongly Enhanced Antitumor Activity of Trastuzumab and Pertuzumab Combination Treatment on HER2-Positive Human Xenograft Tumor Models, 2009, Cancer Research 69(24):9330-9336.

Silva et al., The S228P Mutation Prevents in Vivo and in Vitro IgG4 Fab-arm Exchange as Demonstrated using a Combination of Novel Quantitative Immunoassays and Physiological Matrix Preparation, 2015, The Journal of Biological Chemistry 290(9): 5462-5469.

Symphogen—About, [online], printed on Jan. 25, 2016, Internet < URL: http: http://www.symphogen.com/about> in 2 pages.

Symphogen—Pipeline, [online], printed on Jan. 25, 2016, Internet < URL: http: http://www.symphogen.com/pipeline> in 2 pages.

Thompson et al., Complex mixtures of antibodies generated from a single production qualitatively and quantitatively evaluated by native Orbitrap mass spectrometry, 2014, mAbs, 6(1): 197-203.

Wolchok et al., Nivolumab plus Ipilimumab in Advanced Melanoma, 2013, The New England Journal of Medicine, 369(2): 122-133.

Yamashita-Kashima et al., Pertuzumab in Combination with Trastuzumab Shows Significantly Enhanced Antitumor Activity in HER2-Positive Human Gastric Cancer Xenograft Models, 2011, Clinical Cancer Research, 17(15): 5060-5070.

\* cited by examiner

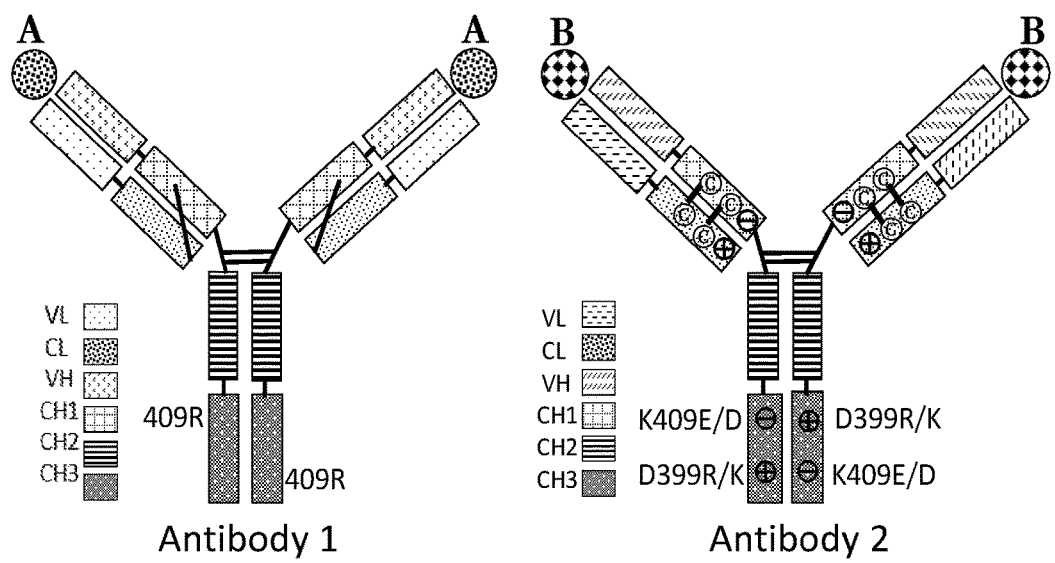
Panel A
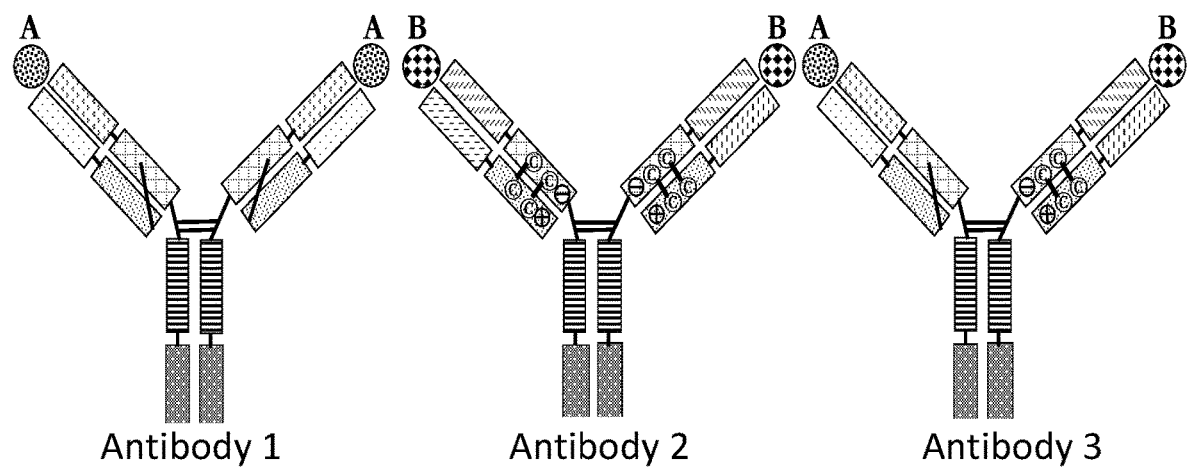
Panel B
Figure 3

| Lane | IgG1 Fc alteration | IgG4 HC alteration | Percent heterodimer |
|---|---|---|---|
| 1 | WT | WT | 59.6 |
| 2 | D399K | WT | 73.2 |
| 3 | D399R | WT | 75.6 |
| 4 | K409D | WT | 72.2 |
| 5 | K409E | WT | 72.8 |
| 6 | D399K, K409E | WT | 4.7 |
| 7 | D399K, K409D | WT | 2.5 |

A
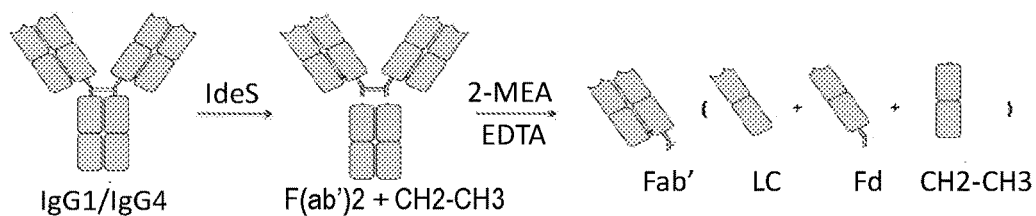
B
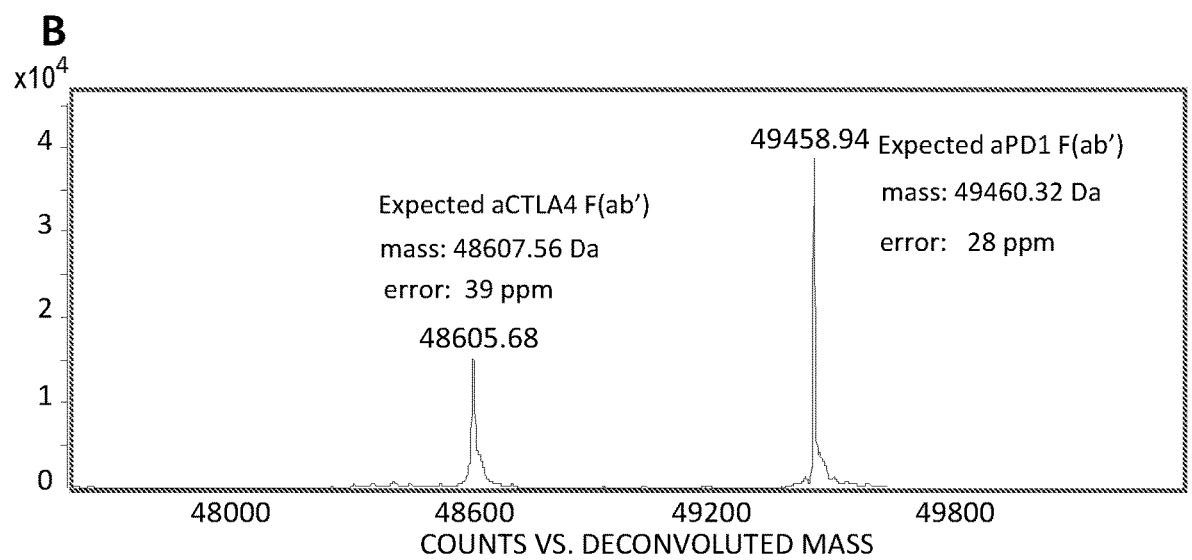
Figure 20

Antibody concentration (nM)

SEQUENCE LISTING

```
<160> NUMBER OF SEQ ID NOS: 46

<210> SEQ ID NO 1
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Consensus amino acid sequence for a human VH
      domain
<220> FEATURE:
<221> NAME/KEY: MOD_RES
<222> LOCATION: (1)..(3)
<223> OTHER INFORMATION: Any amino acid ordinarily found in living
      organisms
<220> FEATURE:
<221> NAME/KEY: MOD_RES
<222> LOCATION: (5)..(7)
<223> OTHER INFORMATION: Any amino acid ordinarily found in living
```

```
      organisms
<220> FEATURE:
<221> NAME/KEY: MOD_RES
<222> LOCATION: (9)..(13)
<223> OTHER INFORMATION: Any amino acid ordinarily found in living
      organisms
<220> FEATURE:
<221> NAME/KEY: MOD_RES
<222> LOCATION: (15)..(16)
<223> OTHER INFORMATION: Any amino acid ordinarily found in living
      organisms
<220> FEATURE:
<221> NAME/KEY: MOD_RES
<222> LOCATION: (17)..(17)
<223> OTHER INFORMATION: serine or threonine
<220> FEATURE:
<221> NAME/KEY: MOD_RES
<222> LOCATION: (18)..(18)
<223> OTHER INFORMATION: valine or leucine
<220> FEATURE:
<221> NAME/KEY: MOD_RES
<222> LOCATION: (19)..(19)
<223> OTHER INFORMATION: Any amino acid ordinarily found in living
      organisms
<220> FEATURE:
<221> NAME/KEY: MOD_RES
<222> LOCATION: (20)..(20)
<223> OTHER INFORMATION: valine or leucine
<220> FEATURE:
<221> NAME/KEY: MOD_RES
<222> LOCATION: (21)..(21)
<223> OTHER INFORMATION: serine or threonine
<220> FEATURE:
<221> NAME/KEY: MOD_RES
<222> LOCATION: (23)..(25)
<223> OTHER INFORMATION: Any amino acid ordinarily found in living
      organisms
<220> FEATURE:
<221> NAME/KEY: MOD_RES
<222> LOCATION: (27)..(35)
<223> OTHER INFORMATION: Any amino acid ordinarily found in living
      organisms
<220> FEATURE:
<221> NAME/KEY: MOD_RES
<222> LOCATION: (36)..(37)
<223> OTHER INFORMATION: Any amino acid ordinarily found in living
      organisms or absent
<220> FEATURE:
<221> NAME/KEY: MOD_RES
<222> LOCATION: (39)..(39)
<223> OTHER INFORMATION: Any amino acid ordinarily found in living
      organisms
<220> FEATURE:
<221> NAME/KEY: MOD_RES
<222> LOCATION: (42)..(43)
<223> OTHER INFORMATION: Any amino acid ordinarily found in living
      organisms
<220> FEATURE:
<221> NAME/KEY: MOD_RES
<222> LOCATION: (45)..(45)
<223> OTHER INFORMATION: lysine or glutamine
<220> FEATURE:
<221> NAME/KEY: MOD_RES
<222> LOCATION: (48)..(48)
<223> OTHER INFORMATION: Any amino acid ordinarily found in living
      organisms
<220> FEATURE:
<221> NAME/KEY: MOD_RES
<222> LOCATION: (50)..(54)
<223> OTHER INFORMATION: Any amino acid ordinarily found in living
      organisms
<220> FEATURE:
<221> NAME/KEY: MOD_RES
<222> LOCATION: (55)..(57)
<223> OTHER INFORMATION: Any amino acid ordinarily found in living
      organisms or absent
<220> FEATURE:
<221> NAME/KEY: MOD_RES
<222> LOCATION: (58)..(70)
```

```
<223> OTHER INFORMATION: Any amino acid ordinarily found in living
      organisms
<220> FEATURE:
<221> NAME/KEY: MOD_RES
<222> LOCATION: (72)..(78)
<223> OTHER INFORMATION: Any amino acid ordinarily found in living
      organisms
<220> FEATURE:
<221> NAME/KEY: MOD_RES
<222> LOCATION: (80)..(84)
<223> OTHER INFORMATION: Any amino acid ordinarily found in living
      organisms
<220> FEATURE:
<221> NAME/KEY: MOD_RES
<222> LOCATION: (86)..(93)
<223> OTHER INFORMATION: Any amino acid ordinarily found in living
      organisms
<220> FEATURE:
<221> NAME/KEY: MOD_RES
<222> LOCATION: (95)..(97)
<223> OTHER INFORMATION: Any amino acid ordinarily found in living
      organisms
<220> FEATURE:
<221> NAME/KEY: MOD_RES
<222> LOCATION: (99)..(99)
<223> OTHER INFORMATION: Any amino acid ordinarily found in living
      organisms
<220> FEATURE:
<221> NAME/KEY: MOD_RES
<222> LOCATION: (101)..(108)
<223> OTHER INFORMATION: Any amino acid ordinarily found in living
      organisms
<220> FEATURE:
<221> NAME/KEY: MOD_RES
<222> LOCATION: (109)..(119)
<223> OTHER INFORMATION: Any amino acid ordinarily found in living
      organisms or absent
<220> FEATURE:
<221> NAME/KEY: MOD_RES
<222> LOCATION: (120)..(121)
<223> OTHER INFORMATION: Any amino acid ordinarily found in living
      organisms
<220> FEATURE:
<221> NAME/KEY: MOD_RES
<222> LOCATION: (123)..(123)
<223> OTHER INFORMATION: Any amino acid ordinarily found in living
      organisms
<220> FEATURE:
<221> NAME/KEY: MOD_RES
<222> LOCATION: (126)..(127)
<223> OTHER INFORMATION: Any amino acid ordinarily found in living
      organisms
<220> FEATURE:
<221> NAME/KEY: MOD_RES
<222> LOCATION: (129)..(129)
<223> OTHER INFORMATION: Any amino acid ordinarily found in living
      organisms
<220> FEATURE:
<221> NAME/KEY: MOD_RES
<222> LOCATION: (132)..(132)
<223> OTHER INFORMATION: Any amino acid ordinarily found in living
      organisms

<400> SEQUENCE: 1

Xaa Xaa Xaa Leu Xaa Xaa Xaa Gly Xaa Xaa Xaa Xaa Pro Xaa Xaa
 1               5                  10                  15

Xaa Xaa Xaa Xaa Xaa Cys Xaa Xaa Xaa Gly Xaa Xaa Xaa Xaa Xaa
                20                  25                  30

Xaa Xaa Xaa Xaa Xaa Trp Xaa Arg Gln Xaa Xaa Gly Xaa Gly Leu Xaa
             35                  40                  45

Trp Xaa Xaa Xaa Xaa Xaa Xaa Xaa Xaa Xaa Xaa Xaa Xaa Xaa
     50                  55                  60

Xaa Xaa Xaa Xaa Xaa Xaa Arg Xaa Xaa Xaa Xaa Xaa Xaa Ser Xaa
65                  70                  75                  80
```

```
Xaa Xaa Xaa Xaa Leu Xaa Xaa Xaa Xaa Xaa Xaa Xaa Asp Xaa Xaa
                 85                  90                  95

Xaa Tyr Xaa Cys Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Trp Xaa Gln Gly Xaa Xaa Val
        115                 120                 125

Xaa Val Ser Xaa
    130
```

```
<210> SEQ ID NO 2
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Consensus amino acid sequence for a CH1 domain
<220> FEATURE:
<221> NAME/KEY: MOD_RES
<222> LOCATION: (1)..(5)
<223> OTHER INFORMATION: Any amino acid ordinarily found in living
      organisms
<220> FEATURE:
<221> NAME/KEY: MOD_RES
<222> LOCATION: (7)..(9)
<223> OTHER INFORMATION: Any amino acid ordinarily found in living
      organisms
<220> FEATURE:
<221> NAME/KEY: MOD_RES
<222> LOCATION: (11)..(15)
<223> OTHER INFORMATION: Any amino acid ordinarily found in living
      organisms
<220> FEATURE:
<221> NAME/KEY: MOD_RES
<222> LOCATION: (16)..(16)
<223> OTHER INFORMATION: arginine or lysine
<220> FEATURE:
<221> NAME/KEY: MOD_RES
<222> LOCATION: (17)..(26)
<223> OTHER INFORMATION: Any amino acid ordinarily found in living
      organisms
<220> FEATURE:
<221> NAME/KEY: MOD_RES
<222> LOCATION: (29)..(29)
<223> OTHER INFORMATION: Any amino acid ordinarily found in living
      organisms
<220> FEATURE:
<221> NAME/KEY: MOD_RES
<222> LOCATION: (31)..(33)
<223> OTHER INFORMATION: Any amino acid ordinarily found in living
      organisms
<220> FEATURE:
<221> NAME/KEY: MOD_RES
<222> LOCATION: (35)..(40)
<223> OTHER INFORMATION: Any amino acid ordinarily found in living
      organisms
<220> FEATURE:
<221> NAME/KEY: MOD_RES
<222> LOCATION: (42)..(50)
<223> OTHER INFORMATION: Any amino acid ordinarily found in living
      organisms
<220> FEATURE:
<221> NAME/KEY: MOD_RES
<222> LOCATION: (52)..(52)
<223> OTHER INFORMATION: Any amino acid ordinarily found in living
      organisms
<220> FEATURE:
<221> NAME/KEY: MOD_RES
<222> LOCATION: (54)..(55)
<223> OTHER INFORMATION: Any amino acid ordinarily found in living
      organisms
<220> FEATURE:
<221> NAME/KEY: MOD_RES
```

```
<222> LOCATION: (57)..(63)
<223> OTHER INFORMATION: Any amino acid ordinarily found in living
      organisms
<220> FEATURE:
<221> NAME/KEY: MOD_RES
<222> LOCATION: (65)..(65)
<223> OTHER INFORMATION: Any amino acid ordinarily found in living
      organisms
<220> FEATURE:
<221> NAME/KEY: MOD_RES
<222> LOCATION: (68)..(82)
<223> OTHER INFORMATION: Any amino acid ordinarily found in living
      organisms
<220> FEATURE:
<221> NAME/KEY: MOD_RES
<222> LOCATION: (84)..(98)
<223> OTHER INFORMATION: Any amino acid ordinarily found in living
      organisms

<400> SEQUENCE: 2

Xaa Xaa Xaa Xaa Xaa Pro Xaa Xaa Xaa Pro Xaa Xaa Xaa Xaa Xaa Xaa
1               5                   10                  15

Xaa Xaa Xaa Xaa Xaa Xaa Xaa Xaa Xaa Cys Leu Xaa Lys Xaa Xaa
            20                  25                  30

Xaa Pro Xaa Xaa Xaa Xaa Xaa Trp Xaa Xaa Xaa Xaa Xaa Xaa Xaa
        35                  40                  45

Xaa Xaa His Xaa Phe Xaa Xaa Val Xaa Xaa Xaa Xaa Xaa Xaa Xaa Thr
    50                  55                  60

Xaa Ser Ser Xaa Xaa Xaa Xaa Xaa Xaa Xaa Xaa Xaa Xaa Xaa Xaa Xaa
65                  70                  75                  80

Xaa Xaa Cys Xaa Xaa Xaa Xaa Xaa Xaa Xaa Xaa Xaa Xaa Xaa Xaa
            85                  90                  95

Xaa Xaa

<210> SEQ ID NO 3
<211> LENGTH: 98
<212> TYPE: PRT
<213> ORGANISM: Homo sapiens

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 4
<211> LENGTH: 98
<212> TYPE: PRT
<213> ORGANISM: Homo sapiens

<400> SEQUENCE: 4

Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val

<210> SEQ ID NO 5
<211> LENGTH: 98
<212> TYPE: PRT
<213> ORGANISM: Homo sapiens

<400> SEQUENCE: 5

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val

<210> SEQ ID NO 6
<211> LENGTH: 98
<212> TYPE: PRT
<213> ORGANISM: Homo sapiens

<400> SEQUENCE: 6

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 7
<211> LENGTH: 232
<212> TYPE: PRT
<213> ORGANISM: Homo sapiens
```

<400> SEQUENCE: 7

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230
```

<210> SEQ ID NO 8
<211> LENGTH: 228
<212> TYPE: PRT
<213> ORGANISM: Homo sapiens

<400> SEQUENCE: 8

```
Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Met Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125
```

```
Val Tyr Thr Leu Pro Pro Ser Arg Glu Glu Met Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
                180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
        210                 215                 220

Ser Pro Gly Lys
225

<210> SEQ ID NO 9
<211> LENGTH: 279
<212> TYPE: PRT
<213> ORGANISM: Homo sapiens

<400> SEQUENCE: 9

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
                20                  25                  30

Glu Pro Lys Ser Cys Asp Thr Pro Pro Cys Pro Arg Cys Pro Glu
            35                  40                  45

Pro Lys Ser Cys Asp Thr Pro Pro Cys Pro Arg Cys Pro Ala Pro
50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
                100                 105                 110

Gly Val Glu Val His Asn Ala Lys Thr Lys Pro Arg Glu Glu Gln Tyr
            115                 120                 125

Asn Ser Thr Phe Arg Val Val Ser Val Leu Thr Val Leu His Gln Asp
        130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
                180                 185                 190

Asn Gln Val Ser Leu Thr Cys Leu Val Lys Gly Phe Tyr Pro Ser Asp
            195                 200                 205

Ile Ala Val Glu Trp Glu Ser Ser Gly Gln Pro Glu Asn Asn Tyr Asn
        210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
```

```
                    260                 265                 270
Leu Ser Leu Ser Pro Gly Lys
                275

<210> SEQ ID NO 10
<211> LENGTH: 229
<212> TYPE: PRT
<213> ORGANISM: Homo sapiens

<400> SEQUENCE: 10

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 11
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Consensus amino acid sequence for a human VL
      domain
<220> FEATURE:
<221> NAME/KEY: MOD_RES
<222> LOCATION: (1)..(15)
<223> OTHER INFORMATION: Any amino acid ordinarily found in living
      organisms
<220> FEATURE:
<221> NAME/KEY: MOD_RES
<222> LOCATION: (17)..(22)
<223> OTHER INFORMATION: Any amino acid ordinarily found in living
      organisms
```

-continued

```
<220> FEATURE:
<221> NAME/KEY: MOD_RES
<222> LOCATION: (24)..(27)
<223> OTHER INFORMATION: Any amino acid ordinarily found in living
      organisms
<220> FEATURE:
<221> NAME/KEY: MOD_RES
<222> LOCATION: (28)..(33)
<223> OTHER INFORMATION: Any amino acid ordinarily found in living
      organisms or absent
<220> FEATURE:
<221> NAME/KEY: MOD_RES
<222> LOCATION: (34)..(40)
<223> OTHER INFORMATION: Any amino acid ordinarily found in living
      organisms
<220> FEATURE:
<221> NAME/KEY: MOD_RES
<222> LOCATION: (42)..(48)
<223> OTHER INFORMATION: Any amino acid ordinarily found in living
      organisms
<220> FEATURE:
<221> NAME/KEY: MOD_RES
<222> LOCATION: (49)..(49)
<223> OTHER INFORMATION: alanine, serine, or proline
<220> FEATURE:
<221> NAME/KEY: MOD_RES
<222> LOCATION: (51)..(63)
<223> OTHER INFORMATION: Any amino acid ordinarily found in living
      organisms
<220> FEATURE:
<221> NAME/KEY: MOD_RES
<222> LOCATION: (64)..(64)
<223> OTHER INFORMATION: isoleucine or valine
<220> FEATURE:
<221> NAME/KEY: MOD_RES
<222> LOCATION: (66)..(66)
<223> OTHER INFORMATION: Any amino acid ordinarily found in living
      organisms
<220> FEATURE:
<221> NAME/KEY: MOD_RES
<222> LOCATION: (72)..(78)
<223> OTHER INFORMATION: Any amino acid ordinarily found in living
      organisms
<220> FEATURE:
<221> NAME/KEY: MOD_RES
<222> LOCATION: (80)..(89)
<223> OTHER INFORMATION: Any amino acid ordinarily found in living
      organisms
<220> FEATURE:
<221> NAME/KEY: MOD_RES
<222> LOCATION: (90)..(90)
<223> OTHER INFORMATION: alanine or glycine
<220> FEATURE:
<221> NAME/KEY: MOD_RES
<222> LOCATION: (91)..(91)
<223> OTHER INFORMATION: Any amino acid ordinarily found in living
      organisms
<220> FEATURE:
<221> NAME/KEY: MOD_RES
<222> LOCATION: (93)..(93)
<223> OTHER INFORMATION: tyrosine or phenylalanine
<220> FEATURE:
<221> NAME/KEY: MOD_RES
<222> LOCATION: (94)..(101)
<223> OTHER INFORMATION: Any amino acid ordinarily found in living
      organisms
<220> FEATURE:
<221> NAME/KEY: MOD_RES
<222> LOCATION: (102)..(102)
<223> OTHER INFORMATION: Any amino acid ordinarily found in living
      organisms or absent
<220> FEATURE:
<221> NAME/KEY: MOD_RES
<222> LOCATION: (103)..(104)
<223> OTHER INFORMATION: Any amino acid ordinarily found in living
      organisms
<220> FEATURE:
<221> NAME/KEY: MOD_RES
<222> LOCATION: (107)..(107)
```

<223> OTHER INFORMATION: glutamine or glycine
<220> FEATURE:
<221> NAME/KEY: MOD_RES
<222> LOCATION: (110)..(117)
<223> OTHER INFORMATION: Any amino acid ordinarily found in living
      organisms

<400> SEQUENCE: 11

Xaa Xaa Xaa Xaa Xaa Xaa Xaa Xaa Xaa Xaa Xaa Xaa Xaa Xaa Xaa Gly
1               5                   10                  15

Xaa Xaa Xaa Xaa Xaa Xaa Cys Xaa Xaa Xaa Xaa Xaa Xaa Xaa Xaa
            20                  25                  30

Xaa Xaa Xaa Xaa Xaa Xaa Xaa Xaa Trp Xaa Xaa Xaa Xaa Xaa Xaa Xaa
        35                  40                  45

Xaa Pro Xaa Xaa Xaa Xaa Xaa Xaa Xaa Xaa Xaa Xaa Xaa Xaa Xaa Xaa
    50                  55                  60

Pro Xaa Arg Phe Ser Gly Ser Xaa Xaa Xaa Xaa Xaa Xaa Xaa Leu Xaa
65                  70                  75                  80

Xaa Xaa Xaa Xaa Xaa Xaa Xaa Xaa Xaa Xaa Tyr Xaa Xaa Xaa Xaa
            85                  90                  95

Xaa Xaa Xaa Xaa Xaa Xaa Xaa Xaa Phe Gly Xaa Gly Thr Xaa Xaa Xaa
            100                 105                 110

Xaa Xaa Xaa Xaa Xaa
        115

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Consensus amino acid sequence for a CL kappa
      domain
<220> FEATURE:
<221> NAME/KEY: MOD_RES
<222> LOCATION: (1)..(5)
<223> OTHER INFORMATION: Any amino acid ordinarily found in living
      organisms
<220> FEATURE:
<221> NAME/KEY: MOD_RES
<222> LOCATION: (7)..(11)
<223> OTHER INFORMATION: Any amino acid ordinarily found in living
      organisms
<220> FEATURE:
<221> NAME/KEY: MOD_RES
<222> LOCATION: (14)..(23)
<223> OTHER INFORMATION: Any amino acid ordinarily found in living
      organisms
<220> FEATURE:
<221> NAME/KEY: MOD_RES
<222> LOCATION: (25)..(25)
<223> OTHER INFORMATION: Any amino acid ordinarily found in living
      organisms
<220> FEATURE:
<221> NAME/KEY: MOD_RES
<222> LOCATION: (28)..(33)
<223> OTHER INFORMATION: Any amino acid ordinarily found in living
      organisms
<220> FEATURE:
<221> NAME/KEY: MOD_RES
<222> LOCATION: (35)..(38)
<223> OTHER INFORMATION: Any amino acid ordinarily found in living
      organisms
<220> FEATURE:
<221> NAME/KEY: MOD_RES
<222> LOCATION: (40)..(40)
<223> OTHER INFORMATION: Any amino acid ordinarily found in living
      organisms <220> FEATURE:
<221> NAME/KEY: MOD_RES
<222> LOCATION: (42)..(52)
<223> OTHER INFORMATION: Any amino acid ordinarily found in living
      organisms
<220> FEATURE:
<221> NAME/KEY: MOD_RES
<222> LOCATION: (54)..(54)
<223> OTHER INFORMATION: Any amino acid ordinarily found in living
      organisms
<220> FEATURE:
<221> NAME/KEY: MOD_RES
<222> LOCATION: (56)..(56)
<223> OTHER INFORMATION: Any amino acid ordinarily found in living
      organisms
<220> FEATURE:
<221> NAME/KEY: MOD_RES
<222> LOCATION: (58)..(66)
<223> OTHER INFORMATION: Any amino acid ordinarily found in living
      organisms
<220> FEATURE:
<221> NAME/KEY: MOD_RES
<222> LOCATION: (68)..(68)
<223> OTHER INFORMATION: Any amino acid ordinarily found in living
      organisms
<220> FEATURE:
<221> NAME/KEY: MOD_RES
<222> LOCATION: (75)..(86)
<223> OTHER INFORMATION: Any amino acid ordinarily found in living
      organisms
<220> FEATURE:
<221> NAME/KEY: MOD_RES
<222> LOCATION: (88)..(90)
<223> OTHER INFORMATION: Any amino acid ordinarily found in living
      organisms
<220> FEATURE:
<221> NAME/KEY: MOD_RES
<222> LOCATION: (92)..(106)
<223> OTHER INFORMATION: Any amino acid ordinarily found in living
      organisms

<400> SEQUENCE: 12

Xaa Xaa Xaa Xaa Xaa Pro Xaa Xaa Xaa Xaa Pro Pro Xaa Xaa Xaa
1               5                   10                  15

Xaa Xaa Xaa Xaa Xaa Xaa Xaa Ser Xaa Val Cys Xaa Xaa Xaa Xaa
                20                  25                  30

Xaa Pro Xaa Xaa Xaa Xaa Val Xaa Trp Xaa Xaa Xaa Xaa Xaa Xaa
            35                  40                  45

Xaa Xaa Xaa Xaa Gln Xaa Ser Xaa Thr Xaa Xaa Xaa Xaa Xaa Xaa
        50                  55                  60

Xaa Xaa Ser Xaa Ser Ser Thr Leu Thr Leu Xaa Xaa Xaa Xaa Xaa
65                  70                  75                  80

Xaa Xaa Xaa Xaa Xaa Xaa Cys Xaa Xaa Xaa His Xaa Xaa Xaa Xaa
                85                  90                  95

Xaa Xaa Xaa Xaa Xaa Xaa Xaa Xaa Xaa Xaa Cys
                100                 105

<210> SEQ ID NO 13
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Consensus amino acid sequence for a CL lambda
      domain
<220> FEATURE:
<221> NAME/KEY: MOD_RES
<222> LOCATION: (1)..(5)
<223> OTHER INFORMATION: Any amino acid ordinarily found in living

```
          organisms
<220> FEATURE:
<221> NAME/KEY: MOD_RES
<222> LOCATION: (7)..(11)
<223> OTHER INFORMATION: Any amino acid ordinarily found in living
          organisms
<220> FEATURE:
<221> NAME/KEY: MOD_RES
<222> LOCATION: (14)..(23)
<223> OTHER INFORMATION: Any amino acid ordinarily found in living
          organisms
<220> FEATURE:
<221> NAME/KEY: MOD_RES
<222> LOCATION: (25)..(25)
<223> OTHER INFORMATION: Any amino acid ordinarily found in living
          organisms
<220> FEATURE:
<221> NAME/KEY: MOD_RES
<222> LOCATION: (28)..(33)
<223> OTHER INFORMATION: Any amino acid ordinarily found in living
          organisms
<220> FEATURE:
<221> NAME/KEY: MOD_RES
<222> LOCATION: (35)..(38)
<223> OTHER INFORMATION: Any amino acid ordinarily found in living
          organisms
<220> FEATURE:
<221> NAME/KEY: MOD_RES
<222> LOCATION: (40)..(40)
<223> OTHER INFORMATION: Any amino acid ordinarily found in living
          organisms
<220> FEATURE:
<221> NAME/KEY: MOD_RES
<222> LOCATION: (42)..(52)
<223> OTHER INFORMATION: Any amino acid ordinarily found in living
          organisms
<220> FEATURE:
<221> NAME/KEY: MOD_RES
<222> LOCATION: (54)..(54)
<223> OTHER INFORMATION: Any amino acid ordinarily found in living
          organisms
<220> FEATURE:
<221> NAME/KEY: MOD_RES
<222> LOCATION: (56)..(56)
<223> OTHER INFORMATION: Any amino acid ordinarily found in living
          organisms
<220> FEATURE:
<221> NAME/KEY: MOD_RES
<222> LOCATION: (58)..(66)
<223> OTHER INFORMATION: Any amino acid ordinarily found in living
          organisms
<220> FEATURE:
<221> NAME/KEY: MOD_RES
<222> LOCATION: (67)..(67)
<223> OTHER INFORMATION: alanine or methionine
<220> FEATURE:
<221> NAME/KEY: MOD_RES
<222> LOCATION: (68)..(68)
<223> OTHER INFORMATION: Any amino acid ordinarily found in living
          organisms
<220> FEATURE:
<221> NAME/KEY: MOD_RES
<222> LOCATION: (75)..(86)
<223> OTHER INFORMATION: Any amino acid ordinarily found in living
          organisms
<220> FEATURE:
<221> NAME/KEY: MOD_RES
<222> LOCATION: (88)..(90)
<223> OTHER INFORMATION: Any amino acid ordinarily found in living
          organisms
<220> FEATURE:
<221> NAME/KEY: MOD_RES
<222> LOCATION: (92)..(106)
<223> OTHER INFORMATION: Any amino acid ordinarily found in living
          organisms

<400> SEQUENCE: 13

Xaa Xaa Xaa Xaa Xaa Pro Xaa Xaa Xaa Xaa Xaa Pro Pro Xaa Xaa Xaa
```

```
                1               5                   10                  15
Xaa Xaa Xaa Xaa Xaa Xaa Ala Xaa Val Cys Xaa Xaa Xaa Xaa
                20                  25                  30

Xaa Pro Xaa Xaa Xaa Val Xaa Trp Xaa Xaa Xaa Xaa Xaa Xaa
        35                  40                  45

Xaa Xaa Xaa Xaa Glu Xaa Thr Xaa Pro Xaa Xaa Xaa Xaa Xaa
    50                  55                  60

Xaa Xaa Xaa Xaa Ser Ser Tyr Leu Ser Leu Xaa Xaa Xaa Xaa Xaa
65                  70                  75                  80

Xaa Xaa Xaa Xaa Xaa Cys Xaa Xaa Xaa His Xaa Xaa Xaa Xaa Xaa
            85                  90                  95

Xaa Xaa Xaa Xaa Xaa Xaa Xaa Xaa Xaa Xaa Cys
                100                 105
```

<210> SEQ ID NO 14
<211> LENGTH: 107
<212> TYPE: PRT
<213> ORGANISM: Homo sapiens

<400> SEQUENCE: 14

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105
```

<210> SEQ ID NO 15
<211> LENGTH: 107
<212> TYPE: PRT
<213> ORGANISM: Homo sapiens

<400> SEQUENCE: 15

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Gly Glu Val Thr His Gln Gly Leu Ser Ser
                85                  90                  95

Pro Val Thr Lys Ser Phe Asn Arg Gly Glu Cys
                100                 105
```

```
<210> SEQ ID NO 16
<211> LENGTH: 107
<212> TYPE: PRT
<213> ORGANISM: Homo sapiens

<400> SEQUENCE: 16

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Arg Lys Val Asp Asn Ala Leu Gln
        35                  40                  45

Ser Gly Asn Ser Gln Glu Ser Val Thr Glu Gln Glu Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 17
<211> LENGTH: 107
<212> TYPE: PRT
<213> ORGANISM: Homo sapiens

<400> SEQUENCE: 17

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 18
<211> LENGTH: 107
<212> TYPE: PRT
<213> ORGANISM: Homo sapiens

<400> SEQUENCE: 18

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Asn Thr Leu Thr Leu Ser Lys Ala Asp Tyr Glu
65                  70                  75                  80
```

```
Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 19
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of the light chain of a
      humanized antibody

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

```
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
        210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
```

Gly Lys
    450

<210> SEQ ID NO 21
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of the heavy chain of a
      humanized antibody

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

```
Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 22
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of the light chain of a
      humanized antibody

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 23
<211> LENGTH: 446
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Amino acid sequence of the heavy chain of an
engineered antibody

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Glu Ile Asp Pro Phe Asp Ser Tyr Thr Asn Tyr Asn Gln Lys Phe
    50                  55                  60

Lys Gly Arg Val Thr Met Thr Ile Asp Lys Ser Thr Asn Thr Val Tyr
65                  70                  75                  80

Met Glu Leu Ser Ser Leu Gly Ser Glu Asp Thr Ala Val Tyr Tyr Cys
                85                  90                  95

Ala Arg Pro Gly Tyr Thr Tyr Gly Gly Met Asp Phe Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro

```
                    340                 345                 350
Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 24
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of the light chain of an
      engineered antibody

<400> SEQUENCE: 24

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Phe Ile Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asn His Tyr Tyr Pro Tyr Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 25
<211> LENGTH: 11
```

-continued

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence of a light chain CDR1 of a
      humanized antibody

<400> SEQUENCE: 25

Arg Ala Ser Gln Asp Val Asn Thr Ala Val Ala
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence of a light chain CDR2 of a
      humanized antibody

<400> SEQUENCE: 26

Ser Ala Ser Phe Leu Trp Ser
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence of a light chain CDR3 of a
      humanized antibody

<400> SEQUENCE: 27

Gln Gln His Tyr Thr Thr Pro Pro Thr
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence of a heavy chain CDR1 of a
      humanized antibody

<400> SEQUENCE: 28

Asp Thr Tyr Ile His
1               5

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence of a heavy chain CDR2 of a
      humanized antibody

<400> SEQUENCE: 29
```

```
Arg Ile Tyr Pro Thr Asn Gly Tyr Thr Arg Tyr Ala Asp Ser Val Lys
1               5                   10                  15
Gly
```

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence of a heavy chain CDR3 of a
      humanized antibody

<400> SEQUENCE: 30

```
Trp Gly Gly Asp Gly Phe Tyr Ala Met Asp Tyr
1               5                   10
```

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence of a light chain CDR1 of a
      humanized antibody

<400> SEQUENCE: 31

```
Lys Ala Ser Gln Asp Val Ser Ile Gly Val Ala
1               5                   10
```

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence of a light chain CDR2 of a
      humanized antibody

<400> SEQUENCE: 32

```
Ser Ala Ser Tyr Arg Tyr Thr
1               5
```

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence of a light chain CDR3 of a
      humanized antibody

<400> SEQUENCE: 33

```
Gln Gln Tyr Tyr Ile Tyr Pro Tyr Thr
1               5
```

<210> SEQ ID NO 34
<211> LENGTH: 5
<212> TYPE: PRT
<213> ORGANISM: Artificial Sequence
<220> FEATURE:

<223> OTHER INFORMATION: Description of Artificial Sequence: Synthetic
    peptide
<220> FEATURE:
<223> OTHER INFORMATION: Amino acid sequence of a heavy chain CDR1 of a
    humanized antibody

<400> SEQUENCE: 34

Asp Thr Tyr Met Asp
1               5

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: Amino acid sequence of a heavy chain CDR2 of a
    humanized antibody

<400> SEQUENCE: 35

Asp Val Asn Pro Asn Ser Gly Gly Ser Ile Tyr Asn Gln Arg Phe Lys
1               5                   10                  15
Gly

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: Amino acid sequence of a heavy chain CDR3 of a
    humanized antibody

<400> SEQUENCE: 36

Asn Leu Gly Pro Ser Phe Tyr Phe Asp Tyr
1               5                   10

<210> SEQ ID NO 37
<211> LENGTH: 1347
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Nucleotide sequence encoding the heavy chain of
    an engineered antibody

<400> SEQUENCE: 37
caggtgcagc ttgtcgaaag cggtggtggg gtagttgaac cagggcgttc tttacgttta      60
tcttgtgcag cctccggttt caccttcagt tcatacggga tgcactgggt tagacaagct     120
ccaggaaaag gattagaatg ggtagctgtt atttggtaca accctagcga aaggattac      180 gccgattcag ctaagggtag gtttaccatt agtagagaca atagtaaaaa cactctatat     240
ctacaaatga acagcttgcg tgccgaggat actgcagttt actactgcgc gagggctggt     300
cttctcggtt atttcgacta ctggggtcag gggacattgg taactgtttc aagcgctagc     360
accaagggcc catccgtctt cccctggcg ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540

```
tactccctca gcagcgtggt gaccgtgccc tccagcagct tgggcaccca gacctacatc    600
tgcaacgtga atcacaagcc cagcaacacc aaggtggaca gaaaagttga gcccaaatct    660
tgtgacaaaa ctcacacatg cccaccgtgc ccagcacctg aactcctggg gggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctccca gccccatcg agaaaaccat ctccaaagcc   1020
aaagggcagc cccgagaacc acaggtgtac accctgcccc catcccggga ggagatgacc   1080
aagaaccagg tcagcctgac ctgcctggtc aaaggcttct atcccagcga catcgccgtg   1140
gagtgggaga gcaatgggca gccggagaac aactacaaga ccacgcctcc cgtgctggac   1200
tccgacggct ccttcttcct ctatagcaag ctcaccgtgg acaagagcag gtggcagcag   1260
gggaacgtct tctcatgctc cgtgatgcat gaggctctgc acaaccacta cacgcagaag   1320
agcctctccc tgtctccggg taaatga                                      1347
```

<210> SEQ ID NO 38
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of the heavy chain of an
      engineered antibody

<400> SEQUENCE: 38

```
Gln Val Gln Leu Val Glu Ser Gly Gly Gly Val Val Glu Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asn Pro Ser Glu Lys Asp Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Leu Leu Gly Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
```

```
              195                 200                 205
Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 39
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence encoding the light chain of
      an engineered antibody

<400> SEQUENCE: 39
gagattgttc tgacacagag tcctggtaca ttatctttgt cccctggtga aagggcaact      60
ctatcttgta gggcctctca atctattagc agctacttgg cttggtatca acaaaaacca    120
ggtcaagcgc cgagaccatt gatttatggt gtctcctcta gagcaacagg gataccagac    180
agatttagtg gaagcggttc aggtactgat ttcactctaa cgattagccg tttagaacct    240
gaagattttg cagtgtacta ttgtcaacag tacggcatga ccccctttac ctttggtcct    300
ggaactaaag tggatataaa gcgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
```

```
ctgagcaaag cagactacga gaaacacaaa gtctacgcct gcgaagtcac ccatcagggc      600
ctgagctcgc ccgtcacaaa gagcttcaac aggggagagt gttga                     645
```

<210> SEQ ID NO 40
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence ofo the light chain of an
      engineered antibody

<400> SEQUENCE: 40

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Pro Leu Ile
        35                  40                  45

Tyr Gly Val Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Met Ser Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 41
<211> LENGTH: 326
<212> TYPE: PRT
<213> ORGANISM: Homo sapiens

<400> SEQUENCE: 41

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 42
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of the CH1, hinge, CH2, and
      CH3 domains of an engineered antibody

<400> SEQUENCE: 42

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Asp Asp Tyr
                20                  25                  30

Phe Pro Glu Pro Val Thr Val Ser Trp Asn Ser Gly Ala Leu Thr Ser
            35                  40                  45

Gly Val His Thr Cys Pro Ala Cys Leu Gln Ser Ser Gly Leu Tyr Ser
        50                  55                  60

Leu Ser Ser Val Val Thr Val Pro Ser Ser Asn Phe Gly Thr Gln Thr

```
                65                  70                  75                  80
Tyr Thr Cys Asn Val Asp His Lys Pro Ser Asn Thr Lys Val Asp Lys
                    85                  90                  95

Thr Val Glu Arg Lys Cys Cys Val Glu Cys Pro Pro Cys Pro Ala Pro
                    100                 105                 110

Pro Val Ala Gly Pro Ser Val Phe Leu Phe Pro Pro Lys Pro Lys Asp
                    115                 120                 125

Thr Leu Met Ile Ser Arg Thr Pro Glu Val Thr Cys Val Val Val Asp
            130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Gln Phe Asn
                    165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
                195                 200                 205

Ala Pro Ile Glu Lys Thr Ile Ser Lys Thr Lys Gly Gln Pro Arg Glu
            210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                    245                 250                 255

Ala Val Glu Trp Glu Ser Asn Gly Gln Pro Glu Asn Asn Tyr Lys Thr
                260                 265                 270

Thr Pro Pro Met Leu Arg Ser Asp Gly Ser Phe Phe Leu Tyr Ser Glu
            275                 280                 285

Leu Thr Val Asp Lys Ser Arg Trp Gln Gln Gly Asn Val Phe Ser Cys
                290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 43
<211> LENGTH: 107
<212> TYPE: PRT
<213> ORGANISM: Homo sapiens

<400> SEQUENCE: 43

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                    85                  90                  95

Pro Val Thr Lys Ser Phe Asn Arg Gly Glu Cys
                100                 105
```

<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of the CL kappa domain of
      an engineered human antibody

<400> SEQUENCE: 44

Arg Thr Val Ala Ala Pro Ser Val Phe Ile Phe Pro Pro Ser Asp Glu
1               5                   10                  15

Gln Leu Lys Ser Gly Thr Ala Lys Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Cys Glu Cys Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser
            100                 105

<210> SEQ ID NO 45
<211> LENGTH: 72
<212> TYPE: PRT
<213> ORGANISM: Homo sapiens

<400> SEQUENCE: 45

Ser Thr Ser Gly Gly Thr Ala Ala Leu Gly Cys Leu Val Asp Tyr
1               5                   10                  15

Phe Pro Glu Pro Val Thr Val Ser Trp Asn Ser Gly Ala Leu Thr Ser
            20                  25                  30

Gly Val His Thr Cys Pro Ala Cys Leu Gln Ser Ser Gly Leu Tyr Ser
        35                  40                  45

Leu Ser Ser Val Val Thr Val Pro Ser Ser Ser Leu Gly Thr Gln Thr
    50                  55                  60

Tyr Ile Cys Asn Val Asn His Lys
65                  70

<210> SEQ ID NO 46
<211> LENGTH: 20
<212> TYPE: PRT
<213> ORGANISM: Homo sapiens

<400> SEQUENCE: 46

Val Asp Asn Ala Leu Gln Ser Gly Asn Ser Cys Glu Cys Val Thr Glu
1               5                   10                  15

Gln Asp Ser Lys
            20

MIXTURES OF ANTIBODIES

CROSS-REFERENCE TO RELATED APPLICATIONS

This is a National Stage application under 35 USC § 371 of International Application No. PCT/US2017/030676, having an international filing date of May 2, 2017, which claims the benefit of U.S. Provisional Patent Application. 62/342,167, filed May 26, 2016, both of which are incorporated herein by reference in their entirety for all purposes.

FIELD

The compositions and methods described herein are in the field of recombinant antibodies and methods for their production.

BACKGROUND

Recombinant monoclonal antibodies have emerged as a very successful class of biological drugs for the treatment of a variety of different diseases during the past two decades. They have been used both with and without the co-administration of small molecule-based drugs. Due to the biological complexity of some diseases, antibody mixtures or bispecific antibodies that target more than one antigen or epitope can be more effective than single antibodies in treating certain conditions. See, e.g., Lindzen et al., (2010), Proc. Natl. Acad. Sci. 107(28): 12550-12563; Nagorsen and Baeuerle (2011), Exp. Cell Res. 317(9): 1255-60.

Antibody mixtures allow flexibility in dosing of two different binding entities. This is not true for an IgG bispecific antibody because each of the two binding entities is present in the same amount since the binding entities are part of the same molecule. This may not be optimal in cases where different doses of each binding entity are desirable in a treatment regimen. See, e.g., Wolchok et al. (2013), New Engl. J. Med. 369(2): 122-133. Similarly, both binding entities will have the same in vivo half life in a bispecific antibody, which may not be optimal in some situations. Therapeutics including mixtures of two or more individual antibodies could allow different doses of antibodies comprising two different binding entities to be administered, and the antibodies could have different pharmacokinetic properties.

The manufacture of recombinant antibody mixtures can be accomplished through the separate production of each antibody from individual host cell lines and the mixture of multiple antibodies post production. Single batch production of multiple antibodies by mixing and co-culturing host cells expressing different antibodies has provided a less costly alternative to this approach. Rasmussen et al. (2012), *Arch Biochem Biophys.* 526: 139-45. Other simple and relatively inexpensive production processes for producing two or more antibodies using a single process are needed.

SUMMARY

The compositions and methods set forth herein are described below in a numbered series of items.

1. A mixture of antibodies comprising two major antibody species including (a) a first antibody comprising two copies of a first heavy chain (HC1) having the same amino acid sequence and two copies of a first light chain (LC1) having the same amino acid sequence and (b) a second antibody comprising two copies of a second heavy chain (HC2) having the same amino acid sequence and two copies of a second light chain (LC2) having the same amino acid sequence, wherein the first and second antibodies are full-length primate IgG antibodies, wherein the HC1 and the HC2 have different amino acid sequences, wherein the LC1 and the LC2 have different amino acid sequences, wherein the mixture comprises not more than three different major species of full-length antibodies, and wherein the mixture has been produced by a single host cell line into which DNA encoding the HC1, HC2, LC1, and LC2 has been introduced.

2. The mixture of item 1, wherein the HC1 and HC2 are human IgG HCs, wherein each is of any one of the following isotypes: IgG1, IgG2, IgG3, or IgG4.

3. The mixture of item 1 or 2, wherein
   the HC1 and/or HC2 contain(s) at least one LC-partner-directing alteration, and
   the LC1 and/or LC2 contain(s) at least one HC-partner-directing alteration at an amino acid contacting the amino acid at which the LC-partner-directing alteration(s) occur(s) in the HC1 and/or HC2, respectively, or contacting a charged amino acid or cysteine present in the HC1 and/or HC2, respectively.

4. The mixture of item 3,
   wherein the HC1 and/or HC2 comprise at least one LC-partner-directing alteration at a heavy chain (HC) residue, wherein the LC partner-directing alteration(s) cause(s) the HC1 and HC2 to comprise a charged amino acid at the same HC residue in both the HC1 and HC2 amino acid sequences, wherein the charged amino acid at the HC residue in the HC1 is opposite in charge to the charged amino acid at the HC residue in the HC2, and
   wherein the LC1 and/or LC2 comprise at least one HC-partner-directing alteration at a light chain (LC) residue contacting the HC residue, wherein the HC-partner-directing alteration(s) causes the LC1 and LC2 to comprise a charged amino acid at the same LC residue in the both the LC1 and LC2 amino acid sequences, wherein the charged amino acid at the LC residue in the LC1 is opposite in charge to the charged amino acid at the LC residue in the LC2, and the charged amino acid at the LC residue in the LC1 is opposite in charge to the amino at the HC residue in the HC1.

5. The mixture of item 3 or 4, wherein the first and second antibodies comprise one or more of the sets of alterations selected from the group consisting of:

(a) the set of alterations wherein positions 44 and 105 in both the HC1 and HC2 and 43 and 100 in both the LC1 and LC2 are each occupied by a charged amino acid, the amino acids at positions 44 and 105 in the HC1 are each opposite in charge from those at the same sites in the HC2, the amino acids at positions 43 and 100 in the LC1 are each opposite in charge from those at the same sites in LC2, the amino acids at position 44 in the HC1 and HC2 are opposite in charge to the amino acids at position 100 in the LC1 and LC2, respectively, and the amino acids at position 105 in the HC1 and HC2 are opposite in charge to the amino acids at position 43 in the LC1 and LC2, respectively;

(b) the set of alterations wherein positions 147 in the HC1 and HC2 and 131 in the LC1 and LC2 are each occupied by a charged amino acid, the amino acid at position 147 in the HC1 is opposite in charge from that at position 147 in the HC2, the amino acid at position 131 in the LC1 is opposite in charge from that at position 131 in the LC2, and the amino acids at position 147 in the HC1 and HC2 are opposite in charge to the amino acids at position 131 in the LC1 and LC2, respectively;

(c) the set of alterations wherein positions 168 in the HC1 and HC2 and 174 in the LC1 and LC2 are each occupied by a charged amino acid, the amino acid at position 168 the HC1 is opposite in charge from that at position 168 in the HC2, the amino acid at position 174 in the LC1 is opposite in charge from that at position 174 in the LC2, and the amino acids at position 168 in the HC1 and HC2 are opposite in charge to the amino acids at position 174 in the LC1 and LC2, respectively; and (d) the set of alterations wherein positions 181 in the HC1 and HC2 and 178 in the LC1 and LC2 are each occupied by a charged amino acid, the amino acid at position 181 in the HC1 is opposite in charge from that at position 181 in the HC2, the amino acid at position 178 in the LC1 is opposite in charge from that at position 178 in the LC2, and the amino acids at position 181 in the HC1 and HC2 are opposite in charge to the amino acids at position 178 in the LC1 and LC2, respectively.

6. The mixture of any one of items 1 to 5, wherein the first and second antibodies comprise one or more of the sets of alterations selected from the group consisting of:

(a) the set of alterations wherein the HC1 comprises 44E/D, the LC1 comprises 100R/K, the HC2 comprises 44R/K, and the LC2 comprises 100D/E; or the HC2 comprises 44E/D, the LC2 comprises 100R/K, the HC1 comprises 44R/K, and the LC1 comprises 100D/E;

(b) the set of alterations wherein the HC1 comprises 105E/D, the LC1 comprises 43R/K, the HC2 comprises 105R/K, and the LC2 comprises 43D/E; or the HC2 comprises 105E/D, the LC2 comprises 43R/K, the HC1 comprises 105R/K, and the LC1 comprises 43D/E;

(c) the set of alterations wherein the HC1 comprises 147R/K, the LC1 comprises 131E/D, the HC2 comprises 147E/D, and the LC2 comprises 131R/K; or the HC2 comprises 147R/K, the LC2 comprises 131E/D, the HC1 comprises 147E/D, and the LC1 comprises 131R/K;

(d) the set of alterations wherein the HC1 comprises 168E/D, the LC1 comprises 174R/K, the HC2 comprises 168R/K, and the LC2 comprises 174D/E; or the HC2 comprises 168E/D, the LC2 comprises 174R/K, the HC1 comprises 168R/K, and the LC1 comprises 174D/E; and (e) the set of alterations wherein the HC1 comprises 181E/D, the LC1 comprises 178R/K, the HC2 comprises 181R/K, and the LC2 comprises 178D/E; or the HC2 comprises 181E/D, the LC2 comprises 178R/K, the HC1 comprises 181R/K, and the LC1 comprises 178D/E.

7. The mixture of item 6, wherein the first and second antibodies comprise one or more of the sets of alterations selected from the group consisting of:

(a) the set of alterations wherein the HC1 comprises 44D and 105R, the LC1 comprises 43D and 100R, the HC2 comprises 44R and 105D, and the LC2 comprises 43R and 100D; or the HC2 comprises 44D and 105R, the LC2 comprises 43D and 100R, the HC1 comprises 44R and 105D, and the LC1 comprises 43R and 100D;

(b) the set of alterations wherein the HC1 comprises 147R, the LC1 comprises 131D, the HC2 comprises 147D, and the LC2 comprises 131R; or the HC2 comprises 147R, the LC2 comprises 131D, the HC1 comprises 147D, and the LC1 comprises 131R;

(c) the set of alterations wherein the HC1 comprises 168D, the LC1 comprises 174R, the HC2 comprises 168R, and the LC2 comprises 174D; or the HC2 comprises 168D, the LC2 comprises 174R, the HC1 comprises 168R, and the LC1 comprises 174D; and (d) the set of alterations wherein the HC1 comprises 181D, the LC1 comprises 178R, the HC2 comprises 181R, and the LC2 comprises 178D; or the HC2 comprises 181D, the LC2 comprises 178R, the HC1 comprises 181R, and the LC1 comprises 178D.

8. The mixture of item 7, wherein the first and second antibodies comprise one or more of the sets of alterations selected from the group consisting of:

(a) the set of alterations wherein the HC1 comprises G44D and Q105R, the LC1 comprises A/V43D and Q/G100R, the HC2 comprises G44R and Q105D, and the LC2 comprises A/V43R and Q/G100D; or the HC2 comprises G44D and Q105R, the LC2 comprises A/V43D and Q/G100R, the HC1 comprises G44R and Q105D, and the LC1 comprises A/V43R and Q/G100D;

(b) the set of alterations wherein the HC1 comprises K147R, the LC1 comprises S131D, the HC2 comprises K147D, and the LC2 comprises S131R; or the HC2 comprises K147R, the LC2 comprises S131D, the HC1 comprises K147D, and the LC1 comprises S131R;

(c) the set of alterations wherein the HC1 comprises H168D, the LC1 comprises S174R, the HC2 comprises H168R, and the LC2 comprises S174D; or the HC2 comprises H168D, the LC2 comprises S174R, the HC1 comprises H168R, and the LC1 comprises S174D; and (d) the set of alterations wherein the HC1 comprises S181 D, the LC1 comprises T178R, the HC2 comprises S181R, and the LC2 comprises T178D; or the HC2 comprises S181D, the LC2 comprises T178R, the HC1 comprises S181R, and the LC1 comprises T178D.

9. The mixture of any one of items 1 to 8, wherein the first and/or the second antibody comprise one or more of the pairs of alterations selected from the group consisting of:

126C in the HC1 and 121C in the LC1, or 126C in the HC2 and 121C in the LC2;

126C in the HC1 and 124C in the LC1, or 126C in the HC2 and 124C in the LC2;

127C in the HC1 and 121C in the LC1, or 127C in the HC2 and 121C in the LC2;

128C in the HC1 and 118C in the LC1, or 128C in the HC2 and 118C in the LC2;

133C in the HC1 and 117C in the LC1, or 133C in the HC2 and 117C in the LC2;

133C in the HC1 and 209C in the LC1, or 133C in the HC2 and 209C in the LC2;

134C in the HC1 and 116C in the LC1, or 134C in the HC2 and 116C in the LC2;

141C in the HC1 and 116C in the LC1, or 141C in the HC2 and 116C in the LC2;

168C in the HC1 and 174C in the LC1, or 168C in the HC2 and 174C in the LC2;

170C in the HC1 and 162C in the LC1, or 170C in the HC2 and 162C in the LC2;

170C in the HC1 and 176C in the LC1, or 170C in the HC2 and 176C in the LC2;

173C in the HC1 and 160C in the LC1, or 173C in the HC2 and 160C in the LC2;

173C in the HC1 and 162C in the LC1, or 173C in the HC2 and 162C in the LC2; and 183C in the HC1 and 176C in the LC1, or 183C in the HC2 and 176C in the LC2.

10. The mixture of any one of items 1 to 9, wherein the first and second antibodies comprise one or more of the sets of alterations selected from the group consisting of:

(1) positions 170 and 183 in the HC1 and HC2, respectively, and 162 and 176 in the LC1 and LC2, respectively, are each substituted with cysteine; or positions 170 and 183 in the HC2 and HC1, respectively, and 162 and 176 in the LC2 and LC1, respectively, are each substituted with cysteine;

(2) positions 173 and 170 in the HC1 and HC2, respectively, and 160 and 162 in the LC1 and LC2, respectively, are each substituted with cysteine; or positions 173 and 170 in the HC2 and HC1, respectively, and 160 and 162 in the LC2 and LC1, respectively, are each substituted with cysteine;

(3) positions 173 and 183 in the HC1 and HC2, respectively, and 160 and 176 in the LC1 and LC2, respectively, are each substituted with cysteine; or positions 173 and 183 in the HC2 and HC1, respectively, and 160 and 176 in the LC2 and LC1, respectively, are each substituted with cysteine;

(4) positions 170 in HC1 and the HC2 and 162 and 176 in the LC1 and LC2, respectively, are each substituted with cysteine; or positions 170 in the HC2 and HC1 and 162 and 176 in the LC2 and LC1, respectively, are each substituted with cysteine;

(5) positions 170 and 173 in the HC1 and HC2, respectively, and the 162 and 160 in LC1 and LC2, respectively, are each substituted with cysteine; or positions 170 and 173 in the HC2 and HC1, respectively, and 162 and 160 in the LC2 and LC1, respectively, are each substituted with cysteine;

(6) positions 173 and 170 in the HC1 and HC2, respectively, and 162 and 176 in the LC1 and LC2, respectively, are each substituted with cysteine; or positions 173 and 170 in the HC2 and HC1, respectively, and 162 and 176 in the LC2 and LC1, respectively, are each substituted with cysteine;

(7) positions 173 in the HC1 and HC2 and 162 and 160 in the LC1 and LC2, respectively, are each substituted with cysteine; or positions 173 in the HC2 and HC1 and 162 and 160 in the LC2 and LC1, respectively, are each substituted with cysteine;

(8) positions 183 and 173 in the HC1 and HC2, respectively, and 176 and 160 in the LC1 and LC2, respectively, are each substituted with cysteine; or positions 183 and 173 in the HC2 and HC1, respectively, and 176 and 160 in the LC2 and LC1, respectively, are each substituted with cysteine;

(9) positions 170 and 173 in the HC1 and HC2, respectively, and 176 and 160 in the LC1 and LC2, respectively, are each substituted with cysteine; or positions 170 and 173 in the HC2 and HC1, respectively, and 176 and 160 in the LC2 and LC1, respectively, are each substituted with cysteine; and

(10) positions 170 and 183 in the HC1 and HC2, respectively and 176 in the LC1 and LC2 are each substituted with cysteine; or positions the 170 and 183 in HC2 and HC1, respectively and 176 in the LC2 and LC1 are each substituted with cysteine.

11. The mixture of any one of items 1 to 10, wherein the first and second antibodies comprise one or more of the sets of alterations selected from the group consisting of:

(1) the HC1 comprises F170C, the LC1 comprises S162C, the HC2 comprises S183C, and the LC2 comprises S176C; or the HC2 comprises F170C, the LC2 comprises S162C, the HC1 comprises S183C, and the LC1 comprises S176C;

(2) the HC1 comprises V173C, the LC1 comprises Q160C, the HC2 comprises F170C, and the LC2 comprises S162C; or the HC2 comprises V173C, the LC2 comprises Q160C, the HC1 comprises F170C, and the LC1 comprises S162C;

(3) the HC1 comprises V173C, the LC1 comprises Q160C, the HC2 comprises S183C, and the LC2 comprises S176C; or the HC2 comprises V173C, the LC2 comprises Q160C, the HC1 comprises S183C, and the LC1 comprises S176C;

(4) the HC1 comprises F170C, the LC1 comprises S162C, the HC2 comprises F170C, and the LC2 comprises S176C; or the HC2 comprises F170C, the LC2 comprises S162C, the HC1 comprises F170C, and the LC1 comprises S176C;

(5) the HC1 comprises F170C, the LC1 comprises S162C, the HC2 comprises V173C, and the LC2 comprises Q160C; or the HC2 comprises F170C, the LC2 comprises S162C, the HC1 comprises V173C, and the LC1 comprises Q160C;

(6) the HC1 comprises V173C, the LC1 comprises S162C, the HC2 comprises F170C, and the LC2 comprises S176C; or the HC2 comprises V173C, the LC2 comprises S162C, the HC1 comprises F170C, and the LC1 comprises S176C;

(7) the HC1 comprises V173C, the LC1 comprises S162C, the HC2 comprises V173C, and the LC2 comprises Q160C; or the HC2 comprises V173C, the LC2 comprises S162C, the HC1 comprises V173C, and the LC1 comprises Q160C;

(8) the HC1 comprises S183C, the LC1 comprises S176C, the HC2 comprises V173C, and the LC2 comprises Q160C; or the HC2 comprises S183C, the LC2 comprises S176C, the HC1 comprises V173C, and the LC1 comprises Q160C;

(9) the HC1 comprises F170C, the LC1 comprises S176C, the HC2 comprises V173C, and the LC2 comprises Q160C; or the HC2 comprises F170C, the LC2 comprises S176C, the HC1 comprises V173C, and the LC1 comprises Q160C; and

(10) the HC1 comprises F170C, the LC1 comprises S176C, the HC2 comprises S183C, and the LC2 comprises S176C; or the HC2 comprises F170C, the LC2 comprises S176C, the HC1 comprises S183C, and the LC1 comprises S176C.

12. The mixture of any one of items 1 to 11, which comprises three major antibody species.

13. The mixture of any one of items 1 to 11, which comprises not more than two major antibody species.

14. The mixture of item 13,
wherein the HC1 and/or HC2 contain(s) one or more alteration(s) that disfavor(s) heterodimers.

15. The mixture of item 14, wherein
(a) (1) the HC1 is an IgG1 HC, the HC2 is an IgG4 HC, the HC1 comprises alterations that disfavor heterodimers at positions 399 and 409, and the HC2 does not contain an alteration that disfavors heterodimers; or (2) the HC2 is an IgG1 HC, the HC1 is an IgG4 HC, the HC2 comprises alterations that disfavor heterodimers at positions 399 and 409, and the HC1 does not contain an alteration that disfavors heterodimers;

(b) (1) the HC1 and HC2 are IgG1 HCs, the HC1 comprises alterations that disfavor heterodimers at positions 399 and 409, and the HC2 comprises the alteration K409R; or (2) the HC1 and HC2 are IgG1 HCs, the HC2 comprises alterations that disfavor heterodimers at positions 399 and 409, and the HC1 comprises the alteration K409R;

(c) (1) the HC1 is an IgG1 HC, the HC2 is an IgG4 HC, and the HC1 comprises alterations that disfavor heterodimers at positions 390 and 400; or (2) the HC1 is an IgG1

HC, the HC2 is an IgG4 HC, and the HC2 comprises alterations that disfavor heterodimers at positions 390 and 400;

(d) (1) the HC1 and HC2 are IgG1 HCs, and the HC1 comprises alterations that disfavor heterodimers at positions 390 and 400; or (2) the HC1 and HC2 are IgG1 HCs, and the HC2 comprises alterations that disfavor heterodimers at positions 390 and 400;

(e) (1) the HC1 is an IgG1 HC, the HC2 is an IgG4 HC, the HC1 comprises alterations that disfavor heterodimers at positions 364 and 370, and the HC2 does not contain an alteration that disfavors heterodimers; or (2) the HC2 is an IgG1 HC, the HC1 is an IgG4 HC, the HC2 comprises alterations that disfavor heterodimers at positions 364 and 370, and the HC1 does not contain an alteration that disfavors heterodimers; or (f) (1) the HC1 and HC2 are IgG1 HCs, the HC1 comprises alterations that disfavor heterodimers at positions 364 and 370, and the HC2 comprises the alteration K409R; or (2) the HC1 and HC2 are IgG1 HCs, the HC2 comprises alterations that disfavor heterodimers at positions 364 and 370, and the HC1 comprises the alteration K409R.

16. The mixture of item 15, wherein (a) (1) the HC1 is an IgG1 HC and comprises alterations D399R/K and K409D/E, and the HC2 is an IgG4 HC does not contain an alteration that disfavors heterodimers or (2) the HC2 is an IgG1 HC and comprises alterations D399R/K and K409D/E, and the HC1 is an IgG4 HC does not contain an alteration that disfavors heterodimers;

(b) the HC1 and HC2 are IgG1 HCs, and one of them comprises alterations D399R/K and K409D/E and the other comprises alteration K409R;

(c) (1) the HC1 is an IgG1 HC that comprises alterations N390R/K and S400D/E or alterations N390D/E and S400R/K, and the HC2 is an IgG4 HC; or (2) the HC1 is an IgG1 HC, and the HC2 is an IgG4 HC that comprises alterations N390R/K and S400D/E or alterations N390D/E and S400R/K;

(d) (1) the HC1 and HC2 are IgG1 HCs, and the HC1 comprises alterations N390R/K and S400D/E or the alterations N390D/E and S400R/K; or (2) the HC1 and HC2 are IgG1 HCs, and the HC2 comprises the alterations N390R/K and S400D/E or the alterations N390D/E and S400R/K;

(e) (1) the HC1 is an IgG1 HC, the HC2 is an IgG4 HC, the HC1 comprises the alterations S364K/R and K370D/E, and the HC2 does not contain an alteration that disfavors heterodimers; or (2) the HC2 is an IgG1 HC, the HC1 is an IgG4 HC, the HC2 comprises alterations S364K/R and K370D/E, and the HC1 does not contain an alteration that disfavors heterodimers; or (f) (1) the HC1 and HC2 are IgG1 HCs, the HC1 comprises alterations S364K/R and K370D/E, and the HC2 comprises alteration K409R; or (2) the HC1 and HC2 are IgG1 HCs, the HC2 comprises alterations S364K/R and K370D/E, and the HC1 comprises alteration K409R.

17. The mixture of any one of items 1 to 16, wherein if the HC1 and/or HC2 is an IgG4 HC, then the IgG4 HC(s) comprise(s) the alteration S228P.

18. The mixture of any one of items 1 to 17, wherein the in vivo half lives of the first and second antibodies differ by at least one week.

19. The mixture of item 18, wherein the in vivo half lives of the first and second antibodies differ by at least ten days.

20. The mixture of item 19, wherein the in vivo half lives of the first and second antibodies differ by at least two weeks.

21. The mixture of any one of items 18 to 20, wherein the antibody with the shorter in vivo half life contains the alteration M252A, M252L, M252S, M252R, R255K or H435R.

22. The mixture of any one items 1 to 21, wherein
the HC1 comprises a CDR1, CDR2, and CDR3 having the amino acid sequences SEQ ID NOs: 28, 29, and 30, respectively, the LC1 comprises a CDR1, CDR2, and CDR3 having the amino acid sequences SEQ ID NOs: 25, 26, and 27, respectively, the HC2 comprises a CDR1, CDR2, and CDR3 having the amino acid sequences SEQ ID NOs: 31, 32, and 33, and the LC2 comprises a CDR1, CDR2, and CDR3 having the amino acid sequences SEQ ID NOs: 34, 35, and 36.

23. The mixture of item 22, wherein
the HC1 comprises a heavy chain variable domain (VH) having the amino acid sequence of amino acids 1-120 of SEQ ID NO:20 comprising the alterations 44D and 105R, the LC1 comprises a light chain variable domain (VL) having the amino acid sequence of amino acids 1-107 of SEQ ID NO:19 comprising the alterations 43D, and 100R, the HC2 comprises a VH having the amino acid sequence of amino acid 1-119 of SEQ ID NO:21 comprising the alterations 44R and 105D, and the LC2 comprises a VL having the amino acid sequence of amino acid 1-107 of SEQ ID NO:22 comprising the alterations 43R and 100D.

24. The mixture of any one items 1 to 23, wherein
(a) one of the first and second antibodies binds to human CTLA4 and the other binds to human PD1,
(b) both the first and second antibodies bind to human HER2, but they do not compete for binding to HER2,
(c) one of the first and second antibodies binds to human LAG3 and the other binds to human PD1,
(d) one of the first and second antibodies binds to human GITR and the other binds to human PD1,
(d) one of the first and second antibodies binds to human VEGF and the other binds to human PD1,
(f) one of the first and second antibodies binds to human CSFR1a and the other binds to human PD1,
(g) one of the first and second antibodies binds to human OX40 and the other binds to human PD1,
(h) one of the first and second antibodies binds to human TIGIT and the other binds to human PD1,
(i) one of the first and second antibodies binds to human CTLA4 and the other binds to human PDL1,
(j) one of the first and second antibodies binds to human VEGF and the other binds to human PDL1,
(k) one of the first and second antibodies binds to human OX40 and the other binds to human PDL1,
(l) one of the first and second antibodies binds to human CSFR1a and the other binds to human PDL1,
(m) one of the first and second antibodies binds to human TIGIT and the other binds to human PDL1,
(n) one of the first and second antibodies binds to human Tim3 and the other binds to human PDL1,
(o) one of the first and second antibodies binds to human CTLA4 and the other binds to human VEGF,
(p) one of the first and second antibodies binds to human CTLA4 and the other binds to human 41BB,
(q) one of the first and second antibodies binds to human CD20 and the other binds to human CD37,
(r) one of the first and second antibodies binds to human ANG2 and the other binds to human VEGF,
(s) one of the first and second antibodies binds to human TNF and the other binds to human IL17a,
(t) one of the first and second antibodies binds to human CD38 and the other binds to human CD138, (u) one of the first and second antibodies binds to human EGFR and the other binds to human HER2, (v) one of the first and second antibodies binds to human EGFR and the other binds to human HER3, (w) one of the first and second antibodies binds to human MET and the other binds to human VEGF (x) one of the first and second antibodies binds to human MET and the other binds to human EGFR, (y) one of the first and second antibodies binds to human TSLP and the other binds to human IL33, or (z) one of the first and second antibodies binds to human IL4 and the other binds to human IL13, or (aa) one of the first and second antibodies binds to human PD1 and the other binds to human CD96.

25. A full-length antibody comprising two primate and/or humanized LCs having the same amino acid sequence and two primate and/or humanized IgG HCs having the same amino acid sequence, wherein the HCs each comprise a charged amino acid at position 181, wherein the LCs each comprise a charged amino acid at position 178, and wherein the charge of the amino acid at the HC position 181 is opposite to the charge of the amino acid at the LC position 178.

26. A method of making the mixture of antibodies of any one of items 1 to 24, comprising the steps of:

(a) culturing the host cell line expressing the antibody species in a culture medium, and (b) recovering the mixture comprising the antibody species from the culture medium.

27. The method of item 26, wherein the host cell line is a mammalian cell line.

28. The method of item 27, wherein the host cell line is a CHO cell line.

29. The method of any one of items 26 to 28, further comprising a step of purifying the mixture from other components present in the culture medium.

30. A host cell line that produces the mixture of antibodies of any one of items 1 to 24.

31. The host cell line of item 30, which is a mammalian cell line.

32. The host cell of item 31, which is a CHO cell line.

33. A nucleic acid or a mixture of nucleic acids encoding the antibody or the mixture of antibodies of any one of items 1 to 25.

34. One or more vector(s) containing the nucleic acid or mixture of nucleic acids of item 33.

35. The vector(s) of item 34, each of which is a mammalian expression vector.

36. The vector(s) of item 34, each of which is a viral vector.

37. The vector(s) of item 36, each of which is an adenovirus, an adeno-associated virus (AAV), a retrovirus, a vaccinia virus, a modified vaccinia virus Ankara (MVA), a herpes virus, a lentivirus, or a poxvirus vector.

38. A method of treating a disease comprising administering to a patient the mixture of any one of items 1 to 24.

39. A method of treating cancer comprising administering to a patient the mixture of item 24(a).

40. A method of treating breast cancer comprising administering to a patient the mixture of item 24(b).

41. The method of item 40, wherein the mixture comprises three major antibody species.

42. The method of item 41, wherein the mixture comprises at most three major antibody species.

43. A method of treating a patient having a tumor comprising injecting into the tumor the mixture of any one of items 1 to 24.

44. A method of treating a patient having a tumor comprising administering directly to the tumor the nucleic acid(s) of item 33 or the vector(s) of any one of items 34 to 37.

45. The method of item 44, wherein the nucleic acid(s) or the vector(s) are injected into the tumor.

46. A mixture of antibodies comprising two major antibody species, which include (a) a first antibody comprising a first heavy chain (HC1) and a first light chain (LC1) and (b) a second antibody comprising a second heavy chain (HC2) and a second light chain (LC2), wherein the first and second antibodies are full-length primate and/or humanized IgG antibodies, wherein the first antibody comprises two chains of the HC1 having the same first amino acid sequence and two chains of the LC1 having the same second amino sequence, wherein the second antibody comprises two chains of the HC2 having the same third amino acid sequence and two chains of the LC2 having the same fourth amino sequence, wherein the HC1 and the HC2 have different amino acid sequences, wherein the LC1 and the LC2 have different amino acid sequences, wherein the mixture comprises not more than ten different major species of full-length IgG antibodies, and wherein the mixture has been produced by a host cell line into which DNA(s) encoding the HC1, HC2, LC1, and LC2 has (have) been introduced.

47. The mixture of item 46, wherein the mixture comprises not more than three different major species of full-length antibodies.

48. The mixture of item 47, wherein the DNA(s) encoding the HC1, HC2, LC1, and LC2 was (were) introduced at the same time.

49. The mixture of item 47, wherein the DNA(s) encoding the HC1 and LC1 was (were) introduced before the DNA(s) encoding the HC2 and LC2, or the DNA(s) encoding the HC2 and LC2 was (were) introduced before the DNA(s) encoding the HC1 and LC1.

50. The mixture of any one of items 46 to 49, wherein the HC1 and HC2 are human and/or humanized IgG heavy chains (HCs), and the LC1 and LC2 are human and/or humanized light chains (LCs).

51. The mixture of any one of items 46 to 50, wherein:

(a) both the first and second antibodies comprise one or more partner-directing alteration;

(b) both the first and second antibodies comprise one or more partner-directing alteration, and at least one of the first and second antibodies comprises at least one alteration that disfavors heterodimers; or (c) either the first antibody comprises one or more partner-directing alteration and the second does not or vice versa.

52. The mixture of item 51(c), wherein either the first antibody comprises one or more alteration that disfavors heterodimers and the second antibody does not, or vice versa.

53. The mixture of item 52, wherein either (1) the first antibody comprises one or more partner-directing alteration and one or more alteration that disfavors heterodimers and the second antibody does not comprise a partner-directing alteration or an alteration that disfavors heterodimers, or (2) the second antibody comprises one or more partner-directing alteration and one or more alteration that disfavors heterodimers and the first antibody does not comprise a partner-directing alteration or an alteration that disfavors heterodimers.

54. The mixture of any one of items 46 to 51, which comprises three major antibody species.

55. The mixture of any one of items 46 to 51, which comprises not more than two major antibody species.

56. The mixture of item 55, wherein the HC1 and/or the HC2 contain(s) one or more alteration that disfavors heterodimers.

57. The mixture of any one of items 46 to 56, wherein
(a) (1) the HC1 is an IgG1 or IgG2 heavy chain (HC), the HC2 is an IgG4 HC, the HC1 comprises alterations that disfavor heterodimers at positions 399 and 409, and the HC2 does not contain an alteration that disfavors heterodimers; or (2) the HC2 is an IgG1 or IgG2 HC, the HC1 is an IgG4 HC, the HC2 comprises alterations that disfavor heterodimers at positions 399 and 409, and the HC1 does not comprise an alteration that disfavors heterodimers; or
(b) (1) the HC1 and HC2 are each an IgG1 or an IgG2 HC, the HC1 comprises alterations that disfavor heterodimers at positions 399 and 409, and the HC2 comprises the alteration K409R; or (2) the HC1 and HC2 are each an IgG1 or an IgG2 HC, the HC2 comprises alterations that disfavor heterodimers at positions 399 and 409, and the HC1 comprises the alteration K409R.

58. The mixture of item 57, wherein
(a) (1) the HC1 is an IgG1 or IgG2 HC and comprises the alterations D399R/K and K409D/E, and the HC2 is an IgG4 HC and does not comprise an alteration that disfavors heterodimers or (2) the HC2 is an IgG1 or IgG2 HC and comprises the alterations D399R/K and K409D/E, and the HC1 is an IgG4 HC and does not comprise an alteration that disfavors heterodimers; or
(b) the HC1 and HC2 are each an IgG1 or an IgG2 HC, and one of them comprises the alterations D399R/K and K409D/E and the other comprises the alteration K409R.

59. The mixture of any one of items 46 to 51 and 54 to 56, wherein the first antibody comprises at least one alteration that disfavors heterodimers and the second antibody does not contain an alteration that disfavors heterodimers, or vice versa.

60. The mixture of any one of items 46 to 59, wherein
(a) the first antibody comprises at least one partner-directing alteration and the second antibody does not; and
(b) (1) the first antibody is a human and/or humanized IgG1 antibody, the cysteine at position 220 in the HC1 is substituted with another amino acid, and the cysteine at position 214 in the LC1 is substituted with another amino acid, or (2) the first antibody is a human and/or humanized IgG2 or IgG4 antibody, the cysteine at position 131 in the HC1 is substituted with another amino acid, and the cysteine at position 214 in the LC1 is substituted with another amino acid.

61. The mixture of item 60, wherein
the first antibody is an IgG1 antibody, and it comprises the alterations C220G/A in the HC1 and C214S/A/G in the LC1; or
the first antibody is an IgG2 or IgG4 antibody, and it comprises the alterations C131S/A/G in the HC1 and C214S/A/G in the LC1.

62. The mixture of item 61, wherein
the first antibody is an IgG1 antibody, and it comprises the alterations C220G in the HC1 and C214S in the LC1; or
the first antibody is an IgG2 or IgG4 antibody, it comprises the alterations C131S in the HC1 and C214S in the LC1.

63. The mixture of any of items 60 to 62,
wherein the first antibody is an IgG1 antibody;
wherein the first antibody comprises at least one pair of cysteine substitutions at a first pair of amino acid positions;
wherein the first pair of amino acid positions comprises a first HC1 position and a first LC1 position; and
wherein the first HC1 and LC1 positions, respectively, are selected from the group consisting of: positions 126 and 124; positions 128 and 118; positions 133 and 117; positions 133 and 209; positions 134 and 116; positions 168 and 174; positions 170 and 162; positions 170 and 176; positions 173 and 160; and positions 183 and 176.

64. The mixture of item 63,
wherein the first HC1 and LC1 positions, respectively, are selected from the group consisting of: positions 168 and 174; positions 173 and 160; and positions 170 and 162.

65. The mixture of item 64, wherein
the first antibody comprises a second pair of cysteine substitutions at a second pair of positions comprising a second HC1 and second LC1 position, which are different from the first HC1 and first LC1 positions, respectively, and
the second HC1 and LC1 positions, respectively, are selected from the group consisting of: positions 126 and 124; positions 128 and 118; positions 133 and 117; positions 133 and 209; positions 134 and 116; positions 168 and 174; positions 170 and 162; positions 170 and 176; positions 173 and 160; and positions 183 and 176.

66. The mixture of item 65, wherein the first HC1 and LC1 positions are, respectively, 173 and 160, and the second HC1 and LC1 positions are, respectively, 170 and 162.

67. The mixture of any one of items 60 to 62,
wherein the first antibody is an IgG4 antibody;
wherein the first antibody comprises at least one pair of cysteine substitutions at a first pair of amino acid positions;
wherein the first pair of amino acid positions comprises a first HC1 position and a first LC1 position; and
wherein the first HC1 and LC1 positions, respectively, are selected from the group consisting of: positions 126 and 121; positions 126 and 124; positions 127 and 121; positions 128 and 118; positions 168 and 174; positions 170 and 162; and positions 173 and 162.

68. The mixture of item 67, wherein
the first antibody comprises a second pair of cysteine substitutions at a second HC1 position and a second LC1 position, which are different from the first HC1 and LC1 positions, respectively, and
the second HC1 and LC1 positions, respectively, are selected from the group consisting of: positions 126 and 121; positions 126 and 124; positions 127 and 121; positions 128 and 118; positions 168 and 174; positions 170 and 162; and positions 173 and 162.

69. The mixture of any one of items 60 to 62,
wherein the first antibody is an IgG2 antibody;
wherein the first antibody comprises at least one pair of cysteine substitutions at a first pair of contacting amino acid positions, wherein one position is in the HC1 and the other is in the LC1.

70. The mixture of item 69, wherein the first pair of contacting amino acid positions in the HC1 and LC1, respectively, is selected from the group consisting of: 170 and 162; and 173 and 160.

71. The mixture of item 69 or 70, wherein the first antibody comprises a second pair of cysteine substitutions at a second pair of contacting amino acid positions, wherein one position in the second pair of contacting amino acid positions is an HC1 position and the other is an LC1 position, and wherein the HC1 and LC1 positions in the second pair of contacting amino acid positions are each different from the HC1 and LC1 positions, respectively, in the first pair of contacting amino acid positions.

72. The mixture of item 71, wherein the second pair of contacting amino acid positions in the HC1 and LC1, respectively, is selected from the group consisting of: 170 and 162; and 173 and 160.

73. The mixture of any one of items 46 to 72, wherein the first antibody comprises at least one partner-directing alteration in which a charged amino acid is substituted for another amino acid.

74. The mixture of item 73,
wherein the first antibody is an IgG1 antibody,
wherein the first antibody comprises a charge pair of amino acids,
wherein one amino acid of the charge pair is in the HC1, and one amino acid of the charge pair is in the LC1,
wherein at least one of the amino acids of the charge pair results from the partner-directing alteration; and
wherein the charge pair consists of one of the following amino acid pairs at the following positions in the HC1 and LC1, respectively: 147D/E and 124K/R; 147D/E and 129K/R; 147D/E and 131K/R; 147D/E and 180K/R; 168D/E and 164K/R; 168D/E and 167K/R; or 168D/E and 174K/R.

75. The mixture of item 73,
wherein the first antibody is an IgG4 antibody,
wherein the first antibody comprises a charge pair of amino acids,
wherein one amino acid of the charge pair is in the HC1, and one amino acid of the charge pair is in the LC1,
wherein at least one of the amino acids of the charge pair results from the partner-directing alteration; and
wherein the charge pair consists of one of the following amino acid pairs at the following positions in the HC1 and LC1, respectively: 133D/E and 117K/R; 137K/R and 114D/E; 137K/R and 116D/E; 147D/E and 124K/R; 147D/E and 129K/R; 147D/E and 131K/R; 147D/E and 178K/R; 147D/E and 180K/R; 168D/E and 164K/R; 168D/E and 167K/R; 168D/E and 173K/R; or 168D/E and 174K/R.

76. The mixture of item 73,
wherein the first antibody is an IgG2 antibody,
wherein the first antibody comprises a charge pair of amino acids,
wherein one amino acid of the charge pair is in the HC1 and one amino acid of the charge pair is in the LC1,
wherein at least one of the amino acids of the charge pair results from the partner-directing alteration.

77. The mixture of item 76, wherein the charge pair consists of 147D/E in the HC1 and 131K/R in the LC1.

78. The mixture of any one of items 46 to 59, wherein
the HC1 and/or the HC2 contain(s) at least one LC-partner-directing alteration at an HC residue, and
the LC1 and/or the LC2 contain(s) at least one HC-partner-directing alteration at an LC residue contacting the HC residue at which the LC-partner-directing alteration(s) occur(s) in HC1 and/or HC2, respectively, or contacting a charged amino acid or cysteine present in the HC1 and/or the HC2, respectively.

79. The mixture of item 78, wherein
the LC partner-directing alteration(s) cause(s) the HC1 and the HC2 to comprise a charged amino acid at the HC residue in both the HC1 and the HC2, the charged amino acid at the HC residue in the HC1 is opposite in charge to the charged amino acid at the HC residue in the HC2,
the HC-partner-directing alteration(s) cause(s) the LC1 and the LC2 to comprise a charged amino acid at the LC residue in both the LC1 and the LC2,
the charged amino acid at the LC residue in the LC1 is opposite in charge to the charged amino acid at the LC residue in the LC2, and
the charged amino acid at the LC residue in the LC1 is opposite in charge to the amino acid at the HC residue in the HC1.

80. The mixture of item 78 or 79, wherein the first and second antibodies comprise one or more of the sets of alterations selected from the group consisting of:
(a) the set of alterations wherein positions 44 and 105 in both the HC1 and the HC2 and 43 and 100 in both the LC1 and the LC2 are each occupied by a charged amino acid, the amino acids at positions 44 and 105 in the HC1 are each opposite in charge from those at the same sites in the HC2, the amino acids at positions 43 and 100 in the LC1 are each opposite in charge from those at the same sites in the LC2, the amino acids at position 44 in the HC1 and the HC2 are opposite in charge to the amino acids at position 100 in the LC1 and the LC2, respectively, and the amino acids at position 105 in the HC1 and the HC2 are opposite in charge to the amino acids at position 43 in the LC1 and the LC2, respectively;
(b) the set of alterations wherein positions 147 in the HC1 and the HC2 and 131 in the LC1 and the LC2 are each occupied by a charged amino acid, the amino acid at position 147 in the HC1 is opposite in charge from that at position 147 in the HC2, the amino acid at position 131 in the LC1 is opposite in charge from that at position 131 in the LC2, and the amino acids at position 147 in the HC1 and the HC2 are opposite in charge to the amino acids at position 131 in the LC1 and the LC2, respectively;
(c) the set of alterations wherein positions 168 in the HC1 and the HC2 and 174 in the LC1 and the LC2 are each occupied by a charged amino acid, the amino acid at position 168 the HC1 is opposite in charge from that at position 168 in the HC2, the amino acid at position 174 in the LC1 is opposite in charge from that at position 174 in the LC2, and the amino acids at position 168 in the HC1 and the HC2 are opposite in charge to the amino acids at position 174 in the LC1 and the LC2, respectively; and
(d) the set of alterations wherein positions 181 in the HC1 and the HC2 and 178 or 180 in the LC1 and the LC2 are each occupied by a charged amino acid, the amino acid at position 181 in the HC1 is opposite in charge from that at position 181 in the HC2, the amino acid at position 178 or 180 in the LC1 is opposite in charge from that at position 178 or 180 in the LC2, and the amino acids at position 181 in the HC1 and the HC2 are opposite in charge to the amino acids at position 178 or 180 in the LC1 and the LC2, respectively.

81. The mixture of any one of items 78 to 80, wherein the first and second antibodies comprise one or more of the sets of alterations selected from the group consisting of:
(a) the set of alterations wherein the HC1 comprises 44E/D, the LC1 comprises 100R/K, the HC2 comprises 44R/K, and the LC2 comprises 100D/E; or the HC2 comprises 44E/D, the LC2 comprises 100R/K, the HC1 comprises 44R/K, and the LC1 comprises 100D/E;
(b) the set of alterations wherein the HC1 comprises 105E/D, the LC1 comprises 43R/K, the HC2 comprises 105R/K, and the LC2 comprises 43D/E; or the HC2 comprises 105E/D, the LC2 comprises 43R/K, the HC1 comprises 105R/K, and the LC1 comprises 43D/E;

(c) the set of alterations wherein the HC1 comprises 147R/K, the LC1 comprises 131E/D, the HC2 comprises 147E/D, and the LC2 comprises 131R/K; or the HC2 comprises 147R/K, the LC2 comprises 131E/D, the HC1 comprises 147E/D, and the LC1 comprises 131R/K;

(d) the set of alterations wherein the HC1 comprises 168E/D, the LC1 comprises 174R/K, the HC2 comprises 168R/K, and the LC2 comprises 174D/E; or the HC2 comprises 168E/D, the LC2 comprises 174R/K, the HC1 comprises 168R/K, and the LC1 comprises 174D/E; and (e) the set of alterations wherein the HC1 comprises 181E/D, the LC1 comprises 178R/K or 180R/K, the HC2 comprises 181R/K, and the LC2 comprises 178D/E or 180D/E; or the HC2 comprises 181E/D, the LC2 comprises 178R/K or 180R/K, the HC1 comprises 181R/K, and the LC1 comprises 178D/E or 180D/E.

82. The mixture of item 81, wherein the first and second antibodies comprise one or more of the sets of alterations selected from the group consisting of:

(a) the set of alterations wherein the HC1 comprises 44D and 105R, the LC1 comprises 43D and 100R, the HC2 comprises 44R and 105D, and the LC2 comprises 43R and 100D; or the HC2 comprises 44D and 105R, the LC2 comprises 43D and 100R, the HC1 comprises 44R and 105D, and the LC1 comprises 43R and 100D;

(b) the set of alterations wherein the HC1 comprises 147R, the LC1 comprises 131D, the HC2 comprises 147D, and the LC2 comprises 131R; or the HC2 comprises 147R, the LC2 comprises 131 D, the HC1 comprises 147D, and the LC1 comprises 131R;

(c) the set of alterations wherein the HC1 comprises 168D, the LC1 comprises 174R, the HC2 comprises 168R, and the LC2 comprises 174D; or the HC2 comprises 168D, the LC2 comprises 174R, the HC1 comprises 168R, and the LC1 comprises 174D; and (d) the set of alterations wherein the HC1 comprises 181D, the LC1 comprises 178R or 180R, the HC2 comprises 181R, and the LC2 comprises 178D or 180D; or the HC2 comprises 181D, the LC2 comprises 178R or 180R, the HC1 comprises 181R, and the LC1 comprises 178D or 178D.

83. The mixture of item 82, wherein the first and second antibodies comprise one or more of the sets of alterations selected from the group consisting of:

(a) the set of alterations wherein the HC1 comprises G44D and Q105R, the LC1 comprises A/V43D and Q/G100R, the HC2 comprises G44R and Q105D, and the LC2 comprises A/V43R and Q/G100D; or the HC2 comprises G44D and Q105R, the LC2 comprises A/V43D and Q/G100R, the HC1 comprises G44R and Q105D, and the LC1 comprises A/V43R and Q/G100D.

(b) the set of alterations wherein the HC1 comprises K147R, the LC1 comprises S131D, the HC2 comprises K147D, and the LC2 comprises S131R; or the HC2 comprises K147R, the LC2 comprises S131D, the HC1 comprises K147D, and the LC1 comprises S131R;

(c) the set of alterations wherein the HC1 comprises H168D, the LC1 comprises S174R, the HC2 comprises H168R, and the LC2 comprises S174D; or the HC2 comprises H168D, the LC2 comprises S174R, the HC1 comprises H168R, and the LC1 comprises S174D; and (d) the set of alterations wherein the HC1 comprises S181 D, the LC1 comprises T/Y178R or T/S180R, the HC2 comprises S181R, and the LC2 comprises T/Y178D or T/S180D; or the HC2 comprises S181D, the LC2 comprises T/Y178R or T/S180R, the HC1 comprises S181R, and the LC1 comprises T/Y178D or T/S180D.

84. The mixture of any one of items 78 to 83,
wherein the first and/or the second antibody comprise one or more pairs of cysteine substitutions at one or more pairs of positions;
wherein each pair of positions comprises one HC position and one LC position;
wherein the HC and LC positions, respectively, in the pairs of positions are selected from the group consisting of: 126 and 121; 126 and 124; 127 and 121; 128 and 118; 133 and 117; 133 and 209; 134 and 116; 141 and 116; 168 and 174; 170 and 162; 170 and 176; 173 and 160; 173 and 162; and 183 and 176; and
wherein the first and second antibodies do not comprise cysteine substitutions at the same pairs of positions.

85. The mixture of item 84, wherein the first and second antibodies comprise one or more of the sets of alterations selected from the group consisting of:

(1) positions 170 and 183 in the HC1 and the HC2, respectively, and 162 and 176 in the LC1 and the LC2, respectively, are each substituted with cysteine; or positions 170 and 183 in the HC2 and the HC1, respectively, and 162 and 176 in the LC2 and the LC1, respectively, are each substituted with cysteine;

(2) positions 173 and 170 in the HC1 and the HC2, respectively, and 160 and 162 in the LC1 and the LC2, respectively, are each substituted with cysteine; or positions 173 and 170 in the HC2 and the HC1, respectively, and 160 and 162 in the LC2 and the LC1, respectively, are each substituted with cysteine;

(3) positions 173 and 183 in the HC1 and the HC2, respectively, and 160 and 176 in the LC1 and the LC2, respectively, are each substituted with cysteine; or positions 173 and 183 in the HC2 and the HC1, respectively, and 160 and 176 in the LC2 and the LC1, respectively, are each substituted with cysteine;

(4) positions 170 in the HC1 and the HC2 and 162 and 176 in the LC1 and the LC2, respectively, are each substituted with cysteine; or positions 170 in the HC2 and the HC1 and 162 and 176 in the LC2 and the LC1, respectively, are each substituted with cysteine;

(5) positions 170 and 173 in the HC1 and the HC2, respectively, and 162 and 160 in the LC1 and the LC2, respectively, are each substituted with cysteine; or positions 170 and 173 in the HC2 and the HC1, respectively, and 162 and 160 in the LC2 and the LC1, respectively, are each substituted with cysteine;

(6) positions 173 and 170 in the HC1 and the HC2, respectively, and 162 and 176 in the LC1 and the LC2, respectively, are each substituted with cysteine; or positions 173 and 170 in the HC2 and the HC1, respectively, and 162 and 176 in the LC2 and the LC1, respectively, are each substituted with cysteine;

(7) positions 173 in the HC1 and the HC2 and 162 and 160 in the LC1 and the LC2, respectively, are each substituted with cysteine; or positions 173 in the HC2 and the HC1 and 162 and 160 in the LC2 and the LC1, respectively, are each substituted with cysteine;

(8) positions 183 and 173 in the HC1 and the HC2, respectively, and 176 and 160 in the LC1 and the LC2, respectively, are each substituted with cysteine; or positions 183 and 173 in the HC2 and the HC1, respectively, and 176 and 160 in the LC2 and the LC1, respectively, are each substituted with cysteine;

(9) positions 170 and 173 in the HC1 and the HC2, respectively, and 176 and 160 in the LC1 and the LC2, respectively, are each substituted with cysteine; or positions 170 and 173 in the HC2 and the HC1, respectively, and 176 and 160 in the LC2 and the LC1, respectively, are each substituted with cysteine;

(10) positions 170 and 183 in the HC1 and the HC2, respectively, and 176 in the LC1 and the LC2 are each substituted with cysteine; or positions 170 and 183 in the HC2 and the HC1, respectively and 176 in the LC2 and the LC1 are each substituted with cysteine; and

(11) positions 173 and 170 in the HC1 and the HC2, respectively, and 162 in both the LC1 and the LC2 are each substituted with cysteine; or positions 173 and 170 in the HC2 and the HC1, respectively, and 162 in both the LC2 and the LC1 are each substituted with cysteine.

86. The mixture of item 85, wherein the first and second antibodies comprise one or more of the sets of alterations selected from the group consisting of:

(1) the HC1 comprises F170C, the LC1 comprises S162C, the HC2 comprises S183C, and the LC2 comprises S176C; or the HC2 comprises F170C, the LC2 comprises S162C, the HC1 comprises S183C, and the LC1 comprises S176C;

(2) the HC1 comprises V173C, the LC1 comprises Q160C, the HC2 comprises F170C, and the LC2 comprises S162C; or the HC2 comprises V173C, the LC2 comprises Q160C, the HC1 comprises F170C, and the LC1 comprises S162C;

(3) the HC1 comprises V173C, the LC1 comprises Q160C, the HC2 comprises S183C, and the LC2 comprises S176C; or the HC2 comprises V173C, the LC2 comprises Q160C, the HC1 comprises S183C, and the LC1 comprises S176C;

(4) the HC1 comprises F170C, the LC1 comprises S162C, the HC2 comprises F170C, and the LC2 comprises S176C; or the HC2 comprises F170C, the LC2 comprises S162C, the HC1 comprises F170C, and the LC1 comprises S176C;

(5) the HC1 comprises F170C, the LC1 comprises S162C, the HC2 comprises V173C, and the LC2 comprises Q160C; or the HC2 comprises F170C, the LC2 comprises S162C, the HC1 comprises V173C, and the LC1 comprises Q160C;

(6) the HC1 comprises V173C, the LC1 comprises S162C, the HC2 comprises F170C, and the LC2 comprises S176C; or the HC2 comprises V173C, the LC2 comprises S162C, the HC1 comprises F170C, and the LC1 comprises S176C;

(7) the HC1 comprises V173C, the LC1 comprises S162C, the HC2 comprises V173C, and the LC2 comprises Q160C; or the HC2 comprises V173C, the LC2 comprises S162C, the HC1 comprises V173C, and the LC1 comprises Q160C;

(8) the HC1 comprises S183C, the LC1 comprises S176C, the HC2 comprises V173C, and the LC2 comprises Q160C; or the HC2 comprises S183C, the LC2 comprises S176C, the HC1 comprises V173C, and the LC1 comprises Q/E160C;

(9) the HC1 comprises F170C, the LC1 comprises S176C, the HC2 comprises V173C, and the LC2 comprises Q160C; or the HC2 comprises F170C, the LC2 comprises S176C, the HC1 comprises V173C, and the LC1 comprises Q160C;

(10) the HC1 comprises F170C, the LC1 comprises S176C, the HC2 comprises S183C, and the LC2 comprises S176C; or the HC2 comprises F170C, the LC2 comprises S176C, the HC1 comprises S183C, and the LC1 comprises S176C; and

(11) the HC1 comprises V173C, the LC1 comprises S162C, the HC2 comprises F170C, and the LC2 comprises S162C; or the HC2 comprises V173C, the LC2 comprises S162C, the HC1 comprises F170C, and the LC1 comprises S162C.

87. The mixture of any one of items 46 to 86, wherein if the HC1 and/or the HC2 is an IgG4 HC, then the IgG4 HC(s) comprise(s) 228P.

88. The mixture of any one of items 46 to 87, wherein the in vivo half lives of the first and second antibodies differ by at least one week.

89. The mixture of item 88, wherein the in vivo half lives of the first and second antibodies differ by at least ten days.

90. The mixture of item 89, wherein the in vivo half lives of the first and second antibodies differ by at least two weeks.

91. The mixture of any one of items 88 to 90, wherein the antibody with the shorter in vivo half life comprises at least one of the following alterations: M252A, M252L, M252S, M252R, R255K or H435R.

92. The mixture of any one items 46 to 59 and 78 to 91, wherein
the HC1 comprises a CDR1, CDR2, and CDR3 having the amino acid sequences SEQ ID NOs: 28, 29, and 30, respectively, the LC1 comprises a CDR1, CDR2, and CDR3 having the amino acid sequences SEQ ID NOs: 25, 26, and 27, respectively, the HC2 comprises a CDR1, CDR2, and CDR3 having the amino acid sequences SEQ ID NOs: 31, 32, and 33, and the LC2 comprises a CDR1, CDR2, and CDR3 having the amino acid sequences SEQ ID NOs: 34, 35, and 36.

93. The mixture of any one items 46 to 91, wherein
(a) one of the first and second antibodies binds to human CTLA4 and the other binds to human PD1,
(b) both the first and second antibodies bind to human HER2, but they do not compete for binding to HER2,
(c) one of the first and second antibodies binds to human LAG3 and the other binds to human PD1,
(d) one of the first and second antibodies binds to human GITR and the other binds to human PD1,
(d) one of the first and second antibodies binds to human VEGF and the other binds to human PD1,
(f) one of the first and second antibodies binds to human CSFR1a and the other binds to human PD1,
(g) one of the first and second antibodies binds to human OX40 and the other binds to human PD1,
(h) one of the first and second antibodies binds to human TIGIT and the other binds to human PD1,
(i) one of the first and second antibodies binds to human CTLA4 and the other binds to human PDL1,
(j) one of the first and second antibodies binds to human VEGF and the other binds to human PDL1,
(k) one of the first and second antibodies binds to human OX40 and the other binds to human PDL1,
(l) one of the first and second antibodies binds to human CSFR1a and the other binds to human PDL1,
(m) one of the first and second antibodies binds to human TIGIT and the other binds to human PDL1,
(n) one of the first and second antibodies binds to human Tim3 and the other binds to human PDL1,
(o) one of the first and second antibodies binds to human CTLA4 and the other binds to human VEGF,
(p) one of the first and second antibodies binds to human CTLA4 and the other binds to human 41BB,
(q) one of the first and second antibodies binds to human CD20 and the other binds to human CD37,
(r) one of the first and second antibodies binds to human ANG2 and the other binds to human VEGF, (s) one of the first and second antibodies binds to human TNF and the other binds to human IL17a, (t) one of the first and second antibodies binds to human CD38 and the other binds to human CD138, (u) one of the first and second antibodies binds to human EGFR and the other binds to human HER2, (v) one of the first and second antibodies binds to human EGFR and the other binds to human HER3, (w) one of the first and second antibodies binds to human MET and the other binds to human VEGF (x) one of the first and second antibodies binds to human MET and the other binds to human EGFR, (y) one of the first and second antibodies binds to human TSLP and the other binds to human IL33, (z) one of the first and second antibodies binds to human IL4 and the other binds to human IL13, (aa) one of the first and second antibodies binds to human PD1 and the other binds to human CD96, (bb) one of the first and second antibodies binds to human PD1 and the other binds to human SIRP-alpha, or (cc) one of the first and second antibodies binds to human PD1 and the other binds to human CCR8.

94. An antibody comprising a primate or humanized IgG CH1 domain and a primate or humanized CL domain,
wherein the CH1 and CL domains comprise a charge pair of amino acids,
wherein one amino acid of the charge pair is in the CH1 domain and the other is in the CL domain, and
wherein
(1) the CH1 domain is an IgG1 CH1 domain, and the HC and LC positions, respectively, of the amino acids of the charge pair are selected from the group consisting of: 181 and 178; and 168 and 174; or
(2) the CH1 domain is an IgG4 CH1 domain, and the HC and LC positions, respectively, of the amino acids of the charge pair are selected from the group consisting of: 181 and 180; and 168 and 174.

95. An antibody comprising a primate or humanized IgG1 CH1 domain and a primate or humanized kappa CL domain,
wherein the CH1 and CL domains comprise a pair of contacting cysteine residues,
wherein one cysteine of the pair is in the CH1 domain and the other is in the CL domain, and
wherein the CH1 and CL positions, respectively, of the pair of cysteines are selected from the group consisting of: (1) 168 and 174; (2) 133 and 117; (3) 173 and 160; (4) 170 and 162; (5) 170 and 176; (6) 126 and 124; (7) 128 and 118; and (8) 134 and 116.

96. The antibody of item 95, wherein the antibody comprises substitutions of the cysteines at positions 220 in the CH1 domain and 214 in the CL domain with other amino acids.

97. An antibody comprising a primate or humanized IgG4 CH1 domain and a primate or humanized kappa CL domain,
wherein the CH1 and CL domains comprise a pair of contacting cysteine residues,
wherein one of the pair of contacting cysteine residues is at a CH1 residue and the other is at a CL residue, and
wherein the CH1 and CL residues, respectively, of the pair of contacting cysteine residues are selected from the group consisting of: (1) 168 and 174; (2) 173 and 162; (3) 170 and 162; (4) 126 and 124; (5) 127 and 121; and (6) 128 and 118.

98. The antibody of item 97, wherein the antibody comprises substitutions of the cysteines at positions 131 in the CH1 domain and 214 in the CL domain with other amino acids.

99. An antibody comprising a primate or humanized IgG2 CH1 domain and a primate or humanized CL domain,
wherein the antibody comprises substitutions of the cysteines at positions 131 in the CH1 domain and 214 in the CL domain with other amino acids, and
wherein the CH1 and CL domains each comprise a cysteine substitution, which creates a pair of contacting cysteine residues.

100. The antibody of item 99, wherein the pair of contacting cysteine residues are selected from the group of positions in the CH1 and CL domains, respectively, consisting of: (1) positions 173 and 162; and (2) positions 170 and 162.

101. The antibody of item 99 or 100, wherein the CH1 and CL domains each comprise a second cysteine substitution, which creates a second, different pair of contacting cysteine residues.

102. The antibody of item 101, wherein the second pair of contacting cysteine residues are selected from the group of positions in the CH1 and CL domains, respectively, consisting of: (1) positions 173 and 162; and (2) positions 170 and 162.

103. The antibody of any one of items 94 to 102, wherein the antibody is a full-length human or humanized IgG antibody.

104. A method of making the mixture of antibodies of any one of items 46 to 93, comprising the steps of:
(a) culturing the host cell line expressing the mixture of antibodies in a culture medium, and
(b) recovering the mixture of antibodies from the cell mass or the culture medium.

105. The method of item 104, wherein the host cell line is a mammalian cell line.

106. The method of item 105, wherein the host cell line is a CHO cell line.

107. The method of any one of items 104 to 106, further comprising a step of purifying the mixture of antibodies from other components present in the cell mass or the culture medium.

108. A host cell line that produces the mixture of antibodies of any one of items 46 to 93.

109. The host cell line of item 108, which is a mammalian cell line.

110. The host cell line of item 109, which is a CHO cell line.

111. One or more nucleic acid(s) encoding the antibody or the mixture of antibodies of any one of items 46 to 103.

112. One or more vector(s) containing the nucleic acid(s) of item 111.

113. The vector(s) of item 112, each of which is a mammalian expression vector.

114. The vector(s) of item 112, each of which is a viral vector.

115. The vector(s) of item 114, each of which is an adenovirus, an adeno-associated virus (AAV), a retrovirus, a vaccinia virus, a modified vaccinia virus Ankara (MVA), a herpes virus, a lentivirus, or a poxvirus vector.

116. A host cell line containing the nucleic acid(s) and/or the vector(s) of any one of items 111 to 115.

117. A method of treating a disease comprising administering to a patient having the disease the mixture of antibodies of any one of items 46 to 93, wherein the disease is a cancer, a metabolic disease, an infectious disease, or an autoimmune or inflammatory disease.

118. The method of item 117, wherein the disease is a cancer.

119. A method of treating a disease comprising administering to a patient having the disease an antibody of any one of items 94 to 103.

120. A method of treating cancer comprising administering to a patient the mixture of antibodies of item 93(a).

121. A method of treating breast cancer comprising administering to a patient the mixture of antibodies of item 93(b).

122. The method of item 121, wherein the mixture of antibodies comprises three major antibody species.

123. A method of treating a patient having a tumor comprising injecting into the tumor the antibody or the mixture of antibodies of any one of items 46 to 103. 124. A method of treating a cancer patient comprising administering to the patient the nucleic acid(s) and/or the vector(s) of any one of items 111 to 115.

125. The method of item 124, wherein the patient has a tumor and the nucleic acid(s) and/or vector(s) is (are) administered directly to the tumor.

126. The method of item 125, wherein the nucleic acid(s) and/or the vector(s) are injected into the tumor.

BRIEF DESCRIPTION OF THE FIGURES

FIG. 3: Alternate strategy used to produce a MabPair (Panel A) or a 3-in-1 mixture (Panel B) of antibodies in one host cell. Markings are as indicated in FIG. 1. Panel A. Antibody 1 is an IgG1, IgG2, or IgG3 antibody, in which residue 409 has been changed to be an arginine, or an IgG4 antibody, which has a naturally occurring arginine at position 409. As indicated, Antibody 1 binds to Antigen A. Antibody 1 does not have any alterations in its Fab region, i.e., the VH-CH1 and VL-CL domains. The naturally occurring disulfide bridge between the HC and LC is indicated by a heavy line between the CH1 domain and the carboxy terminus of the LC. Antibody 2 is an IgG antibody in which residue 399 has been altered to be an arginine or lysine (D399R/K, indicated by a circled "+") and residue 409 has been altered to be aspartic acid or glutamic acid (K409D/E, indicated by a circled "−"). As indicated, Antibody 2 binds to Antigen B. Due to amino acid substitutions Antibody 2 lacks the naturally occurring interchain disulfide bond between the LC and the HC, but has two newly-introduced disulfide bonds between the CL and CH1 domains (indicated by two ©'s joined by a solid line). Further, an introduced charge pair (e.g., S131K/R in CL and K147D/E in CH1 or S174K/R in CL and H168D/E in CH1) is indicated by circled "+" and "−". Panel B. Markings are as in panel A. Note that the alterations in the CH3 domain shown in panel A are absent. Antibody 3 is a bispecific antibody comprising an HC and LC from each of Antibody 1 and Antibody 2.

TABLE 1

Figure 1:
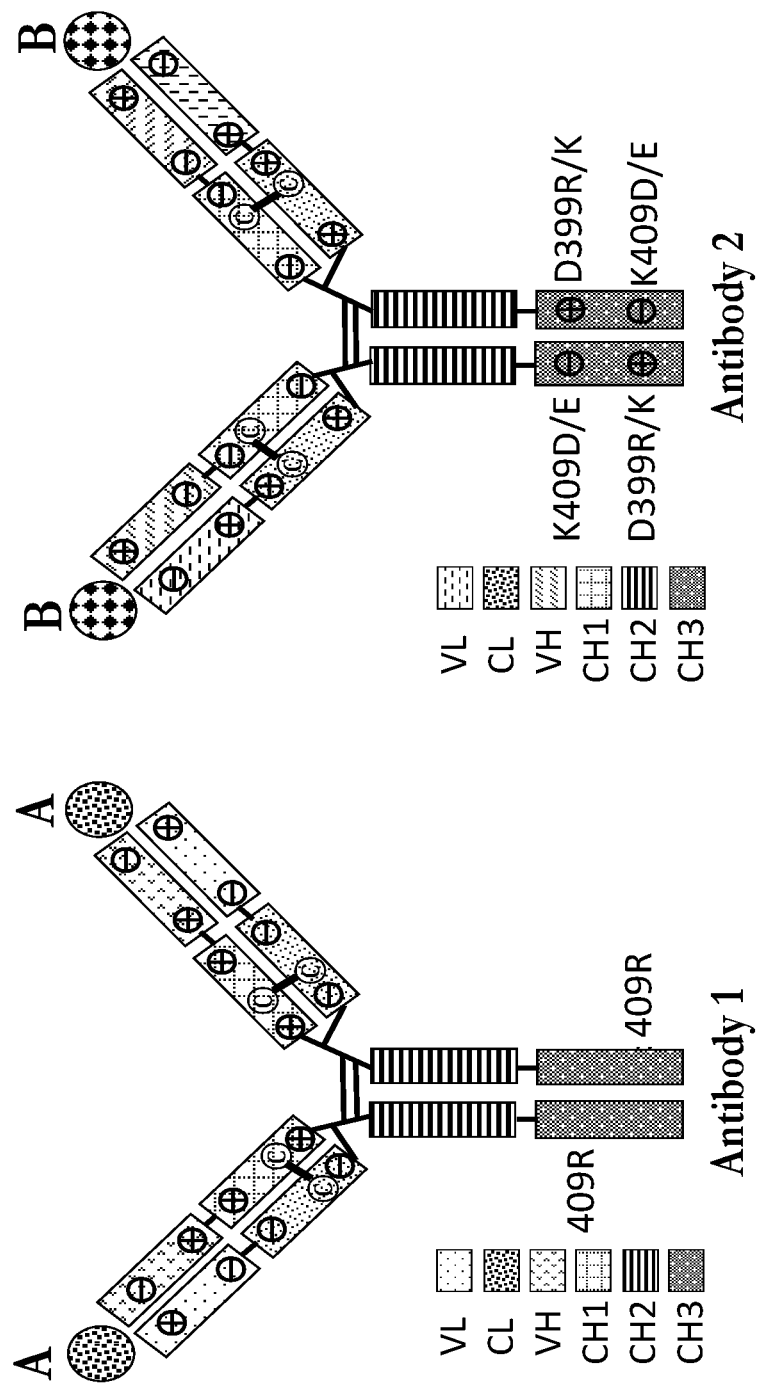
FIG. 1: Alterations used to produce a "MabPair" in a host cell. The various domains of the antibodies are indicated in the figure. Antibody 1 is an IgG1, IgG2, or IgG3 antibody in which residue 409 has been changed to be an arginine or an IgG4 antibody, which has a naturally occurring arginine at position 409. As indicated, Antibody 1 binds to Antigen A (indicated by a circle filled with irregularly-spaced squares). Antibody 2 is an IgG antibody in which residue 409 has been altered to be aspartic acid or glutamic acid (K409D/E, indicated by a circled "−") and residue 399 has been altered to be an arginine or lysine (D399R/K, indicated by a circled "+"). As indicated, Antibody 2 binds to Antigen B (indicated by a circle filled with a checkerboard pattern). As indicated by circled "+" and "−" signs, pairs of charged residues in the VL and VH domains and in the CL and CH1 domains of Antibody 1 and Antibody 2 drive the light chains of Antibodies 1 and 2 to pair with their cognate heavy chains. These charged residues may be present in the original amino acid sequence of the antibody or can be introduced by substituting a charged amino acid for the amino acid present in the original sequence. Moreover, these charged residues create a repulsive force between the heavy chain of Antibody 1 and the light chain of Antibody 2, and between the heavy chain of Antibody 2 and the light chain of Antibody 1. Cysteine residues, which can be introduced by substitution at different locations within the $C_H1$/CL interface of Antibodies 1 and 2, are indicated by two ©'s joined by a solid line. Additional disulfide bridges normally present in the hinge domains of the antibodies are indicated by solid horizontal lines.

Alterations in antibody chains in samples shown in Panel A

| | Anti-PD1 human IgG4 (S228P)* | | Anti-CTLA4 human IgG1 (D399K, K409E)* | |
|---|---|---|---|---|
| Lane | HC1 | LC1 | HC2 | LC2 |
| 1 | WT | WT | WT | WT |
| 2 | WT | WT | | |
| 3 | WT | | | WT |
| 4 | | | WT | WT |
| 5 | | WT | WT | |
| 6 | WT | WT | C220S | C214S |
| 7 | WT | WT | | |
| 8 | WT | | | C214S |
| 9 | | | C220S | C214S |
| 10 | | WT | C220S | |
| 11 | WT | WT | C220S, H168C, V173C | C214S, Q160C, S174C |
| 12 | WT | WT | | |
| 13 | WT | | | C214S, Q160C, S174C |
| 14 | | | C220S, H168C, V173C | C214S, Q160C, S174C |
| 15 | | WT | C220S, H168C, V173C | |
| 16 | WT | WT | C220S, H168C, F170C | C214S, S162C, S174C |
| 17 | WT | WT | | |
| 18 | WT | | | C214S, S162C, S174C |
| 19 | | | C220S, H168C, F170C | C214S, S162C, S174C |
| 20 | | WT | C220S, H168C, F170C | |
| 21 | WT | WT | C220S, F170C, V173C | C214S, Q160C, S162C |
| 22 | WT | WT | | |
| 23 | WT | | | C214S, Q160C, S162C |
| 24 | | | C220S, F170C, V173C | C214S, Q160C, S162C |
| 25 | | WT | C220S, F170C, V173C | |

*Blank boxes indicate the absence of the chain listed in the heading above the box.

TABLE 2

Alterations in antibody chains in samples shown in Panel B

| | Anti-PD1 human IgG4 (S228P)* | | Anti-CTLA4 human IgG1 (D399K, K409E)* | |
|---|---|---|---|---|
| Lane | HC1 | LC1 | HC2 | LC2 |
| 1 | WT | WT | WT | WT |
| 2 | WT | WT | | |
| 3 | WT | | | WT |
| 4 | | | WT | WT |
| 5 | | WT | WT | |
| 6 | WT | WT | C220S, F170C, V173C | C214S, Q160C, S162C |
| 7 | WT | WT | | |
| 8 | WT | | | C214S, Q160C, S162C |
| 9 | | | C220S, F170C, V173C | C214S, Q160C, S162C |
| 10 | | WT | C220S, F170C, V173C | |
| 11 | WT | WT | C220S, F170C, V173C, K147D | C214S, Q160C, S162C, S131K |
| 12 | WT | WT | | |
| 13 | WT | | | C214S, Q160C, S162C, S131K |
| 14 | | | C220S, F170C, V173C, K147D | C214S, Q160C, S162C, S131K |
| 15 | | WT | C220S, F170C, V173C, K147D | |
| 16 | WT | WT | C220S, F170C, V173C, K147D | C214S, Q160C, S162C, S131R |
| 17 | WT | WT | | |
| 18 | WT | | | C214S, Q160C, S162C, S131R |
| 19 | | | C220S, F170C, V173C, K147D | C214S, Q160C, S162C, S131R |
| 20 | | WT | C220S, F170C, V173C, K147D | |

*Blank boxes indicate the absence of the chain listed in the heading above the box

TABLE 3

Alterations in antibody chains in samples shown in Panel C

| | Anti-PD1 human IgG4 (S228P)* | | Anti-CTLA4 human IgG1 (D399K, K409E)* | |
|---|---|---|---|---|
| Lane | HC1 | LC1 | HC2 | LC2 |
| 1 | WT | WT | C220S, F170C, V173C, H168D | C214S, Q160C, S162C, S174K |
| 2 | WT | WT | | |
| 3 | WT | | | C214S, Q160C, S162C, S174K |
| 4 | | | C220S, F170C, V173C, H168D | C214S, Q160C, S162C, S174K |
| 5 | | WT | C220S, F170C, V173C, H168D | |
| 6 | WT | WT | C220S, F170C, V173C, H168D | C214S, Q160C, S162C, S174R |
| 7 | WT | WT | | |
| 8 | WT | | | C214S, Q160C, S162C, S174R |
| 9 | | | C220S, F170C, V173C, H168D | C214S, Q160C, S162C, S174R |
| 10 | | WT | C220S, F170C, V173C, H168D | |
| 11 | WT | WT | C220S, F170C, V173C, K147D, H168D | C214S, Q160C, S162C, S131K, S174K |
| 12 | WT | WT | | |
| 13 | WT | | | C214S, Q160C, S162C, S131K, S174K |
| 14 | | | C220S, F170C, V173C, K147D, H168D | C214S, Q160C, S162C, S131K, S174K |
| 15 | | WT | C220S, F170C, V173C, K147D, H168D | |
| 16 | WT | WT | C220S, F170C, V173C, K147D, H168D | C214S, Q160C, S162C, S131R, S174R |
| 17 | WT | WT | | |
| 18 | WT | | | C214S, Q160C, S162C, S131R, S174R |
| 19 | | | C220S, F170C, V173C, K147D, H168D | C214S, Q160C, S162C, S131R, S174R |
| 20 | | WT | C220S, F170C, V173C, K147D, H168D | |

Figure 11:
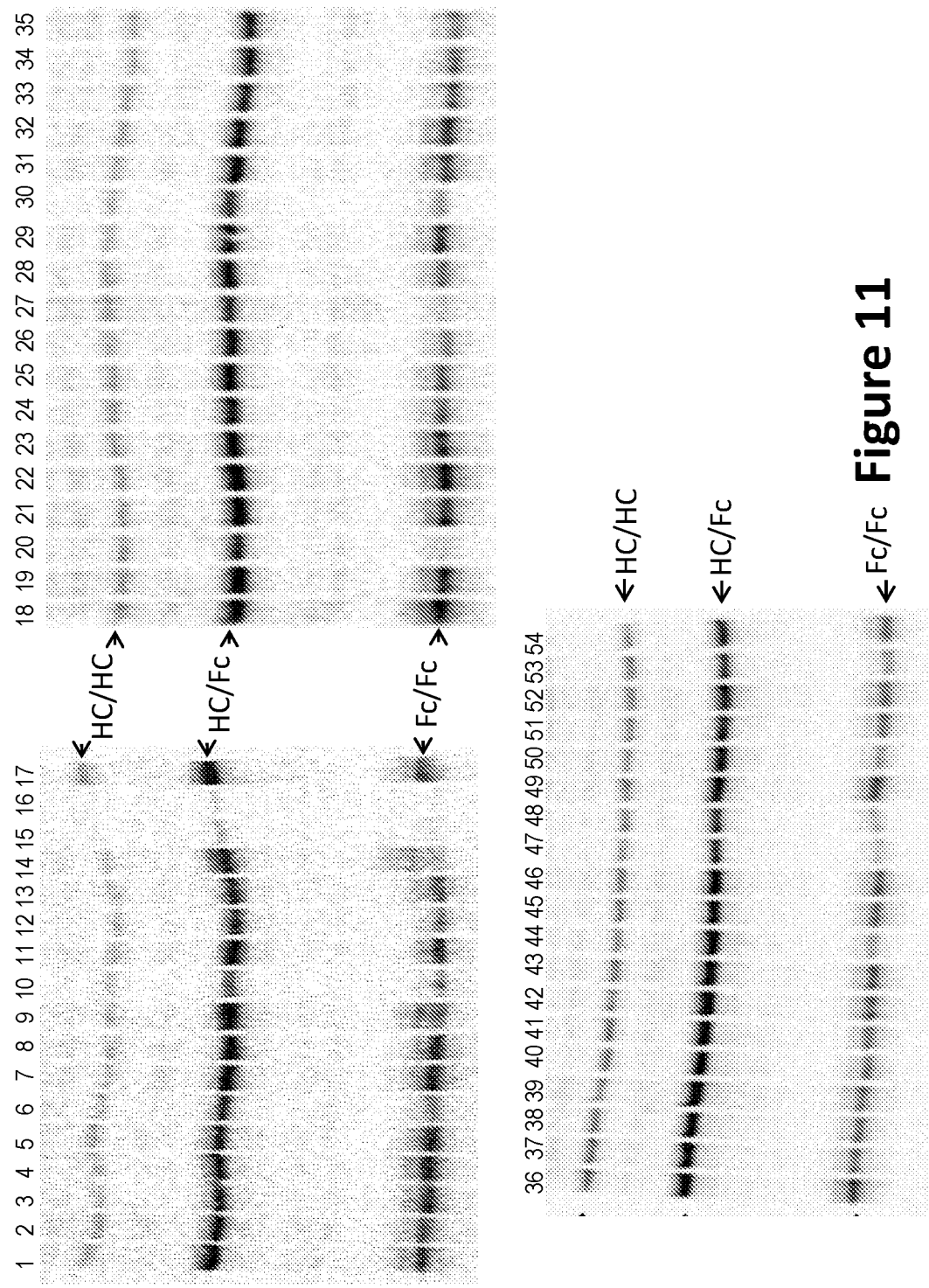

*Blank boxes indicate the absence of the chain listed in the heading above the box FIG. 11: Heterodimer formation of HCs with alterations at position 392, 370, and 397. As described in Example 4, host cells were transfected with DNAs encoding a full-length wild type IgG1 HC and an LC plus a DNA encoding an IgG1 Fc fragment, with or without alterations as indicated below. Antibodies from the culture media of transfectants were subjected to SDS-polyacrylamide gel electrophoresis (SDS-PAGE) under non-reducing conditions and blotted. Antibodies were detected as described in Example 4. Positions of HC-LC/HC-LC homodimer ("HC/HC"), HC-LC/Fc heterodimer ("HC/Fc"), and Fc/Fc ("Fc/Fc") homodimer are indicated. Alterations present in the Fc fragment and the percent HC-LC/Fc heterodimer in each lane are as follows: 1) K392A, 46.9%; 2) K392C, 49.2%; 3) K392D, 42.9%; 4) K392E, 44.1%; 5) K392F, 42.7%; 6) K392G, 50.2%; 7) K392H, 44.0%: 8) K392M, 43.3%; 9) K392N, 50.0%; 10) K392P, 45.9%; 11) K392Q, 48.1%; 12) K392R, 50.3%; 13) K392S, 46.3%; 14) K392T, 56.3%; 15) K392V, 54.0%; 16) K392W, 49.5%; 17) K392Y, 49.6%; 18) WT, 39.7%; 19) K370A, 47.3%; 20) K370C, 62.3%; 21) K370D, 48.8%; 22) K370E, 45.4%; 23) K370F, 43.2%; 24) K370G, 50.7%; 25) K370H, 55.2%; 26) K370I, 59.1%; 27) K370L, 60.6%; 28) K370M, 55.7%; 29) K370N, 47.4%; 30) K370P, 59.3%; 31) K370Q, 49.2%; 32) K370T, 54.1%; 33) K370V, 51.9%; 34) K370W, 39.7%; 35) K370Y, 47.3%; 36) V397A, 46.9%; 37) V397C, 53.7%; 38) V397D, 52.2%; 39) V397E, 57.5%; 40) V397F, 51.4%; 41) V397G, 55.3%; 42) V397H, 55.2%; 43) V397I, 51.4%; 44) V397K, 66.5%; 45) V397L, 48.4%; 46) V397M, 52.1%; 47) V397N, 59.4%; 48) V397P, 56.2%; 49) V397Q, 48.0%; 50) V397R, 61.9%; 51) V397S, 48.9%; 52) V397T, 51.6%; 53) V397W, 49.5%; and 54) V397Y, 49.1%.

Figure 12:
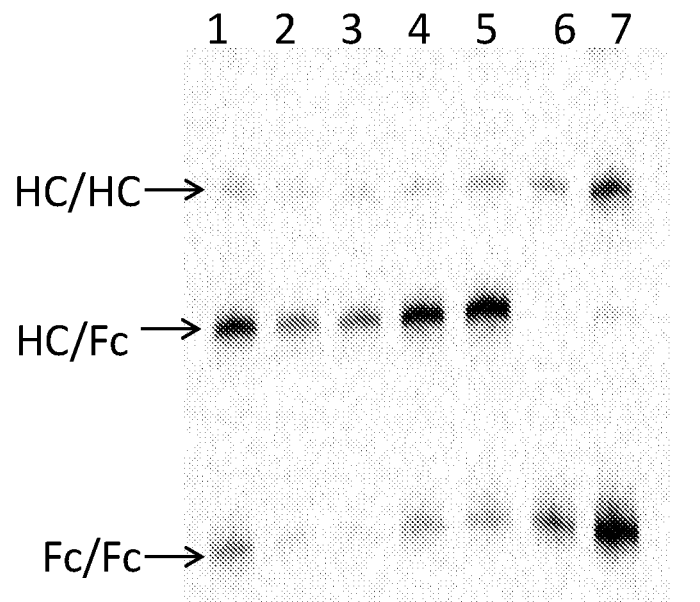

FIG. 12: Heterodimer formation of HCs with alterations at position(s) 399 and/or 409. This experiment is described in Example 4. The experiment and the markings on the figure are the same as in FIG. 11 except that, as indicated in the table below, the various alterations of the Fc fragment are at position(s) 399 and/or 409, and the full-length HC is a wild type IgG4 HC.

Figure 13:
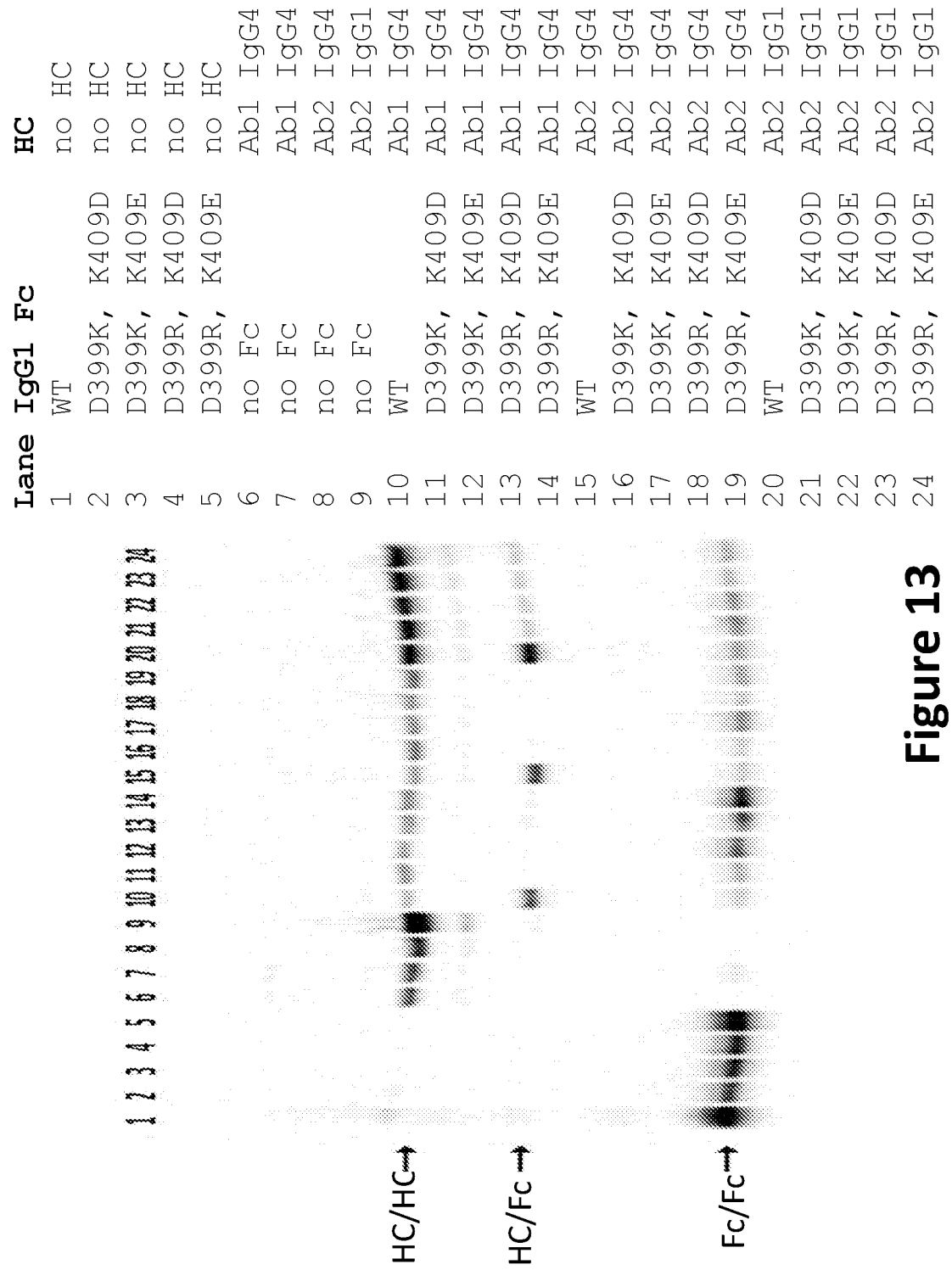

FIG. 13: Heterodimer formation of IgG1 or IgG4 HCs with Fc fragments with or without alterations at positions 399 and/or 409. This experiment is described in Example 4. Markings are as in FIG. 12. A "no HC" or "no Fc" in the table at right indicates that DNA encoding either the HC or the Fc, respectively, was not introduced into the host cells whose antibodies are visualized in that lane. "Ab1" and "Ab2" are two different antibodies. Ab2 IgG4 and Ab2 IgG1 have the same variable domains in an IgG4 and an IgG1 format, respectively.

Figure 14:
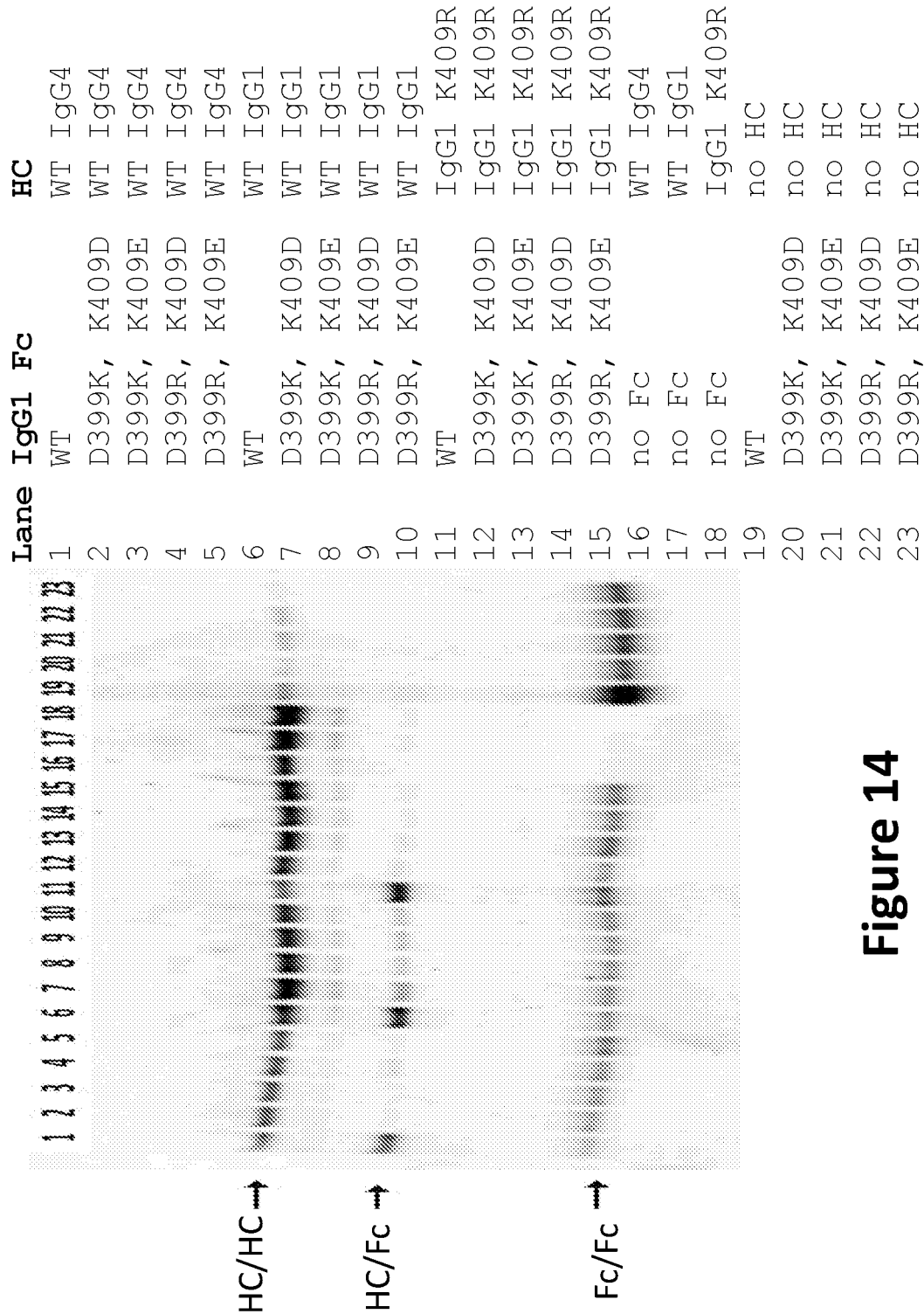

FIG. 14: Heterodimer formation of IgG1 or IgG4 HCs with Fc fragments with or without alterations at positions 399 and/or 409. Experiment is described in Example 4. Markings are as in FIG. 13.

Figure 15:
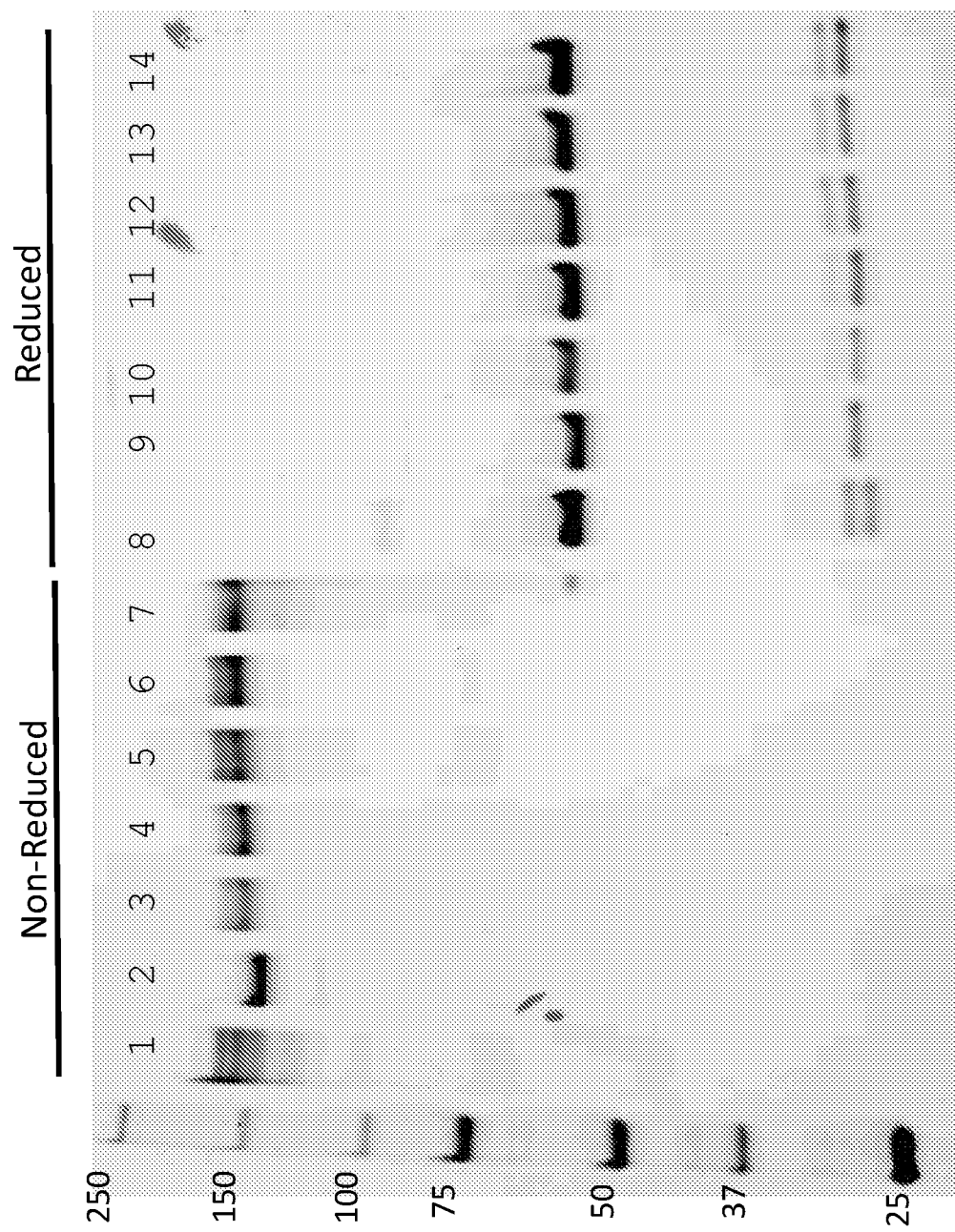

FIG. 15: SDS-PAGE analysis of purified anti-PD1 anti-CTLA4 MabPair antibody mixtures. This experiment is described in Example 5. Non-reduced (left) and reduced (right) samples were run in 4-15% CRITERION™ TGX STAIN-FREE™ Precast SDS-PAGE gel and blotted, and antibodies were detected as described in Example 5. Sizes of protein molecular weight standards were run in the leftmost lane, and sizes in kilodaltons (kDa) are indicated. Lanes 1 and 8 contain samples expected to include three different antibodies, two different anti-HER2 antibodies, 4D5-8 and 2C4, and a bispecific antibody containing one HC and one LC from each of these two antibodies. Lanes 2 and 9 contain samples from cells transfected with DNAs encoding an anti-CTLA4 IgG1 antibody. Other lanes contain samples from transfectants containing DNAs encoding antibody mixtures described in Table 21 as follows: lanes 3 and 10, mixture 17B; lanes 4 and 11, mixture 17C; lanes 5 and 12, mixture 18B; lanes 6 and 13, mixture 18C; and lanes 7 and 14, mixture 19C.

Figure 16:
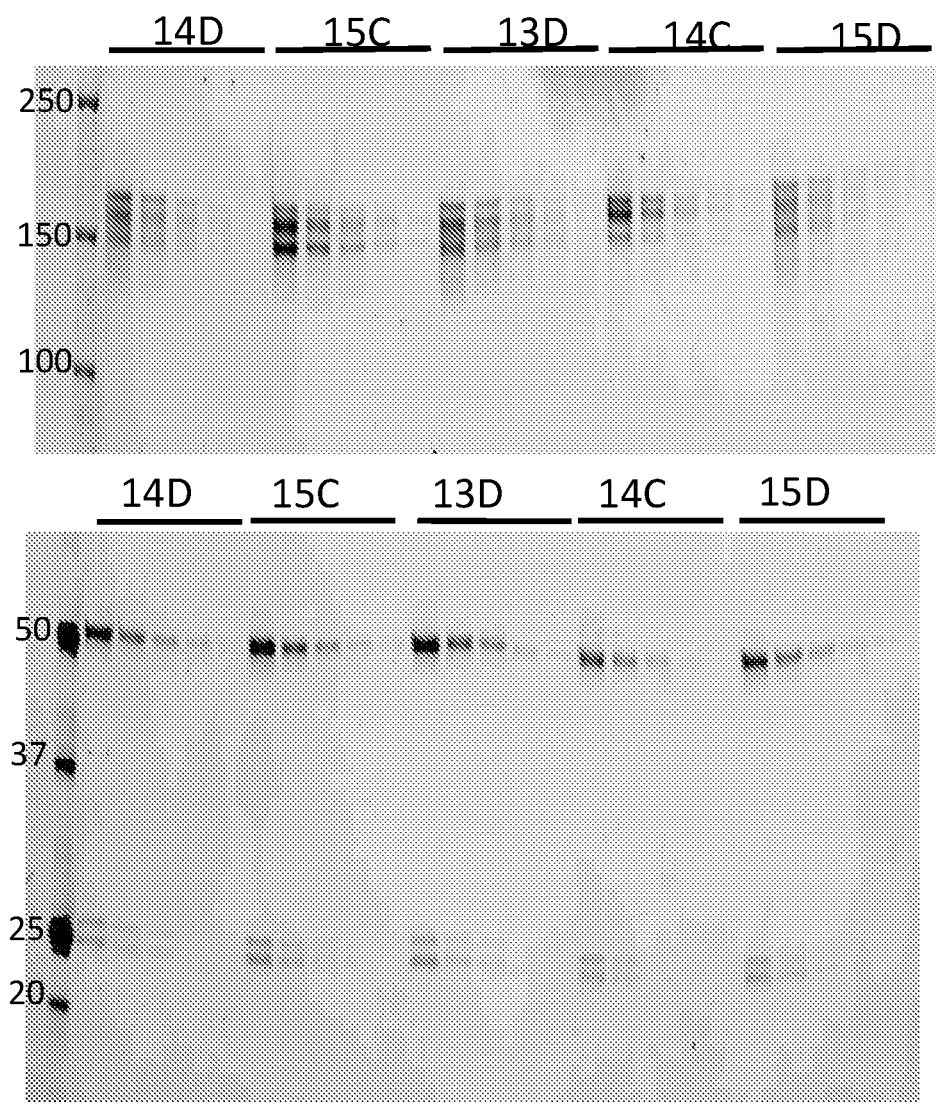

FIG. 16: SDS-PAGE analysis of non-reduced and reduced samples of antibody mixtures. This experiment is described in Example 5. Leftmost lane in top and bottom panels contains molecular weight standards. Each group of five lanes contains varying concentrations of non-reduced (top panel) or reduced (bottom panel) samples of the antibody mixture indicated above the lanes. These antibody mixtures are described in Table 20.

Figure 17:
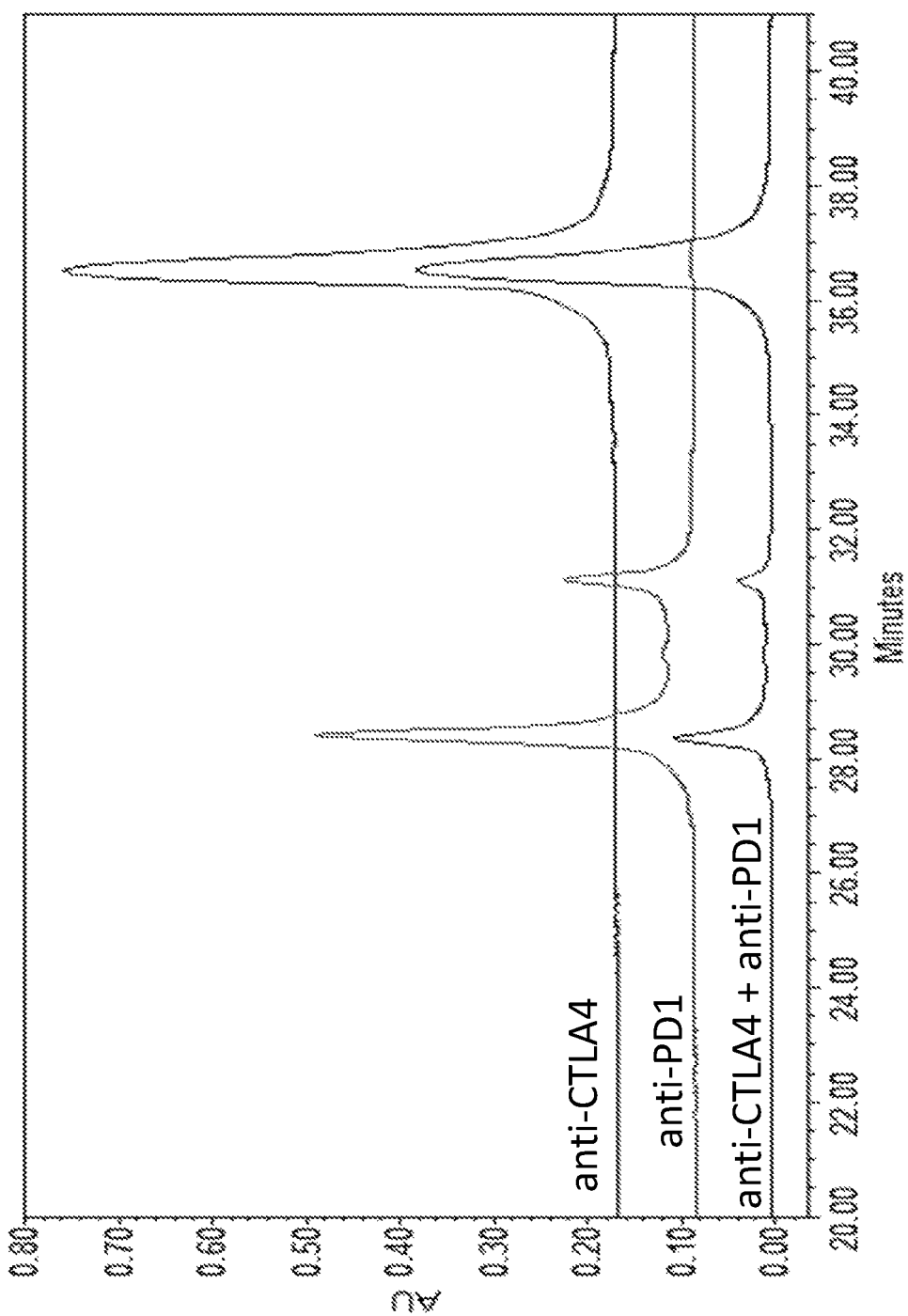

FIG. 17: Analysis of non-reduced antibody mixtures by low pH cation exchange (CEX) chromatography. The figure shows tracings from CEX columns run at low pH as described in Example 5. The horizontal axis shows minutes after the start of the column run, and the vertical axis shows absorbance at 214 nanometers (indicated as "AU," which reflects protein concentration) detected in the column outflow. As indicated, the upper tracing is from an anti-CTLA4 antibody, the middle tracing is from an anti-PD1 antibody, and the bottom tracing is from the 18C variant antibody mixture (described in Table 21), which was produced in host cells transfected with DNA encoding altered versions of anti-PD1 and anti-CTLA4 antibodies.

Figure 18:
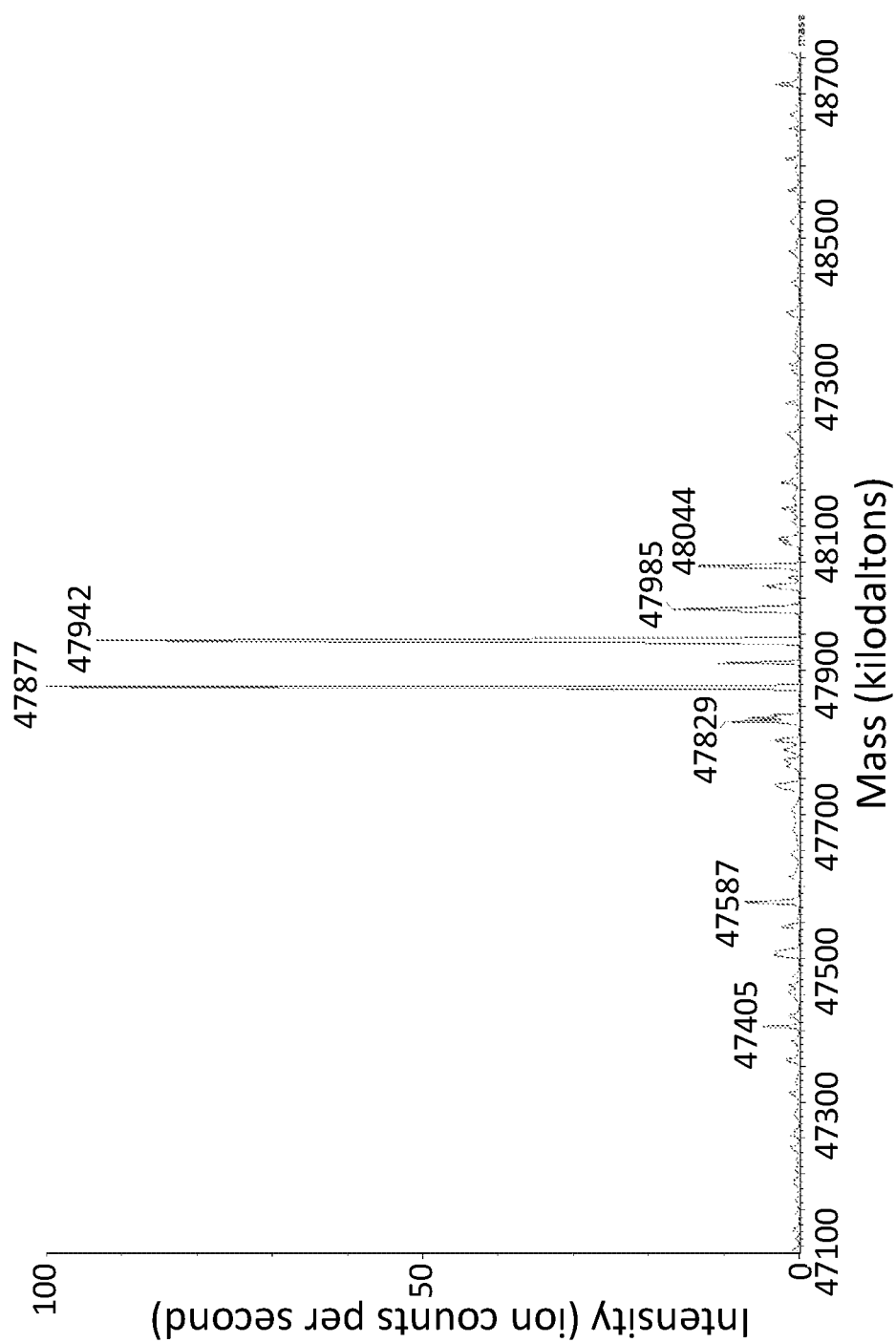

FIG. 18: Mass spectrometry (MS) analysis of Fab fragments from the purified anti-HER2/anti-HER2 14D 3-in-1 mixture of antibodies. The variant 14D mixture is described in Table 20. This experiment is described in Example 5. The Fab fragments generated by papain digestion were analyzed using a Waters SYNAPT™ G2 MS system (Waters Corporation, Milford, Mass., USA). Above the most prominent peaks, the masses (in Daltons) are indicated. As indicated, the vertical axis shows the intensity of the signal (ion counts per second), and the horizontal axis shows mass in kilodaltons.

Figure 19:
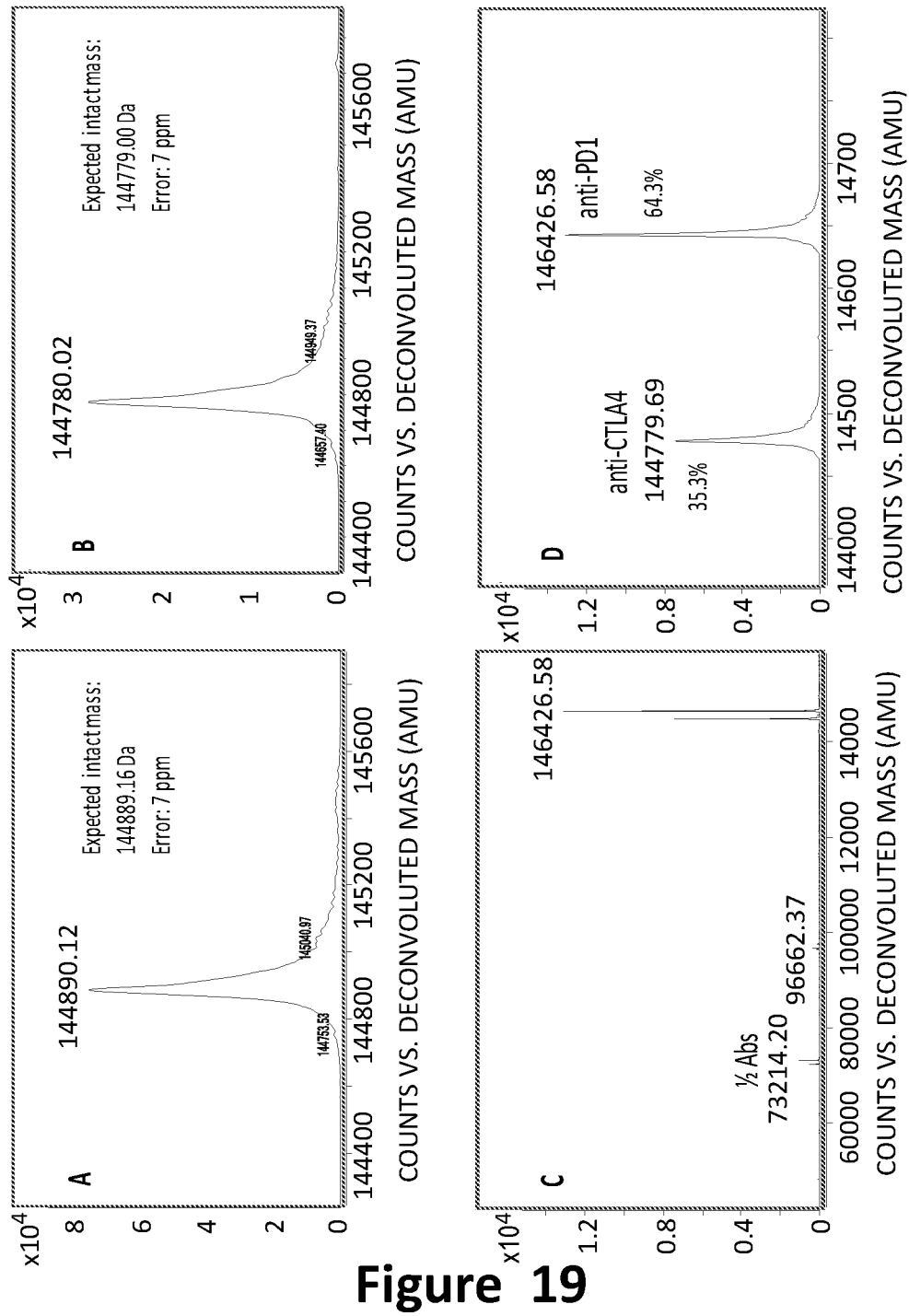

FIG. 19: MS analysis of anti-CTLA4, anti-PD1 MabPair antibody mixture. These experiments are described in Example 6. As indicated, the x axes show deconvoluted mass, and the y axes show counts, which are reflective of the quantity of protein at a given mass. Panel A. This panel shows analysis of the IgG1 anti-CTLA4 111 antibody without alteration. Panel B. This panel shows analysis of the anti-CTLA4 111 antibody containing the alterations K147D, F170C, V173C, C220G, R255K, D399R, and K409E in the HC and S131K, Q160C, S162C, and C214S in the LC. Panel C. This panel shows analysis of a MabPair mixture of an unaltered version of the IgG4 anti-PD1 antibody described in Example 2 and the engineered IgG1 anti-CTLA4 111 antibody analyzed in panel B. Panel D. This panel shows a higher resolution analysis of the MabPair mixture analyzed in panel C. As indicated, Area Under Curve (AUC) analysis was performed to determine the relative amounts of each antibody in this MabPair.

FIG. 20: MS analysis of Fab' fragments from an anti-PD1/anti-CTLA4 MabPair antibody mixture. The experiment is described in Example 6. Panel A. This panel shows a drawing of an IgG antibody (at left) and an IgG antibody digested with IdeS Protease (second from left) and further treated with 2-mercaptoethyl amine (2-MEA) and ethylenediaminetetraacetic acid (EDTA) (at right). The names of the various fragments generated are indicated. Panel B. This panel shows MS analysis of the Fab' fragments generated by IdeS Protease digestion and 2-MEA/EDTA treatment of the same MabPair that was analyzed in panel D of FIG. 19. As indicated, the x axis shows deconvoluted mass, and the y axis shows counts, which are reflective of the quantity of protein at a given mass. Expected masses of the two Fab' fragments containing cognate HC/LC pairs are indicated, as are the actual masses of the fragments detected and the calculated error.

Figure 21:
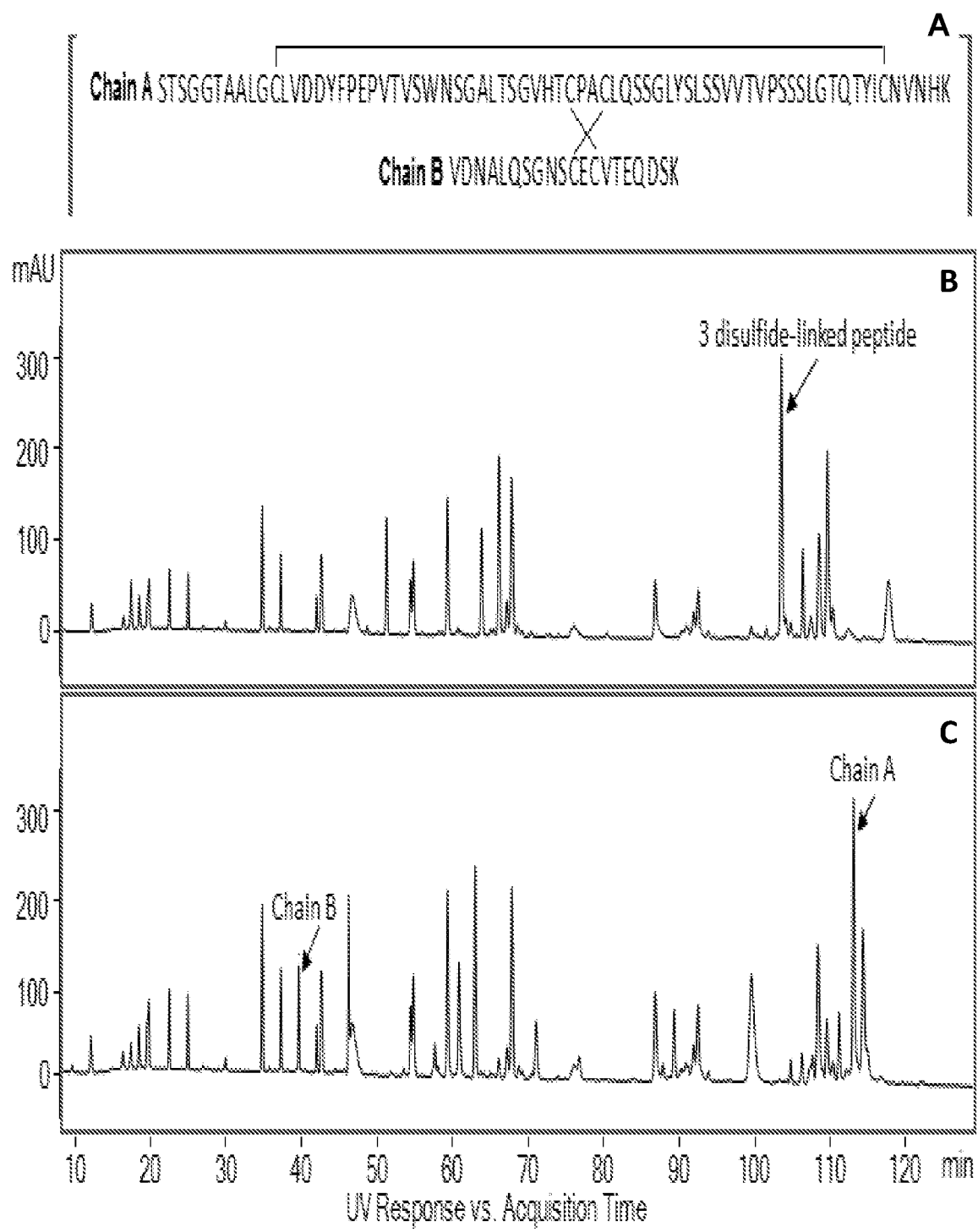

FIG. 21: Liquid chromatography of reduced and non-reduced lysyl endopeptidase digests of an engineered anti-CTLA4 antibody. This experiment is described in Example 6. Panel A. This panel shows the expected amino acid sequences of two of the peptides resulting from lysyl endopeptidase digestion of the engineered anti-CTLA4 antibody analyzed in FIG. 19, panel B. See Tables 7 and 11. Expected disulfide bonds are indicated by lines. Panel B. This panel shows the column profile of a non-reduced sample of the lysyl endopeptidase digestion of the engineered anti-CTLA4 antibody described in Example 6. The x axis indicates the time since the start of the chromatography (expressed as acquisition time in minutes), and the y axis shows the UV Response, which is reflective of the quantity of protein in the column effluent. The peak corresponding to linked chains A (SEQ ID NO:45) and B (SEQ ID NO:46) (see panel A) was identified by its mass and is indicated by an arrow with the label "3 disulfide-linked peptide." Panel C. This panel shows the column profile of a reduced sample of the lysyl endopeptidase digestion of the engineered anti-CTLA4 antibody. X and y axes are the same as in panel B. The new peaks corresponding to chains A and B (see Panel A) were identified by their masses and are indicated.

Figure 22:
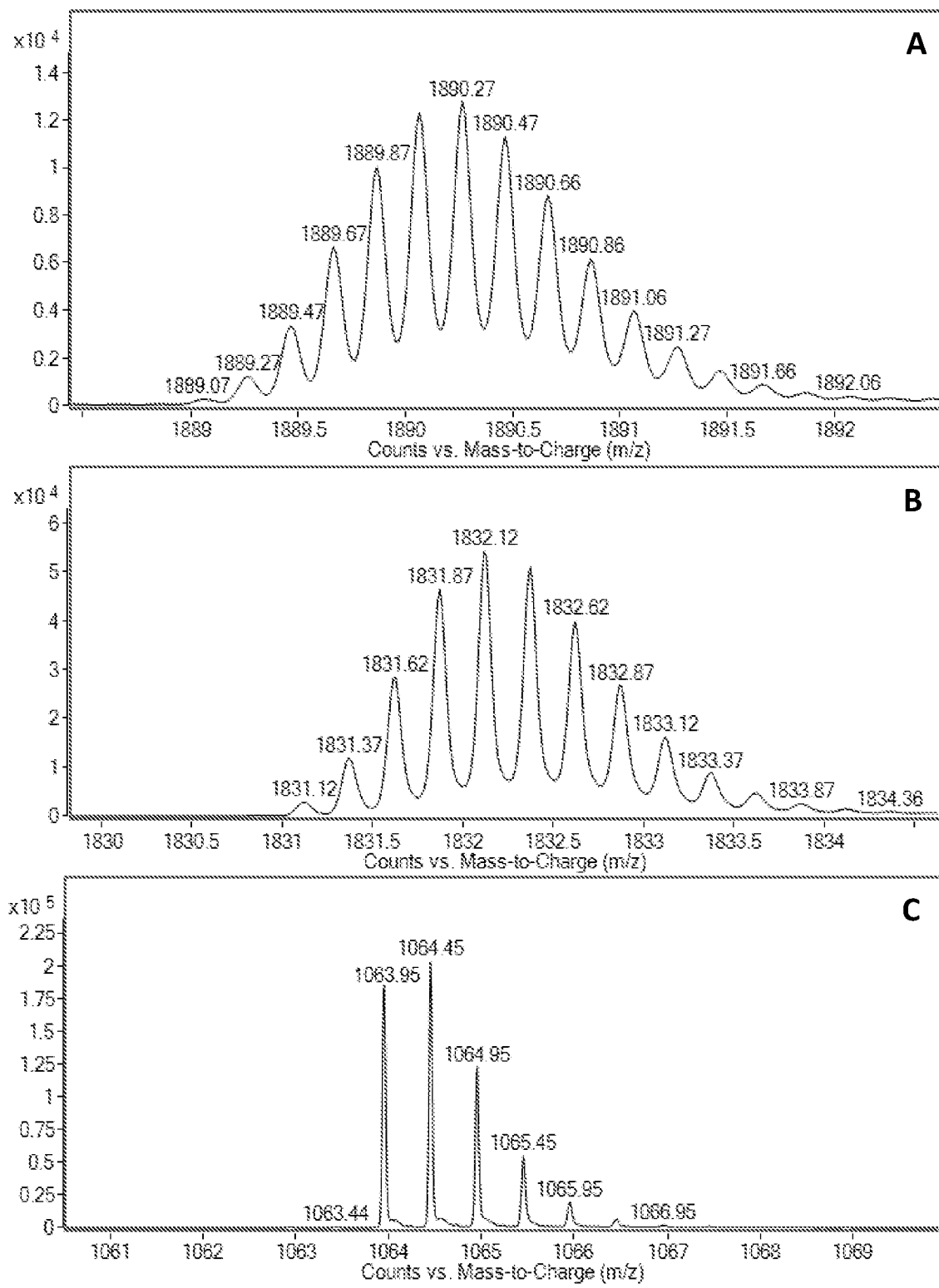

FIG. 22: Determination of monoisotopic masses of peptides resulting from lysyl endopeptidase digestion of an engineered anti-CTLA4 antibody. Experiments are described in Example 6. Panel A. MS analysis of an expected disulfide-linked peptide from a non-reduced lysyl endopeptidase digestion of the engineered anti-CTLA4 antibody (labeled "3 disulfide-linked peptide" in FIG. 21, panel B). The x axis shows mass/charge ratio (m/z ratio), and the y axis shows counts, which reflect the quantity of ions of a given mass. Panel B. This panel shows MS analysis of the chain A peptide (indicated in FIG. 21, panel C) from the reduced lysyl endopeptidase digestion of the engineered anti-CTLA4 antibody. Panel C. This panel shows MS analysis of the chain B peptide (indicated in FIG. 21, panel C) from the reduced lysyl endopeptidase digestion of the engineered anti-CTLA4 antibody.

Figure 23:
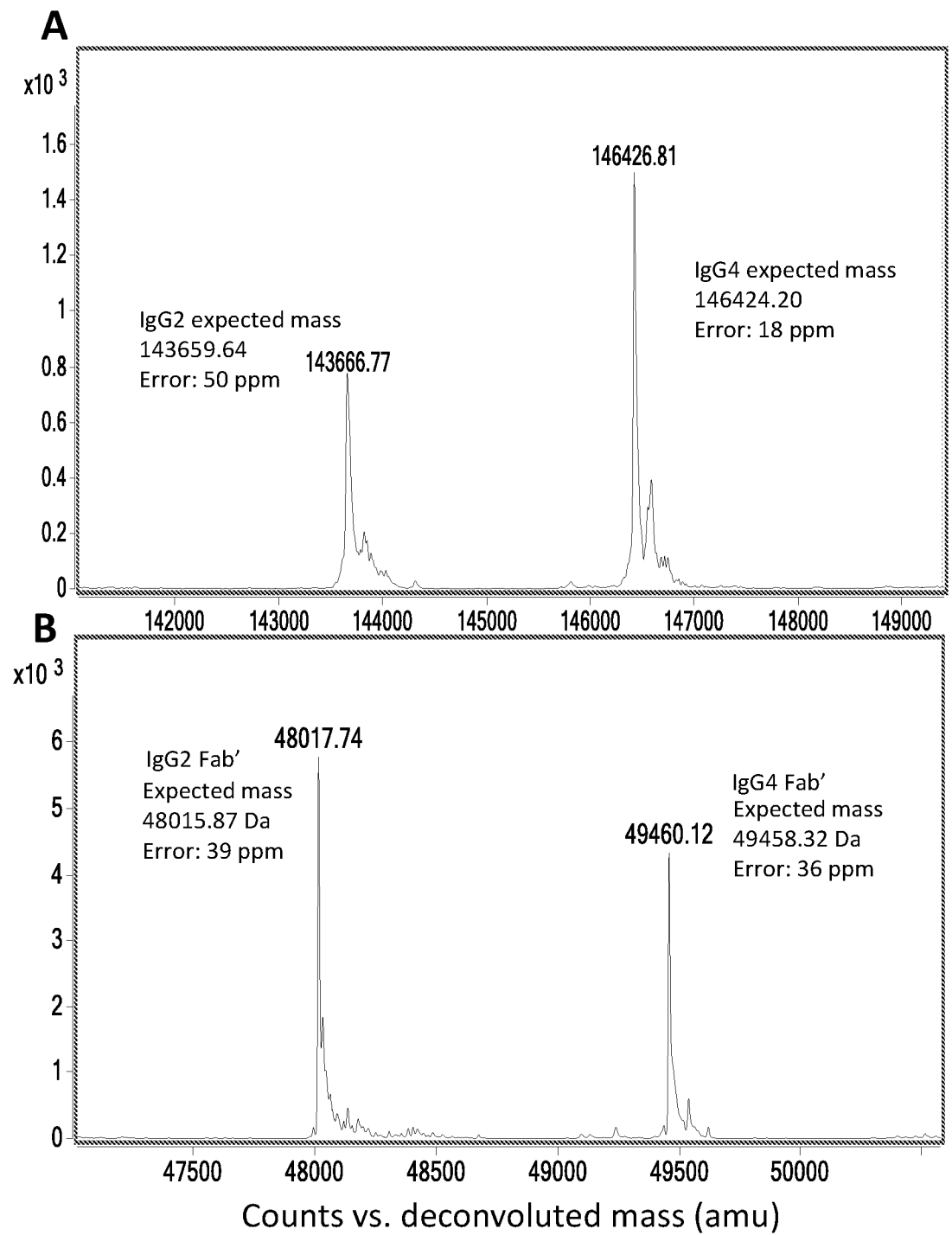

FIG. 23: Mass spectrometry analysis of an IgG2/IgG4 MabPair. These experiments are described in Example 7. As indicated, the x axes show deconvoluted mass in atomic mass units (amu), and the y axes show counts, which are reflective of the quantity of protein at a given mass. Panel A. This panel shows mass spectrometry analysis of deglycosylated antibodies produced by cells transfected with DNAs encoding the engineered IgG2 and unaltered IgG4 antibodies described in Example 7. Panel B. This panel shows mass spectrometry analysis of the Fab' fragments generated from antibodies produced by cells transfected with DNAs encoding the engineered IgG2 and unaltered IgG4 antibodies described in Example 7.

Figure 24:
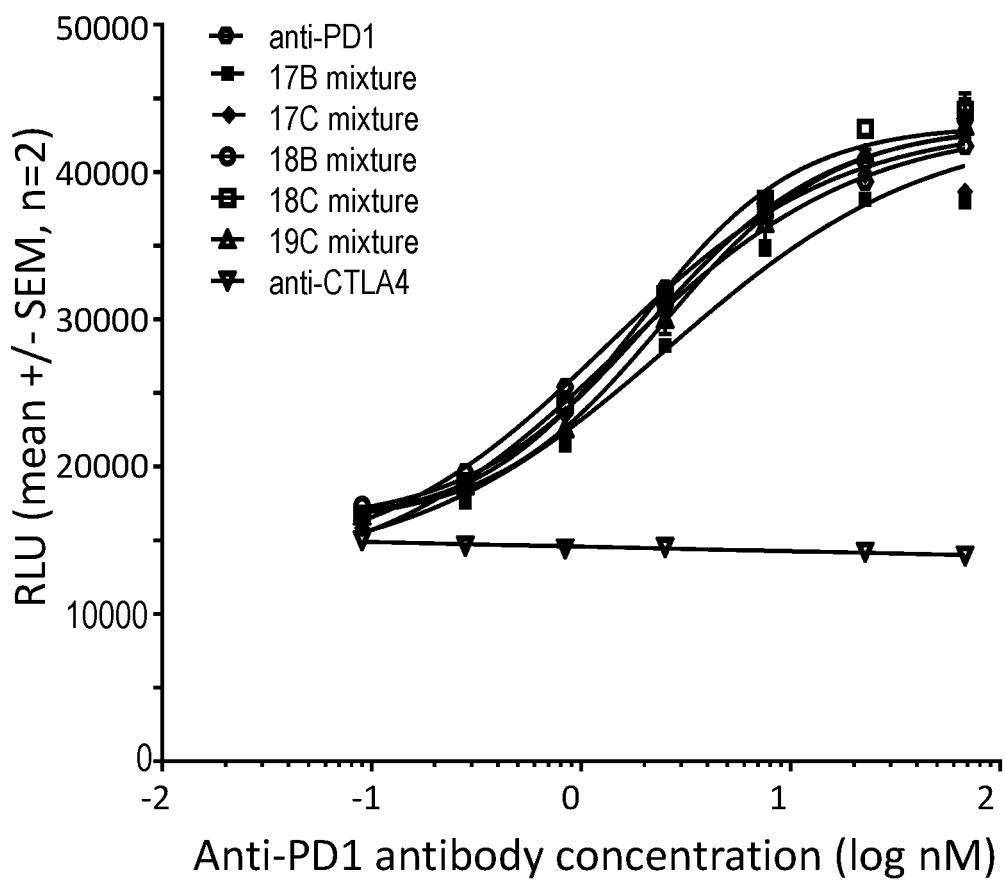

FIG. 24: Anti-PD1 potency of antibody mixtures. This experiment is described in Example 8. The samples represented by the various curves are indicated. The horizontal axis indicates the log of the anti-PD1 antibody concentration. In the case of the antibody mixtures, this amount was based on the antibody concentration determination made in Example 7. The vertical axis indicates the mean plus or minus the standard error of the mean of the relative luminescence units (RLU±SEM).

Figure 25:
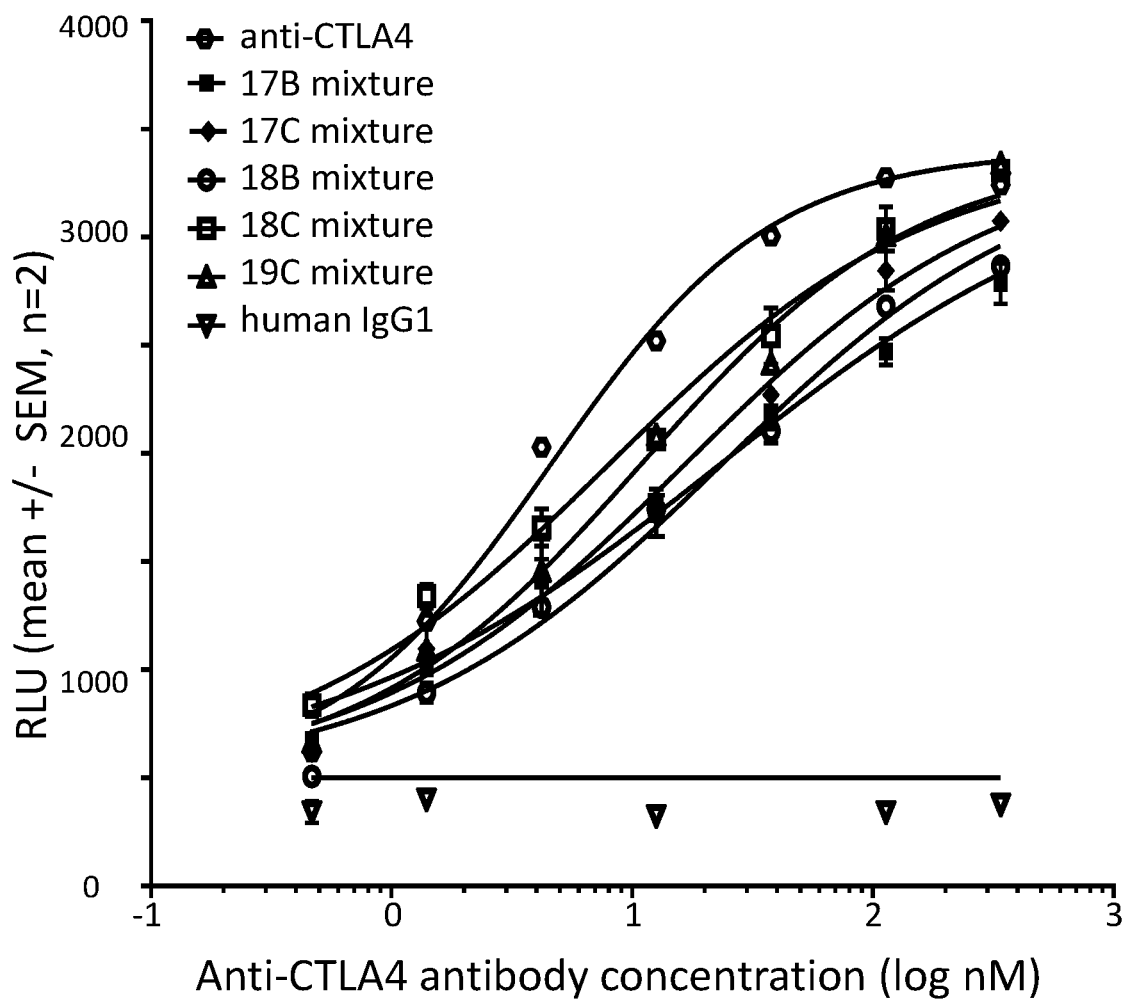

FIG. 25: Anti-CTLA4 potency of antibody mixtures. This experiment is described in Example 9. The samples represented by the various curves are indicated. The horizontal and vertical axes are designated as in FIG. 16, except that the horizontal axis represents the log of the anti-CTLA4 antibody concentration rather than the log of the anti-PD1 antibody concentration.

Figure 26:
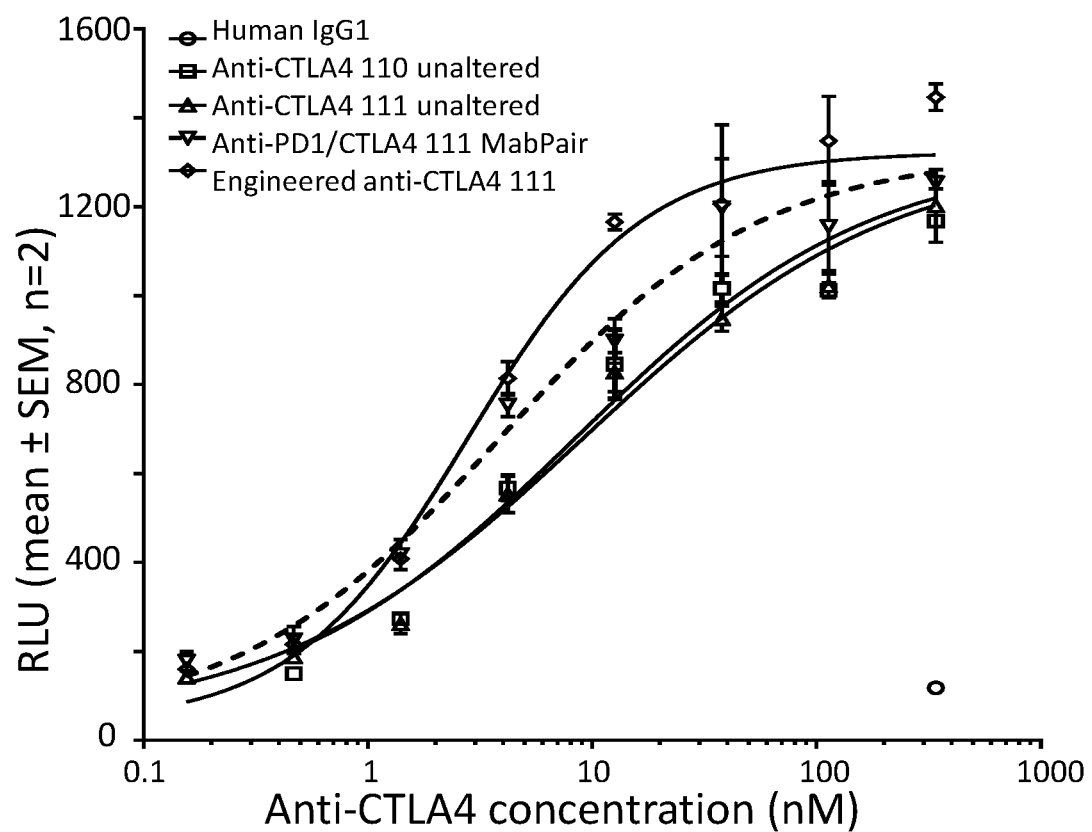

FIG. 26: Potency of an anti-CTLA4 antibody in an anti-CTLA4/anti-PD1 MabPair. Procedures are described in Example 10. The x axis shows the concentration of anti-CTLA4 antibody used in each assay, and the y axis shows the RLU±SEM. The symbols and lines identify the samples as indicated in the legend in the upper left corner of the graph and explained in Example 10. The single filled circle in the lower right corner represents data from an unrelated human IgG1 antibody.

Figure 27:
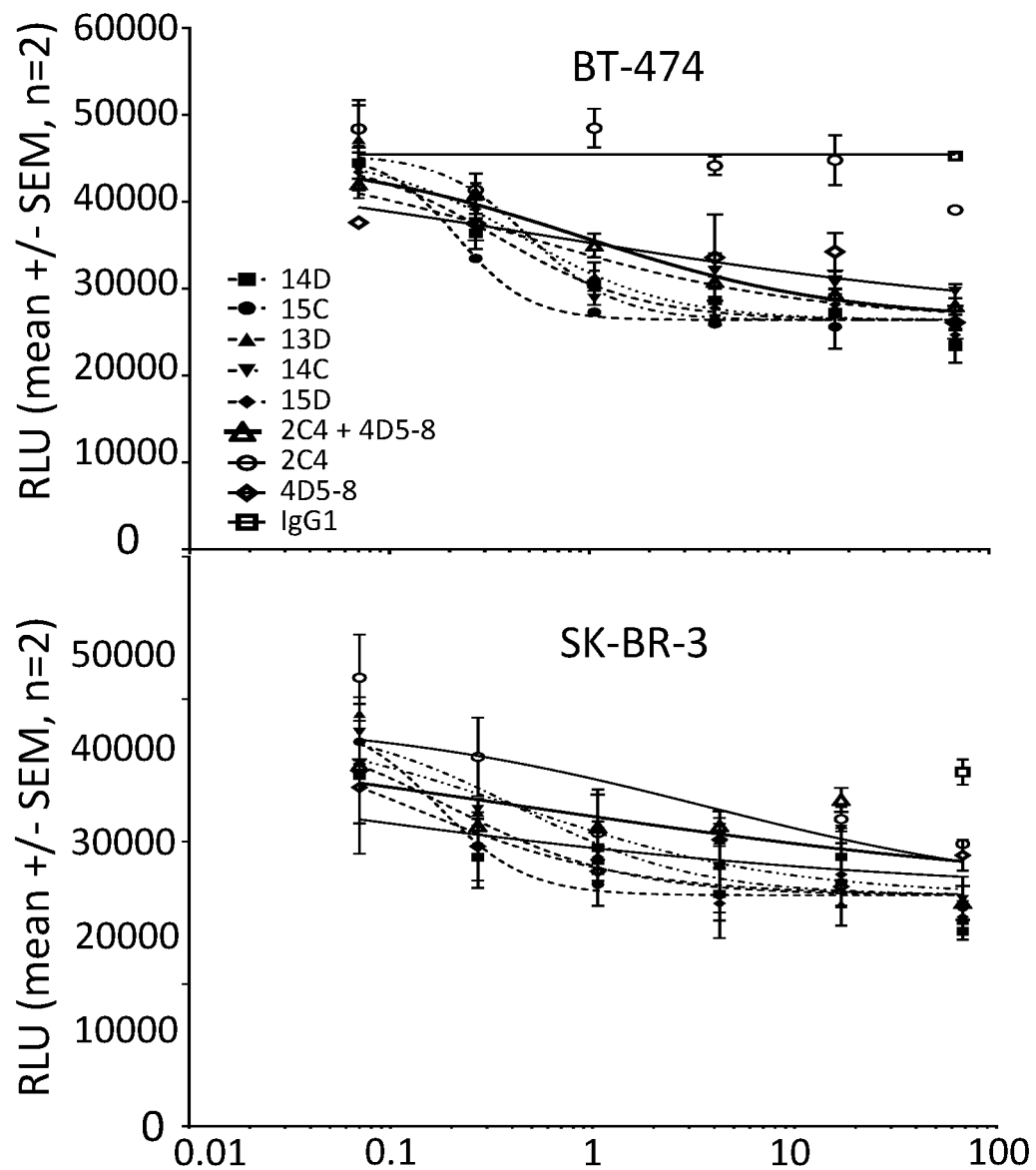

FIG. 27: Effects of anti-HER2 antibody mixtures on breast cancer cell viability. This experiment is described in Example 11. The antibodies and antibody mixtures used as samples in the experiment are indicated as follows. IgG1, a control IgG1/κLC antibody; 4D5-8, anti-HER antibody 4D5-8; 2C4, anti-HER2 antibody 2C4; 2C4+4D5-8, a mixture of the two anti-HER2 antibodies 4D5-8 and 2C4; and 14D, 15C, 13D, 14C, and 15D, the anti-HER2 antibody mixtures described in Table 20. The vertical axis indicates the RLU±SEM. The horizontal axis indicates the concentration of the antibody or the antibody mixture in the sample in nanomoles/liter (nM). As indicated, the top and bottom panels contain data from samples using BT-474 cells and SK-BR-3 cells, respectively.

BRIEF DESCRIPTION OF THE SEQUENCE LISTING

| Sequence Listing Number | Description |
| --- | --- |
| SEQ ID NO: 1 | Consensus amino acid sequence for human VH domains |
| SEQ ID NO: 2 | Consensus amino acid sequence for CH1 domains |
| SEQ ID NO: 3 | Amino acid sequence of a human IgG1 CH1 domain |
| SEQ ID NO: 4 | Amino acid sequence of a human IgG2 CH1 domain |
| SEQ ID NO: 5 | Amino acid sequence of a human IgG3 CH1 domain |
| SEQ ID NO: 6 | Amino acid sequence of a human IgG4 CH1 domain |
| SEQ ID NO: 7 | Amino acid sequence of a human IgG1 Fc fragment |
| SEQ ID NO: 8 | Amino acid sequence of a human IgG2 Fc fragment |
| SEQ ID NO: 9 | Amino acid sequence of a human IgG3 Fc fragment |
| SEQ ID NO: 10 | Amino acid sequence of a human IgG4 Fc fragment |
| SEQ ID NO: 11 | Consensus amino acid sequence of a human VL domain |
| SEQ ID NO: 12 | Consensus amino acid sequence of a CLκ domain |
| SEQ ID NO: 13 | Consensus amino acid sequence of a CLλ domain |
| SEQ ID NO: 14 | Amino acid sequence of a human CLκ domain (IMGT accession no. J00241) |
| SEQ ID NO: 15 | Amino acid sequence of a human CLκ domain (IMGT accession no. M11736) |
| SEQ ID NO: 16 | Amino acid sequence of a human CLκ domain (IMGT accession no. M11737) |
| SEQ ID NO: 17 | Amino acid sequence of a human CLκ domain (IMGT accession no. AF0017732) |
| SEQ ID NO: 18 | Amino acid sequence of a human CLκ domain (IMGT accession no. AF11387) |
| SEQ ID NO: 19 | Amino acid sequence of the LC of 4D5-8 |
| SEQ ID NO: 20 | Amino acid sequence of the HC of 4D5-8 |
| SEQ ID NO: 21 | Amino acid sequence of the HC of 2C4 |
| SEQ ID NO: 22 | Amino acid sequence of the LC of 2C4 |
| SEQ ID NO: 23 | Amino acid sequence of the HC of anti-PD1 antibody 16137 |
| SEQ ID NO: 24 | Amino acid sequence of the LC of anti-PD1 antibody 16137 |
| SEQ ID NO: 25 | Amino acid sequence of the LC CDR1 of the anti-HER2 antibody 4D5-8 |
| SEQ ID NO: 26 | Amino acid sequence of the LC CDR2 of the anti-HER2 antibody 4D5-8 |
| SEQ ID NO: 27 | Amino acid sequence of the LC CDR3 of the anti-HER2 antibody 4D5-8 |
| SEQ ID NO: 28 | Amino acid sequence of the HC CDR1 of the anti-HER2 antibody 4D5-8 |

-continued

BRIEF DESCRIPTION OF THE SEQUENCE LISTING

| Sequence Listing Number | Description |
|---|---|
| SEQ ID NO: 29 | Amino acid sequence of the HC CDR2 of the anti-HER2 antibody 4D5-8 |
| SEQ ID NO: 30 | Amino acid sequence of the HC CDR3 of the anti-HER2 antibody 4D5-8 |
| SEQ ID NO: 31 | Amino acid sequence of the HC CDR1 of the anti-HER2 antibody 2C4 |
| SEQ ID NO: 32 | Amino acid sequence of the HC CDR2 of the anti-HER2 antibody 2C4 |
| SEQ ID NO: 33 | Amino acid sequence of the HC CDR3 of the anti-HER2 antibody 2C4 |
| SEQ ID NO: 34 | Amino acid sequence of the LC CDR1 of the anti-HER2 antibody 2C4 |
| SEQ ID NO: 35 | Amino acid sequence of the LC CDR2 of the anti-HER2 antibody 2C4 |
| SEQ ID NO: 36 | Amino acid sequence of the LC CDR3 of the anti-HER2 antibody 2C4 |
| SEQ ID NO: 37 | Nucleotide sequence encoding the heavy chain of anti-CTLA4 antibody 1E1 |
| SEQ ID NO: 38 | Amino acid sequence of the heavy chain of the anti-CTLA4 antibody 1E1 |
| SEQ ID NO: 39 | Nucleotide sequence encoding the light chain of the anti-CTLA4 antibody 1E1 |
| SEQ ID NO: 40 | Amino acid sequence of the light chain of the anti-CTLA4 antibody 1E1 |
| SEQ ID NO: 41 | Amino acid sequence of the CH1, hinge, CH2, and CH3 domains of an unaltered human IgG2 antibody |
| SEQ ID NO: 42 | Amino acid sequence of the CH1, hinge, CH2, and CH3 domains of an engineered human IgG2 antibody |
| SEQ ID NO: 43 | SEQ ID NO: 43: Amino acid sequence of the CL kappa domain of a human antibody |
| SEQ ID NO: 44 | SEQ ID NO: 43: Amino acid sequence of the CL kappa domain of an engineered human antibody |

REFERENCE TO SEQUENCE LISTING

This application includes a sequence listing submitted electronically, in a file entitled 126861-0001US01_SL.txt, created on May 26, 2021 and having a size of 71.2 kilobytes (KB), which is incorporated by reference herein.

DETAILED DESCRIPTION

Figure 2:
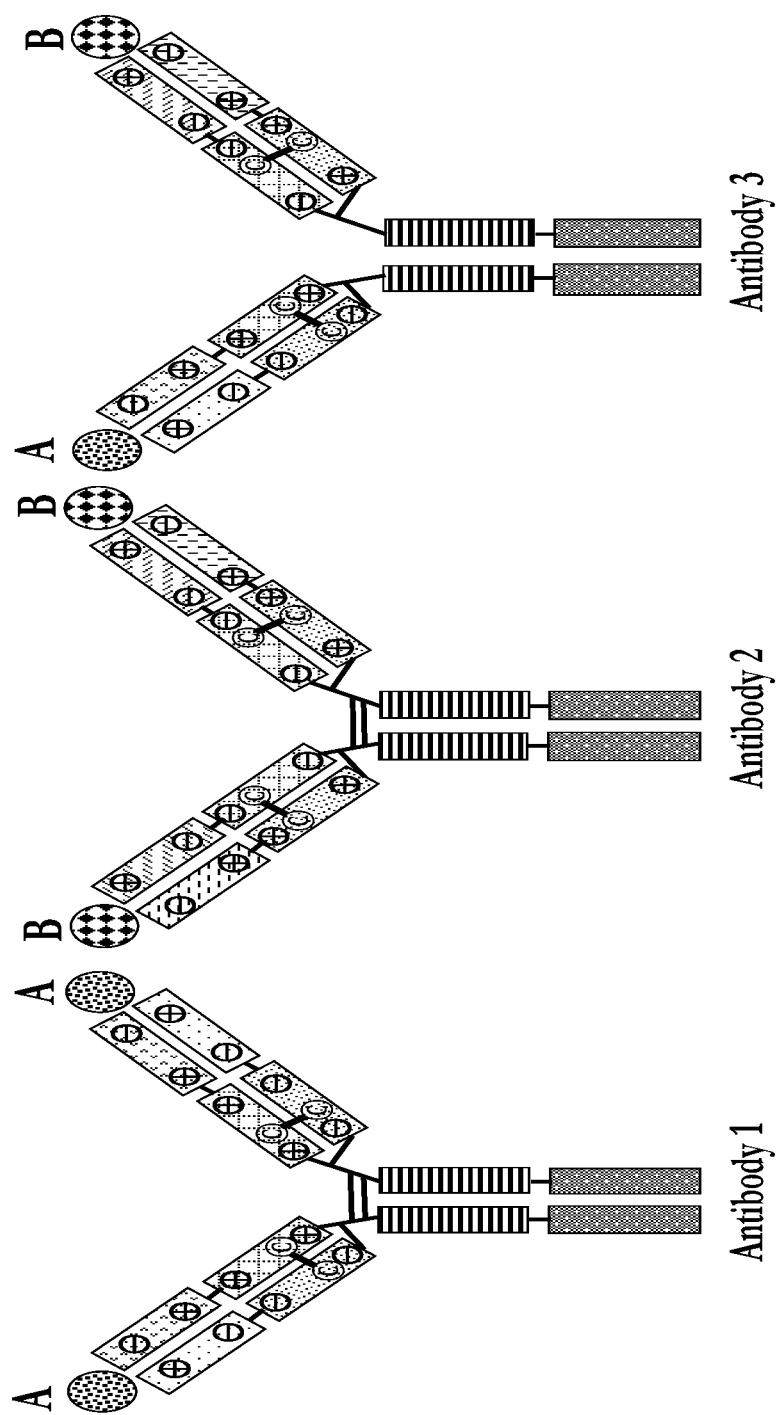
FIG. 2: Alterations used to produce three different antibodies (a "3-in-1 mixture") in one host cell. Markings are as in FIG. 1. Antibody 1 (at left) is an IgG1 antibody that binds to Antigen A, Antibody 2 is an IgG1 antibody that binds to Antigen B, and Antibody 3 is a bispecific antibody that binds to both Antigens A and B, as indicated. Unlike the embodiment shown in FIG. 1, alterations in the CH3 domain to disfavor heterodimer formation are not present in Antibody 2.

Described herein are mixtures of antibodies and methods for producing mixtures of antibodies containing a limited number of major species of antibodies, optionally not more than two, three, four, five, six, seven, eight, nine, or ten, from host cells, optionally cells from a single host cell line, that have been transfected with DNA encoding at least two different antibodies, optionally full-length primate IgG antibodies, with different binding specificities. In some embodiments, DNAs encoding at least two different heavy chains (HCs) and at least two different light chains (LCs) can be introduced into the host cells. In some embodiments, the host cells can be transfected with DNAs encoding at least two, but not more than four, different antibodies with different binding specificities. In some embodiments, DNAs encoding at least two, but not more than four, different HCs and at least two, but not more than four, different LCs can be introduced into the host cells. In some embodiments, the sequences of all of the transfected DNAs encoding HCs and LCs can be mutated so that the amino acid sequences of the antibodies are altered such that non-cognate HC/LC pairings are disfavored and cognate HC/LC pairings are highly favored. See FIGS. 1 and 2. Where two different HCs are introduced into the host cells, one or both of the two different HCs can, optionally, be altered such that heterodimer formation is disfavored. In some embodiments, only one heavy chain is altered to discourage heterodimer formation. In some embodiments where DNAs encoding only two different antibodies are introduced into the host cells, only one of the antibodies encoded by the DNAs comprises one or more partner-directing alterations such that cognate HC/LC pairing is favored, whereas the other antibody does not comprise such alterations. See FIG. 3. In such embodiments, this altered antibody can also comprise one or more alterations that disfavor heterodimer formation. See FIG. 3. In some embodiments, one of the antibodies does not comprise alterations that disfavor heterodimer formation or alterations that favor cognate HC/LC pairing. See FIG. 3. In some further embodiments, only one of the two antibodies comprises one or more partner-directing alteration(s), and only one of the two antibodies comprises one or more alteration(s) that disfavor heterodimer formation. In such embodiments, the antibody that comprises the partner-directing alteration(s) may not comprise the alteration(s) that disfavor heterodimer formation and vice versa. Alternatively, one antibody can be unaltered and the other can comprise one or more partner-directing alteration(s) and one or more alteration(s) disfavoring heterodimer formation. In some embodiments, only two major antibody species are produced by the host cell, where each HC is paired predominantly to its cognate LC, and most of the antibodies are tetramers containing two heavy chains having the same amino acid sequence and two light chains having the same amino acid sequence (referred to herein as "MabPairs"). See FIGS. 1 and 3. In other embodiments, the host cell produces three different major species of antibodies, two different monospecific antibodies each comprising two HCs with the same amino acid sequence and two LCs with the same amino acid sequence plus a functional bispecific antibody comprising two different HCs and two different LCs (referred to herein as a "3-in-1 mixture" of antibodies). See FIGS. 2 and 3. Described herein are (1) methods for producing mixtures of antibodies comprising a limited number of major species in host cells, optionally in a host cell line, (2) antibodies and mixtures of antibodies comprising alterations that facilitate cognate HC/LC pairing and, in some embodiments, alterations that disfavor formation of heterodimeric HC/HC pairs, (3) host cells and/or host cell lines transfected with DNA encoding at least two different HCs and two different LCs altered as described herein, (4) nucleic acids, e.g., DNAs, encoding such antibodies and mixtures, which may be carried on one or more vectors, and (5) methods of treatment using such antibodies, mixtures of antibodies, and/or nucleic acids encoding them.

Definitions

A "3-in-1 mixture" of antibodies, as meant herein, refers to a mixture of antibodies made in a host cell line into which DNAs encoding two different IgG antibodies has been introduced. A 3-in-1 mixture comprises three different major species of antibodies, that is, the two different IgG antibodies plus a bispecific antibody comprising a cognate HC/LC pair from each of the two IgG antibodies. A 3-in-1 mixture does not refer to mixtures of antibodies made by separate populations of host cells into which different DNAs encoding the different antibodies have been separately introduced.

An "alteration that disfavors heterodimers," as meant herein, is a substitution, insertion, or deletion of a single amino acid within a CH3 domain amino acid sequence in an antibody, optionally a human, humanized, or primate CH3 domain amino acid sequence, where the substitution, insertion, or deletion disfavors the formation of heterodimers in the context of a mixture of antibodies. An antibody can comprise more than one alteration that disfavors heterodimers, and multiple alterations that disfavor heterodimers can occur at multiple sites in one or more antibodies in a mixture of antibodies. A single alteration that disfavors heterodimer formation need not be completely effective in eliminating heterodimers, or effective by itself, to be considered an "alteration that disfavors heterodimers," as long as it is partially effective and/or effective when paired with one or more other alterations. Included among the alterations can be the substitution of a charged residue for the residue present in the wild type sequence. Alternatively, a substitution can create a steric obstacle to proper HC/HC pairing such as a "protuberance" abutting against another "protuberance." Protuberances or knobs are described in U.S. Pat. No. 8,679,785, col. 12, line 12 to col. 13, line 2, which is incorporated herein by reference.

Whether one or more alteration(s) has (have) an effect on HC/HC heterodimer formation can be determined by the methods described in Example 4. Data from such experiments is shown in FIGS. 11-14. Alterations that disfavor heterodimers occur at "domain interface residues." Domain interface residues are discussed in U.S. Pat. No. 8,592,562 in Table 1 and accompanying text, which are incorporated herein by reference. Such domain interface residues are said to be "contacting" residues or are said to "contact" each other if they are predicted to be physically close, i.e., at most 12 angstroms (Å) between the alpha carbons (Cα, i.e., the carbon between the amino and the carboxyl moiety of the amino acid) of the two amino acids or at most 5.5 Å between a side chain heavy atom (any atom other than hydrogen) of one amino acid and any heavy atom of the other amino acid according to known structure models. Such structures are available online, for example, through the Protein Data Bank (available at rcsb.org/pdb/home/home.do) or through the INTERNATIONAL IMMUNOGENETICS INFORMATION SYSTEM® (IMGT; available at imgt.org). In Table 4 below, examples of contacting residues at the CH3/CH3 interface in a human IgG antibody are listed.

TABLE 4

Contacting residues at a human IgG CH3/CH3 interface

| Contacting residue in first CH3* | Residues in second CH3* having a heavy atom within 4.5 angstroms of a side chain heavy atom of the contacting amino acid in first CH3 |
|---|---|
| Q347 | K360 |
| Y349 | S354, D356, E357, K360 |
| T350 | S354, R355 |
| L351 | L351, P352, P353, S354, T366 |
| S354 | Y349, T350, L351 |
| R355 | T350 |
| D356 | Y349, K439 |
| E357 | Y349, K370 |
| K360 | Q347, Y349 |
| S364 | L368, K370 |
| T366 | L351, Y407 |
| L368 | S364, K409 |
| K370 | E357, S364 |
| N390 | S400 |
| K392 | L398, D399, S400, F405 |
| T394 | T394, V397, F405, Y407 |
| P395 | V397 |
| V397 | T393, T394, P395 |
| D399 | K392, K409 |
| S400 | N390, K392 |
| F405 | K392, T394, K409 |
| Y407 | T366, T394, Y407, S408, K409 |

TABLE 4-continued

Contacting residues at a human IgG CH3/CH3 interface

| Contacting residue in first CH3* | Residues in second CH3* having a heavy atom within 4.5 angstroms of a side chain heavy atom of the contacting amino acid in first CH3 |
|---|---|
| K409 | L368, D399, F405, Y407 |
| K439 | D356 |

*Numbering is according to Edelman et al. (1969), Proc. Natl. Acad. Sci. USA 63: 78-85, which is incorporated herein in its entirety Examples of alterations that disfavor heterodimers include, e.g., D399K/R plus K/R409D/E in a primate and/or humanized IgG heavy chain, optionally in the context of a mixture of antibodies that includes another IgG antibody comprising 409R. As shown in Table 8 below, human IgG4 antibodies have an arginine (R) at position 409, while human IgG1, IgG2, and IgG3 antibodies have a lysine (K) at position 409. In particular instances where an IgG1, IgG2, or IgG3 antibody comprises the alteration K409R, this alteration is not considered to be an "alteration that disfavors heterodimers" (which is an exception to the definition above), as meant herein, since there is a naturally occurring R at position 409 in human IgG4 HCs.

An "amino acid," an "amino acid residue," a "residue," or a "position," within a HC or LC amino acid sequence refers to an amino acid at a position numbered as shown in Tables 5-11. Thus, for example, it is possible for two different HC amino acid sequences to have the same or different amino acids at a particular position in the two HC amino acid sequences. Further, an "HC position," an "HC residue," an "LC position," or an "LC residue" refers to an amino acid at a position in any HC or LC amino acid sequence numbered as shown in Tables 5-11.

An "antibody," as meant herein, is a protein that contains at least one heavy chain variable (VH) domain or light chain variable (VL) domain. An antibody often contains both VH and VL domains. VH and VL domains are described in full detail in, e.g., Kabat et al., SEQUENCES OF PROTEINS OF IMMUNOLOGICAL INTEREST, FIFTH EDITION, U.S. Department of Health and Human Services, Public Health Service, National Institutes of Health, NIH Publication No. 91-3242, 1991, pp. xvi-xix and pp. 103-533, which are incorporated by reference herein. "Antibody" includes molecules having different formats such as single chain Fv antibodies (scFv, which contain VH and VL regions joined by a linker), Fab, F(ab)$_2$, Fab', scFv:Fc antibodies (as described in Carayannopoulos and Capra, Ch. 9 in FUNDAMENTAL IMMUNOLOGY, 3.sup.rd ed., Paul, ed., Raven Press, New York, 1993, pp. 284-286, which is incorporated herein by reference), bispecific antibodies and monovalent antibodies in any of a variety of formats, and full-length and IgG antibodies as defined below, among other possible formats for an antibody.

A "bispecific antibody," as meant herein, binds to two different epitopes, which can reside on one target molecule or on two separate target molecules. A bispecific antibody can be a full-length antibody, IgG antibody, or an antibody having a different format.

A "bivalent antibody," as meant herein, can simultaneously bind to two epitopes, which can be identical or different and can reside on one target molecule or on two separate target molecules.

A "charge pair," of amino acids, as meant herein, is a pair of oppositely charged amino acids at "contacting" amino acid residues as defined herein. Such charged amino acids can be on the same polypeptide chain or on different polypeptide chains.

A "charged" amino acid, as meant herein, is an acidic or basic amino acid that can have a charge at near-physiologic pH. These include the acidic amino acids glutamic acid (E) and aspartic acid (D), which are negatively charged at physiologic pH, and the basic amino acids arginine (R) and lysine (K), which are positively charged at physiologic pH. The weakly basic amino acid histidine, which can be partially charged at near-physiologic pH, is not within the definition of "charged" amino acid herein. To avoid confusion, a positive charge is considered to be "opposite" to a negative charge, as meant herein. Thus, for example, amino acid residues E and R are opposite in charge.

A "cognate" HC in the context of a mixture of antibodies, as meant herein, is the HC that a particular LC is known to pair with to form a binding site for a particular antigen. For example, if a known full-length Antibody X binds to Antigen X, the Antibody X HC is the cognate HC of the Antibody X LC, and vice versa, in the context of a mixture of antibodies that comprises Antibody X, among other antibodies. Further, if the mixture also comprises an Antibody Y, the antibody Y HC is "non-cognate" with respect to the Antibody X LC and vice versa.

A "complementarity determining region" (CDR) is a hypervariable region within a VH or VL domain. Each VH and VL domain contains three CDRs called CDR1, CDR2, and CDR3. The CDRs form loops on the surface of the antibody and are primarily responsible for determining the binding specificity of an antibody. The CDRs are interspersed between four more conserved framework regions (called FR1, FR2, FR3, and FR4) as follows: FR1-CDR1-FR2-CDR2-FR3-CDR3-FR4. Positions of CDRs in a VH and a VL are indicated in Tables 5 and 9, respectively. Kabat et al. position the VH CDRS as follows: CDR1 is at positions 31-35 (with possible insertions numbered 35A and 35B); CDR2 is at positions 50-65 (with possible insertions numbered 52A-52C); and CDR3 is at positions 95-102 (with possible insertions numbered 100A-100K). Kabat et al., supra, at xvii. Kabat et al. position the VL CDRs as follows: CDR1 is at positions 24-34 (with possible insertions numbered 27A-27F); CDR2 is at positions 50-56; and CDR3 is at positions 89-97 (with possible insertions numbered 95A-95F).

A "cysteine substitution," as meant herein, refers to an amino acid substitution in a protein where a cysteine is substituted for any other amino acid.

Amino acid alterations within two or more related sequences "differ," as meant herein, (1) if they occur at different sites within two amino acid sequences that are the same or within two amino acid sequences that belong to the same class (e.g., VH domains) and can be aligned to a common numbering system via conserved amino acids, and/or (2) if the alteration is different, e.g., a different amino acid is substituted at the same site within two amino acid sequences that are otherwise the same or that belong to the same class or different numbers of amino acids and/or different amino acids are inserted into or deleted from two amino acid sequences that are otherwise the same or that belong to the same class. Of course, amino acid alterations in two or more unrelated sequences also "differ" from each other. Two or more antibodies are "different," as meant herein, if the amino acid sequences of all the polypeptide chains included in the antibody are not "the same," as meant herein.

Two or more amino acid sequences are "different," as meant herein, if they could not be encoded by the same DNA sequence. Thus, amino acid sequences that differ only because of post-translational modifications are not "different" as meant herein.

An "Fc fragment," as meant herein, comprises most or all of a hinge domain, plus a CH2 and a CH3 domain from an HC. For example, amino acid sequences of human IgG Fc fragments are shown in Table 8.

A "full-length antibody," as meant herein, comprises (1) two heavy chains of any isotype each comprising at least a VH domain, a first heavy chain constant (CH1) domain, a hinge domain, a second heavy chain constant (CH2) domain, and a third heavy chain constant (CH3) domain, and (2) two light chains, which can be either kappa (κ) or lambda (λ) chains, each comprising a VL and a light chain constant (CL) domain. These domains are described in detail Kabat et al., supra, pp. xv-xix and 647-699, which pages are incorporated herein by reference. The numbering system of Kabat et al., supra, is used for the VH and VL domains (see Tables 5 and 9 below), and the EU system (Edelman et al. (1969), Proc. Natl. Acad. Sci. USA 63: 78-85, which is incorporated herein in its entirety) is used for the CL, CH1, hinge, CH2, and CH3 domains. See Tables 6-8, 10, and 11.

A "heavy chain (HC)," as meant herein, comprises at least VH, CH1, hinge, CH2, and CH3 domains. An HC including all of these domains could also be referred to as a "full-length HC." Some isotypes such as IgA or IgM can contain additional sequences, such as the IgM CH4 domain. The numbering system of Kabat et al., supra, is used for the VH domain (see Table 5 below), and the EU system (Edelman et al. (1969), Proc. Natl. Acad. Sci. USA 63: 78-85, which is incorporated herein in its entirety) is used for the CH1, hinge, CH2, and CH3 domains. Tables 5 to 8 below provide a more specific picture of HC amino acid sequences.

TABLE 5

Consensus sequence of human VHs
(SEQ ID NO: 1)

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
|   |   |   | L |   |   | G |   |   |    |    |    |    | P  |    |

| 16 | 17 | 18 | 19 | 20 | 21 | 22 | 23 | 24 | 25 | 26 | 27 |
|----|----|----|----|----|----|----|----|----|----|----|----|
|    | S  | V  |    | L  | S  | C  |    |    |    | G  |    |
|    | T  | L  |    | V  | T  |    |    |    |    |    |    |

| 28 | 29 | 30 | 31 | 32 | 33 | 34 | 35 | 35A | 35B | 36 |
|----|----|----|----|----|----|----|----|-----|-----|----|
|    |    |    |    |    |    |    |    |     |     | W  |

| 37 | 38 | 39 | 40 | 41 | 42 | 43 | 44 | 45 | 46 | 47 | 48 |
|----|----|----|----|----|----|----|----|----|----|----|----|
|    | R  | Q  |    |    | G  | K  | G  | L  |    | W  |    |
|    |    |    |    |    |    |    | Q  |    |    |    |    |

| 49 | 50 | 51 | 52 | 52A | 52B | 52C | 53 | 54 | 55 | 56 |
|----|----|----|----|-----|-----|-----|----|----|----|----|

| 57 | 58 | 59 | 60 | 61 | 62 | 63 | 64 | 65 | 66 | 67 | 68 |
|----|----|----|----|----|----|----|----|----|----|----|----|
|    |    |    |    |    |    |    |    |    | R  |    |    |

| 69 | 70 | 71 | 72 | 73 | 74 | 75 | 76 | 77 | 78 | 79 | 80 |
|----|----|----|----|----|----|----|----|----|----|----|----|
|    |    |    |    |    | S  |    |    |    |    |    | L  |

| 81 | 82 | 82A | 823 | 82C | 83 | 84 | 85 | 86 | 87 | 88 |
|----|----|-----|-----|-----|----|----|----|----|----|----|
|    |    |     |     |     |    |    |    |    | D  |    |

| 89 | 90 | 91 | 92 | 93 | 94 | 95 | 96 | 97 | 98 | 99 | 100 |
|----|----|----|----|----|----|----|----|----|----|----|-----|
|    | Y  |    | C  |    |    |    |    |    |    |    |     |

| 100A | 100B | 100C | 100D | 100E | 100F | 100G |
|------|------|------|------|------|------|------|

| 100H | 100I | 100J | 100K | 101 | 102 | 103 | 104 |
|------|------|------|------|-----|-----|-----|-----|
|      |      |      |      |     |     |     | W   |

| 105 | 106 | 107 | 108 | 109 | 110 | 111 | 112 | 113 |
|-----|-----|-----|-----|-----|-----|-----|-----|-----|
| Q   | G   |     |     | V   |     | V   | S   |     |

Table 5 shows conserved amino acids based on the human VH amino acid sequences (I-III) in Kabat et al. (supra). Numbering is according to Kabat et al., supra. Site numbers within the CDRs are written in bold italics. Position numbers with letters after them, e.g., 100A, may or may not be filled by an amino acid due to the varying lengths of CDRs. A single boldface amino acid at a particular position indicates an "invariant" amino acid in all three classes of human VH domains as described by Kabat et al. (supra). At sites of interest where the amino acid at a given position is most commonly one amino acid or either of two amino acids, those amino acids are indicated in plain text. Site numbers in underlined boldface indicate positions that are described as being altered herein. Positions where no amino acid is designated did not meet the criteria stated above.

Table 5 shows that there are numerous conserved amino acids that would allow alignment of any VH sequence with the conserved amino acids spaced as shown above by eye. Alternatively, a novel sequence could be aligned with a known VH sequence using alignment software, for example, alignment software available on the International ImMunoGeneTics (IMGT) Information System® (for example, IMGT/DomainGapAlign, which is available at imgt.org or CLUSTAL Omega (Sievers et al., (2011), Molecular Systems Biology 7(1): 539).

Table 6 below shows a consensus amino acid sequence of CH1 domains.

TABLE 6

CH1 consensus
(SEQ ID NO: 2)
118 119 120 121 122 123 124 125 126 127 128 129 130
                            P               P TABLE 6-continued

131 132 133 134 134 136 137 138 139 140 141 142 143
L       R/K 144 145 146 147 148 149 150 151 152 153 154 155 156
C   L       K               P 157 158 159 160 161 162 163 164 165 166 167 168 169
    W                                           H

170 171 172 173 174 175 176 177 178 179 180 181 182
F           V           A                       T

183 184 185 186 187 188 189 190 191 192 193 194 195
S   S 196 197 198 199 200 201 202 203 204 205 206 207 208
            C 209 210 211 212 213 214 215

TABLE 6: The numbering is the numbering according to Edelman et al. (supra). The single amino acids shown in boldface below the numbers are "invariant" residues according to Kabat et al. (supra) from alignments of CH1 domains from a variety of species. Sites selected for alteration herein (131, 133, 147, 168, 170, 173, 176, 181, and 183) are shown in underlined boldface. At these sites, the most common one or two amino acids in the 63 primate CH1 sequences reported in Kabat et al. (supra) are shown in plain text. Positions where no amino acid is designated were not "invariant" and were not selected for alteration.

Table 7 below shows an alignment human CH1 domains of the IgG1, IgG2, IgG3 and IgG4 isotypes. This alignment highlights the very strong conservation of sequence among these closely-50 related CH1 domains.

TABLE 7

Alignment of human IgG1,
IgG2, IgG3, and IgG4 CH1 domains

```
        118 120       130       140       150       160       170     177
         *  *          *         *         *         *         *       *
IgG1    ASTKGPSVFPLAPSSKSTSGGTAALGCLVKDYFPEPVTVSWNSGALTSGVHTFPAVLQSS
IgG2    ASTKGPSVFPLAPCSRSTSESTAALGCLVKDYFPEPVTVSWNSGALTSGVHTFPAVLQSS
IgG3    ASTKGPSVFPLAPCSRSTSGGTAALGCLVKDYFPEPVTVSWNSGALTSGVHTFPAVLQSS
IgG4    ASTKGPSVFPLAPCSRSTSESTAALGCLVKDYFPEPVTVSWNSGALTSGVHTFPAVLQSS 178 180       190       200       210  215
         *  *          *         *         *    *
IgG1    GLYSLSSVVTVPSSSLGTQTYICNVNHKPSNTKVDKKV (SEQ ID NO: 3)
IgG2    GLYSLSSVVTVPSSNFGTQTYTCNVDHKPSNTKVDKTV (SEQ ID NO: 4)
IgG3    GLYSLSSVVTVPSSSLGTQTYTCNVNHKPSNTKVDKRV (SEQ ID NO: 5)
IgG4    GLYSLSSVVTVPSSSLGTKTYTCNVDHKPSNTKVDKRV (SEQ ID NO: 6)
```

Table 7: The amino acid sequences of representative CH1 domains of human IgG1, IgG2, IgG3 and IgG4 antibodies were obtained from IMGT web page, accession numbers J00228, J00230, X03604, and K01316, respectively, and aligned with CLUSTALW software. Residues are numbered according to the EU system of Edelman et al., supra. "Invariant" residues according to Kabat et al., supra are shown in boldface. These residues are highly conserved, but not completely invariant. Residues that are underlined and in boldface italics are sites at which substitutions have been made and tested as reported in the Examples below.

Table 8 below shows an alignment of human IgG Fc regions of the four human IgG subclasses, IgG1, IgG2, IgG3, and IgG4. This alignment shows the differences between these subclasses, as well as the high sequence conservation.

"human" amino acid sequence or protein does not contain more than 10 insertions, deletions, and/or substitutions of a single amino acid per every 100 amino acids. Similarly, a human nucleic acid (e.g., DNA) or nucleotide sequence does not contain more than 30 insertions, deletions, and/or substitutions of a single nucleotide per every 300 nucleotides. In the particular case of a VH or VL sequence, the CDRs are expected to be extremely variable, and, for the purpose of determining whether a particular VH or VL amino acid sequence (or the nucleotide sequence encoding it) is a "human" sequence, the CDRs (or the nucleotides encoding them) are not considered part of the sequence.

A "humanized" nucleotide sequence encoding an antibody or antibody domain or a "humanized" amino acid sequence of an antibody or antibody domain, as meant herein, is a sequence that originated in a non-human organ-

TABLE 8

Amino acid sequences of human IgG Fc regions

```
IgG1   ------------------------------------------------
IgG2   ------------------------------------------------
IgG3   ELKTPLGDTTHTCPRCPEPKSCDTPPPCPRCPEPKSCDTPPPCPRCP
IgG4   ------------------------------------------------

216       226       236       246       256       266
        *         *         *         *         *         *
IgG1   EPKSCDKTHTCPPCPAPELLGGPSVFLFPPKPKDTLMISRTPEVTCVVVDVSHEDPEVKF
IgG2   ERKCCVE---CPPCPAPPVA-GPSVFLFPPKPKDTLMISRTPEVTCVVVDVSHEDPEVQF
IgG3   EPKSCDTPPPCPRCPAPELLGGPSVFLFPPKPKDTLMISRTPEVTCVVVDVSHEDPEVQF
IgG4   ESKYG---PPCPSCPAPEFLGGPSVFLFPPKPKDTLMISRTPEVTCVVVDVSQEDPEVQF 276       286       296       306       316       326
        *         *         *         *         *         *
IgG1   NWYVDGVEVHNAKTKPREEQYNSTYRVVSVLTVLHQDWLNGKEYKCKVSNKALPAPIEKT
IgG2   NWYVDGMEVHNAKTKPREEQFNSTFRVVSVLTVVHQDWLNGKEYKCKVSNKGLPAPIEKT
IgG3   KWYVDGVEVHNAKTKPREEQYNSTFRVVSVLTVLHQDWLNGKEYKCKVSNKALPAPIEKT
IgG4   NWYVDGVEVHNAKTKPREEQFNSTYRVVSVLTVLHQDWLNGKEYKCKVSNKGLPSSIEKT 336       346       356       366       376       386
        *         *         *         *         *         *
IgG1   ISKAKGQPREPQVYTLPPSREEMTKNQVSLTCLVKGFYPSDIAVEWESNGQPENNYKTTP
IgG2   ISKTKGQPREPQVYTLPPSREEMTKNQVSLTCLVKGFYPSDIAVEWESNGQPENNYKTTP
IgG3   ISKTKGQPREPQVYTLPPSREEMTKNQVSLTCLVKGFYPSDIAVEWESSGQPENNYNTTP
IgG4   ISKAKGQPREPQVYTLPPSQEEMTKNQVSLTCLVKGFYPSDIAVEWESNGQPENNYKTTP 396       406       416       426       436       446
        *         *         *         *         *         *
IgG1   PVLDSDGSFFLYSKLTVDKSRWQQGNVFSCSVMHEALHNHYTQKSLSLSPGK   (SEQ ID NO: 7)
IgG2   PMLDSDGSFFLYSKLTVDKSRWQQGNVFSCSVMHEALHNHYTQKSLSLSPGK   (SEQ ID NO: 8)
IgG3   PMLDSDGSFFLYSKLTVDKSRWQQGNIFSCSVMHEALHNRFTQKSLSLSPGK   (SEQ ID NO: 9)
IgG4   PVLDSDGSFFLYSRLTVDKSRWQEGNVFSCSVMHEALHNHYTQKSLSLSLGK   (SEQ ID NO: 10)
```

A "host cell line" into which DNA(s) encoding one or more proteins has been introduced refers to a cell line derived from a single cell following the introduction of the DNA, e.g., by transfection. Methods for isolating such clonal cell lines following the introduction of DNA are well known in the art and include limiting dilution, among other possible methods that can include visually determining the existence of only one cell in a particular sample. See, e.g., Wewetzer (1995), J. Immunol. Methods 179(1): 71-76, Underwood and Bean (1988), J. Immunol. Meth. 107(1): 119-128.

"Human," nucleotide or amino acid sequences or nucleic acids or proteins include those that occur naturally in a human. Many human nucleotide and amino acid sequences are reported in, e.g., Kabat et al., supra, which illustrates the use of the word "human" in the art. A "human" amino acid sequence or protein, as meant herein, can contain one or more insertions, deletions, or substitutions relative to a naturally-occurring sequence, with the proviso that a ism but was engineered to be as similar as possible to a human sequence as possible without sacrificing the desired properties of the antibody, e.g., binding to a certain antigen with a certain avidity, among many possible desired properties. The process of humanization generally involves changing all constant domains to be human constant domains. In the variable domains, the original CDRs can be used to replace the CDRs of a human antibody sequence that is as similar as possible to the original variable domain (a process often referred to as CDR grafting). However, one or more changes in the framework regions may also be required. Thus, the amino acid sequence of a humanized antibody may or may not fall within the definition of "human" immediately above. This process is described in, e.g., Zhang and Ho, Scientific Reports 6: 33878; doi: 10.1038/srep33878 (2016) and Miethe et al. PLOS One; doi: 10.137/journal.pone.0161446 (2016), both of which are incorporated herein by reference.

An "IgG antibody," as meant herein, refers to a full-length antibody, as defined herein, of the IgG isotype, including human, humanized, and primate antibodies of the IgG1, IgG2, IgG2, and IgG4 isotype subclasses.

The term "isotype," as meant herein, refers to whether the heavy chain constant regions in an antibody, i.e., the CH1, hinge, CH2, and CH3 domains, are of the IgG, IgD, IgM, IgA, or IgE class or a subclass thereof, such as IgG1, IgG2, IgG3, or IgG4. Such isotypes are known in the art and are described and explained in detail in, e.g., Janeway et al., The Immune System in Health and Disease, 5th ed., sections 4-15 to 4-19, Garland Science, New York, 2001 (available at ncbi.nlm.nih.gov/books/NBK27106/).

A "light chain (LC)," as meant herein, comprises a VL domain and a light chain constant (CL) domain, which can be a kappa (CLκ) or lambda (CLλ) domain. These domains, including exemplary amino acid sequences thereof, are described in Kabat et al., supra, pages xiii-lix, 103-309, and 647-660, which are incorporated herein by reference. The numbering system used herein for the light chain is that described in Kabat et al., supra for the VL domain and that described in Edelman et al., supra for the CL domain, as illustrated in Tables 9-11 below.

TABLE 9

```
Consensus sequence of human VL domains
                                     (SEQ ID NO: 11)
 1  2  3  4  5  6  7  8  9 10 11 12 13 14 15

16 17 18 19 20 21 22 23 24 25 26 27
 G                    C
```

TABLE 9-continued

```
27A 27B 27C 27D 27E 27F 28 29 30 31

32 33 34 35 36 37 38 39 40 41 42 43
 W                                    A
                                      S
                                      P 44 45 46 47 48 49 50 51 52 53 54 55
 P 56 57 58 59 60 61 62 63 64 65 66 67
   I/V P       R  F  S  G  S 68 69 70 71 72 73 74 75 76 77 78 79
                L 80 81 82 83 84 85 86 87 88 89 90 91
              A/G  Y Y/F 92 93 94 95 95A 96 97 98 99 100 101
                 F  G     Q/G  G 102 103 104 105 106 106A 107 108 109
 T
```

TABLE 9: The numbering is according to Kabat et al. (supra). Numbers in bold italics indicate the positions of the CDRs. Position numbers with letters after them, e.g., 27A, may or may not be filled by an amino acid, due to the varying lengths of CDRs. Invariant residues for all human light chains in Kabat et al. (supra) are shown as bold letters indicating the amino acid found at that position. At selected sites, the one to three most common amino acids found at that site are indicated in plain text. In addition, many other amino acids are invariant or highly conserved within some subgroups of kappa or lambda VL domains, which can aid in categorizing a particular amino acid sequence as a VL domain. Sites selected for alteration herein, as reported in the Examples below, are indicated by boldface underlined type. Positions where no amino acid is designated and/or the number is not shown in boldface underlined type do not meet the criteria stated above.

TABLE 10

Consensus sequence and numbering for CL domains

|   | 108 | 109 | 110 | 111 | 112 | 113 | 114 | 115 | 116 | 117 | 118 | 119 | 120 | 121 | 122 | 123 |
|---|-----|-----|-----|-----|-----|-----|-----|-----|-----|-----|-----|-----|-----|-----|-----|-----|
| κ |     |     |     |     |     | P   |     |     |     | I   |     |     | P   | P   |     |     |
| λ |     |     |     |     |     | P   |     |     |     | L   |     |     | P   | P   |     |     |

|   | 124 | 125 | 126 | 127 | 128 | 129 | 130 | 131 | 132 | 133 | 134 | 135 | 136 | 137 | 138 | 139 |
|---|-----|-----|-----|-----|-----|-----|-----|-----|-----|-----|-----|-----|-----|-----|-----|-----|
| κ |     |     |     |     |     |     |     | S   |     | V   | C   |     |     |     |     |     |
| λ |     |     |     |     |     |     |     | A   |     | V   | C   |     |     |     |     |     |

|   | 140 | 141 | 142 | 143 | 144 | 145 | 146 | 147 | 148 | 149 | 150 | 151 | 152 | 153 | 154 | 155 |
|---|-----|-----|-----|-----|-----|-----|-----|-----|-----|-----|-----|-----|-----|-----|-----|-----|
| κ |     | P   |     |     |     |     | V   |     | W   |     |     |     |     |     |     |     |
| λ |     | P   |     |     |     |     | V   |     | W   |     |     |     |     |     |     |     |

|   | 156 | 157 | 158 | 159 | 160 | 161 | 162 | 163 | 164 | 165 | 166 | 167 | 168 | 169 | 170 | 171 |
|---|-----|-----|-----|-----|-----|-----|-----|-----|-----|-----|-----|-----|-----|-----|-----|-----|
| κ |     |     |     |     | Q   |     | S   |     | T   |     |     |     |     |     |     |     |
| λ |     |     |     |     | E   |     | T   |     | P   |     |     |     |     |     |     |     |

|   | 172 | 173 | 174 | 175 | 176 | 177 | 178 | 179 | 180 | 181 | 182 | 183 | 184 | 185 | 186 | 187 |
|---|-----|-----|-----|-----|-----|-----|-----|-----|-----|-----|-----|-----|-----|-----|-----|-----|
| κ |     |     | S   |     | S   | S   | T   | L   | T   | L   |     |     |     |     |     |     |
| λ |     |     | A/M |     | S   | S   | Y   | L   | S   | L   |     |     |     |     |     |     |

|   | 188 | 189 | 190 | 191 | 192 | 193 | 194 | 195 | 196 | 197 | 198 | 199 | 200 | 201 | 202 | 203 |
|---|-----|-----|-----|-----|-----|-----|-----|-----|-----|-----|-----|-----|-----|-----|-----|-----|
| κ |     |     |     |     |     |     | C   |     |     |     | H   |     |     |     |     |     |
| λ |     |     |     |     |     |     | C   |     |     |     | H   |     |     |     |     |     |

|   | 204 | 205 | 206 | 207 | 208 | 209 | 210 | 211 | 212 | 213 | 214 |                  |
|---|-----|-----|-----|-----|-----|-----|-----|-----|-----|-----|-----|------------------|
| κ |     |     |     |     |     | F   |     |     |     |     | C   | (SEQ ID NO: 12)  |
| λ |     |     |     |     |     | V   |     |     |     |     | C   | (SEQ ID NO: 13)  |

TABLE 10: The numbering is according to Edelman et al. (supra), which is the same as the numbering of Kabat et al. (supra) for CL domains. The amino acids shown in bold below the numbers are "invariant" residues according to Kabat et al. (supra) from alignments of both kappa and lambda CL domains from a variety of species. As indicated at selected sites (131, 160, 162, 174, 176, and 178), amino acids conserved in the ten human kappa chains (top) and 28 human lambda chains (below) reported in Kabat et al. (supra) are shown in plain text. In cases where either of two different amino acids are found at one of these sites, the more common amino acid is shown prior to the less common, e.g., A/M. Bold underlined numbers indicate sites that were altered as reported in the Examples below. In addition, many other amino acids are invariant or highly conserved within some subgroups of CLκ or CLλ domains, which can aid in categorizing a particular amino acid sequence as a CL domain. Positions where no amino acid is designated and/or the number is not shown in boldface underlined type do not meet the criteria stated above.

optionally a substitution of a charged amino acid or a cysteine for the naturally occurring amino acid, which causes an LC, optionally a human, humanized, and/or primate kappa or lambda LC, containing the altered VL or CL amino acid sequence to associate more strongly with an HC, optionally one containing an LC-partner-directing alteration at a contacting amino acid residue. In some embodiments, a contacting pair of HC- and LC-partner-directing alterations can be substitutions of charged amino acids having opposite charges, which form a "charge pair," as defined above. In other embodiments, a charged amino acid already exists at one of the contacting sites of the HC or LC so that alteration of only one chain is required to create a charge pair favoring formation of a cognate HC/LC pair. In other embodiments, cysteine residues can be introduced at contacting sites so that disulfide bridges between a cognate HC/LC pair can form. In further embodiments, HC- and LC-partner-directing alterations can be substitutions or pre-existing amino acids that create a knob and a hole (or a protuberance and a cavity) at contacting residues as described in U.S. Pat. No.

TABLE 11

Alignment of human kappa chain CL domains

```
              108        120        130        140        150        160    167
                *          *          *          *          *          *      *
J00241        RTVAAPSVFIFPPSDEQLKSGTASVVCLLNNFYPREAKVQWKVDNALQSGNSQESVTEQD
M11736        RTVAAPSVFIFPPSDEQLKSGTASVVCLLNNFYPREAKVQWKVDNALQSGNSQESVTEQE
M11737        RTVAAPSVFIFPPSDEQLKSGTASVVCLLNNFYPREAKVQRKVDNALQSGNSQESVTEQE
AF017732      RTVAAPSVFIFPPSDEQLKSGTASVVCLLNNFYPREAKVQWKVDNALQSGNSQESVTEQD
AF113887      RTVAAPSVFIFPPSDEQLKSGTASVVCLLNNFYPREAKVQWKVDNALQSGNSQESVTEQD 168 170    180        190        200        210 214
               *   *      *          *          *          *   *
J00241        SKDSTYSLSSTLTLSKADYEKHKVYACEVTHQGLSSPVTKSFNRGEC (SEQ ID NO: 14)
M11736        SKDSTYSLSSTLTLSKADYEKHKVYAGEVTHQGLSSPVTKSFNRGEC (SEQ ID NO: 15)
M11737        SKDSTYSLSSTLTLSKADYEKHKVYACEVTHQGLSSPVTKSFNRGEC (SEQ ID NO: 16)
AF017732      SKDSTYSLSSTLTLSKADYEKHKLYACEVTHQGLSSPVTKSFNRGEC (SEQ ID NO: 17)
AF113887      SKDSTYSLSNTLTLSKADYEKHKVYACEVTHQGLSSPVTKSFNRGEC (SEQ ID NO: 18)
```

Table 11: The amino acid sequences of human CL$_{[\ ]}$ domains in this table are from the International ImMunoGeneTics information System® (IMGT) web page (imgt.org). The accession number of each sequence is shown to the left of the sequence, and the sequences were aligned with CLUSTALW software (available at genome.jp/tools/clustalw/). Numbering is according to Edelman et al. supra. The boldface residues are invariant residues according to Kabat et al., supra. Invariant sites where substitutions were made and the resulting antibodies were tested as reported in the Examples below are indicated by boldface and underlined amino acids. The bolded, italicized, and underlined residues are other sites where substitutions were made and the resulting antibodies were tested as reported in the Examples below.

An "LC-partner-directing alteration," as meant herein, is a substitution, insertion, or deletion of a single amino acid at the HC/LC interface within a VH or CH1 amino acid sequence, optionally a substitution of a charged amino acid or a cysteine for the naturally occurring amino acid, which causes an HC, optionally a human, humanized, and/or primate IgG HC, containing the altered VH and/or CH1 amino acid sequence to associate more strongly with an LC, optionally one containing an "HC-partner-directing alteration" at a contacting amino acid residue.

Similarly, an "HC-partner-directing alteration" is the substitution, insertion, or deletion of a single amino acid in the HC/LC interface within a VL or CL amino acid sequence, 8,679,785, the relevant portions of which are incorporated herein by reference. The HC can be of the IgG, IgA, IgD, IgM, or IgE isotype, optionally IgG1, IgG2, IgG3, or IgG4. HC- and LC-partner-directing alterations occur at contacting amino acid positions that form part of the HC/LC interface. Interface residues in the CL and CH1 domains include those within 4.5 Å, as explained in U.S. Pat. No. 8,592,562, Tables 4 and 5 and accompanying text in columns 10 and 11, all of which is incorporated herein by reference. Contacting residues in the CH1 and CL domains are catalogued in Table 12 below.

TABLE 12

Contacting residues between CH1 and CL

| CH1 residue | CLκ residue | CLλ residue |
|---|---|---|
| 125 | 123 | 119 |
| 126 | 121, 123, 124 | 117, 119, 120 |
| 127 | 121 | 117, 119 |
| 128 | 118, 133 | 114, 129 |
| 129 | 118 | 114 |
| 130 | 118 | |
| 139 | 116 | |
| 140 | 116 | |
| 141 | 116, 118, 135 | 112, 114 |
| 142 | 118 | 114 |
| 143 | | 114 |
| 145 | 124, 131 | 127, 129, 173 |
| 147 | 124, 131 | 125, 127 |

TABLE 12-continued

Contacting residues between CH1 and CL

| CH1 residue | CLκ residue | CLλ residue |
|---|---|---|
| 148 | | 125 |
| 168 | 137, 138, 174 | 133, 163, 169 |
| 169 | 164 | |
| 170 | 135, 162, 164, 174, 176 | 131, 133, 169, 171 |
| 171 | 162, 164 | 158, 161, 171 |
| 172 | | 158 |
| 173 | 160, 162 | 156, 158, 173 |
| 174 | 160 | 156 |
| 175 | 160 | 156 |
| 176 | | 156 |
| 181 | | 173 |
| 182 | | 173 |
| 183 | 176 | 129, 131, 173 |
| 185 | 135 | 114, 131 |
| 187 | 137 | |
| 213 | 123 | 119 |
| 218 | 122 | |

In the case of contacting residues on the interface between the VH and VL domains, pairs of residues, one in the VH and one in the VL domain, suitable for alteration were selected using the follow criteria: (1) the residues are buried or partially buried, i.e., inaccessible in the tertiary structure of a full-length antibody, (2) the residues are spatially close, that is, where the Cα's of the two amino acids are within about 12 Å, or where there is at most 5.5 Å between a side chain heavy atom (any atom other than hydrogen) of one amino acid and any heavy atom of the other amino acid according to known structure models, (3) the residues are highly conserved, although they need not be totally invariant, and (4) the residues are not within or interacting with the complementarity determining regions (CDRs). Examples of such contacting residues include, without limitation, the following: position 44 (VH) and position 100 (VL); position 39 (VH) and position 38 (VL); and position 105 (VH) and position 43 (VL). A change in the strength of HC/LC association due to HC- and/or LC-partner-directing alterations can be measured by determining the relative amounts of various antibody species in a host cell into which DNA encoding at least two different antibodies has been introduced. As explained in detail in Examples 5 and 6 and shown in FIGS. 18, 20, and 23, panel B, the size differences between Fab fragments arising from antibodies having different HC/LC pairings can usually be distinguished by mass spectrometry (MS). Use of MS to identify various antibody species is discussed in, e.g., Thompson et al. (2014), mAbs 6:1, 197-203, which is incorporated herein in its entirety. To quickly screen many different variants, chain drop out experiments as described in Example 3 and shown in FIGS. 7-10 were performed, particularly in cases where expected Fab fragments are essentially identical in size or where expected Fab fragments do not appear in MS results and thus may be uniquely susceptible to papain. Examples of contacting pairs of LC- and HC-partner-directing alterations include, without limitation, the following: K147D/E in an HC and S131R in an LC; and H168D/E in an HC and S174R in an LC. As these examples illustrate "contacting" pairs of LC- and HC-partner directing alterations can include amino acids opposite in charge. Many other examples are disclosed in the Description and Examples below. Alternatively, LC- and HC-partner-directing alterations could be "protuberance in cavity" style alterations as described in U.S. Pat. No. 8,679,785. The portions of this patent describing these kinds of alterations, especially col. 12, line 12 to col. 14, line 5, are incorporated herein by reference. The term "partner-directing alteration" refers to HC- and/or LC-partner-directing alterations.

A "MabPair," as meant herein, is a mixture of antibodies comprising two, and not more than two, major species of antibodies. A MabPair can be made in a host cell line (as defined above) into which DNA encoding two different IgG antibodies, i.e., two different heavy chains and two different light chains, has been introduced. A MabPair can also be made in a cell population into which DNA(s) encoding two different IgG antibodies has (have) been introduced, where a clonal host cell line is not purified from the cells into which the DNA(s) was (were) introduced. An example of this kind of situation could involve transiently transfecting DNA(s) encoding two different IgG antibodies into, e.g., 293 or ExpiCHO cells, and subsequently obtaining the antibodies produced by the cells from the cell supernatant of the transfected cells. Mixtures of two antibodies that are made from more than one host cell line are not MabPairs as meant herein. Further, mixtures of two antibodies made from two separate populations of cells, where DNA encoding one antibody has been introduced into one cell population and DNA encoding the other antibody has been introduced into the other cell population, are also not MabPairs as meant herein.

A "major species" of antibody in the context of a mixture of antibodies, as meant herein, is a particular antibody species that makes up at least 10% of the total amount of antibodies within the mixture. To determine how many major species are in a mixture of antibodies, low pH CEX chromatography as described in Example 5 and shown in FIG. 17 can be performed. The percentage of the total amount of antibody that each species in an antibody mixture comprises can be determined using the areas under the peaks of absorbance in the column outflow.

A "minor species" of antibody within a mixture of antibodies, as meant herein, comprises less than 10% of the total amount of antibodies in an antibody mixture. This can be determined by low pH CEX chromatography as described in the definition of "major species."

A "primate," nucleotide or amino acid sequence or nucleic acid or protein includes molecules and sequences that occur naturally in a primate. Primates include animals from a number of families including, without limitation, prosimians (including lemurs), new world monkeys, chimpanzees, humans, gorillas, orangutans, gibbons, and old world monkeys. Specific primate species include, without limitation, *Homo sapiens, Macaca mulata* (rhesus macaque), *Macaca fascicularis* (cynomolgus monkey), and *Pan troglodytes* (chimpanzee), among many others. Many primate nucleotide and amino acid sequences are known in the art, e.g., those reported in, e.g., Kabat et al., supra. Generally, "primate" amino acid sequence, as meant herein, can contain one or more insertions, deletions, or substitutions relative to a naturally-occurring primate sequence, with the proviso that a "primate" amino acid sequence does not contain more than 10 insertions, deletions, and/or substitutions of a single amino acid per every 100 amino acids. Similarly, a primate nucleotide sequence can contain insertions, deletions, or substitutions relative to a naturally-occurring primate sequence, but does not contain more than 30 insertions, deletions, and/or substitutions of a single nucleotide per every 300 nucleotides. In the particular case of a VH or VL sequence, the CDRs are expected to be extremely variable, and, for the purpose of determining whether a particular VH or VL amino acid sequence (or the nucleotide sequence encoding it) is a "primate" sequence, the CDRs (or the nucleotides encoding them) are not considered part of the sequence.

Two amino acid sequences are "the same," as meant herein, if the two sequences could be encoded by the same DNA sequence. That is, amino acid sequences that differ only as a result of post-translational modifications, e.g., elimination of a carboxyl-terminal lysine or cyclization of N-terminal glutamate or glutamine residues, are "the same" as meant herein.

A "target molecule," as meant herein, is a molecule to which an antibody, e.g., an antibody in a mixture described herein, specifically binds. In some embodiments, a target molecule is a "target protein," i.e., a protein to which an antibody specifically binds.

Mixtures of Antibodies and Methods of Producing Them

Described herein are mixtures of antibodies having different binding specificities that are produced in host cells into which DNA(s) encoding the antibodies has (have) been introduced. The antibodies can be human, humanized, and/or primate full-length IgG antibodies. Also described are methods for producing such mixtures. The number of different major species of antibodies in the mixtures can be limited, e.g., not more than 2, 3, 4, 5, 6, 7, 8, 9, or 10 major species. The HCs and/or LCs of one or more of the antibodies can comprise LC- and/or HC-partner-directing alterations. In some embodiments, the HCs of one or more of the antibodies can comprise one or more alterations that disfavor heterodimers. In some embodiments, one or more major species of antibody in a mixture can be without such alterations. These alterations can serve to limit the number of major species of antibodies produced by the host cells.

The method for producing the mixtures of antibodies can comprise introducing DNA encoding the mixtures of antibodies described herein into host cells, culturing the host cells, and recovering the mixture of antibodies from the cell mass or culture medium. DNA encoding the different antibodies in a mixture can be introduced into host cells at the same time or at different times. For example, DNA encoding a second antibody can be introduced into a host cell population that already produces a first antibody encoded by DNA that was previously introduced into the host cell population. Alternatively, DNA encoding both antibodies can be introduced into the host cells at the same time. Further, after introduction of DNAs encoding multiple antibodies into the host cells, a clonal "host cell line" (as defined above) that produces the antibodies can be isolated from the population of cells into which the DNAs were introduced. Alternatively, mixtures of antibodies can be produced by a host cell population into which the DNAs were introduced. As explained in detail below, the alteration(s) in the antibodies can limit the number of major species of antibodies produced by the host cells. The mixture can be obtained from a host cell culture supernatant or the cell mass, can be further purified, and can be formulated as appropriate for use as a pharmaceutical.

More specifically, DNAs encoding at least two, three, or four different antibodies, optionally full-length IgG antibodies, binding to different epitopes and/or targets can be introduced into a host cell. The encoded antibodies can each comprise two HCs with the same amino acid sequence and two LCs with the same amino acid sequence, and each of the encoded antibodies can have both HCs and LCs that differ in amino acid sequence from the HCs and LCs of the other encoded antibody or antibodies. In some embodiments, the antibodies can be two full-length antibodies, each comprising two heavy chains having the same amino acid sequence and two light chains having the same amino acid sequence. Optionally, the antibodies are primate and/or human and/or humanized IgG antibodies. In some embodiments, at least one pair of oppositely charged residues, i.e., charge pairs, or cysteine residues at contacting sites in a cognate HC/LC pair (where at least one of these charged residues or cysteines results from an alteration) can be found in the interface between the LC of each antibody and its cognate HC. In other embodiments, such charge pairs and/or pairs of contacting cysteine residues can be found in one or more of the antibodies in the mixture, but need not be present in all antibodies in the mixture. Alterations in the LC and HC that create such pairs are called HC-partner-directing alterations and LC-partner-directing alterations, respectively. Each antibody can comprise multiple contacting pairs of LC- and/or HC-partner-directing alterations or can comprise no pairs of LC- and/or HC-partner-directing alterations. Optionally, there can be additional alterations in the CH3 domains that disfavor the formation of heterodimeric HC/HC pairs. Such alterations can be present in one or more of the antibodies and can be absent from one or more antibodies. The host cell population or host cell line can be cultured, and the mixture of antibodies can be recovered in the cell mass and/or the culture medium. The mixture of antibodies can be further purified, and the mixture can be formulated as is appropriate for its pharmaceutical use.

In embodiments where DNAs encoding only two full-length antibodies (Ab1 and Ab2) are introduced into the host cells and each antibody comprises one or more HC- and/or LC-partner-directing alteration(s) such that few if any non-cognate HC/LC pairs form, either two (called herein "MabPair") or three (called herein "3-in-1 mixture") major species of antibodies can be produced by the host cells. See FIGS. 1-4. If the HCs can form heterodimeric HC/HC pairs, a 3-in-1 mixture comprising Ab1, Ab2, and a bispecific antibody comprising one HC and one LC from each antibody can be produced by the host cells. If the antibodies do not form heterodimeric HC/HC pairs (optionally, because of one or more alterations that disfavor heterodimer formation), a MabPair mixture comprising Ab1 and Ab2 will result.

In an alternate strategy where DNAs encoding two full-length antibodies (Ab1 and Ab2) are introduced in the host cells, only one of the antibodies comprises one or more HC- and/or LC-partner-directing alteration(s), and either one or neither of the antibodies comprises alterations that disfavor heterodimers. See FIG. 3. Thus, in some embodiments, one of the antibodies can comprise no partner-directing alterations and no alterations that disfavor heterodimers, and the other can comprise one or more partner-directing alterations and one or more alterations that disfavor heterodimers. See FIG. 3, panel A. Alternatively, one of the antibodies can comprise one or more partner-directing alteration(s) and no alterations that disfavor heterodimers, while the other antibody may comprise no partner-directing alteration(s) but may comprise one or more alterations that disfavor heterodimers. In a further embodiment, neither antibody comprises an alteration that disfavors heterodimers, and only one antibody comprises one or more partner-directing alteration. See FIG. 3, panel B.

Further purification of an antibody mixture made by a host cell population or host cell line can involve a number of steps. In some embodiments, the mixture is applied to a Protein A or Protein G affinity column and subsequently eluted. Other column chromatography steps such as cation or anion exchange chromatography, including low pH cation exchange chromatography as described below, size exclusion chromatography, reverse phase chromatography, or hydrophobic interaction chromatography (HIC) could also be used. Further purification steps can include diafiltration, among many possibilities.

Further, an antibody mixture or nucleic acids encoding an antibody mixture can be formulated for its intended use. For use as a therapeutic, the antibody mixture could be formulated as a liquid for parenteral administration, optionally for injection. Other kinds of formulations, e.g., gels, pastes, creams, or solids, are also possible. Formulations can include ingredients that can, for example, maintain, modify, or preserve the antibodies or nucleic acids and/or control factors such as pH, osmolarity, viscosity, clarity, odor, color, sterility, and/or rate of release or absorption in vivo. As such, it could include any buffer and/or excipient ordinarily used in such formulations. Examples of such ingredients include buffers, anti-microbials, chelating agents, salts, amino acids, and sugars, among many possibilities. The pH of the formulated mixture could be within a range from about pH 5 to about pH 8.5 or from about pH 6 to about pH 8.

The binding specificity of the antibodies can be determined by a binding assay similar to that described in Example 8.

A method to determine whether two antibodies compete for a particular binding site or epitope on an antigen generally includes the following steps. First, a biotinylated antigen is incubated in the presence of varying amounts of a competitor antibody (mAb2). These combinations are referred to as "samples." The samples, which may include mAb2/antigen complexes as well as unbound mAb2 and/or antigen, are then added to wells in a microtiter plate coated with another antibody that binds the antigen (mAb1). As a control, samples including biotinylated antigen incubated without mAb2 can be added some wells. The plate is then washed to remove unbound antigen. If mAb1 and mAb2 do not compete, mAb1 can bind to the mAb2/antigen complexes, as well as free antigen. In this case, signal intensity (which is proportional to the amount of bound antigen or mAb2/antigen complexes) will not be diminished by the presence of mAb2 in a sample. In some cases mAb1 and mAb2 may compete completely, meaning that mAb1 will bind to free antigen, but not to mAb2/antigen complexes. In some cases, competition may occur but be less complete. In such a case, binding of mAb1 to mAb2/antigen complexes may be decreased rather than completely absent. In either case, signal intensity will be decreased by the presence of mAb2/antigen complexes in a sample. The signal is detected by adding streptavidin coupled to horse radish peroxidase (HRP), washing the plate, and adding a substrate for HRP that can be detected by colorimetric measurements. The plate is washed, and the reaction is stopped to prevent saturation of the signal. The colorimetric signal is detected. As meant herein, if two antibodies compete (either completely or partially) for binding to an antigen by the test described here, they are said to bind to the same epitope on the antigen.

The HCs of the antibodies in the mixture can be of any isotype, such as IgG (including either IgG1, IgG2, IgG3, or IgG4), IgA, IgM, IgE, or IgD. When an IgG4 HC is used, the HC can comprise the alteration S228P, which prevents Fab arm exchange. Silva et al. (2015), J. Biol. Chem. 290(9): 5462-5469. Sequences for such heavy chains are known in the art. See, e.g., Kabat et al., supra, at pages 661-723, which is incorporated herein by reference. The amino acid sequence of the heavy chain an IgG4 antibody containing the S228P alteration is provided in SEQ ID NO:23. The heavy chains can be from any species, e.g., a mammal, a human, a primate, a mouse, or a rat, or the heavy chains can be artificially produced, for example using phage display or using a humanization process.

Similarly, the two different light chains can be lambda (λLC) or kappa (κLC) chains, which can be from any species and, optionally, can be mammalian, for example, human or humanized, primate, murine, or rat antibodies. The light chain could also be produced artificially, for example using phage display or a humanization process. Numerous examples of amino acid sequences of λLCs and κLCs are known in the art, for example those reported in Kabat et al., supra, pages 647-660, which are incorporated herein by reference. Positions in these sequences are determined according to the Kabat (Kabat et al., supra) numbering system for VL domains and the Edelman (Edelman et al., supra) numbering system for CL domains, as shown in Tables 9-11 and discussed in the accompanying text.

Both heavy and light chains can contain one or more alterations as described herein. Each alteration of can be a substitution, insertion, or deletion of a single amino acid. In some embodiments, each alteration is the substitution of one amino acid with another. Optionally, the alteration is the substitution of a charged amino acid or a cysteine for the amino acid originally present at that site. In some embodiments, the substituted amino acid can be any amino acid. In some embodiments, an amino acid other than cysteine can be substituted for cysteine. The amino acid other than cysteine can be any amino acid, although it can be serine, glycine, or alanine in some embodiments. In some embodiments the choice of the amino acid used to replace that in the original amino acid sequence is limited. For example, in such embodiments the amino acid used to replace the original amino acid can be any amino acid except one or more of the following amino acids: alanine (A), arginine (R), asparagine (N), aspartic acid (D), cysteine (C), glutamine (Q), glutamic acid (E), glycine (G), histidine (H), isoleucine (I), leucine (L), lysine (K), methionine (M), phenylalanine (F), proline (P), serine (S), threonine (T), tryptophan (W), tyrosine (Y), and valine (V). In other embodiments, an original amino acid can be replaced with any other amino acid from among the group of twenty recited immediately above. In other embodiments, an original amino acid can be replaced with either of two, three or four amino acids and/or any amino acid within a group of amino acids having similar properties, such as the "conservative" amino acid substitutions described below. For example, such groups include (1) arginine and lysine, (2) serine and threonine, (3) aspartate and glutamate, or (4) asparagine and glutamine, among others.

One of skill in the art is aware that the amino acids present in living things can be grouped according to their properties and that replacement of an original amino acid with an amino acid having similar properties is called a "conservative substitution." The alterations described herein can, in some embodiments, include conservative substitutions. As meant herein, conservative substitutions include replacement of (1) A with V, L, or I, (2) R with K, Q, or N, (3) N with Q, (4) D with E, (5) C with S or A, (6) Q with N, (7) E with D, (8), G with P or A, (9) H with N, Q, K, or R, (10) I with L, V, M, A, or F, (11) L with I, V, M, A, or F, (12) K with R, Q, or N, (13) M with L, F, or I, (14) F with L, V, I, A, or Y, (15) P with A, (16) S with T, A, or C, (17) T with S, (18) W with Y or F, (19) Y with W, F, T, or S, and (20) V with I, M, L, F, or A.

Amino acids and amino acid substitutions at particular sites in a sequence are denoted herein as follows. The original amino acid in a sequence is followed by the position number in the heavy or light chain amino acid sequence (using the numbering systems illustrated in Table 5-11), which is followed by the amino acid used as a replacement. For example, K409E in an HC means that the lysine originally present at position 409 in the HC is replaced by glutamic acid. If position 409 in the heavy chain can originally contain either of two different amino acids, e.g., K or R, and these can be replaced with either of two amino acids, e.g., D or E, that could be denoted as K/R409D/E. This designation means that the lysine or arginine originally present at position 409 can be replaced with either an aspartic acid or a glutamic acid. In some cases, the original amino acid is not defined. For example, 409D in an HC would mean amino acid 409 is an aspartic acid, and the identity of the original amino acid is not defined and can be any amino acid, including aspartic acid. Similarly, a designation of K409 means that the original amino acid at position 409 is a lysine (and there is no alteration).

Tables 5-11 illustrate the level of sequence consensus among HCs and LCs, in some cases among human or primate HCs and LCs. The amino acid sequences of the variable regions vary particularly in the complementarity determining regions (CDRs, which are shown by bold italic numbers in Tables 5 and 9). However, the framework regions that surround the CDRs are more conserved and contain highly conserved amino acids at a number of positions. Many of the universally conserved or almost universally conserved amino acids, for example positions 4, 36, 38, and 39 in VH and 98, 99, 101, 102 in VL, are also conserved in VH and VL regions from non-human species. In addition, many other sites in VHs and VLs are highly conserved within specific groups of variable domains, although not across all VHs and VLs. Constant domains in HCs and LCs show a higher degree of sequence conservation than variable domains and contain a number of highly conserved amino acids. See Tables 6-8 and 10-11. Using these highly conserved amino acids, one of skill in the art would be able to align most immunoglobulin domains with the sequences disclosed in Kabat et al., supra to assign a numbering of those VHs and VLs according to the system of Kabat et al., supra or Edelman et al., supra.

The antibodies in the mixtures described herein can comprise HC- and/or LC-partner-directing alterations. HC- and/or LC-partner-directing alterations serve the function of ensuring that each LC pairs with its cognate HC and vice versa. In the absence of such alterations, up to ten different species of antibodies could potentially form in a host cell transfected with DNA encoding only two different full-length antibodies that have different HCs and LCs. See FIG. 4. Of course, many more species could potentially form in a host cell transfected with DNA encoding three or four different full-length antibodies having different HCs and LCs and lacking partner-directing alterations. However, if only cognate HC/LC pairing occurs, these numbers would be drastically reduced. If only homodimeric HC/HC pairing occurs, the number of species would be further reduced. Since many of the possible species in the absence of partner-directing alterations would have non-cognate HC/LC pairings, some of the resulting antibodies might not bind to any epitope and might therefore lack a desired function. Given the very strict requirements for uniformity of a pharmaceutical product, such a complex mixture is unlikely to receive regulatory approval as a therapeutic.

HC- and LC-partner-directing alterations can occur at contacting sites in the CH1 and CL domains, which are listed in Table 12 above, and/or at contacting sites in VH and VL domains, as explained herein. Antibodies in the mixtures described herein can comprise one or more LC- and/or HC-partner-directing alteration(s) in their HC and/or LC, for example, 1, 2, 3, 4, 5, 6, 7, 8, 9, 10, 11, 12, 13, 14, 15, 16, 17, 18, 19, or 20 such alterations and/or not more than 1, 2, 3, 4, 5, 6, 7, 8, 9, 10, 11, 12, 13, 14, 15, 16, 17, 18, 19, or 20 such alterations. In some embodiments, at least one antibody in the mixture can lack such alterations.

In some embodiments, these alterations include a substitution of a charged amino acid at a site that did not originally have a charged amino acid or substitution of a charged amino acid at a site that originally contained an amino acid of opposite charge. In embodiments where DNA encoding two different full-length antibodies, where the HCs and the LCs of the two antibodies are different, is introduced into a host cell, the LC- and HC-partner-directing alterations can occur at the same sites in the two different LCs and HCs, resulting in a situation where (1) the two different LCs have oppositely charged amino acids at the same LC site, (2) the two different HCs have oppositely charged amino acids at an HC site contacting the LC site, and (3) for each cognate LC/HC pairing, the charged amino acid at the LC site is opposite in charge to the amino acid at the contacting HC site. In such a situation, the interaction between cognate LCs and HCs is strengthened by an interaction between oppositely-charged amino acids, and the interaction between non-cognate LC/HC pairings is highly disfavored due to repulsion of amino acids having the same charges situated at contacting sites in non-cognate HC/LC pairs. See FIGS. 1-2. In other embodiments, only one antibody comprises a charge pair that favors cognate HC/LC pairing. See FIG. 3. In such a case, one of the amino acids in the charge pair may result from a partner-directing alteration where a charged amino acid residue is substituted for an oppositely charged amino acid residue. In this case, some non-cognate HC/LC pairs would be expected to be disfavored due to repulsive charge interactions. Examples of contacting charge pairs optionally resulting from HC- and/or LC-partner-directing alterations include, without limitation, the following: 44D/E (HC) and 100R/K (LC); 44R/K (HC) and 100D/E (LC); 105E/D (HC) and 43R/K (LC); 105R/K (HC) and 43E/D (LC); 133R/K (HC) and 117D/E (LC); 133D/E (HC) and 117R/K (LC); 137R/K (HC) and 114D/E (LC); 137D/E (HC) and 114R/K (LC); 137R/K (HC) and 116D/E (LC); 137D/E (HC) and 116R/K (LC); 147R/K (HC) and 124D/E (LC); 147D/E (HC) and 124R/K (LC); 147R/K (HC) and 129D/E (LC); 147D/E (HC) and 129R/K (LC); 147R/K (HC) and 131D/E (LC); 147D/E (HC) and 131R/K (LC); 147R/K (HC) and 178D/E (LC); 147D/E (HC) and 178R/K (LC); 147R/K (HC) and 180D/E (LC); 147D/E (HC) and 180R/K (LC); 168D/E (HC) and 164R/K (LC); 168R/K (HC) and 164D/E (LC); 168D/E (HC) and 167R/K (LC); 168R/K (HC) and 167D/E (LC); 168D/E (HC) and 174R/K (LC); 168R/K (HC) and 174D/E (LC); 170D/E (HC) and 162R/K (LC); 170R/K (HC) and 162D/E (LC); 173D/E (HC) and 160R/K (LC); 173R/K (HC) and 160D/E (LC); 173D/E (HC) and 162R/K (LC); 173R/K (HC) and 162D/E (LC); 175D/E (HC) and 160R/K (LC); 175R/K(HC) and 160D/E (LC); 175D/E (HC) and 180R/K (LC); 175R/K (HC) and 180D/E (LC); 176D/E (HC) and 160R/K (LC); 176R/K (HC) and 160D/E (LC); 181R/K (HC) and 178D/E (LC); 181D/E (HC) and 178R/K (LC); 183R/K (HC) and 176D/E (LC); 183D/E (HC) and 176R/K (LC); 190R/K (HC) and 116D/E (LC); 190D/E (HC) and 116R/K (LC); 190R/K (HC) and 137D/E (LC); 190D/E (HC) and 137R/K (LC).

In, for example, embodiments where DNA encoding two full-length antibodies (a first antibody comprising HC1 and LC1 and a second antibody comprising HC2 and LC2) has been introduced into a host cell, one or both sites in a pair of contacting sites in an HC/LC pair may already contain a charged amino acid. For example, in some cases LC1 may comprise a charged amino acid at a site that contacts a site in the cognate HC1 that does not comprise a charged amino acid, or vice versa. In a specific example, position 160 in a human CL domain can comprise a glutamic acid (E), whereas contacting sites 173, 174, and 175 in a human CH1 domain commonly comprise V, L, and Q, respectively. In this case, one of the contacting CH1 sites, e.g., 173, can be altered such that it is opposite in charge to that of the E at position 160 in the CL domain, i.e. position 173 can be substituted with an R or a K. The same site in HC2 can be altered to a charged amino acid opposite in charge to that at the site in HC1 (i.e., this site can be substituted with a D or an E), and the contacting site in LC2 can be altered to a charged amino acid opposite in charge to that in LC1 (i.e., position 160 in LC2 can be substituted with an R or a K).

Other scenarios where one or more of the contacting sites in a cognate HC/LC pair already comprise one or more charged amino acid(s) could be treated similarly with the end goal of creating oppositely charged amino acids at contacting sites in cognate HC/LC pairs. In some embodiments, the same pair of contacting sites can be altered such that they comprise oppositely charged amino acids in both antibodies, with the proviso that the charges of the amino acids at the HC site is opposite in HC1 and HC2 and the charges at the LC site are also opposite in the LC1 and LC2.

Similarly, for example in embodiments where DNA encoding two full-length antibodies (a first antibody comprising HC1 and LC1 and a second antibody comprising HC2 and LC2) has been introduced into a host cell, if contacting sites in HC1 and LC1 comprise oppositely charged amino acids, the same sites in HC2 and LC2 can be replaced with amino acids opposite in charge to those found in HC1 and LC1, respectively.

In other embodiments where DNA encoding two different full-length antibodies is introduced into a host cell, the LC- and HC-partner-directing alterations can occur at different sites in the two different LCs and HCs, resulting in a situation where (1) one LC and its cognate HC each have oppositely-charged amino acids at contacting sites and (2) the other LC and its cognate HC each have oppositely-charged amino acids at contacting sites that differ from those used in the first LC/HC pair. In these embodiments, the HC- and LC-partner-directing alterations serve to strengthen the interaction between cognate HC/LC pairs.

In still other embodiments, one or more of the antibodies in a mixture as described herein may not comprise a partner-directing alteration. In such embodiments, another of the antibodies in the mixture can comprise one or more partner-directing alterations.

In other embodiments, HC- and LC-partner-directing alterations can result in the creation of disulfide bridges due to cysteine substitutions at contacting sites in cognate HC/LC pairs. In, for example, embodiments where DNA encoding two different full-length antibodies is introduced into a host cell, such LC- and HC-partner-directing alterations can occur at different sites in the two different LCs and HCs, resulting in a situation where cognate LC/HC pairs have cysteine substitutions at contacting sites, whereas non-cognate LC/HC pairs do not have cysteine substitutions at contacting sites. See FIGS. 1-3. Thus, the two different cognate HC/LC pairs will have disulfide bridges at different places at the HC/LC interface, whereas a non-cognate HC/LC pair would not have such a disulfide bridge because the substituted cysteine residues would not be close enough to form a bridge. Hence, in these embodiments, the HC- and LC-partner-directing alterations serve to strengthen the interaction between cognate HC/LC pairs. In other embodiments, one or more antibodies in a mixture, but not all antibodies in the mixture, can comprise cysteines at contacting sites in a cognate HC/LC pair. Examples of pairs of cysteine substitutions at contacting residues include, for example, the following pairs of alterations: 126C (HC) and 121C (LC); 126C (HC) and 124C (LC); 127C (HC) and 121C (LC); 128C (HC) and 118C (LC); 133C (HC) and 117C (LC); 133C (HC) and 209C (LC); 134C (HC) and 116C (LC); 141C (HC) and 116C (LC); 168C (HC) and 174C (LC); 170C (HC) and 162C (LC); 170C (HC) and 176C (LC); 173C (HC) and 160C (LC); 173C (HC) and 162C (LC); and 183C (HC) and 176C (LC).

In some embodiments, one or more cysteine residues that normally form part of a disulfide bridge between an HC and an LC can be replaced with another amino acid in at least one of the antibodies in a mixture as described herein. For example, in a human IgG1 antibody, the cysteines at position 220 in the HC and 214 in the LC form a disulfide bridge between the HC and LC. These amino acids can be replaced with other amino acids, for example serine, alanine, or glycine, thereby eliminating an HC/LC disulfide bridge. Similar alterations can be made in antibodies of other IgG isotypes, i.e., IgG2, IgG3, or IgG4, with similar or different patterns of disulfide bond formation, in which the cysteine residues that participate in HC/LC disulfide bond formation can be substituted with other amino acids. For example, in human IgG2 and IgG4 antibodies, the cysteines at positions 131 (HC) and 214 (LC) can be substituted with other amino acids. Such alterations can weaken non-cognate HC/LC pairing, as well as cognate HC/LC pairing, since non-cognate pairs will also be unable to form the usual interchain disulfide bridges. Cognate HC/LC pairing can be strengthened by, e.g., adding partner-directing alterations to the cognate HC/LC pair lacking it usual disulfide bridge(s). Such partner-directing alterations can include cysteine substitutions at contacting residues in the HC and/or the LC so as to create new disulfide bridges and/or substitutions that introduce charged amino acids at contacting residues in the HC and/or LC so as to create charge pairs. See FIG. 3.

Where DNA encoding at least two and not more than four different full-length antibodies having different HCs and LCs has been introduced into a host cell, if the HCs of the antibodies do not contain any alterations to disfavor the formation of heterodimers, heterodimeric HC/HC pairings can generally occur. If DNA encoding only two different full-length antibodies has been introduced and only cognate HC/LC pairs can form (due to HC- and/or LC-partner directing alterations), this will lead to the formation of three different major antibody species (called "3-in-1 mixture" herein), the two starting antibodies plus a bispecific antibody comprising a cognate HC/LC pair from each of the starting antibodies. See FIGS. 2-4. As explained below with reference to a mixture containing two anti-HER2 antibodies that bind to different epitopes, this may be an advantageous situation for some mixtures.

In some embodiments where DNA encoding two different full-length antibodies having different HCs and LCs has been introduced into a host cell, the HCs of at least one of the two antibodies can comprise one or more alteration(s)

that disfavors the formation of HC/HC heterodimeric pairings. If essentially only homodimeric HC/HC pairs can form and essentially only cognate HC/LC pairs can form (due to HC- and/or LC-partner-directing alterations and/or the elimination of HC/LC disulfide bridges in at least one of the antibodies), this will lead to the formation of only two different major antibody species (called "MabPair" mixtures herein), the two starting full-length antibodies. See FIGS. 1 and 3. In the context of a pharmaceutical production process, this leads to the advantageous situation where a pharmaceutical product consisting essentially of two different antibodies can be produced in a single cell line using a single production process. Examples of alterations (including in some cases amino acids present in the original sequence) that disfavor the formation of heterodimers include, without limitation, the following: 409D/E plus 399R/K in one HC where the other HC has an arginine at position 409 (e.g., as in a human IgG4 antibody); 409D/E, 399R/K, plus 392D/L/Y/M/W/I/V/F in one HC where the other HC has an arginine at position 409; 392E/D plus 399R/K in one HC and 392K/R plus 399D/E other HC; 399K/R, 409D/E, plus 392D/E in one HC and 399D/E, 409K/R, plus 392K/R in the other HC; 399K/R, 409D/E, 356K/R, plus 392D/E in one HC and 399D/E, 409K/R, 356D/E, plus 392K/R in the other HC; 399K/R, 409D/E, 357K/R, plus 392D/E in one HC and 399D/E, 409K/R, 357D/E, plus 392K/R in the other HC; 399K/R, 409D/E, 356K/R, plus 438D/E in one HC and 399D/E, 409K/R, 356D/E, plus 438K/R in the other HC; 399K/R, 409D/E, 357K/R, plus 370D/E in one HC and 399D/E, 409K/R, 357D/E, plus 370K/R in the other HC; 399K/R, 409D/E, 356K/R, 392D/E, 357K/R, plus 370D/E in one HC and 399D/E, 409K/R, 356D/E, 392K/R, 357D/E, plus 370K/R in the other HC; 399K/R, 409D/E, 356K/R, 392D/E, 357K/R, plus 439D/E in one HC and 399D/E, 409K/R, 356D/E, 392K/R, 357D/E, plus 439K/R in the other HC; 366Y/W plus 407T/A in one HC and 366T/A plus 407Y/W in the other HC; 405A/T plus 394W/Y in one HC and 405W/Y plus 394A/T in the other HC; 407Y/W in one HC and 366Y/W in the other HC; 366Y/W, 407T/A, plus 405A/T, 394W/Y in one HC and 366T/A, 407Y/W, plus 405Y/W, plus 394A/T in the other; and 366W/Y, 368A/T, plus 407V/T/A in one HC and 366T/A/S, 368L, plus 407Y/W in the other HC.

In further embodiments, one or more alterations that affect the pharmacokinetic properties of one or more of the antibodies a mixture as described herein can be introduced. For example, the in vivo half life or the area under the curve (AUC) can be shortened by alterations such as M252A, M252L, M252S, M252R, R255K or H435R. Other alterations that affect pharmacokinetic properties of one or more antibody in an antibody mixture can be introduced.

Antibodies

Described herein are antibodies that comprise partner-directing alterations described herein. Such antibodies can be antibodies of any format that comprises VH, CH1, VL, and CL domains. In some embodiments, such antibodies can be full-length IgG antibodies that can be IgG1, IgG2, IgG3, or IgG4 antibodies, which can be mammalian antibodies, e.g., primate, human, and/or humanized antibodies. These include, for example, an antibody comprising, for example, a primate, human, and/or humanized CL and IgG1 CH1 domains that comprise one or more charge pairs (which can result from partner-directing alteration(s)) at one or more of the following pairs of sites in the HC and LC, respectively: 147 and 131; 168 and 174; and 181 and 178. Further embodiments include an antibody comprising, for example, primate, human, and/or humanized CL and IgG4 CH1 domains that comprise one or more charge pairs (which can result from partner-directing alteration(s)) at one or more of the following pairs of sites in the HC and LC, respectively: 147 and 131; 168 and 174; and 181 and 180. In further embodiments, described herein are an antibody comprising, for example, primate, human, and/or humanized CL and IgG1 CH1 domains, wherein the antibody comprises one or more pairs of cysteine residues at contacting sites in the CH1 and CL domains, wherein the CH1 and CL positions, respectively, of these cysteine residues can be at any one or more of the following pairs: 126 and 124; 128 and 118; 133 and 117; 134 and 116; 168 and 174; 170 and 162; 170 and 176; and 173 and 160. In still other embodiments, described herein are an antibody comprising, for example, primate, human, and/or humanized CL and IgG4 CH1 domains, wherein the antibody comprises one or more pairs of cysteine residues at contacting sites in the CH1 and CL domains, wherein the CH1 and CL positions, respectively, of these cysteine residues can be at any one or more of the following pairs of residues: 126 and 124; 127 and 121; 128 and 118; 168 and 174; 170 and 162; and 173 and 162;

In a further embodiment, described herein is an IgG2 antibody, optionally a human, primate, and/or humanized antibody, lacking the naturally occurring disulfide bridge linking the HC and LC and containing one or more substitutions in both the HC and the LC that can create one or more new disulfide bridge. For example, the cysteine at position 131 in a human, humanized, and/or primate IgG2 HC can be replaced with another amino acid, e.g., serine, alanine, or glycine, and the cysteine at position 214 in the cognate LC can be replaced with another amino acid, e.g., serine, alanine, or glycine. These substitutions would eliminate the naturally occurring disulfide bridge between an IgG2 HC and its cognate LC. A new disulfide bridge could be created by introducing a cysteine substitution at each residue of a pair of contacting residues, where one residue is in the IgG2 HC and other is in the LC. For example, the substitutions F170C in the HC and S162C in the LC are such a pair of cysteine substitutions at contacting residues, as are V173C in the HC and Q160C in the LC. Other cysteine substitutions at other pairs of contacting residues could also be used. This approach could avoid the formation of multiple IgG2 structural isomers due to disulfide bond shuffling, which has been observed in native human IgG2 antibodies. See, e.g., Lightle et al. (2010), Protein Science 19: 753-762. Formation of multiple structural isomers can be disadvantageous when manufacturing an antibody for use as a therapeutic since a homogeneous preparation is generally preferred.

Any of the antibodies described above can be made using standard methods in the art. For example, an antibody can be made by (1) introducing one or more DNAs encoding the antibody, optionally in one or more appropriate vectors, into host cells, (2) culturing the host cells under conditions conducive to expression of the antibody, and (3) obtaining the antibody from the cell supernatant or host cell mass.

Target Molecules Bound by the Antibodies and/or Mixtures of Antibodies

The different antibodies in the mixtures described herein bind to different epitopes and can bind to one or more target molecule. The target molecules, optionally proteins, for antibodies and/or antibody mixtures described herein can be chosen in light of knowledge of the role of various molecules in a disease state. In some embodiments, the disease is a human disease, and the target molecule(s) is (are) one or more human protein(s). Similarly, the antibodies described above can bind to one of these target molecules.

In one example, the target protein(s) for an antibody mixture can be one or more protein(s) that serve(s) as a checkpoint that inhibits or blocks the activity of the immune system. Since cancers and infections can be recognized by the immune system and the immune system may regulate and even eliminate tumors and infections, preventing regulation or blockage of immune system activity could potentially limit growth of cancer cells or eliminate infections, in some embodiments, viral infections. Checkpoint-blocking antibodies, such as those directed against cytotoxic T-lymphocyte antigen 4 (CTLA4) and programmed death 1 receptor (PD1), have demonstrated promise in the treatment of an expanding list of malignancies. While both CTLA4 and PD1 function as negative regulators, each plays a non-redundant role in modulating immune responses. CTLA4 attenuates the early activation of naïve and memory T cells, and PD1 is primarily involved in modulating T cell activity in peripheral tissues via interaction with its ligands, PD-L1 and PD-L2. A single antibody could also bind to any of these target proteins.

Accumulating clinical evidence points toward a promising role for checkpoint-blocking antibodies in a rapidly expanding spectrum of solid tumors, including non-small cell lung cancer, renal cell cancer, ovarian cancer, bladder cancer, head and neck cancer, and gastric cancer. While blocking either the CTLA4 or the PD1 pathway inhibits growth of multiple tumor types, the overall response rate is still low, underscoring the importance of improving upon present options. Combined checkpoint blockade, to date explored with anti-CTLA4 (ipilimumab) and anti-PD1 (nivolumab) pathway blocking agents, has shown better clinical efficacy than ipilimumab alone or nivolumab alone in patients with untreated melanoma. Larkin et al. (2015), New Eng. J. Med. 373: 23-34. In melanoma patients with programmed cell death 1 ligand (PD-L1; also known as PDCD1LG1, PDCD1L1, B7H1, and CD274)-positive tumors, progression-free survival using treatment with nivolumab alone was essentially the same as that observed using treatment with nivolumab plus ipilimumab and was higher than that observed using treatment with ipilimumab alone. Larkin et al., supra. In patients with PD-L1-negative tumors, combination therapy resulted in longer progression-free survival than was observed with nivolumab or ipilimumab alone. Larkin et al, supra. These data provide a strong rationale for anti-cancer therapeutics that include two or more antibodies that block two or more immune system checkpoint proteins. Similar studies using another anti-PD1 antibody, prembrolizumab, are currently ongoing. Such mixtures could be made using the methods described herein to make, for example, a MabPair mixture or a 3-in-1 antibody mixture.

In the context of making mixtures of different immune checkpoint-blocking antibodies, the isotype of the antibodies can be of importance because different isotypes can elicit different effector functions. Of the five immunoglobulin isotypes, immunoglobulin G (IgG) is most abundant in human serum. The four IgG subclasses, IgG1, IgG2, IgG3, and IgG4, differ in their constant regions, especially in their hinge and upper CH2 domains. These regions are involved in binding to IgG-Fc receptors (FcγR), which can initiate antibody-dependent cell-mediated cytotoxicity (ADCC) and/or phagocytosis (ADCP), and C1q, which can initiate complement dependent cytotoxicity (CDC). Hence, the different subclasses have different effector functions. IgG1 and IgG3 antibodies can elicit potent effector responses including ADCC, ADCP, and CDC, whereas IgG2 and IgG4 antibodies elicit much more subtle effector responses and only do so in certain cases. Antibody responses to soluble protein antigens and membrane proteins primarily induce production of IgG1 antibodies, accompanied by lower levels of other IgG subclasses, mostly IgG3 and IgG4. Ferrante et al. (1990), Pediatr. Infect. Dis. J. 9(8 Suppl):S16-24.

For therapeutic antibodies, IgG1 has been the most popular choice by far. Antibodies designed for selective eradication of cancer cells typically require an isotype that can elicit potent complement activation and effector-mediated cell killing by ADCC. Although IgG1 and IgG3 both meet these criteria, IgG3 has not been used for therapeutic antibody development, probably because of a shorter half-life, susceptibility of the relatively long hinge region to proteolysis, and extensive allotypic polymorphism.

Antibody isotype can be an important consideration for anti-CTLA4 antibodies used to treat cancer. Preclinical data suggests that a checkpoint-blocking anti-CTLA4 antibody might deliver much of its therapeutic effect through killing of T regulatory (Treg) cells within tumors, thus releasing CD8 T cell-mediated anti-tumor immunity. Simpson et al. (2013), J Exp Med. 210(9): 1695-1710. Similar mechanisms may operate in human patients. Ipilimumab, a human IgG1 anti-CTLA4 antibody, was recently shown to lead to ADCC-mediated lysis of human Tregs ex vivo. Romano et al. (2015), Proc. Natl. Acad. Sci. 112(19): 6140-6145. Further, in a small clinical study, melanoma patients responding to ipilimumab had significantly higher baseline frequencies of nonclassical monocytes and more activated tumor-associated macrophages expressing FcγRIII, which correlated with lower intratumoral Treg numbers after therapy, suggesting that Treg deletion occurs in these patients. Therefore, an IgG1 or IgG3 isotype may be favored for an anti-CTLA4 antibody used in the treatment of cancer since the antibody might have the greatest effect if it causes potent killing of the Treg cells within the tumor.

The IgG isotype of choice for anti-PD1 antibodies is typically IgG4 or a mutated IgG1 with minimal FcγR interactions. PD1 is expressed on the surface of activated T cells, B cells, and macrophages, and negatively regulates immune responses. Since PD1 is expressed on these effector cells, it may not be desirable to use an isotype that can elicit strong effector functions, i.e., IgG1 or IgG3, because this could result in killing activated T cells, which might otherwise kill cancer cells.

Hence, in making an anti-cancer therapeutic containing a mixture of an anti-CTLA4 and an anti-PD1 antibody, the inclusion of a bispecific anti-CTLA4 anti-PD1 antibody may be inappropriate because, as explained above, different effector functions are appropriate for each of the two binding domains. Moreover, the effects of bringing regulatory T cells and effector T cells into close physical proximity by means of an anti-PD1 and anti-CTLA4 bispecific antibody are unpredictable. A mixture consisting essentially of a monospecific IgG1 anti-CTLA4 antibody and a monospecific IgG4 (or modified IgG1) anti-PD1 antibody may be desirable. Such a MabPair mixture could be made in a single host cell as described herein using alterations to disfavor heterodimers and LC- and HC-partner-directing alterations described herein.

Moreover, other combinations of immune checkpoint proteins could serve as targets for MabPair mixtures or 3-in-1 mixtures of antibodies. In situations where different isotypes are appropriate for each binding domain (as in the case of CTLA4 and PD1), a MabPair mixture could be preferred so that each binding domain would be attached to the desired constant region in most or all cases. In cases where the same isotype is appropriate for both binding domains, either a MabPair mixture or a 3-in-1 mixture could be used.

In another example, the human epidermal growth factor receptor (HER) family of proteins, i.e., HER1, HER2, HER3, and HER4, plays an important role in cell survival and proliferation and has been implicated in oncogenesis. These proteins are capable of forming heterodimers and homodimers, which can activate signal transduction pathways that regulate many cellular processes, including growth, proliferation, and survival. Overexpression of HER2 is associated with aggressive disease and poor prognosis in human breast cancer patients. Treatment of such patients with anti-HER2 antibodies, such as HERCEPTIN® (the brand name for a humanized anti-HER2 antibody called trastuzumab), with or without lapatinib (a small molecule tyrosine kinase inhibitor), has improved survival. Trastuzumab binds domain IV of HER2 and inhibits HER2-mediated cell proliferation by activating antibody-dependent cellular cytotoxicity (ADCC), preventing formation of p95HER2 (a truncated and constitutively active form of HER2), blocking ligand-independent HER2 signaling, and inhibiting HER2-mediated angiogenesis.

A different humanized anti-HER2 antibody called pertuzumab binds to a different epitope (in domain II of HER2) than trastuzumab and inhibits HER2 dimerization with other HER family members such as HER3 and HER1, thus inhibiting the downstream signaling processes that are associated with tumor growth and progression. The combination of pertuzumab and trastuzumab has a strongly enhanced antitumor effect compared to either agent alone and induces tumor regression in xenograft models (Yamashita-Kashima (2011), *Clin. Cancer Res.* 17(15): 5060-5070; Scheuer et al. (2009), *Cancer Res* 69: 9330-9336), something that cannot be achieved by either monotherapy. The enhanced efficacy of the combination was also observed after tumor progression during anti-HER2 trastuzumab monotherapy. Binding of pertuzumab to tumors is not impaired by trastuzumab pretreatment. Furthermore, both trastuzumab and pertuzumab potently activate ADCC. The strongly enhanced antitumor activity is likely due to the differing and complementary mechanisms of action of trastuzumab and pertuzumab. Potentially, a bispecific antibody that could bind to both epitopes on one or more molecules of HER2 protein simultaneously might have different activity, possibly greater or lesser, than the two separate antibodies. In some cases, a bispecific antibody binding to two different epitopes on a single target protein might not be able to simultaneously bind to the two epitopes on a single target protein. Thus, there is reason to believe that treatment with two or more anti-HER2 antibodies that bind to different epitopes, optionally including a bispecific antibody, can be more effective than treatment with a single antibody.

Hence, the methods described herein could be used to make mixtures containing two or more different anti-HER2 antibodies. For example, a MabPair mixture or a 3-in-1 antibody mixture could be made. Such mixtures could be used to treat a subset of breast cancer patients, i.e., those with cancers that overexpress HER2, and possibly other cancer patients with HER2-mediated cancers.

Further, the methods described herein could be used to make mixtures of antibodies that bind to other cancer antigens, i.e., proteins that are overexpressed on cancer cells. In most of these cases, IgG1 and/or IgG3 isotype(s) would be desirable because killing of the cancer cells is a therapeutic objective. For example, the antibodies in the mixtures could bind to different epitopes on a single cancer antigen. Alternatively, the antibodies in the mixtures could bind to different cancer antigens if the cancer cells express multiple different cancer antigens. In either case, the mixtures could be, for example, MabPair or 3-in-1 mixtures, depending on the biological role of the target proteins.

Examples of pairs of target molecules for the antibody mixtures described herein include, without limitation, the following pairs of target proteins (shown as first target protein/second target protein), which can be human proteins: PD1/CTLA4, PD1/lymphocyte activation gene 3 (LAG3), PD1/glucocorticoid-induced tumor necrosis factor receptor-related gene (GITR; also known as AITR or TNFRSF18), PD1/vascular endothelial growth factor A (VEGF; also known as VEGFA), PD1/colony-stimulating factor 1 receptor (CSF1R; also known as FMS, c-FMS and CD115), PD1/OX40 (also known as TNFRSF4, ACT35, and CD134), PD1/T-cell immunoreceptor with immunoglobulin and ITIM domains (TIGIT), PDL1/CTLA4, PDL1/VEGF, PDL1/OX40, PDL1/CSF1R, PDL1/TIGIT, PDL1/T-cell immunoglobulin and mucin domains-containing protein 3 (TIM3, also known as HAVCR2), CTLA4/VEGF, CTLA4/41BB (also known as TNFRSF9, ILA, and CD137), membrane-spanning 4 domains, subfamily A, member 1 (CD20; also known as MS4A1 and B1)/leukocyte surface antigen CD37 (CD37), angiopoietin 2 (ANG2; also known as ANGPT2)/VEGF, tumor necrosis factor (TNF; also known as TNFA and cachetin)/interleukin 17a (IL17a; also known as CTLA8), CD38 antigen (CD38)/CD138 antigen (CD138; also known as SDC1 and SYND1), epidermal growth factor receptor (EGFR; also known as ERBB1, HER1, and SA7)/HER2, EGFR/HER3, MET protooncogene (MET; also known as HGFR)/VEGF, MET/EGFR, thymic stromal lymphopoietin (TSLP)/interleukin 33 (IL33; also known as C9ORF26, NFHEV, and IL1F11), interleukin 4 (IL4; also known as BSF1)/interleukin 13 (IL13), HER2/HER2, PD1/CD96, PD1/Protein-tyrosine phosphatase, nonreceptor type, substrate-1 (also known as SIRP-alpha-1, PTPNS1, SIRPA, SHPS1, MYD1, and MFR), and PD1/Chemokine, CC motif, receptor 8 (also known as CCR8, Chemokine, CC motif, receptor-like 2 (CMKBRL2), Chemokine receptor-like 1 (CKRL1), and CMKBR8). Single antibodies could also bind to any of these target molecules.

The examples of particular targets discussed above are exemplary. Antibodies and/or antibody mixtures that bind to any target or combination of these targets could be made using methods described herein.

Nucleic Acids and Vectors Encoding Antibodies and Mixtures of Antibodies

Provided are nucleic acids, e.g., DNA, encoding the antibodies and mixtures of antibodies described herein. Numerous nucleic acid sequences encoding immunoglobulin domains, for example VH, VL, hinge, CH1, CH2, and CH3 domains are known in the art. See, e.g., Kabat et al., supra. Using the guidance provided herein, one of skill in the art could combine known or novel nucleic acid sequences encoding antibodies and modify them by known methods to create nucleic acids encoding the antibodies and mixtures of antibodies described herein, which comprise alterations as described herein.

Methods of modifying nucleic acids are well-known in the art. Perhaps the most straightforward method for creating a modified nucleic acid is to synthesize a nucleic acid having the desired sequence. A number of companies, e.g., DNA 2.0 (Menlo Park, Calif., USA), BlueHeron (Bothell, Wash.), Genewiz (South Plainfield, N.J.), Gen9 (Cambridge, Mass.), and Integrated DNA Technologies (Coralville, Iowa; IDT), provide this service. Other known methods of introducing mutations, for example site-directed mutagenesis using polymerase chain reaction (PCR), can also be employed. See, e.g., Zoller (1991), Curr. Opin. Biotechnol. 2(4): 526-531; Reikofski and Tao (1992), Biotechnol. Adv. 10(4): 535-547. For example, Example 2 below describes the use of a commercial kit to introduce specific mutations into a starting DNA.

The DNA vector(s) that contain(s) the DNA encoding the HCs and LCs of the antibodies can be any vector(s) suitable for expression of the antibodies in a chosen host cell. The vector can include a selectable marker for selection of host cell cells containing the vector and/or for maintenance and/or amplification of the vector in the host cell. Such markers include, for example, (1) genes that confer resistance to antibiotics or other toxins, e.g., ampicillin, tetracycline, or kanamycin for prokaryotic host cells, (2) genes that complement auxotrophic deficiencies of the cell, or (3) genes whose operation supplies critical nutrients not available from complex or defined media. Specific selectable markers include the kanamycin resistance gene, the ampicillin resistance gene, and the tetracycline resistance gene. A neomycin resistance gene may also be used for selection in both prokaryotic and eukaryotic host cells. A dihydrofolate reductase (DHFR) gene and/or a promoterless thymidine kinase gene can be used in mammalian cells, as is known in the art.

In addition, a vector can contain various other sequence elements necessary for the maintenance of the vector and/or the expression of the inserted sequences encoding the antibodies and/or antibody mixtures described herein, e.g., the HCs and LCs of the antibody mixtures described herein. Such elements include, for example, an origin of replication, a promoter, one or more enhancers, a transcriptional terminator, a ribosome binding site, a polyadenylation site, and a polylinker insertion site for exogenous sequences (such as the DNA encoding the antibody mixtures described herein). These sequence elements can be chosen to function in the desired host cells so as to promote replication and/or amplification of the vector and expression of the heterologous sequences inserted into the vector. Such sequence elements are well known in the art and available in a large array of commercially available vectors. Many vectors are commercially available from companies including Promega Corporation (Madison, Wis., USA) and Agilent Technologies (Santa Clara, Calif., USA), among many others.

DNA encoding each of two or more antibodies can be introduced into a population of host cells using any appropriate method including, for example, transfection, transduction, transformation, bombardment with microprojectiles, microinjection, or electroporation. In some embodiments, DNA encoding two full-length IgG antibodies is introduced into the host cells. Such methods are known in the art and described in, e.g., Kaestner et al. (2015), Bioorg. Med. Chem. Lett. 25: 1171-1176, which is incorporated herein by reference.

In some embodiments, nucleic acids encoding an antibody or a mixture of antibodies can be carried on one or more viral vectors. Examples of such viral vectors include adenovirus, adeno-associated virus (AAV), retrovirus, vaccinia virus, modified vaccinia virus Ankara (MVA), herpes virus, lentivirus, or poxvirus vectors. In such embodiments, these viral vectors containing nucleic acids encoding the mixtures or antibodies can be administered to patients to treat a disease. In a cancer patient, such viral vectors containing nucleic acids encoding the mixture of antibodies can be administered directly to a tumor or a major site of cancer cells in the patient, for example by injection, inhalation (for a lung cancer), topical administration (for a skin cancer), and/or administration to a mucus membrane (through which the nucleic acids can be absorbed), among many possibilities.

Similarly, nucleic acids encoding a mixture of antibodies as described herein, which can be encased in liposomes, can be administered to a patient suffering from a disease.

Host Cells that can Produce Mixtures of Antibodies

The host cells into which DNA(s) encoding antibodies are introduced can be any of a variety of cells suitable for the expression of a recombinant protein. These include, for example, gram negative or gram positive prokaryotes, for example, bacteria such as Escherichia coli, Bacillus subtilis, or Salmonella typhimurium. In other embodiments, the host cells can be eukaryotic cells, including such species as Saccharomyces cerevisiae, Schizosaccharomyces pombe, or eukaryotes of the genus Kluyveromyces, Candida, Spodotera, or any cell capable of expressing heterologous polypeptides. In further embodiments, the host cells can be mammalian cells. Many mammalian cells suitable for expression of heterologous polypeptides are known in the art and can be obtained from a variety of vendors including, e.g., American Type Culture Collection (ATCC). Suitable mammalian cells include, for example, the COS-7 line (ATCC CRL 1651) (Gluzman et al., 1981, Cell 23:175), L cells, C127 cells, 3T3 cells (ATCC CCL 163), Chinese hamster ovary (CHO) cells, or their derivatives such as Veggie CHO and related cell lines which grow in serum-free media (Rasmussen et al., 1998, Cytotechnology 28: 31), HeLa cells, baby hamster kidney (BHK) cells (e.g., ATCC CRL 10), the CVI/EBNA cell line derived from the African green monkey kidney cell line CVI (ATCC CCL 70) as described by McMahan et al., 1991, EMBO J. 10: 2821, human embryonic kidney (HEK) cells such as 293, 293 EBNA or MSR 293, human epidermal A431 cells, human Colo205 cells, HL-60 cells, U937 cells, HaK cells, Jurkat cells, HepG2/3B cells, KB cells, NIH 3T3 cells, or S49 cells. Other mammalian cell types that are capable of expression of a heterologous polypeptide could also be used.

In some embodiments, an antibody mixture, e.g., a MabPair or 3-in-1 mixture, can be obtained from a population of host cells into which DNA encoding the antibody mixture has been introduced, for example, by transfection. In some embodiments, a single cell is isolated from the population of cells into which the DNA has been introduced. This cell is propagated to create a "host cell line," as defined herein, that can produce the antibody mixture.

Methods of Treatment

The antibodies and/or mixtures of antibodies described herein or nucleic acids encoding them can be used to treat a variety of diseases, optionally human diseases. As would be readily understood by one of skill in the art, the disease that a particular antibody or mixture of antibodies, or nucleic acids encoding the antibody or mixture, could be used to treat could be determined by a variety of factors including the identity of the target protein to which each antibody in the mixture binds, the particular epitope on each target protein bound by each antibody in the mixture, the relative amounts of each antibody in the mixture, the isotype of each antibody, and the in vivo half life of each antibody in the mixture, among other possible factors. The target proteins bound by the antibody or the antibodies in a mixture as described herein may play a direct or indirect role in driving the course of a disease being treated. For example, a target protein may be part of a biological pathway that drives a disease or be a protein that serves as an immune checkpoint, and/or a target protein may serve as a means to target disease cells for destruction by the immune system. Other scenarios are also possible.

In a general sense, the mixtures of antibodies, or nucleic acids encoding them, described herein can be used to treat diseases driven by multiple biological pathways, diseases driven by a molecule that has multiple mechanisms of action (e.g., HER2 in breast cancer), or diseases driven by multiple molecules that feed into a single biological pathway, among other possibilities. These diseases include, without limitation, cancers, metabolic diseases, infectious diseases, and autoimmune or inflammatory diseases, among many possibilities.

The antibodies, mixtures of antibodies, or nucleic acids encoding them described herein can, for example, be used to treat a cancer. In such a case, the antibody or the mixture of antibodies can be administered to a cancer patient, optionally directly to a tumor. As is known in the art, different cancers are different and require different treatments. Thus, different antibodies or mixtures of antibodies may be suitable for different cancers. Cancers that can be treated with the mixtures of antibodies described herein include, for example, hematolytic cancers, solid tumors including carcinomas and sarcomas, breast cancer, skin cancers including melanoma, lung cancers, pancreatic cancer, prostate cancer, cancer of the head and neck, thyroid cancer, brain cancer, among many others.

The antibodies, the mixtures of antibodies, or the nucleic acids encoding them can be formulated, for example, as a liquid, a paste or a cream, or a solid. Oral administration is possible. The antibody, antibody mixture, or nucleic acids can be administered via parenteral injection. For example, an injection of the antibody mixtures or nucleic acids can be subcutaneous, intravenous, intra-arterial, intralesional (including into a tumor or other major site of a cancer), peritoneal, or intramuscular. Topical administration, e.g., of a liquid, paste, or cream, is possible, especially for diseases of the skin. Administration through contact with a mucus membrane, such as by intra-nasal, sublingual, vaginal, or rectal administration, is also possible. Alternatively, an antibody, antibody mixture, or nucleic acid(s) encoding an antibody or antibody mixture can be administered as an inhalant.

In some embodiments, the nucleic acids encoding the antibody or the mixture of antibodies can be carried on one or more viral vectors. In such embodiments, these viral vectors containing nucleic acids encoding the antibody or the mixture of antibodies can be administered to patients to treat a disease, e.g., by oral administration or by injection (including, for example, subcutaneous, intramuscular, intravenous, intra-tumoral or peritoneal injection), inhalation, topical administration, and/or by administration to a mucus membrane (through which the nucleic acids can be absorbed), among many possibilities. In a cancer patient, such viral vectors containing nucleic acids encoding the antibody or the mixture of antibodies can be administered directly to a tumor or a major site of cancer cells in the patient, for example by injection, inhalation (for a lung cancer), topical administration (for a skin cancer), and/or administration to a mucus membrane (through which the nucleic acids can be absorbed), among many possibilities. The viral vector(s) can be, for example, adenovirus, adeno-associated virus (AAV), retrovirus, vaccinia virus, modified vaccinia virus Ankara (MVA), herpes virus, lentivirus, or a poxvirus vector(s).

Dosing and frequency of dosing of the antibody, the mixture of antibodies, or the nucleic acids encoding them can be adjusted by one skilled in the art according to the condition being treated, the concentration of the antibodies or nucleic acids, the binding properties (such as affinity and avidity) of the antibodies, the in vivo abundance and accessibility of the target molecules to which the antibodies bind, and the in vivo half lives of the antibodies, among many other possible considerations. The dose of the antibody or mixture of antibodies administered to a patient can be, for example, from about 0.0036 milligrams (mg) to about 450 mg, from about 0.000051 mg/kg to about 6.4 mg/kg, or from about 0.002 $mg/mm^2$ to about 250 $mg/mm^2$. Similarly, dosing of nucleic acids, e.g., DNA, encoding the antibody or antibody mixture can be, for example, from about $10^9$ to about $10^{13}$ copies of the DNA(s) encoding the antibody or antibody per kilogram of patient weight. Dosing can occur every day, every other day, twice per week, once per week, every other week, once every 3, 4, 5, 6, 7, 8, 9, 10, 11, or 12 weeks, 4 times per year, twice per year, once every nine months, or once per year, among other possible schedules.

Having described the invention in general terms above, the specific Examples described below are offered to exemplify, not limit, the scope of the invention. It is understood that various changes and modifications may be made to the invention that are in keeping with the spirit of the invention described herein and would be apparent to one of skill in the art. Such changes and modifications are within the scope of the invention described herein, including in the appended claims.

EXAMPLES

Example 1: Designing HC- and LC-Partner-Directing Alterations

Preventing non-cognate HC/LC pairing would greatly limit the number of species of antibodies produced by a host cell transfected with DNAs encoding multiple full-length antibodies. See, e.g., FIG. 4. To ensure that only cognate LC/HC pairs form, it is critical to find an effective way to control the kinetics of the HC/LC assembly process so that each LC strongly favors pairing with its cognate HC but disfavors the non-cognate HC. Since both VH/VL and CH1/CL interfaces are involved in HC/LC recognition and engagement (see Knarr et al. (1995), J. Biol. Chem. 270: 27589-27594; Feige et al. (2009), Mol. Cell 34: 569-579; Reiter et al. (1996), Nat. Biotechnol. 14: 1239-1245; Potapov et al. (2004), J. Mol. Biol. 342: 665-679; Rothlisberger et al. (2005), J. Mol. Biol. 347: 773-789, all of which are incorporated herein by reference in their entirety), both interfaces were engineered to force cognate HC/LC pairing as explained in detail below.

Existing X-ray crystal structures were used to identify residues on the VH/VL and CH1/CL interfaces for modification. Co-crystal structures of two humanized IgG1 anti-HER2 Fab fragments complexed with HER2 have been reported, that is, the structure of the trastuzumab Fab fragment, (available at imgt.org/3Dstructure-DB/ by searching with the Protein Data Bank accession number 1N8Z; see also Cho et al. (2003), Nature 421(6924): 756-760, which is incorporated herein by reference) and the structure of the pertuzumab Fab fragment, (available at imgt.org/3Dstructure-DB/ by searching with the Protein Data Bank accession number 1S78; see also Franklin et al. (2004), Cancer Cell 5(4): 317-328, which is incorporated herein by reference). The crystal structure of a human IgG4 Fab has also been reported (available at imgt.org/3Dstructure-DB/ by searching with the Protein Data Bank accession number 1BBJ; see also Brady et al. (1992), J. Mol. Biol., 227(1): 253-264, which is incorporated herein by reference).

For the purpose of selecting residues involved in the HC/LC interaction that would be suitable to test as sites for substitution with charged amino acids, physical contact as determined by a distance limit criterion and solvent accessible surface area were considered. Using the physical contact method, interface residues for substitution with charged amino acids were defined as residues whose side chain heavy atoms, i.e., atoms other than hydrogen, are positioned closer than a specified limit (5 Å) from side chain heavy atoms of any residue in the second chain. In some cases, this could mean that the α-carbon atoms (Cα) of the two amino acids, i.e., the carbon in the position adjacent to the carboxyl group of the amino acid, could be as far as about 12 Å away from each other. Such distances were determined using Molecular Operating Environment (MOE) software, obtained from Chemical Computing Group Inc. (1010 Sherbooke St. West, Suite #910, Montreal, QC, Canada, H3A 2R7). The second method involves calculating solvent accessible surface area (ASA) of the residues in the presence and absence of the second chain. See, e.g., Liu et al. (2015), J. Biol. Chem. 290(12): 7535-7562, the relevant portions of which are incorporated herein by reference. The residues that show difference >1 Å$^2$ in ASA between the two calculations were identified as interface residues. Both the methods identified similar set of interface residues. The following additional criteria were further applied to select VH/VL interface residue pairs for mutagenesis: (1) they are not in CDRs and do not make contact with any CDR residues, (2) they are highly conserved among IgG antibody subtypes, and (3) they are mostly solvent inaccessible (i.e., buried or partially buried).

In variable domains, G44 and Q105 in the VH domain are spatially close to Q100 and A43 in the VL domain, respectively, regardless of the germline sequences from which a particular variable domain is derived. Moreover, these are solvent inaccessible, spatially conserved residues, i.e., residues whose spatial location within the tertiary structure of the antibody is conserved among different antibodies. Hence these sites were chosen for making substitutions to create charge-charge interactions between VH and VL. We refer to such substitutions herein as "charge pair" alterations or substitutions.

The residues at the CH1/CL interface of an IgG1 or IgG4 Fab fragment that are close enough, i.e., less than about 12 Å between Cα atoms and about 5 Å between side chain heavy atoms, to be appropriate for charge pair substitutions are summarized in Tables 13 and 14 below. Contacting residues are shown in the same row, along with the distance between the α-carbons of the residues.

TABLE 13

Contacting residues at IgG1 CH1/CLκ interface

| CH1 | | | Cα-Cα distance | CLκ | | |
|---|---|---|---|---|---|---|
| Residue | Location* | EU #@ | (Å) | EU #@ | Location* | Residue |
| K | B-strand | 147 | 9.74 | 124 | A-strand | Q |
| K | B-strand | 147 | 10.55 | 129 | B-strand | T |
| K | B-strand | 147 | 9.28 | 131 | B-strand | W |
| K | B-strand | 147 | 10.71 | 180 | E-strand | T |
| H | D-strand | 168 | 7.33 | 164 | D-strand | T |
| H | D-strand | 168 | 9.49 | 167 | DE-turn | D |
| H | D-strand | 168 | 7.41 | 174 | DE-turn | S |
| T | D-strand | 169 | 7.54 | 164 | D-strand | T |
| Q | DE-turn | 175 | 8.29 | 160 | D-strand | Q |
| Q | DE-turn | 175 | 9.79 | 180 | E-strand | T |
| S | DE-turn | 176 | 10.41 | 160 | D-strand | Q |
| S | DE-turn | 181 | 9.71 | 178 | E-strand | T |
| S | E-strand | 183 | 7.87 | 176 | E-strand | S |
| T | E-strand | 187 | 10.84 | 116 | A-strand | F |
| T | E-strand | 187 | 8.88 | 137 | B-strand | N |

*The locations of the various strands and turns in an immunoglobulin structure are known in the art and illustrated in, e.g., Wang (2013), Protein Cell. 4(8): 569-572, the relevant portions of which are incorporated herein by reference.
@Numbering is according to Edelman et al., supra, as illustrated in Table 6 (CH1) and Table 10 (CL).

TABLE 14

Contacting residues at IgG4 CH1/CLκ interface

| CH1 | | | Cα-Cα distance | CLκ | | |
|---|---|---|---|---|---|---|
| Residue | Location* | EU #@ | (Å) | EU #@ | Location* | Residue |
| R | A-strand | 133 | 11.51 | 117 | A-strand | I |
| E | B-strand | 137 | 8.30 | 114 | A-strand | S |
| E | B-strand | 137 | 9.94 | 116 | A-strand | F |
| K | B-strand | 147 | 9.65 | 124 | A-strand | Q |
| K | B-strand | 147 | 10.83 | 129 | B-strand | T |
| K | B-strand | 147 | 9.44 | 131 | B-strand | S |
| K | B-strand | 147 | 10.96 | 178 | E-strand | T |
| K | B-strand | 147 | 11.39 | 180 | E-strand | T |
| H | D-strand | 168 | 7.37 | 164 | D-strand | T |
| H | D-strand | 168 | 9.52 | 167 | DE-turn | D |
| H | D-strand | 168 | 9.71 | 173 | DE-turn | Y |
| H | D-strand | 168 | 7.66 | 174 | DE-turn | S |
| F | D-strand | 170 | 7.41 | 176 | E-strand | S |
| V | D-strand | 173 | 7.68 | 160 | D-strand | Q |
| V | D-strand | 173 | 6.66 | 162 | D-strand | S |
| Q | DE-turn | 175 | 8.16 | 160 | D-strand | Q |
| Q | DE-turn | 175 | 9.61 | 180 | E-strand | T |
| S | DE-turn | 181 | 9.32 | 180 | E-strand | T |
| S | E-strand | 183 | 7.61 | 176 | E-strand | S |

*The locations of the various strands and turns in an immunoglobulin structure are illustrated in, e.g., Wang (2013), Protein Cell. 4(8): 569-572.
@Numbering is according to Edelman et al., supra, as illustrated in Table 6 (CH1) and Table 10 (CL).

Due to the presence of the CH1 domain, HCs are retained in the endoplasmic reticulum (ER) by immunoglobulin heavy chain binding protein (BiP, also known as GRP78 and HSPA5) until they are engaged by LCs for the assembly of a full-length IgG. BiP generally recognizes and binds to hydrophobic residues and, to lesser extent, to hydrophilic and charged residues. Knarr et al. (1995), *J Biol Chem* 270: 27589-27594. Hence, destabilization of HC/LC interactions could cause an antibody to be retained in the ER, thus reducing secretion of the antibody into culture medium.

Examination of the VH/VL and CH1/CL interface tertiary structures revealed that hydrogen bonds and van der Waals interactions are important parts of these interfaces. Unlike the CH3/CH3 interface, electrostatic charge-charge residue interactions are rare between the LC and HC. For example, a CLκ/CH1 interface has one and a CLλ/CH1 interface has two positive-negative charge interactions involving E/D and K residues. All of these existing charge pair interactions involve partially or fully solvent exposed positions, a situation that weakens an electrostatic interaction due to interference of solvent molecules.

To utilize an electrostatic steering effect to drive cognate HC/LC pairing, we hypothesized that it may be important to keep the VH/VL and CH1/CL interfaces stable and that residue substitutions could destabilize these structures, thereby decreasing antibody expression. Therefore, we preferentially used at least one conserved, naturally occurring charged residue (for example, K147 and H168 in the CH1 domain of both IgG1 and IgG4) for exploration. We hypothesized that changing a conserved charged residue in the CH1 domain to a residue having the opposite charge might cause little or no disruption of the CH1/CL interface.

Our analysis of the tertiary structures described above indicated that K147 in the CH1 domains of both IgG1 and IgG4 contacts Q124, T129, S131, and T180 in a CLκ domain and H168 in a CH1 domain of both IgG1 and IgG4 contacts T164, D167, and S174 in a CLκ domain. We hypothesized that an oppositely charged pair of amino acids interacting across a CL/CH1 interface might have maximum electrostatic steering effect if one of the oppositely charged residues is located on the inner β-sheet of the CL and/or CH1 domain, which includes Strand-B, Strand D, and Strand E. Examples of such residues include S131, T180, T164, and S174 on the inner β-sheet of a CLκ domain. We focused on (1) substitutions at S131 and/or T180 in a CLκ domain that would promote an electrostatic interaction with the residue at position 147 in a CH1 domain (which may or may not have a substitution), (2) substitutions at T164 and/or S174 in a CLκ domain that would promote an electrostatic interaction with the residue at 168 in a CH1 domain (which may or may not have a substitution).

Example 2: Designing and Testing Added Disulfide Bridges in the HC/LC Interface

We hypothesized that alterations that create additional HC/LC interchain disulfide bridges might strengthen the association of cognate HC/LC pairs. In unmodified antibodies, interchain disulfide bonds are solvent exposed while intrachain disulfide bonds are buried between the two layers of anti-parallel β-sheet structures within each domain, i.e., not solvent exposed. For example, the interchain disulfide bonds in the hinge region are solvent exposed, as is the disulfide bond between the HC and the LC. Solvent exposed cysteine residues are considered more reactive than non-exposed cysteine residues. Hence, in making cysteine substitutions, we tried to create disulfide bridges that were partially or fully solvent exposed.

Introduced disulfide bridges have been shown to stabilize Fv fragments by stabilizing VH/VL interactions, leading to higher production and solubility of the resulting Fv fragments. Reiter et al. (1996), Nature Biotechnol. 14(10): 1239-1245. The altered residues for these cysteine substitutions were well-conserved amino acids in framework regions, specifically VH residues G44 and Q105 and the contacting VL residues Q100 and A43, respectively.

We have tried a similar approach in the CH1 and CL domains. Our analysis of the tertiary structure described in Example 1 indicates that the following residue pairs located at the CH1/CL interface of human IgG1 or IgG4 HC with a κLC are close enough to potentially form a disulfide bond if substituted with cysteine.

TABLE 15

IgG1 CH1/CLκ interface residues suitable for cysteine substitution

| IgG1 CH1 | | | Cα-Cα distance | CLκ | | |
|---|---|---|---|---|---|---|
| EU #@ | Location* | Residue | (Å) | Residue | Location* | EU #@ |
| 126 | A-strand | F | 6.41 | S | A-strand | 121 |
| 126 | A-strand | F | 6.41 | Q | A-strand | 124 |
| 128 | A-strand | L | 6.03 | F | A-strand | 118 |
| 133 | A-strand | K | 5.52 | I | A-strand | 117 |
| 133 | A-strand | K | 7.09 | F | G-strand | 209 |
| 134 | A-strand | S | 4.62 | F | A-strand | 116 |
| 141 | B-strand | A | 7.49 | F | A-strand | 116 |
| 168 | D-strand | H | 7.40 | S | DE-turn | 174 |
| 170 | D-strand | F | 6.11 | S | D-strand | 162 |
| 170 | D-strand | F | 7.42 | S | E-strand | 176 |
| 173 | D-strand | V | 7.39 | Q | D-strand | 160 |
| 183 | E-strand | S | 7.66 | S | E-strand | 176 |

*The locations of the various strands and turns in an immunoglobulin structure are illustrated in, e.g., Wang (2013), Protein Cell. 4(8): 569-572.
@Numbering is according to Edelman et al., supra, as illustrated in Table 6 (CH1) and Table 10 (CL).

TABLE 16

IgG4 CH1/CLκ interface residues suitable for cysteine substitution

| IgG4 CH1 | | | Cα-Cα distance | CLk | | |
|---|---|---|---|---|---|---|
| EU #@ | Location* | Residue | (Å) | Residue | Location* | EU #@ |
| 126 | A-strand | F | 6.76 | S | A-strand | 121 |
| 126 | A-strand | F | 6.47 | Q | A-strand | 124 |
| 127 | A-strand | P | 6.36 | S | A-strand | 121 |
| 128 | A-strand | L | 6.00 | F | A-strand | 118 |
| 141 | B-strand | A | 7.31 | F | A-strand | 116 |
| 168 | D-strand | H | 7.66 | S | DE-turn | 174 |
| 170 | D-strand | F | 6.32 | S | D-strand | 162 |
| 173 | D-strand | V | 6.80 | S | D-strand | 162 |

*The locations of the various strands and turns in an immunoglobulin structure are illustrated in, e.g., Wang (2013), Protein Cell. 4(8): 569-572.
@Numbering is according to Edelman et al., supra, as illustrated in Table 6 (CH1) and Table 10 (CL).

To determine whether antibodies having cysteine substitutions in their HCs and LCs at one or more pairs of sites set forth in Table 15 and 16 and lacking the disulfide bridge normally present between an HC and LC would form HC/LC pairs sufficiently stable for escape from the ER, DNA constructs encoding such antibodies were made as follows. A DNA fragment encoding a signal peptide (SP) followed by VH and CH1 domains from an anti-CTLA4 antibody 1E1 (the "1E1 antibody") was synthesized by Integrated DNA Technologies (IDT), Inc. (Iowa, USA). The amino acid sequence of the VH and CH1 domains of the 1E1 antibody are shown in amino acids 1-216 of SEQ ID NO:38. It was fused by Gibson reaction (see, e.g., Gibson Assembly® Master Mix Instruction Manual, New England Biolabs Inc. (NEB), Version 3.3, NEB catalog no. #E2611S/L, NEB Inc. Ipswich, Mass., USA) with a downstream DNA fragment encoding the hinge, CH2, and CH3 domains of a human IgG1 antibody in a mammalian expression vector. The CH3 domain included the substitutions D399K and K409E, which are discussed in more detail in Example 4.

A second DNA fragment encoding an SP followed by VL and CL domains from the 1E1 antibody was synthesized by IDT, Inc. and fused by Gibson reaction with a mammalian expression vector. The amino acid sequence of the VL and CL domains of the 1E1 antibody are shown in amino acids 1-214 of SEQ ID NO:40. The reaction mixture was transformed into competent E. coli XL1 Blue by electroporation and plated out onto the LB-agar plates containing antibiotic carbernicillin. Resulting colonies were picked and cultured, and plasmid DNA was isolated. The plasmid insert sequence was confirmed by DNA sequencing.

Mutations encoding amino acid substitutions were introduced into these DNA constructs by mutagenesis reactions with QuikChange Lightning multi site-directed mutagenesis kit (Agilent Technologies, cat no. 210516). In the DNA encoding the HC, mutations encoding a C220S alteration (which is replacement of the cysteine at position 221 in SEQ ID NO:38 with serine, since the EU numbering system is used herein to describe constant domain alterations) were made. Mutations encoding a C214S alteration (which is replacement of the cysteine at position 214 in SEQ ID NO:40 with serine) were made in the DNA encoding the LC. Together, these alterations completely eliminate the naturally occurring interchain disulfide bridge between the cysteine residues normally present at these positions. Further, DNA encoding the HC was mutated to encode the alteration F126C, L128C, S134C, H168C, K133C, F170C, V173C, or S183C. Positions 126, 128, 134, 168, 133, 170, 173, and 183 according to the EU numbering scheme are equivalent to positions 127, 129, 135, 169, 134, 171, 174, and 184 in SEQ ID NO:38, respectively. Similarly, DNA encoding the LC was mutated to encode the alteration F116C, I117C, F118C, Q124C, Q160C, S162C, S174C, S176C, or F209C. Positions 116, 117, 118, 124, 160, 162, 174, 176, and 209 according to the EU numbering are equivalent to these same positions in SEQ ID NO:40

A second set of DNA constructs encoding altered versions of an anti-PD1 antibody was also made in a similar manner. A DNA fragment encoding an SP followed by a VH domain and an IgG4 CH1 domain from the anti-PD1 102 antibody were synthesized by IDT, Inc. and fused by Gibson reaction with a downstream DNA fragment encoding the hinge, CH2, and CH3 domains of a human IgG4 antibody in a mammalian expression vector. SEQ ID NO:23 provides the amino acid sequence of the HC of the anti-PD1 antibody 16137, which differs from that of the anti-PD1 102 antibody HC only in the CDRs and at three additional amino acids in the framework regions of the VH domain. Like the anti-PD1 102 antibody HC, the anti-PD1 antibody 16137 HC has a proline at position 228 (using EU numbering) to prevent Fab arm exchange (Silva et al. (2015), J. Biol. Chem. 290(9): 5462-5469, which is incorporated herein by reference)). A second DNA fragment encoding an SP followed by VL and CL domains from the anti-PD1 102 antibody was synthesized by IDT, Inc. and fused by Gibson reaction with a mammalian expression vector. SEQ ID NO:24 provides the amino acid sequence of the LC of the anti-PD1 antibody 16137, which differs from that of the anti-PD1 102 antibody LC only in the CDRs and at five additional amino acids in the framework regions of the VL domain. The reaction mixture was transformed into competent E. coli XL1 Blue by electroporation and plated out onto the LB-agar plates containing antibiotic carbernicillin. The resulting colonies were picked and cultured, and the insert sequence of the isolated plasmid DNA was confirmed by DNA sequencing.

Amino acid substitutions were introduced into the anti-PD1 antibody using a QuikChange Lightning multi site-directed mutagenesis kit (Agilent Technologies, cat no. 210516). To eliminate the disulfide bridge between C131 (HC) and C214 (LC), mutations in the HC and LC DNA constructs encoding antibodies with the alterations C131S (HC) and C214S (LC) were made. Further, DNA constructs encoding antibodies with the HC alteration F126C, P127C, L128C, H168C, F170C, V173C, or S183C and the LC alteration F118C, S121C, Q124C, S162C, S174C, or S176C were made. High quality plasmid DNAs (0D260/280=1.90-2.00) were prepared by using Qiagen Midi-prep kit. The plasmid DNAs were diluted in water and mixed in EPPENDORF TUBES®.

All of the altered antibodies described immediately above were missing the disulfide bridge normally present between C131 (IgG4 HC) or C220 (IgG1 HC) and C214 (LC) but have an additional pair of cysteine residues in the HC and LC that could potentially form a disulfide bridge. Two DNAs encoding an HC/LC pair were combined to transfect EXPI293™ cells (ThermoFisher Scientific Inc., Waltham, Mass., USA), and the antibodies secreted by the transfectants into the culture medium were visualized by Western blotting. If the transfectants produced full-length antibody of about 150 kilodaltons (kDa) in size, disulfide bridge formation was judged to be successful.

In more detail, the EXPI293™ cells were transfected with the plasmid DNAs encoding the test antibody with LIPOFECTAMINE® 2000 in 24-well deep well blocks. Cells were continuously shaken at 150 revolutions per minute (rpm) at 37° C. for 4 days. The supernatants were harvested by spinning down cells at 1500 rpm for 20 minutes. For non-reduced samples, 5 microliters (μl) of supernatant and 5 μl of 2× Laemmli Sample Buffer (65.8 mM Tris-HC1, pH 6.8, 2.1% sodium lauryl sulfate (SDS), 26.3% (w/v) glycerol, 0.01% bromophenol blue) were heated at 70° C. for 10 minutes. For the reduced samples, 5 μl of supernatant and 5 μl of 2× Laemmli Sample Buffer in the presence of 100 mM dithiothreitol (DTT) were heated at 70° C. for 10 minutes. In the Western blots shown in FIGS. 5 and 6, all samples were non-reduced. The treated samples were loaded into the wells of 4-15% CRITERION™ TGX STAIN-FREE™ Precast SDS-PAGE gels (Bio-Rad Laboratories, Inc., Hercules, Calif., cat no. 567-8085). Electrophoresis was run for 45 minutes at 200 V. The proteins were transferred onto a nitrocellulose membrane with TRANS-BLOT® TURBO™ Transfer System (Bio-Rad Laboratories, Inc.) and blocked in 3% non-fat milk in 1× phosphate buffered saline with 0.05% TWEEN® 20 (PBST). The nitrocellulose membrane was washed, and the antibodies were detected with HRP-conjugated polyclonal goat-anti-human IgG (Fc-specific) (Sigma-Aldrich Corporation, St. Louis, Mo., cat. no. A0170). The image was visualized with a CHEMIDOC™ XRS+ imager from Bio-Rad Laboratories, Inc.

Figure 5:
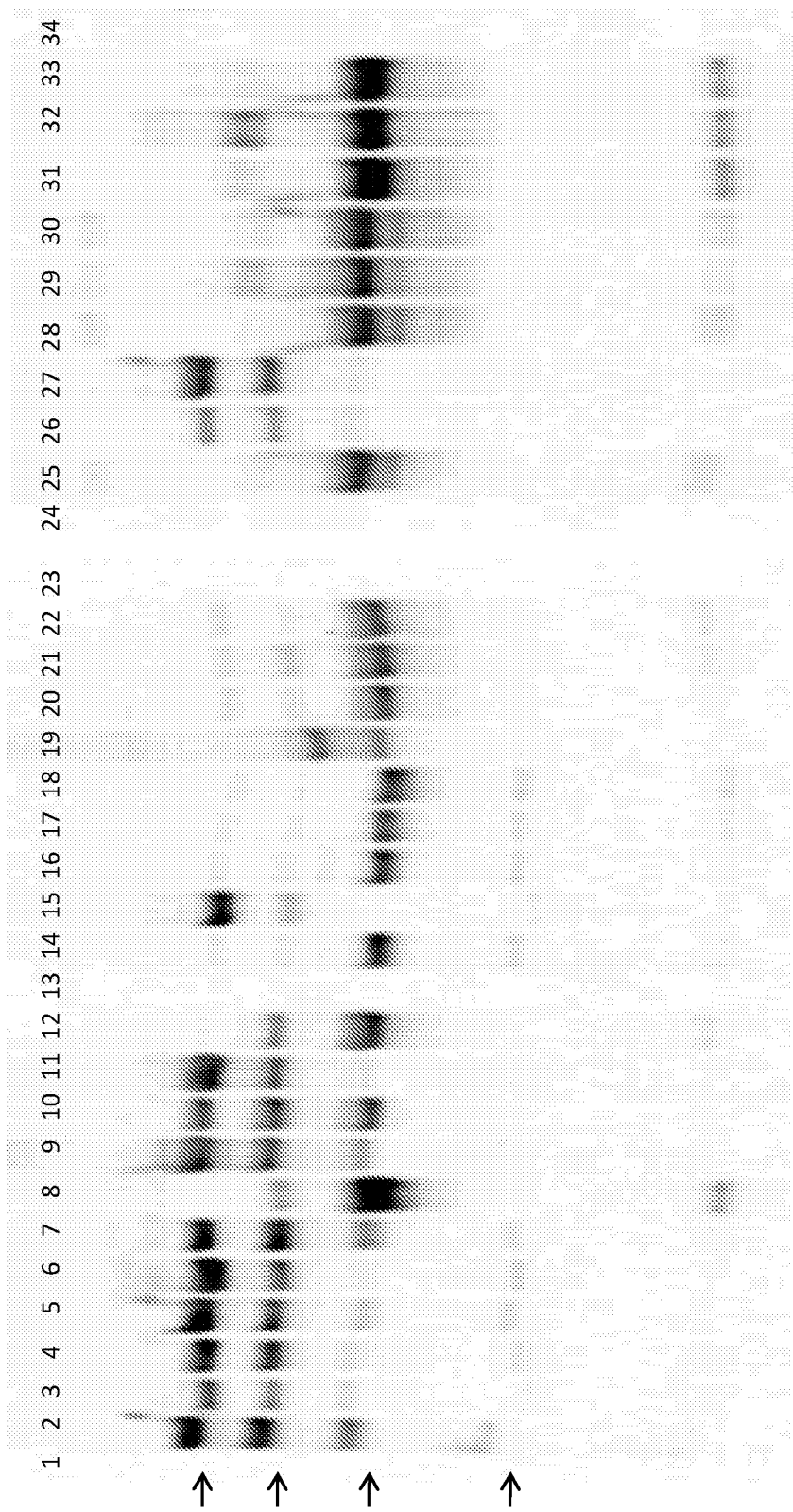
FIG. 5: Analysis of antibody species formed in the presence of cysteine substitutions at contacting residues in the HC and the LC. Experiments are described in Example 2. Briefly, DNAs encoding an HC with or without alterations and a kappa LC (kLC) with or without alterations were introduced into a host cell, and the antibodies produced by the host cell were analyzed by Western blotting. The designation "aCTLA4(IgG1)KE" used below refers to the HC of an IgG1 anti-CTLA4 antibody with the alterations C220S (which eliminates the naturally occurring HC/LC disulfide bridge), D399K, and K409E. The designation "aPD1 (IgG4)" used below refers to the HC of an IgG4 anti-PD1 antibody that comprises the alterations C131S (which eliminates the naturally occurring HC/LC disulfide bridge) and S228P (which prevents IgG4 Fab arm exchange). The designations "aCTLA4-kLC" and "aPD1-kLC" used below refer to the cognate light chains of these antibodies, and both comprise the alteration C214S (which eliminates the naturally occurring HC/LC disulfide bridge). Other alterations, e.g., (H168C), in these polypeptides or no further alterations (WT) are indicated in parenthesis following this description of the polypeptide. Lanes 1, 13, 23, 24, and 34 contain size markers that are not visible in this image. Other lanes contain samples from transfectants containing DNAs encoding the following: lane 2, aCTLA4(IgG1)KE(H168C) and aCTLA4-kLC(S174C); lane 3, aCTLA4(IgG1)KE(K133C) and aCTLA4-kLC(I117C); lane 4, aCTLA4(IgG1)KE (K133C) and aCTLA4-kLC(F209C); lane 5, aCTLA4 (IgG1)KE(V173C) and aCTLA4-kLC(Q160C); lane 6, aCTLA4(IgG1)KE(F170C) and aCTLA4-kLC(S162C); lane 7, aCTLA4(IgG1)KE(F170C) and aCTLA4-kLC (S176C); lane 8, aCTLA4(IgG1)KE(S183C) and aCTLA4-kLC(S176C); lane 9, aPD1(IgG4)(H168C) and aPD1-kLC (S174C); lane 10, aPD1(IgG4)(V173C) and aPD1-kLC (S162C); lane 11, aPD1(IgG4)(F170C) and aPD1-kLC (S162C); lane 12, aPD1(IgG4)(S183C) and aPD1-kLC (S176C); lane 14, aCTLA4(IgG1)KE(H168C) and aPD1-kLC(WT); lane 15, aCTLA4(IgG1)KE(K133C) and aPD1-kLC(WT); lane 16, aCTLA4(IgG1)KE(V173C) and aPD1-kLC(WT); lane 17, aCTLA4(IgG1)KE(F170C) and aPD1-kLC(WT); lane 18, aCTLA4(IgG1)KE(S183C) and aPD1-kLC(WT); lane 19, aPD1(IgG4)(H168C) and aCTLA4-kLC (WT); lane 20, aPD1(IgG4)(V173C) and aCTLA4-kLC (WT); lane 21, aPD1(IgG4)(F170C) and aCTLA4-kLC (WT); lane 22, aPD1(IgG4)(S183C) and aCTLA4-kLC (WT); lane 25, aPD1(IgG4)(WT) and aCTLA4-kLC (S174C); lane 26, aPD1(IgG4)(WT) and aCTLA4-kLC (I117C); lane 27, aPD1(IgG4)(WT) and aCTLA4-kLC (F209C); lane 28, aPD1(IgG4)(WT) and aCTLA4-kLC (Q160C); lane 29 aPD1(IgG4)(WT) and aCTLA4-kLC (S162C); lane 30, aPD1(IgG4)(WT) and aCTLA4-kLC (S176C); lane 31, aCTLA4(IgG1)KE(WT) and aPD1-kLC (S174C); lane 32, aCTLA4(IgG1)KE(WT) and aPD1-kLC (S162C); and lane 33 aCTLA4(IgG1)KE(WT) and aPD1-kLC(S176C). Arrows at left point to various bands as follows: top arrow, HC-LC/HC-LC, full-length antibody; second arrow, HC/HC-LC, a three quarters antibody containing two HCs and one LC; third arrow, HC/HC, an antibody species containing only two HCs; and bottom arrow, HC-LC, a half antibody containing one HC and one LC.
Figure 6:
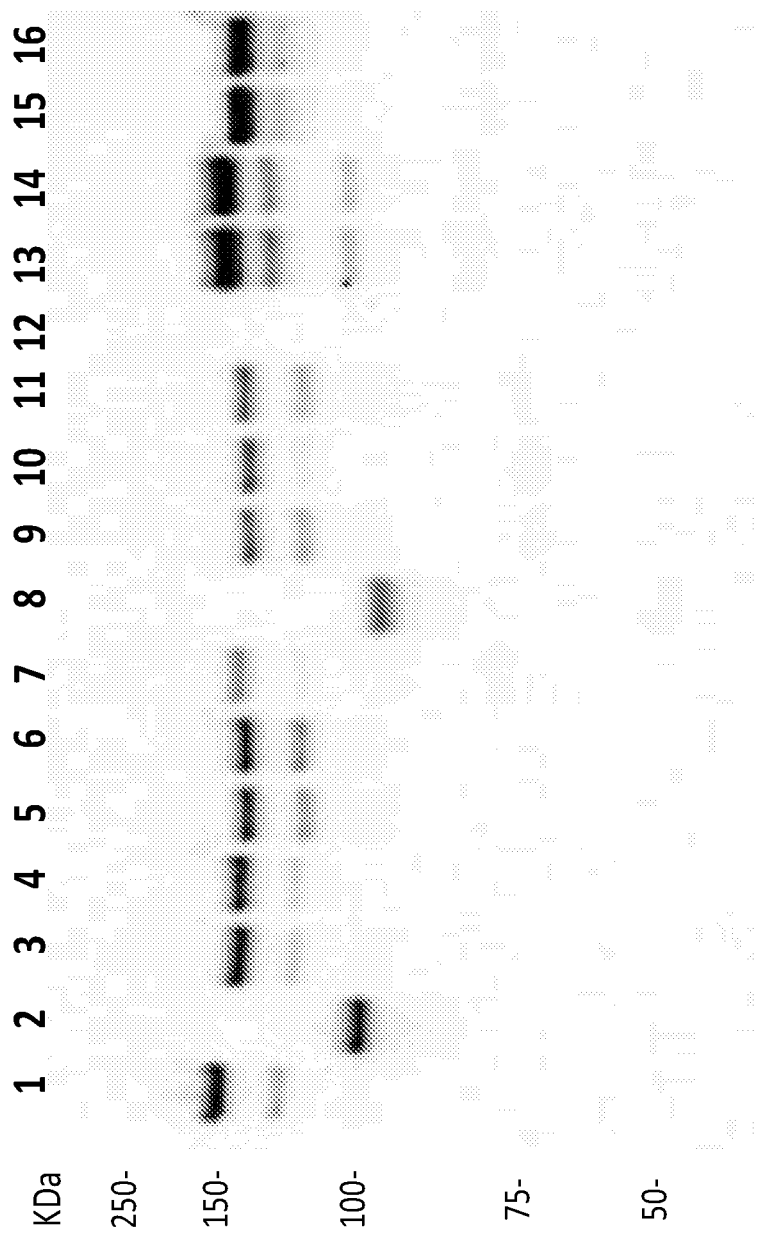
FIG. 6: Analysis of antibody species formed in the presence of cysteine substitutions at contacting residues in the HC and the LC. Experiments are described in Example 2. Lanes 1-6 contain cell supernatants from cells co-transfected with DNAs encoding the HC and LC of the IgG4 anti-PD1 antibody described in Example 2. All the anti-PD1 HCs comprise S228P. Other alterations in these antibodies are as follows: lane 1, wild type (wt) (HC) and (LC); lane 2, C131S (HC) and C214S (LC); lane 3, C131S plus F126C (HC) and C214S a plus S121C (LC); lane 4, C131S plus F126C (HC) and C214S plus Q124C (LC); lane 5, C131S plus P127C (HC) and C214S plus S121C (LC); and lane 6, C131S plus L128C (HC) and C214S plus F118C (LC). Lanes 7-11 contain cell supernatants from cells co-transfected with DNAs encoding the wild wt or altered HC and LC of the IgG1 anti-CTLA4 antibody described in Example 2. The alterations in these antibodies are as follows: lane 7, wt (HC) and (LC); lane 8, C220S (HC) and C214S (LC); lane 9, C220S plus F126C (HC) and C214S plus Q124C (LC); lane 10, C220S plus L128C (HC) and C214S plus F118C (LC); and lane 11, C220S plus S134C (HC) and C214S plus F116C (LC). Lane 12 contains a cell supernatant from a mock transfection in which no DNA was used. Lanes 13 and 14 contain cell supernatants from transfections using the IgG1 anti-HER2 antibody 4D5-8 (comprising the amino acid sequences SEQ ID NOs. 19 and 20). Lanes 15 and 16 contain cell supernatants from transfections using the IgG1 anti-HER2 antibody 2C4 (which contains the amino acid sequences of SEQ ID NOs. 21 and 22). The positions of size (in kilodaltons (kDa)) markers are indicated on the left size of the image of the Western blot.

Results are shown in FIGS. 5 and 6. As explained in Example 1, HCs are generally retained in the ER unless they are engaged by LCs. Hence, if the introduced cysteine residues were forming disulfide bridges, it would be expected that the HCs would be engaged by the LCs and that the transfectants would therefore produce primarily full-length antibody of about 150 kDa, indicated by the top arrow in FIG. 5 and the 150 kDa size marker in FIG. 6. However, other species could possibly be produced, such as a half-antibody consisting of 1 HC and 1 LC (75 kDa; bottom arrow in FIG. 5), a three quarters antibody containing 2 identical HCs and 1 LC (125 kDa; second arrow from top in FIG. 5) and 2 HCs (100 kDa; third arrow from top in FIG. 5 and the 100 kDa size marker in FIG. 6). Such species might be produced in situations where the introduced cysteine residues are not completely effective in forming a disulfide bridge.

It was expected that antibodies lacking the cysteine residues normally present at C131 (IgG4 HC) or C220 (IgG1 HC) and C214 (LC) (which form the naturally-occurring interchain disulfide bridge) would not form full-length antibodies unless both the HC and LC were substituted with cysteine at contacting sites. Data using antibodies lacking the naturally-occurring disulfide bridge and not containing any cysteine substitutions are shown in FIG. 6, lanes 2 and 8. Only 100 kDa species (likely HC/HC) were detected. Results using antibodies lacking the naturally-occurring disulfide bridge and containing a cysteine substitution in their HC, but not in their LC, or vice versa, are shown in lanes 14-22 and lanes 25-33 of FIG. 5. As expected, most of these HC/LC combinations did not produce significant quantities of full-length antibody, producing mostly a 100 kDa species (likely HC/HC). Surprisingly, three of these HC/LC combinations formed full-length antibody, i.e., K133C in the CH1 domain and no substitution in the LC (FIG. 5, lane 15) and I117C or F209C in the LC and no substitution in the HC CH1 domain (FIG. 5, lanes 26 and 27, respectively). Lanes 2-12 of FIG. 5 show data from HC/LC combinations where both the HC and the LC contained cysteine substitutions at contacting sites as indicated in the description of FIG. 5 and lacked the cysteines that form the naturally-occurring disulfide bridge. All but two of these HC/LC combinations (both of which contained S183C (HC) plus S176C (LC) (lanes 8 and 12)) formed significant quantities of full-length antibody. Similarly, analysis of further samples lacking the naturally-occurring disulfide bridge and comprising cysteine substitutions at contacting residues detected mostly full-length antibody. FIG. 6, lanes 3-6 and 9-11.

Thus, these data suggest that most, but not all, of the introduced pairs of cysteine residues did form disulfide bridges, although the presence of detectable quantities of smaller-than-full-length antibody species suggests that kinetics of antibody secretion may be affected by the introduced cysteine residues. Specifically, the results suggest that in a human IgG1 antibody, cysteine substitutions F126C (CH1)-Q124C (CLκ), L128C (CH1)-F118C (CLκ), S134C (CH1)-F116C (CLκ), H168C (CH1)-S174C (CLκ), K133C (CH1)-I117C (CLκ), K133C (CH1)-F209C (CLκ), V173C (CH1)-Q160C (CLκ), F170C (CH1)-S162C (CLκ), and F170C (CH1)-S176C (CLκ) can mediate disulfide bond formation. Further, the results suggest that in a human IgG4 antibody, cysteine substitutions F126C (CH1)-S121C (Cκ), F126C (CH1)-Q124C (Cκ), P127C (CH1)-S121C (Cκ), L128C (CH1)-F118C (Cκ), H168C (CH1)-S174C (Cκ), V173C (CH1)-S162C (Cκ), and F170C (CH1)-S162C (Cκ) can mediate disulfide bond formation.

Example 3: Testing Antibody Mixtures Containing LC- and HC-Partner-Directing Alterations that are Charge Pair Substitutions and/or Cysteine Substitutions Having determined through analysis of published tertiary structures the identity of a number of contacting pairs of residues in the HC and LC suitable for making charge-pair or cysteine substitutions (Examples 1 and 2) and having made and tested some cysteine substitutions, a number of such substitutions and combinations thereof were made and tested to determine their effects on cognate HC/LC pairing. To quickly assess the efficacy of various LC- and HC-partner-directing alterations in forcing cognate HC/LC pairing, "chain drop out" experiments as described below were performed.

DNA constructs encoding the antibodies were made using methods similar to those described in Example 2. A DNA fragment encoding the human IgG1 HC of the human anti-CTLA4 111 antibody (the "111 antibody") was made as described for the HC of the anti-CTLA4 1E1 antibody in Example 2. The CH1, hinge, CH2 and CH3 domains and the framework regions of the VH domain of the 111 antibody have the same amino acid sequences as those of the HC of the 1E1 antibody. The amino acid sequence of the HC of the 1E1 antibody is provided in SEQ ID NO:38. Another DNA fragment encoding an SP and the VL and CLκ domains of the LC of the human anti-CTLA4 111 antibody was also made as described for the anti-CTLA4 1E1 antibody in Example 2. The CL domain and the framework regions of the VL domain of the 111 antibody have the same amino acid sequence as those of the LC of the 1E1 antibody, the sequence of which is provided in SEQ ID NO:40.

The construction of vectors containing DNA inserts encoding the HC and LC of the anti-PD1 102 antibody are described in Example 2.

Similar constructions were made to obtain DNA encoding a pair of anti-HER2 antibodies called 4D5-8 and 2C4. The antibody 4D5-8 contains the variable regions from the antibody humAb4D5-8 described in Carter et al. (1992), Proc. Natl. Acad. Sci. USA 89:4285-4289, which is incorporated herein in its entirety, and constant regions from a human IgG1 HC and a human κLC. The antibody 2C4 contains the variable regions from the antibody rhuMAb 2C4 described in Adams et al. (2006), Cancer Immunol. Immunother. 55(6): 717-727, which is incorporated herein in its entirety, and constant regions from a human IgG1 HC and a human κLC. The amino acid sequences of the light and heavy chains of 4D5-8 are provided in SEQ ID NOs: 19 and 20, respectively. The amino acid sequences of the heavy and light chains of 2C4 are provided in SEQ ID NOs: 21 and 22, respectively.

Amino acid substitutions were introduced into the DNAs encoding the anti-CTLA4 and anti-PD1 antibodies or the two anti-HER2 antibodies by mutagenesis reactions with QuikChange Lightning multi site-directed mutagenesis kit (Agilent Technologies, Santa Clara, Calif., cat no. 210516). Each QuikChange process resulted in a vector DNA containing an insert comprising the desired mutation(s), which was then transformed into *E. coli* XL1-Blue cells. Colonies from these transformations were picked and cultured to obtain plasmid DNA for transfection into mammalian cells. Sequences of all constructs were confirmed by DNA sequencing.

The plasmid DNAs from these cultured colonies were purified using a Qiagen® Midi-prep kit (Qiagen N.V., the Netherlands). The resulting DNAs were diluted in water and mixed in EPPENDORF TUBES®. For each variant pair, a set of 5 tubes of mixed DNAs were transiently transfected into EXPI293™ cells (ThermoFisher Scientific Inc.) to monitor the fidelity of HC/LC pairings. Tube 1 contained DNAs encoding both full-length antibodies, e.g., DNA encoding the anti-PD1 HC and LC (HC1 and LC1) and the anti-CTLA4 HC and LC (HC2 and LC2)). Tube 2 contained DNAs encoding only one antibody (HC1 and LC1). Tube 3 contained the DNAs encoding a non-cognate HC/LC pair (HC1 and LC2). Tube 4 contained DNAs encoding only one antibody (HC2 and LC2). Tube 5 contained DNAs encoding a non-cognate HC/LC pair (HC2 and LC1). DNAs encoding unrelated antibodies were transfected in parallel to assess transfection efficiency.

The mammalian EXPI293™ cells were transfected with the DNAs described above using LIPOFECTAMINE® 2000 (ThermoFisher Scientific, Waltham, Mass., USA) in 24-well deep well plates. Cells were continuously shaken at 150 rpm at 37° C. for 4 days. The supernatants were harvested for analysis by spinning down cells at 1500 rpm for 20 min. Samples were prepared and subjected to electrophoresis, the gels were blotted, the nitrocellulose membranes were blocked and washed, and the antibodies were detected as explained in Example 2.

The mammalian EXPI293™ cells used for transfection can transcribe DNAs, translate mRNAs and secret antibodies into the culture medium. Western blotting of non-reduced samples of antibodies in the culture media was carried out to monitor the HC/LC pairings. As explained above, there were five co-transfections using the five different DNA mixtures described above for each pair of variants. As an initial criterion (see Table 17), a particular pair of variants was judged to be successful if the levels of full-length antibody produced by transfectants containing DNAs encoding cognate HC/LC pairs was higher than the levels produced by transfectants containing only DNAs encoding non-cognate HC/LC pairs, i.e., Tubes 3 and 5 described above. Ultimately (see Tables 20 and 21), a particular variant mixture was judged to be successful in forcing mostly or only cognate HC/LC pairing if the samples from transfectants containing DNA encoding LC1 and HC1 (Tube 2 described above), LC2 and HC2 (Tube 4), and LC1, HC1, LC2, and HC2 (Tube 1) all produced good levels of full-length antibody, whereas the samples from transfectants containing DNA encoding HC1 and LC2 (Tube 3 described above) and HC2 and LC1 (Tube 5) produced little or no detectable full-length antibody.

Figure 7:
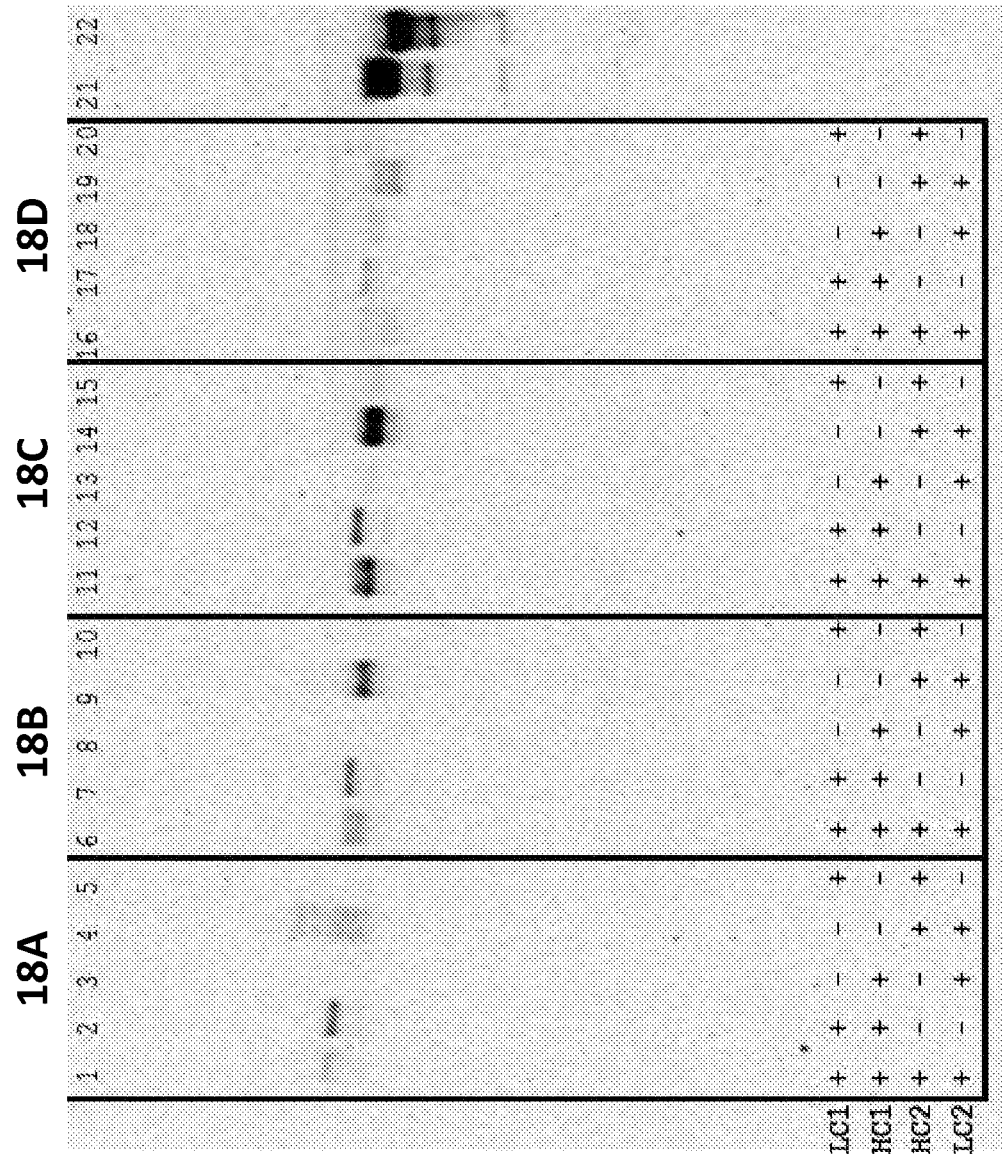
FIG. 7: Chain drop-out transient transfections to assess HC/LC pairing. Experiments are described in Example 3. Each set of five samples comes from transfections using various combinations of the DNAs encoding a first heavy chain (HC1) and a first light chain (LC1), which together encode a first antibody (an anti-PD1 antibody), and a second heavy chain (HC2) and a second light chain (LC2), which together encode a second antibody (an anti-CTLA4 antibody). As indicated in the figure, the combinations are as follows: 1) HC1, LC1, HC2, and LC2; 2) HC1 and LC1; 3) HC1 and LC2; 4) HC2 and LC2; and 5) HC2 and LC1. The designations 18A-18D above each set of five lanes indicate that the HCs and LCs in these lanes have the alterations described for the designations 18A-18D in Table 21. Lanes 21 and 22 contain supernatants from cells transfected with the full-length anti-HER2 antibodies, 4D5-8 (comprising the amino acid sequences SEQ ID NOs: 19 and 20) and 2C4 (which contains the amino acid sequences of SEQ ID NOs: 21 and 22), respectively, included as a control to monitor transfection efficiency.

Examples of such Western blots are shown in FIGS. 7-10. In FIG. 7, lanes 21 and 22 show samples from transfectants that received DNA encoding the anti-HER2 antibodies 4D5-8 and 2C4, respectively, which are full-length antibodies included as controls for transfection efficiency. The DNA contents of the test transfectants are indicated below lanes 1-20 of FIG. 7, and the name of the pair of variants tested is indicated above. The identity of the alterations in the pairs of variants is stated in Table 21 below. The results shown in FIG. 7 indicate that the variant mixtures 18B and 18C were more effective at forcing cognate HC/LC pairing than mixtures 18 Å and 18D. Transfectants containing only non-cognate 18B or 18C HC/LC pairs produced little or no detectable full-length antibody (FIG. 7, lanes 8, 10 13, and 15), while transfectants containing cognate 18B or 18C HC/LC pairs produced detectable full-length antibody (FIG. 7, lanes 6, 7, 9, 11, 12, and 14). In contrast, 18 Å Tube 1 and Tube 4 transfectants, which contain DNA encoding cognate HC/LC pairs produced relatively low amounts of full-length antibody, which was diffuse in size in Tube 4 transfectants. FIG. 7, lanes 1 and 4. Further, 18D transfectants containing DNA encoding only one non-cognate HC/LC pair produced low amounts of full-length antibody (FIG. 7, lane 18), while transfectants containing DNAs encoding cognate HC/LC pairs produced only relatively low amounts of full-length antibody (FIG. 7, lanes 16, 17, and 19).

Figure 8:
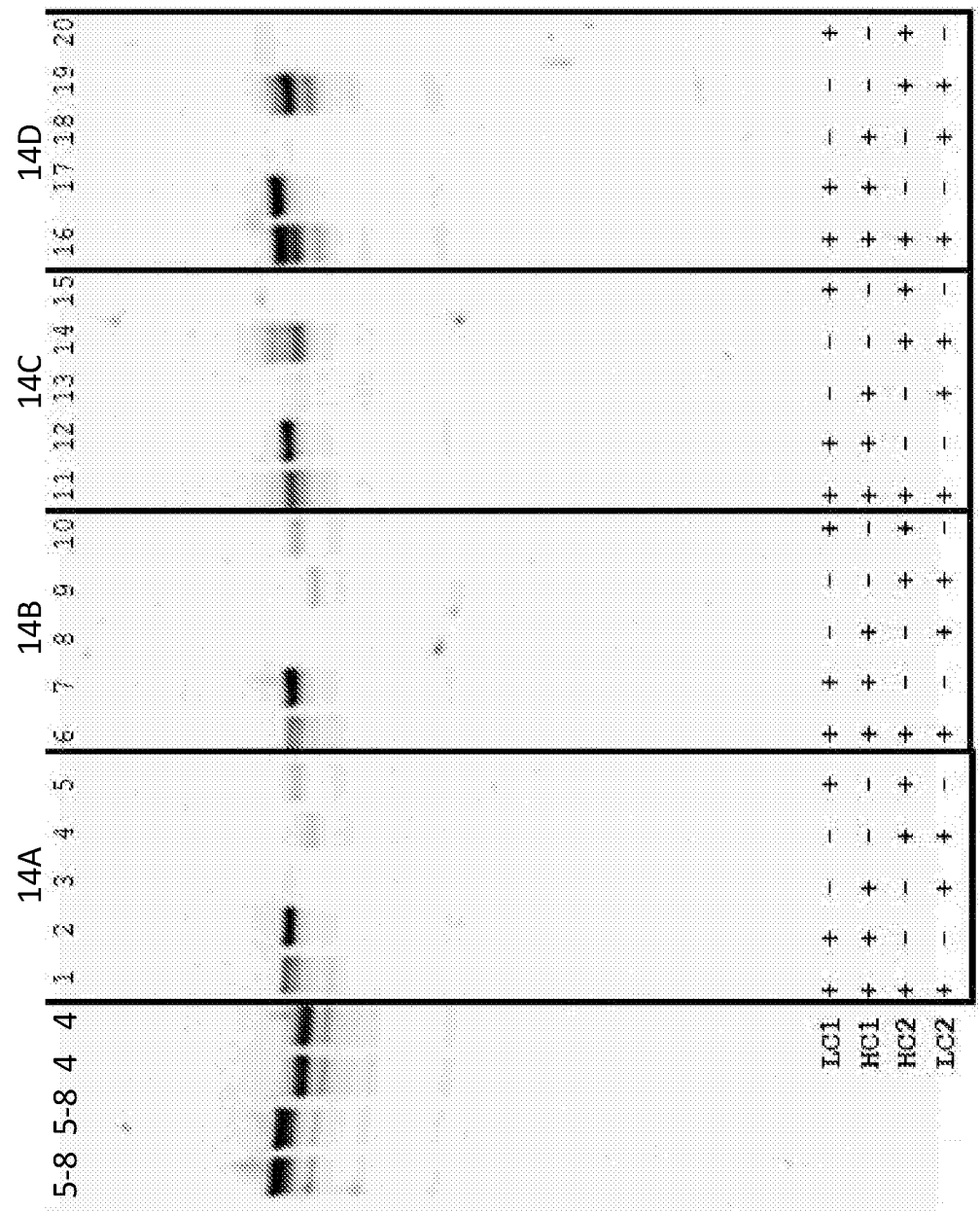
FIG. 8: Chain drop-out transient transfections to assess HC/LC pairing. Experiments are described in Example 3. As indicated under lanes 1-20, for each pair of variants a set of five DNA combinations (as described above for FIG. 7) was transfected into the host cells. The designations 14A-14D above each set of five lanes indicate that the HCs and LCs in these lanes have the alterations described for these designations in Table 20. DNAs encoding anti-HER2 antibodies 4D5-8 and 2C4 were transfected in duplicate at the same time to monitor transfection efficiency, and cell supernatants from these transfectants were analyzed in lanes labeled 5-8 (4D5-8) and 4 (2C4).

Similarly, a Western blot containing data for variant mixtures 14 Å to 14D (see Table 20) is shown in FIG. 8. Variants 14C and 14D showed only cognate HC/LC pairing since there was no detectable antibody expression when only non-cognate HC/LC pairs (LC1+HC2 or LC2+HC1) were combined (FIG. 8, lanes 13, 15, 18, and 20), whereas cognate HC/LC pairs (LC1+HC1 or LC2+HC2) or a mixture of all four chains (LC1+HC1+LC2+HC2) produced significant amounts of full-length antibodies (FIG. 8, lanes 11, 12, 14, 16, 17, and 19). In contrast, mixtures 14 Å and 14B did show detectable full-length antibody in some lanes containing samples from transfectants containing only non-cognate HC/LC pair (FIG. 8, lanes 5 and 10).

Figure 9:
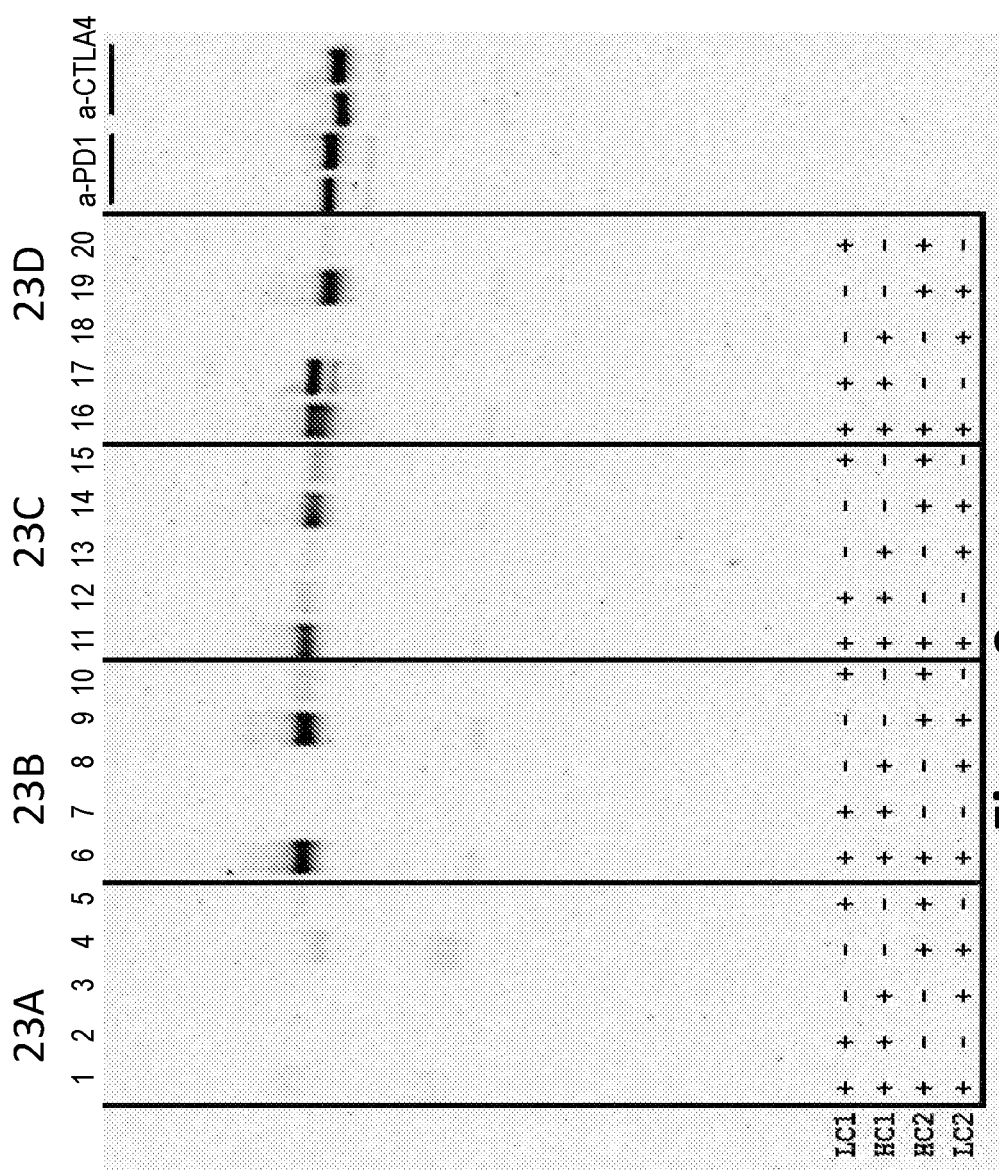
FIG. 9: Chain drop-out transient transfections to assess HC/LC pairing. Experiments are described in Example 3. As indicated under lanes 1-20, for each pair of variants a set of five DNA combinations (as described above for FIG. 7) was transfected into the host cells. The designations 23A-23D above each set of five lanes indicate that the HCs and LCs analyzed in these lanes have the alterations described for these designations in Table 21. DNAs encoding an anti-PD1 antibody and anti-CTLA4 antibody were transfected at the same time to monitor transfection efficiency, and cell supernatants from these transfectants were analyzed in lanes labeled a-PD1 and a-CTLA4.

In FIG. 9, similar data for variant pairs 23A-23D are shown. The alterations in these pairs of anti-PD1 and anti-CTLA4 antibodies are shown in Table 21. As indicated under lanes 1-20, for each pair of variants a set of five DNA combinations (as described above) was transfected into the host cells. DNAs encoding the anti-PD1 antibody (lanes labeled "a-PD1") and anti-CTLA4 antibody (lanes labeled "a-CTLA4") were transfected at the same time to monitor transfection efficiency. Host cells receiving DNA encoding antibody chains of variant pair 23 Å produced little full-length antibody, regardless of whether the cells were transfected with DNAs encoding cognate or non-cognate HC/LC pairs. FIG. 9, lanes 1-5. Host cells receiving DNA encoding chains of variant pairs 23B and 23C produced little or no full-length antibody when DNAs encoding the cognate pair HC1 and LC1 were introduced into the host cells (FIG. 9, lanes 7 and 12) and small but detectable amounts of full-length antibody in the presence of DNAs encoding the non-cognate pair HC2 and LC1 (FIG. 9, lanes 10 and 15). In contrast, host cells receiving DNAs encoding antibody chains of variant pair 23D produced significant amounts of full-length antibody when DNAs encoding cognate HC/LC pairs were present (FIG. 9, lanes 16, 17, and 19) and little or no full-length antibody when only DNAs encoding non-cognate HC/LC pairs were present (FIG. 9, lanes 18 and 20).

Many pairs of variants were tested in similar chain drop out experiments, starting with alterations introducing charged amino acids only in the VH and VL domains or only in the CH1 and CL domains and then combining alterations in VH, CH1, VL, and CL. In some cases alterations creating additional disulfide bridges were added. The identity of such pairs of alterations and the results of the Western blots are catalogued in Tables 17-21.

TABLE 17

Charge pair alterations tested in chain drop out experiments

| | anti-HER2 4D5-8 | | | | anti-HER2 2C4 | | | | Accurate HC/LC |
|---|---|---|---|---|---|---|---|---|---|
| | HC1 | | LC1 | | HC2 | | LC2 | | partner |
| Variant# | VH | CH1 | VL | CL | VH | CH1 | VL | CL | selection* |
| 1A | G44E | | A43R | | G44R | | A43E | | N |
| | Q105E | | Q100R | | Q105R | | Q100E | | |
| 1B | G44E | | A43E | | G44R | | A43R | | Y |
| | Q105R | | Q100R | | Q105E | | Q100E | | |
| 1C | G44R | | A43R | | G44E | | A43E | | N |
| | Q105E | | Q100E | | Q105R | | Q100R | | |
| 1D | G44R | | A43E | | G44E | | A43R | | N |
| | Q105R | | Q100E | | Q105E | | Q100R | | |

TABLE 17-continued

Charge pair alterations tested in chain drop out experiments

| | anti-HER2 4D5-8 | | | | anti-HER2 2C4 | | | | Accurate HC/LC partner selection* |
|---|---|---|---|---|---|---|---|---|---|
| | HC1 | | LC1 | | HC2 | | LC2 | | |
| Variant# | VH | CH1 | VL | CL | VH | CH1 | VL | CL | |
| 2A | | K147E | | S131R | | K147R | | S131E | N |
| 2B | | K147E | | T180R | | K147R | | T180E | N |
| 2C | | K147R | | S131E | | K147E | | S131R | Y |
| 2D | | K147R | | T180E | | K147E | | T180R | N |
| 3A | | H168E | | T164R | | H168R | | T164E | N |
| 3B | | H168E | | S174R | | H168R | | S174E | Y |
| 3C | | H168E | | S174R | | H168R | | S174D | Y |
| 3D | | H168R | | T164E | | H168E | | T164R | N |
| 4A | | H168R | | S174E | | H168E | | S174R | N |
| 4B | | H168R | | S174D | | H168E | | S174R | N |
| 4C | | S181E | | T178R | | S181R | | T178E | N |
| 4D | | S181R | | T178E | | S181E | | T178R | Y |

This column provides the designation for the particular pair of altered variant antibodies.
*A "Y" indicates pairs of variants where transfectants containing DNAs encoding cognate HC/LC pairs had robust expression of full-length antibody and produced more full-length antibody than transfectants containing only DNAs encoding non-cognate HC/LC pairs. Such rows are shown in boldface. An "N" indicates that this criterion was not met.

The data in Table 17 indicate that certain alterations in the VH and VL and in the CH1 and CL were more effective than others at forcing cognate HC/LC pairings. The 1B pair of variants was chosen as a starting point for further experiments to test various combinations of alterations introducing charged amino acids in the VH, CH1, VL, and CL domains as reported in Table 18 below.

TABLE 18

Charge pair alterations tested in chain drop out experiments

| | anti-HER2 4D5-8 | | | | anti-HER2 2C4 | | | | Accurate HC/LC partner selection* |
|---|---|---|---|---|---|---|---|---|---|
| | HC1 | | LC1 | | HC2 | | LC2 | | |
| Variant# | VH | CH1 | VL | CL | VH | CH1 | VL | CL | |
| 5A | G44E Q105R | K147R | A43E Q100R | S131D | G44R Q105E | K147D | A43R Q100E | S131R | N |
| 5B | G44E Q105R | K147D | A43E Q100R | S131R | G44R Q105E | K147R | A43R Q100E | S131D | N |
| 5C | G44E Q105R | H168R | A43E Q100R | S174D | G44R Q105E | H168D | A43R Q100E | S174R | N |
| 5D | G44E Q105R | H168D | A43E Q100R | S174R | G44R Q105E | H168R | A43R Q100E | S174D | N |
| 6A | G44E Q105R | S181R | A43E Q100R | T178D | G44R Q105E | S181D | A43R Q100E | T178R | N |
| 6B | G44E Q105R | S181D | A43E Q100R | T178R | G44R Q105E | S181R | A43R Q100E | T178D | N |
| 6C | G44E Q105R | K147R H168R | A43E Q100R | S131D S174D | G44R Q105E | K147D H168D | A43R Q100E | S131R S174R | Y |
| 6D | G44E Q105R | K147R H168D | A43E Q100R | S131D S174R | G44R Q105E | K147D H168R | A43R Q100E | S131R S174D | N |
| 7A | G44E Q105R | K147D H168R | A43E Q100R | S131R S174D | G44R Q105E | K147R H168D | A43R Q100E | S131D S174R | N |
| 7B | G44E Q105R | K147D H168D | A43E Q100R | S131R S174R | G44R Q105E | K147R H168R | A43R Q100E | S131D S174D | Y |
| 7C | G44E Q105R | K147R | A43E Q100R | S131E | G44R Q105E | K147E | A43R Q100E | S131R | N |
| 7D | G44E Q105R | | A43E Q100R | | G44R Q105E | | A43R Q100E | | N |
| 8A | G44E Q105R | K147R | A43E Q100R | S131E | G44R Q105E | K147E | A43R Q100E | S131E | N |
| 8B | G44E Q105R | K147E | A43E Q100R | S131R | G44R Q105E | K147R | A43R Q100E | S131E | N |
| 8C | G44E Q105R | H168R | A43E Q100R | S174E | G44R Q105E | H168E | A43R Q100E | S174R | N |

TABLE 18-continued

Charge pair alterations tested in chain drop out experiments

| | anti-HER2 4D5-8 | | | | anti-HER2 2C4 | | | | Accurate HC/LC partner selection* |
|---|---|---|---|---|---|---|---|---|---|
| | HC1 | | LC1 | | HC2 | | LC2 | | |
| Variant# | VH | CH1 | VL | CL | VH | CH1 | VL | CL | |
| 8D | G44E Q105R | H168E | A43E Q100R | S174R | G44R Q105E | H168R | A43R Q100E | S174E | N |
| 9A | G44E Q105R | S181R | A43E Q100R | T178E | G44R Q105E | S181E | A43R Q100E | T178R | N |
| 9B | G44E Q105R | S181E | A43E Q100R | T178R | G44R Q105E | S181R | A43R Q100E | T178E | N |
| 9C | G44E Q105R | K147R H168R | A43E Q100R | S131D S174D | G44R Q105E | K147D H168D | A43R Q100E | S131R S174R | N |
| 9D | G44E Q105R | K147D H168D | A43E Q100R | S131R S174R | G44R Q105E | K147R H168R | A43R Q100E | S131D S174D | N |

*A "Y" indicates pairs of variants where transfectants containing DNAs encoding cognate HC/LC pairs were more clearly distinguished from transfectants containing DNAs encoding only non-cognate HC/LC pairs (with the former showing expression of full-length antibody and the latter showing less or no expression) than was observed in the 1B pair of variants. Such rows are shown in boldface. A "N" indicates that this criterion was not met.
This column provides the designation for the particular pair of altered antibodies.

Starting with the alterations present in the 6C and 7B pairs of variants, all glutamic acid residues that had been introduced were changed to aspartic acid to determine whether these changes would have an effect on the selectivity of HC/LC pairing. These alterations and their effects are cataloged in Table 19.

TABLE 19

E to D substitutions tested in chain drop out experiments

| | anti-HER2 4D5-8 | | | | anti-HER2 2C4 | | | | Accurate HC/LC partner selection* |
|---|---|---|---|---|---|---|---|---|---|
| | HC1 | | LC1 | | HC2 | | LC2 | | |
| Variant# | VH | CH1 | VL | CL | VH | CH1 | VL | CL | |
| 10A | G44E Q105R | K147R H168R | A43E Q100R | S131D S174D | G44R Q105E | K147D H168D | A43R Q100E | S131R S174R | N |
| 10B | G44D Q105R | K147R H168R | A43D Q100R | S131D S174D | G44R Q105D | K147D H168D | A43R Q100D | S131R S174R | Y |
| 10C | G44E Q105R | K147R H168R | A43E Q100R | Q124D S174D | G44R Q105E | K147D H168D | A43R Q100E | Q124R S174R | N |
| 11A | G44E Q105R | K147D H168D | A43E Q100R | S131R S174R | G44R Q105E | K147R H168R | A43R Q100E | S131D S174D | N |
| 11B | G44D Q105R | K147D H168D | A43D Q100R | S131R S174R | G44R Q105D | K147R H168R | A43R Q100D | S131D S174D | Y |
| 11C | G44E Q105R | K147D H168D | A43E Q100R | Q124D S174R | G44R Q105E | K147R H168R | A43R Q100E | Q124R S174D | N |

*A "Y" indicates pairs of variants where transfectants containing DNAs encoding cognate HC/LC pairs were more clearly distinguished from transfectants containing DNAs encoding only non-cognate HC/LC pairs (with the former showing expression of full-length antibody and the latter showing less or no expression) than was observed in the 6C and 7B pair of variants. Such rows are shown in boldface. A "N" indicates that this criterion was not met.
This column provides the designation for the particular pair of altered variant antibodies.

The results in Table 19 indicate that the substitution of D for E in pairs of variants further strengthened cognate HC/LC pairing as compared to non-cognate HC/LC pairing. We hypothesize that the smaller molecular size of D as compared to E may be less disruptive to interactions across the VH/VL and CH1/CL interfaces.

Starting from the alterations present in the 10B pair of variants, we made further alterations that were designed to create an additional disulfide bridge between the HC and the LC. We hoped that such additional disulfide bridges would increase antibody expression from transfectants containing DNAs encoding cognate HC/LC pairs, many of which were not expressing the desired high levels antibody. We hypothesized that the charge pair alterations were somehow destabilizing cognate HC/LC pairs, causing retention of the antibodies in the ER, and that an additional disulfide bridge might stabilize the cognate pairs, thereby increasing secretion of the antibodies into the culture medium where they could be detected. As reported in Example 2, these cysteine substitutions also have been tested in the absence of charge pair substitutions to ascertain their ability to form HC/LC disulfide bonds. These combinations of alterations and their effects are cataloged in Table 20 below.

TABLE 20

Charge pairs plus cysteine pairs tested in chain drop out experiments

| | anti-HER2 4D5-8 | | | | anti-HER2 2C4 | | | | Accurate HC/LC partner selection* |
|---|---|---|---|---|---|---|---|---|---|
| | HC1 | | LC1 | | HC2 | | LC2 | | |
| Variant# | VH | CH1 | VL | CL | VH | CH1 | VL | CL | |
| 12A | G44D Q105R | K133C K147R H168R | A43D Q100R | F209C S131D S174D | G44R Q105D | F170C K147D H168D | A43D Q100D | S162C S131R S174R | N |
| 12B | G44D Q105R | K133C K147R H168R | A43D Q100R | F209C S131D S174D | G44R Q105D | V173C K147D H168D | A43R+ Q100D | Q160C S131R S174R | N |
| 12C | G44D Q105R | K133C K147R H168R | A43D Q100R | F209C S131D S174D | G44R Q105D | F170C K147D H168D | A43R+ Q100D | S176C S131R S174R | N |
| 12D | G44D Q105R | K133C K147R H168R | A43D Q100R | F209C S131D S174D | G44R Q105D | S183C K147D H168D | A43R+ Q100D | S176C S131R S174R | N |
| 13A | G44D Q105R | F170C K147R H168R | A43D Q100R | S162C S131D S174D | G44R Q105D | K133C K147D H168D | A43R+ Q100D | I117C S131R S174R | N |
| 13B | G44D Q105R | F170C K147R H168R | A43D Q100R | S162C S131D S174D | G44R Q105D | K133C K147D H168D | A43R+ Q100D | F209C S131R S174R | N |
| 13C | G44D Q105R | F170C K147R H168R | A43D Q100R | S162C S131D S174D | G44R Q105D | V173C K147D H168D | A43R+ Q100D | Q160C S131R S174R | N |
| 13D | G44D Q105R | F170C K147R H168R | A43D Q100R | S162C S131D S174D | G44R Q105D | S183C K147D H168D | A43R Q100D | S176C S131R S174R | Y |
| 14A& | G44D Q105R | V173C K147R H168R | A43D Q100R | Q160C S131D S174D | G44R Q105D | K133C K147D H168D | A43R Q100D | I117C S131R S174R | N |
| 14B& | G44D+ Q105R | V173C K147R H168R | A43D Q100R | Q160C S131D S174D | G44R Q105D | K133C K147D H168D | A43R Q100D | F209C S131R S174R | N |
| 14C& | G44D Q105R | V173C K147R H168R | A43D Q100R | Q160C S131D S174D | G44R+ Q105D | F170C K147D H168D | A43R Q100D | S162C S131R S174R | Y |
| 14D& | G44D Q105R | V173C K147R H168R | A43D Q100R | Q160C S131D S174D | G44R Q105D | S183C K147D H168D | A43R Q100D | S176C S131R S174R | Y |
| 15A | G44D Q105R | F170C K147R H168R | A43D Q100R | S176C S131D S174D | G44R Q105D | K133C K147D H168D | A43R Q100D | I117C S131R S174R | N |
| 15B | G44D Q105R | F170C K147R H168R | A43D Q100R | S176C S131D S174D | G44R Q105D | K133C K147D H168D | A43R Q100D | F209C S131R S174R | N |
| 15C | G44D Q105R | F170C K147R H168R | A43D Q100R | S176C S131D S174D | G44R Q105D | V173C K147D H168D | A43R Q100D | Q160C S131R S174R | Y |
| 15D | G44D Q105R | F170C K147R H168R | A43D Q100R | S176C S131D S174D | G44R Q105D | S183C K147D H168D | A43R Q100D | S176C S131R S174R | Y |
| 16A | G44D Q105R | K133C K147R H168R | A43D Q100R | I117C S131D S174D | G44R Q105D | F170C K147D H168D | A43R Q100D | S162C S131R S174R | N |
| 16B | G44D Q105R | K133C K147R H168R | A43D Q100R | I117C S131D S174D | G44R Q105D | F170C K147D H168D | A43R Q100D | S176C S131R S174R | N |
| 16C | G44D Q105R | K133C K147R H168R | A43D Q100R | I117C S131D S174D | G44R Q105D | V173C K147D H168D | A43R Q100D | Q160C S131R S174R | N |
| 16D | G44D Q105R | K133C K147R H168R | A43D Q100R | I117C S131D S174D | G44R Q105D | S183C K147D H168D | A43R Q100D | S176C S131R S174R | N |

*A "Y" indicates that the host cells (1) produced easily detectable amounts of full-length antibody when DNAs encoding one or both cognate HC/LC pairs were present and (2) produced little or no full-length antibody when only DNAs encoding non-cognate HC/LC pairs were present. Such rows are in boldface. A "N" indicates that not all these criteria were not met.

This column provides the designation for the particular pair of altered variant antibodies.

&Data shown in FIG. 8.

To extend these results to a different antibody pair, pairs of altered antibodies containing the altered IgG4 anti-PD1 102 antibody described in Example 2 and an altered version of the IgG1 anti-CTLA4 111 antibody described above, which contained the alterations D399K and K409E (to disfavor the formation of HC/HC heterodimers), were tested in a similar manner. Using some of the combinations of alterations explored in the chain drop out experiments reported in Table 20, DNAs encoding altered pairs of the anti-PD1 and anti-CTLA4 antibodies were made and tested in chain drop out transfection experiments as described above. These results are cataloged in Table 21 below.

TABLE 21

Alterations tested in chain drop out experiments

| Variant[#] | anti-PD1 (IgG4) | | | | anti-CTLA4 (IgG1; D399K, K409E) | | | | Accurate HC/LC partner selection* |
|---|---|---|---|---|---|---|---|---|---|
| | HC1 | | LC1 | | HC2 | | LC2 | | |
| | VH | CH1 | VL | CL | VH | CH1 | VL | CL | |
| 17A | G44D Q105R | F170C K147R H168R | V43D G100R | S162C S131D S174D | G44R Q105D | F170C K147D H168D | A43R P100D | S162C S131R S174R | N |
| 17B | G44D Q105R | F170C K147R H168R | V43D G100R | S162C S131D S174D | G44R Q105D | F170C K147D H168D | A43R P100D | S176C S131R S174R | Y |
| 17C | G44D Q105R | F170C K147R H168R | V43D G100R | S162C S131D S174D | G44R Q105D | V173C K147D H168D | A43R P100D | Q160C S131R S174R | Y |
| 17D | G44D Q105R | F170C K147R H168R | V43D G100R | S162C S131D S174D | G44R Q105D | S183C K147D H168D | A43R P100D | S176C S131R S174R | N |
| 18A[&] | G44D Q105R | V173C K147R H168R | V43D G100R | S162C S131D S174D | G44R Q105D | F170C K147D H168D | A43R P100D | S162C S131R S174R | N |
| 18B[&] | G44D Q105R | V173C K147R H168R | V43D G100R | S162C S131D S174D | G44R Q105D | F170C K147D H168D | A43R P100D | S176C S131R S174R | Y |
| 18C[&] | G44D Q105R | V173C K147R H168R | V43D G100R | S162C S131D S174D | G44R Q105D | V173C K147D H168D | A43R P100D | Q160C S131R S174R | Y |
| 18D[&] | G44D Q105R | V173C K147R H168R | V43D G100R | S162C S131D S174D | G44R Q105D | S183C K147D H168D | A43R P100D | S176C S131R S174R | N |
| 19A | G44D Q105R | S183C K147R H168R | V43D G100R | S176C S131D S174D | G44R Q105D | F170C K147D H168D | A43R P100D | S162C S131R S174R | N |
| 19B | G44D Q105R | S183C K147R H168R | V43D G100R | S176C S131D S174D | G44R Q105D | F170C K147D H168D | A43R P100D | S176C S131R S174R | N |
| 19C | G44D Q105R | S183C K147R H168R | V43D G100R | S176C S131D S174D | G44R Q105D | V173C K147D H168D | A43R P100D | Q160C S131R S174R | Y |
| 19D | G44D Q105R | S183C K147R H168R | V43D G100R | S176C S131D S174D | G44R Q105D | S183C K147D H168D | A43R P100D | S176C S131R S174R | N |
| 20A | G44D Q105R | K147R H168R | V43D G100R | S131D S174D | G44R Q105D | K147D H168D | A43R P100D | S131R S174R | N |
| 23A[@] | G44D Q105R | K147R H168R | V43D G100R | S131D S174D | G44R Q105D | K147D H168D | A43R P100D | S131R S174R | N |
| 23B[@] | G44D Q105R | K147R H168R | V43D G100R | S131D S174D | G44R Q105D | F170C K147D H168D | A43R P100D | S176C S131R S174R | N |
| 23C[@] | G44D Q105R | K147R H168R | V43D G100R | S162C S131D S174D | G44R Q105D | F170C K147D H168D | A43R P100D | S176C S131R S174R | N |
| 23D[@] | G44D Q105R | V173C K147R H168R | V43D G100R | S162C S131D S174D | G44R Q105D | F170C K147D H168D | A43R P100D | S176C S131R S174R | Y |

*A "Y" indicates that the host cells (1) produced easily detectable amounts of full-length antibody when DNAs encoding one or both cognate HC/LC pairs were present and (2) produced little or no full-length antibody when only DNAs encoding non-cognate HC/LC pairs were present. Such rows are shown in boldface. A "N" indicates that not all these criteria were met.
[@]Data from these variants are shown in FIG. 9.
[&]Data from these variants are shown in FIG. 7.
[#]This column provides the designation for the particular pair of altered variant antibodies.

These data indicate that some of the same sites for charged pairs and cysteine pairs that were effective in forcing cognate HC/LC pairing in the anti-HER2 antibody mixtures containing two full-length IgG1 antibodies were also effective in the mixtures described in Table 21 containing both an IgG1 and an IgG4 full-length antibody. Compare 14C and 14D in Table 20 to 17C and 19C in Table 21.

In addition, the variant mixtures 23A-23D show a clear effect from the addition of disulfide bonds. The antibodies in the 23A mixture have no added cysteine residues, while the antibodies in the 23B and 23C mixtures would be expected to have an additional disulfide bond (due to cysteine substitutions) in the anti-CTLA4 antibody only. The 23D mixture would be expected to have an additional disulfide bond in each of the two antibodies in the mixture. Table 21. DNAs encoding these four antibody mixtures encoded mixtures that were the same except for these differences in cysteine substitutions. Table 21. Expression of the antibody having cysteine substitutions in both the HC and LC is strong in the 23B and 23C mixtures compared to that observed in 23A mixture. FIG. 9, compare lanes 1 and 4 to lanes 6 and 9 and to lanes 11 and 14. However, some expression of non-cognate pairs is detectable in transfectants from mixtures 23B and 23C. FIG. 9, lanes 10 and 15. In mixture 23D, good expression of full-length antibody was observed in all transfectants containing DNA encoding cognate HC/LC pairs (FIG. 9, lanes 16, 17, and 19), and little or no expression was detected in transfectants containing only DNA encoding non-cognate pairs (FIG. 9, lanes 18 and 20). These data indicate that addition of disulfide bonds to antibodies in a mixture increases both expression (likely due to a stronger HC/LC interaction that allows escape from the ER) and selectivity of pairing.

Figure 10:
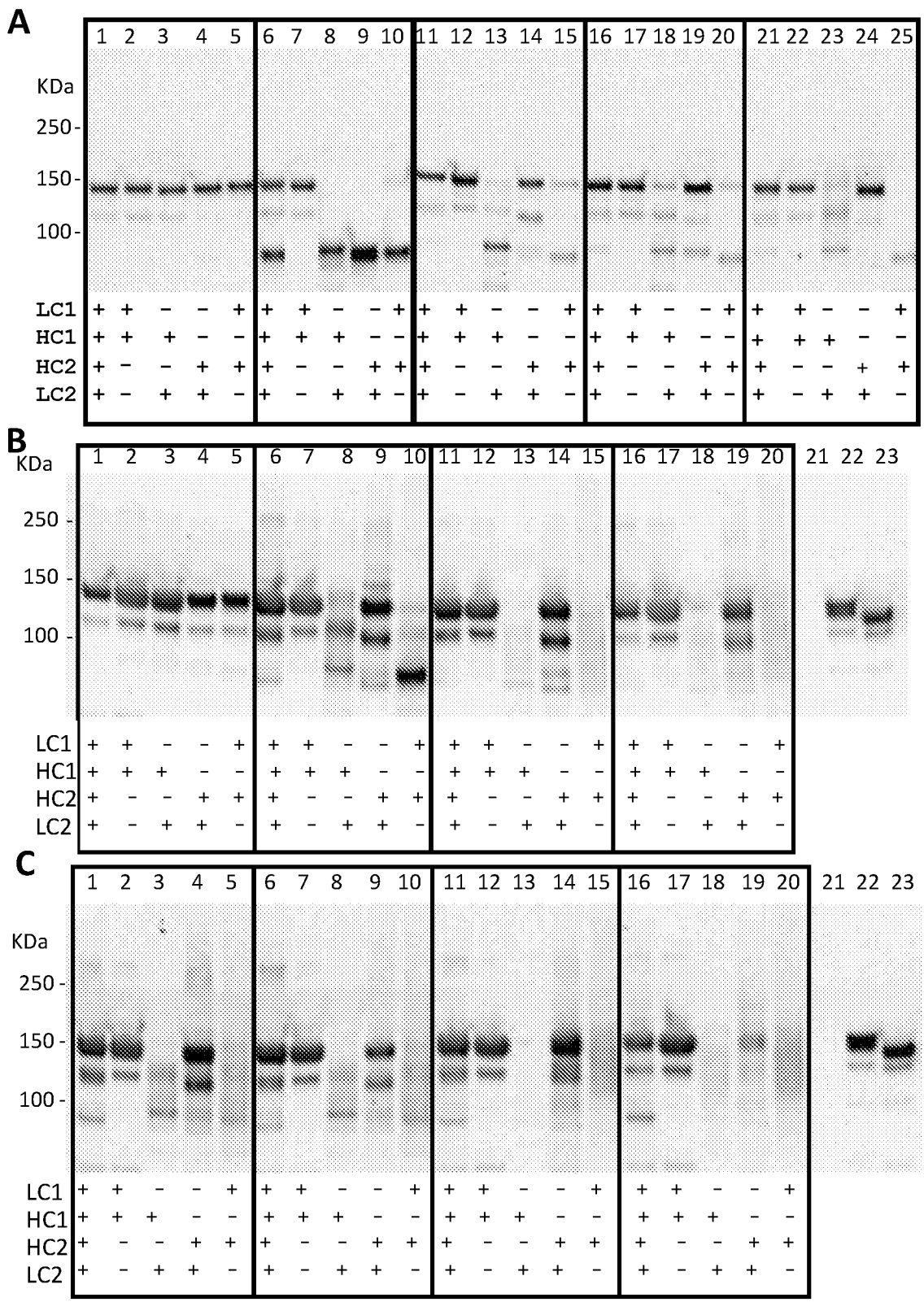
FIG. 10: Chain drop-out transient transfections to assess LC/HC pairing in the presence of cysteine substitutions at contacting residues. Experiments are described in Example 3. Lanes 21-23 in panels B and C contain cell supernatants from control transfections containing no DNA (lane 21), IgG1 anti-HER2 antibody 4D5-8 (comprising the amino acid sequences SEQ ID NOs. 19 and 20; lane 22), and IgG1 anti-HER2 antibody 2C4 (which contains the amino acid sequences of SEQ ID NOs. 21 and 22; lane 23). As indicated, all other samples are in groups of five and contain cell supernatants from transfections containing the DNAs encoding various combinations of HC1, LC1, HC2, and LC2, as explained in Example 3 and the description of FIG. 7. HC1 and LC1, together, make up the IgG4 anti-PD1 antibody described in Example 2 comprising no alterations other than S228P (HC1). HC2 and LC2, together, make up the IgG1 anti-CTLA4 antibody described in Example 2, which comprises only the alterations D399K and K409R (HC). These antibodies are either comprise no further alterations (designated "WT") or are altered in various ways in different lanes as indicated in the tables below. Positions of molecular weight standards are indicated at left.

In further experiments, methods of producing no more than two or three major species of antibodies in a host cell line containing DNAs encoding two IgG antibodies, one of which contained no partner-directing alterations, were explored. In test samples, one of the antibodies did not contain any partner-directing alterations, and the other lacked the naturally-occurring HC/LC disulfide bond (due to the substitutions C220S/G (HC2) and C214S (LC2)) and, in some samples, had two potential HC/LC disulfide bonds (due to cysteine substitutions at contacting residues) and, in some cases, also an HC/LC charge pair (due to substitutions of charged amino acids at contacting residues). Chain drop out experiments were performed as explained above using DNAs encoding the IgG4 anti-PD1 102 antibody (comprising HC1 and LC1) comprising only the alteration S228P (to prevent Fab arm exchange) and the IgG1 anti-CTLA 4 antibody 111 (comprising HC2 and LC2), which, in test samples, was engineered to lack the naturally-occurring disulfide bridge and comprise alterations disfavoring heterodimers (D399K and K409E in the HC) plus partner-directing alterations including alterations potentially creating two HC/LC disulfide bridges and, in some cases, also an HC/LC charge pair. The cysteine substitutions tested included the following pairs of alterations in HC2 and LC2, respectively: H168C and S174C; V173C and Q160C; and F170C and S162C. The substitutions of charged amino acids tested included the following pairs of alterations in the HC2 and LC2, respectively: K147D and S131R/K; and H168D and S174K/R. Samples were subjected to SDS-PAGE under non-reducing conditions and further analyzed by Western blot using goat-anti-human IgG Fc specific polyclonal antibodies for detection as described above. Results are shown in FIG. 10.

Cells transfected with DNAs encoding various chains of unaltered versions of the two antibodies produced full-length IgG antibodies of about 150 kDa. FIG. 10, panel A, lanes 1-5. These data indicate that non-cognate HC/LC pairs can produce full-length antibodies in the absence of alterations preventing such pairing. Elimination of the naturally-occurring disulfide bond in an engineered anti-CTLA4 111 antibody (comprising HC2 and LC2) prevented formation of full-length IgG antibody in any transfectant that did not contain DNA encoding both chains of the unaltered IgG4 anti-PD1 antibody, i.e., HC1 and LC1. FIG. 10, panel A, lanes 6-10. Adding two new potential disulfide bonds to an engineered anti-CTLA4 111 antibody lacking the naturally-occurring disulfide bond restored the ability of transfected containing DNA encoding HC2 and LC2 to produce full-length antibody while greatly decreasing production of full-length IgG antibody when only DNA encoding non-cognate pairs was present. FIG. 10, panel A, lanes 11-25. Among the combinations of pairs of cysteine substitutions tested, the alterations F170C plus V173C (HC2) and Q160C plus S162C (LC2) led to the best expression of full-length IgG in the presence of a cognate HC2/LC2 pair (compare lane 24 to lanes 14 and 19 in panel A) and the least expression of full-length IgG in the presence of only non-cognate HC/LC pairs (compare lanes 23 and 25 to lanes 13 and 15 or lanes 18 and 20 in panel A). However, the other two combinations of pairs of cysteine substitutions tested were almost as effective. See lanes 11-20 of FIG. 10, panel A. These alterations were as follows: H168C plus V173C (HC2) and Q160C plus S174C (LC2); and H168C plus V170C (HC2) and S162C plus S174C (LC2). Thus, these results suggest that the elimination of the naturally-occurring HC/LC disulfide bridge and the addition of two pairs of cysteine substitutions at contacting residues in the HC and LC can lead to robust expression of cognate HC/LC pairs and little expression of non-cognate pairs.

In another set of experiments, the effect of adding an HC/LC charge pair, in addition to two disulfide bridges, to the second antibody (which lacked the naturally-occurring disulfide bridge) was tested. We chose the conserved (see Tables 7 and 10) contacting pair of amino acids K147 (HC2) and S131 (LC2) because K147 is a charged amino acid. We hypothesized that a K147D/E alteration (HC2) and an S131K/R alteration (LC2) would create pairs of contacting amino acids having the same polarity in HC1/LC2 pairs and having unfavorable interactions in HC2/LC1 pairs, thus further discouraging the formation of non-cognate pairs. As explained in Example 1, we also hypothesized that changing a charged amino acid to a different charged amino acid might be tolerated without causing a steric clash in the HC/LC interface. If such a steric clash occurred, it might destabilize the antibody. The alterations would, of course, create an additional charge pair in cognate HC2/LC2 pairs, thus hopefully, would favor formation of this cognate pair without destabilizing the antibody.

Chain drop-out transfections and were performed and analyzed by Western blotting under non-reducing conditions as described above. Results are shown in FIG. 10, panel B. As expected, transfectants containing various combinations of the chains of the two antibodies, unaltered except for S228P in HC1 and D399K plus K409E in HC2, produced full-length IgG antibody of about 150 kDa, regardless of whether cognate or non-cognate HC/LC pairs were present. FIG. 10, panel B, lanes 1-5. In the presence of the alterations C220S (HC2) and C214S (LC2), addition of two pairs of cysteine substitutions to HC2 and LC2 (F170C plus V173C (HC2) and Q160C plus S162C (LC2)) led to strong expression of full-length IgG in the presence of only HC2 and LC2 (FIG. 10, panel B, lane 9) and barely detectable expression of full-length IgG in the presence of only non-cognate pairs, i.e., HC1/LC2 and HC2/LC1 (FIG. 10, panel B, lanes 8 and 10). Further addition, of K147D (HC2) and either S131K or S131R (LC2) led to even less, if any, expression of full-length IgG in the presence of only non-cognate pairs. FIG. 10, panel B, lanes 13, 15, 18, and 20. Hence these results, in combination with those in panel A, suggest that the addition of the tested charge pairs led to robust expression of the HC2/LC2 pair and little if any expression of non-cognate pairs.

In a third set of experiments, the effects of adding a different charge pair, i.e., H168D (HC2) and S174K/R (LC2), to the second antibody (lacking the naturally-occurring disulfide bridge and having two introduced disulfide bridges), optionally along with K147D (HC2) and S131K/R (LC2), on efficiency and specificity of HC/LC pairing were tested. As with K147D (HC2) and S131K/R (LC2), we hypothesized that H168D/E (HC2) and an S174K/R (LC2) would create pairs of contacting amino acids having the same charge polarity in HC1/LC2 pairs (since H168 in HC1 and S174K/R in LC2 are both positively charged) and possibly some repulsion for HC2/LC1 pairing, thus further discouraging the formation of non-cognate pairings. In addition, these alterations would, of course, create additional charge pairs in cognate HC2/LC2 pairs, thus potentially stabilizing this cognate pair.

Chain drop-out transfections and were performed and analyzed by Western blotting under non-reducing conditions as described above. Results are shown in FIG. 10, panel C. When the second antibody comprises H168D (HC2) and S174K (LC2) (in addition to lacking the naturally-occurring disulfide bridge and having two pairs of cysteine substitutions at contacting residues), expression of cognate HC2/LC2 pairs is robust (FIG. 10, panel C, lane 4), whereas little if any expression of non-cognate HC/LC pairs is detected (FIG. 10, panel C, lanes 3 and 5). Similar results are obtained when the second antibody comprises H168D (HC2) and S174R (LC2), although expression of cognate HC2/LC2 pairs is not as robust. FIG. 10, panel C, lanes 6-10. When the second antibody comprises H168D plus K147D (HC2) and S174K plus S131K (LC2) (in addition to lacking the naturally-occurring disulfide bridge and having two pairs of cysteine substitutions at contacting residues), expression of HC2/LC2 is robust (FIG. 10, panel C, lane 14) and little or no expression of non-cognate pairs is observed (FIG. 10, panel C, lanes 13 and 15), an effect that is particularly clear in lane 13. This last result may be explained by the fact that an HC1/LC2 pair will, in this situation, contain two pairs of contacting amino acids having the same charge. Interestingly, when the second antibody comprises H168D plus K147D (HC2) and S174R plus S131R (LC2) (in addition to lacking the naturally-occurring disulfide bridge and having two pairs of cysteine substitutions at contacting residues), expression of HC2/LC2 pairs is not nearly as robust (compare FIG. 10, panel C, lane 19 to lane 14), although expression of non-cognate pairs is similarly very low (FIG. 10, panel C, lanes 18 and 20).

Taken together, the results in FIG. 10 suggest the following conclusions. First, in a host cell transfected with DNAs encoding two different IgG antibodies, elimination of the naturally-occurring interchain HC/LC disulfide bridge in the second of the antibodies essentially prevents expression of that full-length antibody (HC2/LC2), as well as the expression of non-cognate pairs including either chain of the second antibody (HC2/LC1 and HC1/LC2). However, further addition of cysteine substitutions (potentially creating two new disulfide bridges in the second antibody) restores expression of HC2/LC2 without substantially restoring the expression of non-cognate pairs. Further addition of one or two HC2/LC2 charge pairs to the second antibody further enhances the expression HC2/LC2 and further decreases expression of non-cognate pairs. Finally, HC2/LC2 charge pairs containing lysine plus aspartate led to higher expression of HC2/LC2 than did charge pairs containing arginine plus aspartate. Taken together, these data suggest that a host cell transfected with DNAs encoding two different IgG antibodies can produce predominantly antibodies having cognate HC/LC pairs, even when only one of the antibodies comprises partner-directing alterations. In the absence of alterations that disfavor heterodimers, only three major species of antibody could potentially be produced, and only two major species of antibody could potentially be produced in the presence of alterations that disfavor HC1/HC2 heterodimers.

Example 4: Identifying Alterations that Disfavor HC/HC Heterodimers

Figure 4:
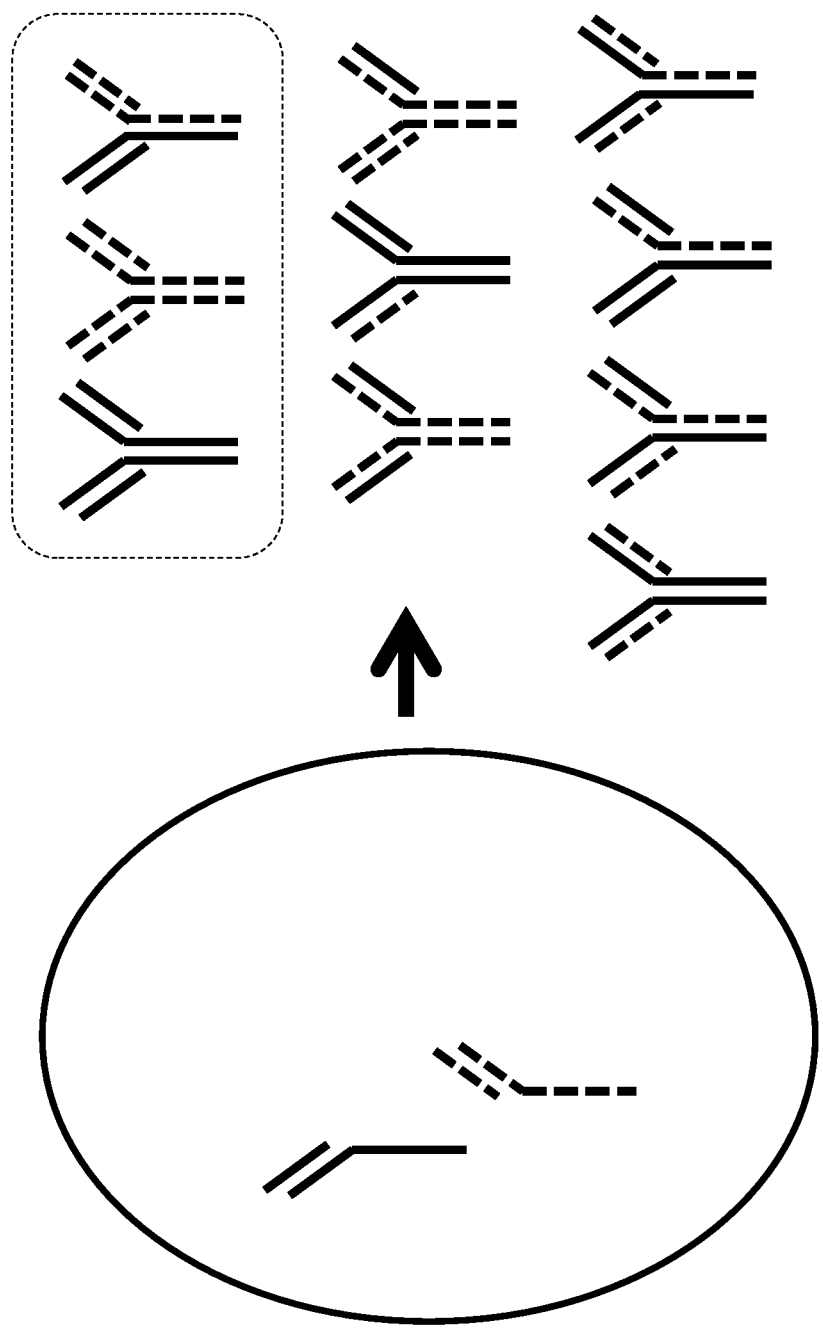
FIG. 4: Antibody species potentially produced by a host cell transfected with DNA encoding two full-length antibodies. The circle at left represents a host cell. The longer solid, bent line and shorter solid line represent the HC and LC of a first antibody, and the longer dashed, bent line and shorter dashed line represent the HC and LC of a second antibody. These polypeptides are encoded by DNAs that have been introduced into the host cell. Outside the circle at right are shown all the potential antibody species that could be produced if promiscuous pairings of the various chains are not prevented by some mechanism. The three species encircled by a dotted-line rectangle are the species that contain only cognate HC/LC pairs. All other species include at least one non-cognate HC/LC pair.

When DNAs encoding two different full-length antibodies, i.e., DNAs encoding two different HCs and two different LCs, are introduced into a host cell, the cell could potentially produce ten different antibodies having different combinations of HCs and LCs. FIG. 4; Carter (2001), J. Immunol. Methods 248: 7-15. To reduce the number of antibody species produced in such a host cell, the two different HCs could be engineered so that they form mostly, if not exclusively, HC/HC homodimers, and the HCs and LCs could be engineered such that mostly or only cognate HC/LC pairings would occur. Examples 1-3 address this latter issue. This Example describes making and testing various alterations in HCs designed to disfavor, if not completely eliminate, HC/HC heterodimer formation between the two different HCs.

To identify alterations that would achieve the goal of eliminating heterodimeric HC/HC pairs, a panel of DNAs encoding pairs of proteins including one Fc fragment and one cognate HC/LC pair, which had different alterations in their CH3 domains, were made. These DNAs were introduced into host cells that could express them, and the antibodies produced by the host cells were analyzed by SDS-PAGE and Western blotting as described above to determine the relative amounts of HC-LC/Fc heterodimers, HC-LC/HC-LC homodimers, and Fc/Fc homodimers produced by host cells into which the DNAs were introduced.

DNA constructs encoding Fc fragments and HC/LC pairs with different alterations in the CH3 domain were generated using PCR and Gibson assembly as explained in Examples 2 and 3. The resulting DNAs encoding the Fc fragment and the full-length HC and LC, which included different alterations, were co-transfected into HEK293 host cells and expressed using EXPI293™ Expression System from ThermoFisher Scientific (Waltham, Mass., USA). Conditioned media, which contained the antibodies produced by the host cells, were harvested from the transfectants after four days of culture.

The antibodies in the media were detected by Western blotting under non-reducing conditions as explained in Examples 2 and 3. After visualization using a CHEMIDOC™ XRS+ System with IMAGE LAB™ Software from Bio-Rad Laboratories, Inc., IMAGE LAB™ Software was used to calculate the percentage HC-LC/Fc heterodimers produced by the host cells transfected with DNA encoding the various pairs of altered proteins.

FIG. 11 shows Western blots of samples taken from culture media of transfectants containing pairs of DNAs encoding an LC and a wild type human IgG4 HC plus an altered human IgG1 Fc fragment having various single substitutions at position K370 (top right panel), K392 (top left panel), or V397 (bottom left panel). Each of these positions is at the CH3/CH3 interface (see, e.g., WO 2015/017548, Table 1 on page 8, which is incorporated herein by reference), and K370 and K392 are also close to position 409 (which is an R in IgG4 and a K in IgG1) in the tertiary structure. V397 is close to K392. Therefore, it was possible that these residues might play a role in strengthening or weakening interactions between CH3 domains, especially where one heavy chain is an IgG4 and the other is an IgG1. However, the data in FIG. 11 indicate that none of the substitutions tested substantially reduced the percentage of heterodimers (indicated as "HC/Fc") compared to that observed when the Fc fragment was not altered, even though some of the substitutions at all three sites replaced the original amino acid with one that was larger. Compare lane 18 of FIG. 11 to all other lanes in FIG. 11.

In further experiments, culture media from transfectants containing DNAs encoding a human IgG4 HC (which was wild type other than the single alteration S228P included to prevent Fab arm exchange) and a human IgG1 Fc fragment with alterations at D399 and/or K409 were analyzed. Results are shown in FIG. 12. Single substitutions D399K, D399R, K409D, and K409E in the IgG1 Fc fragment increased heterodimer formation. Compare lane 1 of FIG. 12 to lanes 2-5 of FIG. 12. However, when the IgG1 Fc fragment contained D399K and K409E or D399K and K409D, heterodimers comprised less than 5% of the total antibodies produced by the transfectants. FIG. 12, lanes 6 and 7.

The data shown in FIG. 13 address the question of whether use of an IgG4 full-length HC, rather than, for example, an IgG1 HC, played a role in the results shown in FIG. 12. In FIG. 13, lanes 10-19 show data from transfectants containing DNA encoding a wild type (lanes 10 and 15) or altered (lanes 11-14 and 16-19) human IgG1 Fc fragment and two different human IgG4 HCs (one (Ab1) in lanes 10-14 and the other (Ab2) in lanes 15-19). Data from Ab2 IgG4 (lanes 15-19) and Ab2 IgG1 (lanes 20-24) are directly comparable since these antibodies contain the same variable domains in an IgG4 or IgG1 format, respectively. The alterations in the Fc were at positions D399 and K409, as indicated in the table in FIG. 13. Little or no heterodimer was detected in transfectants producing an altered Fc fragment and a full-length human IgG4 HC. FIG. 13, lanes 11-14 and 16-19. In contrast, heterodimers are detectable in media from transfectants producing an altered Fc fragment and a full-length human IgG1 HC. FIG. 13, lanes 21-24. Thus, these data indicate that the use of an IgG4 HC rather than an IgG1 HC is important for obtaining the lowest levels of heterodimers.

As shown in Table 8, a human IgG4 HC has an arginine at position 409, whereas a human IgG1 HC has a lysine at position 409. The following experiment investigated whether this difference plays a role in the effect observed in FIG. 13, i.e., that host cells producing a human IgG4 HC plus an altered (D399K/R, K409E/D) human IgG1 Fc made lower levels of HC-LC/Fc heterodimers than did host cells producing a human IgG1 HC plus the same altered IgG1 Fc. Host cells were transfected with DNAs encoding a human IgG1 Fc fragment and a human HC plus LC. The Fc was wild type (WT) or contained alterations as indicated in FIG. 14. As indicated, the HC was either a WT IgG1, a WT IgG4, or an IgG1 containing the alteration K409R, which makes an IgG1 like an IgG4 at this position. The data in FIG. 14 show that levels of heterodimers (indicated as "HC/Fc") were lowest when the host cells were producing an Fc containing D399K/R and K409D/E and an HC that was either a wild type (WT) IgG4 or an IgG1 containing the alteration K409R. Compare lanes 2-5 and 12-15 to lanes 7-10 in FIG. 14. When a WT IgG1 HC was used with an Fc containing D399K/R and K409D/E, higher levels of heterodimers were observed.

FIG. 14, lanes 7-10. Thus, alterations that essentially eliminate detectable heterodimer formation have been identified in these experiments.

Example 5: Assessing Antibody Mixtures by Size

To determine how many species of antibodies were present in some of the altered antibody mixtures described above, the sizes of the antibodies in the mixtures were determined. First, the sizes of the full-length antibody species in these mixtures were assessed by SDS-PAGE under non-reducing conditions, and the sizes of individual HCs and LCs were assessed by SDS-PAGE under reducing conditions. The presence of multiple bands at about 150 kDa (full-length antibody) under non-reducing conditions and/or at about 50 kDa (HC) and/or 25 kDa (LC) under reducing conditions would be supportive of the concept that mixture contains multiple full-length antibody species. To further resolve full-length antibody species, cation exchange (CEX) chromatography was performed at low pH, which provided clear resolution of species in a size range near 150 kD. In addition, sizes of Fab fragments from a handful antibody mixtures were determined by mass spectrometry (MS), which can distinguish mass differences in the range expected for most of the different Fab fragments that could possibly form in the antibody mixtures containing cognate and/or non-cognate HC/LC pairs.

To assess the sizes of the full-length antibodies and the individual HCs and LCs produced in cells transfected with DNAs encoding the variant MabPairs 17B, 17C, 18B, 18C and 19C (see Table 21), EXPI293™ cells were transfected with DNAs encoding the HC and the LC of each of the two antibodies of these MabPairs. Following transfection, the culture supernatant was harvested after 4 days of incubation with shaking. Antibodies were purified with a Protein A column, analyzed in 4-15% CRITERION™ TGX STAIN-FREE™ Precast SDS-PAGE gel as described in Example 3, and blotted and detected as described in Example 2. Results are shown in FIG. 15.

As indicated, lanes 1-7 of FIG. 15 contain non-reduced samples, and lanes 8-14 contain reduced samples. As a control, lanes 1 and 8 contain an antibody mixture expected to contain two different anti-HER2 antibodies (4D5-8 and 2C4 with alterations described in Table 20 as variant 14D) plus a bispecific containing one HC and one LC from each antibody. Under non-reducing conditions, this sample shows three bands of about 150 kDa, suggesting the presence of the three different antibodies. As a further control, lanes 2 and 9 (labeled IgG1) contain an IgG1 anti-CTLA4 antibody, which shows a single band of about 150 kDa under non-reducing conditions, suggesting that this sample contains a single antibody species. Under non-reducing conditions, the MabPair variants 17B, 17C, 18B and 18C showed two bands of about 150 kDa (lanes 3-6), suggesting that these samples contained two antibody species. This is in line with expectations because one of the antibodies in these mixtures contains alterations disfavoring heterodimer formation, and the mixtures would therefore be expected to be MabPairs, i.e., mixtures containing only two major species of antibodies. Variant 19C showed only one band under non-reducing conditions (lane 7), suggesting that multiple antibody species comigrate in this sample.

When reduced, the control sample showed one band of about 50 kDa and two bands of about 25 kDa (FIG. 15, lane 8), suggesting that the two different HCs migrated at same place, whereas the two different LCs migrated separately. The IgG1 control under reducing conditions (lane 9) showed a single band of about 50 kDa and a single band of about 25 kDa. All reduced MabPair variants samples showed a single band at size of 50 KDa and two bands of about 25 kDa (lanes 10-14), suggesting that the two different HCs migrated together, whereas the two different LCs migrated separately. Thus, the data in FIG. 15, when taken together with data in Examples 3 and 4 and the data below, strongly suggest that the 17B, 17C, 18B, 18C, and 19C mixtures contain no more than two major species of antibodies.

Since the two IgG1 anti-HER2 antibodies used as a starting point for designing the variant antibody mixtures 1A-16D (Tables 17-20) did not contain any alterations disfavoring heterodimer formation, these variant mixtures could contain three different major antibody species when produced by a host cell, that is, two different monospecific antibodies containing two identical HCs and two identical LCs and a bispecific antibody containing two different HCs and two different LCs. To test this hypothesis, DNAs encoding both HCs and both LCs of five variant 3-in-1 mixtures, i.e., 13D, 14C, 14D, 15B, and 15C (see Table 20 and FIG. 8), were transfected into 30-50 milliliters (ml) of EXPI293™ cells in shaking flasks. The supernatants were harvested and antibodies were purified using a standard Protein A column. Different amounts of purified antibodies in 1:2 series dilution starting from 200 ng per lane were analyzed on 4-15% CRITERION™ TGX STAIN-FREE™ Precast SDS-PAGE gel (Bio-Rad Laboratories, Inc.) and blotted and detected as described in Example 2. Under non-reducing conditions (FIG. 16, top panel), all purified antibody mixtures showed 3 distinct bands of about 150 kDa, suggesting that these mixtures contain three different antibodies. Under reducing conditions (FIG. 16, bottom panel), all purified mixtures showed 1 band of around 50 kDa and 2 bands of around 25 kDa, suggesting that the two different HCs migrate together, whereas the two different LCs migrate separately.

To get better resolution of the full-length antibody species in the size range around 150 kD, low pH cation exchange chromatography (CEX) was performed on a sample containing the variant antibody mixture 18C (described in Table 21), which contains an anti-PD1, anti-CTLA4 MabPair. This method is described by Chen et al. (2010), Protein Science, 19:1191-1204, which is incorporated herein in its entirety. Briefly, it employs a Thermo PROPAC™ WCX-10 weak CEX column, 4×250 mm, preceded by a 50 mm guard column (PROPAC™ WCX-10G) using a Waters Alliance 2695 high performance liquid chromatography (HPLC) system. The chromatography was run with a linear gradient from 100% Buffer A (20 mM sodium acetate pH 5.2) to 100% Buffer B (20 mM sodium acetate with 250 mM sodium chloride pH 5.2) over 30 minutes. The column is washed with high salt (1M sodium chloride) and re-equilibrated to starting condition of Buffer A. The sample contained 18.8 mg of protein, and the antibodies were detected in the column outflow by absorbance at 214 nm.

Results are shown in FIG. 17. As indicated in FIG. 17, the top two tracings result from chromatography of the anti-CTLA4 (top) and anti-PD1 (second from top) antibodies that were the starting point for the alterations described in Examples 3 and 4. The bottom tracing results from chromatography of the variant antibody mixture 18C (see Table 21). The relative percentages of the components in the 18C mixture were calculated from the areas of the peaks using EMPOWER™ software from Waters Corporation (Milford, Mass., USA), which also served to control the HPLC system. In the bottom tracing resulting from the mixture 18C, the earlier, smaller peak corresponding to the anti-PD1 antibody comprised 21% of the mixture, and the later, larger peak corresponding to the anti-CTLA4 antibody comprised 79% of the mixture. These data show that low pH CEX easily distinguishes between different full-length antibodies species and can be used to quantitate relative amounts of specific antibody species in a mixture.

To obtain data that could distinguish cognate from non-cognate HC/LC pairs, supernatants of transfectants containing DNA encoding five different variant antibody mixtures (13D, 14C, 14D, 15C, and 15D) were analyzed by MS. The mixtures were digested with papain (Thermo Scientific, cat no. 44985) to generate Fab fragments. When IgG molecules are incubated with papain in the presence of cysteine, one or more peptide bonds in the hinge region (generally between His224-Thr 225) are broken, producing three fragments of similar size (about 50 kD): two Fab fragments and one Fc fragment. Immobilized enzyme is advantageous because digestion can be immediately stopped with simple separation of the IgG solution from the papain-coated resin by centrifugation, resulting in a digest that is essentially enzyme-free. The digestion products were analyzed on a SYNAPT™ G2 MS system (Waters Corporation, Milford, Mass., USA). Given the high resolution of MS, the Fab and Fc fragments were easily distinguishable. The analysis described below focuses on masses near the expected masses of the Fab fragments.

Only four different Fab fragments can be made from two different HCs (HC1 and HC2) and two different LCs (LC1 and LC2), that is, an HC1/LC1 Fab, an HC1/LC2 Fab, an HC2/LC2 Fab, and an HC2/LC1 Fab. In most cases, these different Fab fragments can be separated using MS. Table 22 below shows calculated masses of the four possible Fab fragments for 13D, 14C, 14D, 15B, and 15C antibody mixtures

TABLE 22

Calculated masses of Fab fragments

| Variant mixture | HC/LC combination | Calculated mass of Fab (daltons)* |
|---|---|---|
| 13D | HC1/LC1 | 47868.08 |
|  | HC2/LC2 | 47943.22 |
|  | HC1/LC2 | 47777.9 |
|  | HC2/LC1 | 48044.4 |
| 14C | HC1/LC1 | 47875.07 |
|  | HC2/LC2 | 47883.12 |
|  | HC1/LC2 | 47676.65 |
|  | HC2/LC1 | 48081.44 |
| 14D | HC1/LC1 | 47875.07 |
|  | HC2/LC2 | 47943.22 |
|  | HC1/LC2 | 47736.85 |
|  | HC2/LC1 | 48081.44 |
| 15C | HC1/LC1 | 47868.08 |
|  | HC2/LC2 | 47890.12 |
|  | HC1/LC2 | 47765.85 |
|  | HC2/LC1 | 47992.35 |
| 15D | HC1/LC1 | 47868.08 |
|  | HC2/LC2 | 47943.22 |
|  | HC1/LC2 | 47777.9 |
|  | HC2/LC1 | 48033.4 |

*These mass estimates do not take into account any potential post-translational modifications such as, for example, glycosylation. However, no N-glycoscylation is predicted in these Fab fragments.

If only cognate HC/LC pairs were present in the 14D mixture, only two Fab fragments, HC1/LC1 and HC2/LC2 Fabs, would be present in the Fab fragments recovered from the papain digestion. FIG. 18 shows the results of the MS analysis of the Fab fragments from the 14D antibody mixture. Two major species were detected, one at about 47,877 daltons and the other at about 47,942 daltons. FIG. 18. These likely are the HC1/LC1 Fab (predicted size 47,875.07 daltons) and the HC2/LC2 Fab (predicted size 47,943.22 daltons). If appreciable quantities non-cognate HC/LC pairs had been present in the mixture, then two other peaks at around 48,081.44 daltons and/or 47,736.85 daltons would have been detected. Since such peaks were not detected and would be easily separable from the peaks actually detected using MS, these data strongly suggest that most if not all HC/LC pairs in the 14D mixture are cognate HC/LC pairs.

Of the four other samples analyzed by MS, the 13D and 15D mixtures gave results similar to those shown in FIG. 18, i.e., only two major peaks were observed at almost the same masses as those calculated for the Fab fragments from cognate HC/LC pairs. In mixtures 14C and 15C, only one major peak was observed, which was almost the same mass as that calculated for the Fab fragment from one of the cognate HC/LC pairs in each of these mixtures. We hypothesize that the Fab fragment from the other cognate HC/LC pair in these samples was digested by the papain used to generate the Fab fragments since the cognate pairs in question formed full-length antibody in the chain drop-out experiments described above.

Example 6: Characterization of IgG1/IgG4 MabPairs where One Antibody Contains No Partner-Directing Alterations Data described above suggest that it is possible for a single host cell line transfected with DNAs encoding two different IgG antibodies to produce only two major species of antibodies. In those experiments, one or both antibodies were engineered to achieve this result. The following experiments were aimed at further characterizing MabPairs where one of the antibodies comprises no partner-directing alterations or alterations disfavoring heterodimers, and the other antibody comprises one or more partner-directing alterations, as well as one or more alterations disfavoring heterodimers. To determine the number of major species formed in transfectants containing DNAs encoding such antibodies, the following experiments were performed.

The human IgG1 anti-CTLA4 111 antibody was used as a starting place to create an engineered antibody. The amino acid sequences of the constant domains and the framework regions of the variable domains of anti-CTLA4 111 antibody are identical to those of anti-CTLA4 antibody 1E1 reported in SEQ ID NO:38 (HC) and SEQ ID NO:40 (LC). A DNA was constructed that encoded the HC of anti-CTLA4 111 antibody including the following alterations: K147D, F170C, V173C, C220G, R255K, D399R, and K409E. Generally, IgG antibodies comprising the alteration R255K are cleared faster from serum as compared to antibodies without this alteration, and the alterations D399R and K409E disfavor HC/HC heterodimer formation. Another DNA was constructed that encoded the light chain of the anti-CTLA4 111 antibody comprising the following alterations: S131K, Q160C, S162C, and C214S.

Plasmid DNAs encoding this engineered anti-CTLA4 111 antibody, an unaltered anti-CTLA4 111 antibody, and an unaltered version of the humanized IgG4 anti-PD1 102 antibody described in Example 2 were recovered from cultured bacteria containing them and were purified using a Qiagen® Midi-prep kit (Qiagen N.V., the Netherlands). Mammalian EXPI293™ cells were transfected with the plasmid DNAs encoding each antibody separately or encoding a mixture of antibodies containing the engineered anti-CTLA4 111 antibody and the anti-PD1 102 antibody using LIPOFECTAMINE®2000 (ThermoFisher Scientific, Waltham, Mass., USA) in 125-mL shaking flasks. Cells were continuously shaken at 150 rpm at 37° C. for 4 days. The supernatant was harvested by spinning down cells at 1500 rpm for 20 min, and antibodies in the supernatant were purified using a standard Protein A column. The purified antibodies were analyzed by MS using an Agilent 6224 accurate-mass time-of-flight (TOF) mass spectrometer equipped with an electrospray ionization (ESI) source. The results are shown in FIG. 19.

MS analysis of deglycosylated antibodies resulting from EXPI293™ cells transfected with DNAs encoding the unaltered anti-CTLA4 111 antibody indicated that this antibody had a mass of 144,890.12 daltons, which is within 7 parts per million (ppm) from the predicted mass of 144,889.16 daltons. FIG. 19, panel A. MS analysis of deglycosylated antibodies resulting from EXPI293™ cells transfected with DNAs encoding the engineered anti-CTLA4 111 antibody showed that this antibody had a mass of 144,780.02 daltons, which is within 7 ppm from the predicted mass of 144,779.00 daltons. FIG. 19, panel B. MS analysis of deglycosylated antibodies resulting from EXPI293™ cells transfected with DNAs encoding the HC and LC of both the anti-PD1 102 antibody and the engineered anti-CTLA4 111 antibody yielded two major peaks of about 146,000 daltons. A small amount of a species likely comprising one HC and one LC (73,214.20 daltons) was also detected. FIG. 19, panel C. Zooming in on the major peaks revealed one peak of 144,779.69 daltons and another of 146,426.58 daltons. FIG. 19, panel D. These masses match the predicted masses of the engineered anti-CTLA4 111 antibody (144,779.00 daltons) and the anti-PD1 102 antibody (146,426.20 daltons) within 4.8 ppm and 2.6 ppm, respectively. Hence, these data indicated that only two major species of antibody were produced in host cells containing DNA encoding the anti-PD1 102 antibody and the engineered anti-CTLA4 111 antibody.

The purified pair of antibodies resulting from transfection of EXPI293™ cells with DNAs encoding the HC and LC of both the anti-PD1 102 antibody and the engineered anti-CTLA4 111 antibody was further analyzed to confirm that only cognate HC/LC pairs were present. The pair of antibodies was digested with IdeS Protease (Promega, cat no. V7511, which cleaves an IgG antibody at a single site below the hinge region, yielding $F(ab')_2$ fragments and fragments comprising the CH2 and CH3 domains) and further treated with 2-mercaptoethyl amine (2-MEA) in the presence of ethylenediaminetetraacetic acid (EDTA). The treatment with 2-MEA and EDTA reduces hinge region disulfide bridges without substantially affecting HC/LC disulfide bridges. Thus, this treatment would be expected to yield Fab' and fragments comprising the CH2 and CH3 domains, possibly accompanied by minor quantities of LC and Fd fragments. LCs and Fd fragments are designated LC1 (anti-PD1) or LC2 (anti-CTLA4) and Fd1 (anti-PD1) or Fd2 (anti-CTLA4), depending on whether they are derived from the first or second antibody. See FIG. 20, panel A. Potentially, the Fab' fragments could contain LC1 and Fd1, LC2 and Fd2, LC2 and Fd1, and/or LC1 and Fd2. The calculated masses of these Fab' fragments are shown in the table below.

TABLE 23

Calculated masses of potential Fab' fragments of anti-PD1, anti-CTLA4 antibody pair

| Fd/LC combination | Calculated mass of Fab' (daltons) |
|---|---|
| Fd1/LC1 | 49,460.32 |
| Fd2/LC2 | 48,607.56 |
| Fd1/LC2 | 49,272.08 |
| Fd2/LC1 | 48,795.82 |

Analysis of the digested and 2-MEA plus EDTA-treated pair of antibodies by MS yielded peaks at 48,605.68 and 49,458.94 daltons, which matched the calculated Fd2/LC2 mass (within 39 ppm) and Fd1/LC1 Fab' mass (within 28 ppm), respectively. FIG. 20, panel B. No other peaks were observed in the size range surrounding the calculated masses of the Fab' fragments. Thus, these data indicate that both observed HC/LC pairs were cognate pairs.

To confirm formation of the two newly introduced disulfide bonds in the engineered anti-CTLA4 111 antibody, 100 μg of this antibody was incubated in phosphate buffer at pH 7.2 containing 5 mM N-ethylmaleimide (NEM) (Thermo-Scientific, cat no. 23030) at room temperature for 2 hours. NEM can alkylate free thiols, e.g., cysteine residues that are not part of a disulfide bridge. After excess NEM was removed by buffer exchange, lysyl endopeptidase (Wako Chemicals, cat no. 125-05061, which cleaves proteins on the carboxyl side of lysine residues) was added at a 1:10 (enzyme:protein) ratio, and the reaction mixture was incubated at 37° C. for 16 hrs. Then half of the mixture was reduced using 25 mM of Tris-(2-carboxyethyl)phosphine (TCEP, ThermoScientific, cat no. 20490) at room temperature for 30 min.

Liquid chromatography-mass spectrometry (LC-MS) analysis of lysyl endopeptidase digestion products was performed as follows. Reverse phase (RP) HPLC of reduced and non-reduced samples was performed on an Agilent Polaris C18-A column (2.0×250 mm, 5 μm, Agilent Technologies, Inc.). A sample of 50 μg was injected onto the column, and. the column was initially held at 98% mobile phase A (0.1% trifluoroacetic acid (TFA) in water) and 2% mobile phase B (0.1% TFA in 90% acetonitrile (ACN)) for 5 minutes. Separation was achieved with a 2-22% mobile phase B linear gradient in 40 minutes followed by a 22-52% mobile phase B linear gradient in 160 minutes. The column temperature and flow rate were maintained at 50° C. and 0.2 mL/min, respectively.

Online MS analysis of the column effluent was performed in positive ion mode on an Agilent 6224 accurate-mass TOF mass spectrometer equipped with an ESI source. The drying gas temperature, drying gas flow and nebulizer were set at 350° C., 12 L/min and 40 psig, respectively. The capillary, fragmentor, skimmer1 and Oct RF Vpp were set at 4500V, 250V, 60V and 750V, respectively. The instrument was calibrated in an m/z range of 100 to 3000 at 4 GHz high resolution. Data from LC/MS were analyzed using Agilent MASSHUNTER® Qualitative and BioConfirm software.

Whether the substituted cysteine residues F170C (HC)-S162C (LC) and V173C (HC)-Q160C (LC) were actually forming disulfide bonds in the altered anti-CTLA4 antibody was determined by comparison of the column profiles and mass analyses of reduced versus non-reduced lysyl endopeptidase digests. Under non-reducing conditions, a peak at a retention time of 103.48 minutes on the reverse phase column was detected (labeled "3 disulfide-linked peptide," FIG. 21, panel B), but this peak was not present under reducing conditions (FIG. 21, panel C). If the predicted disulfide bonds form, the two peptides shown in FIG. 21, panel A would be covalently linked by one intrachain and two interchain disulfide bonds after lysyl endopeptidase digestion. The peptide in the peak detected at 103.48 minutes under non-reducing conditions had a real monoisotopic mass of 9441.35 daltons (5×1889.07−4=9441.35, since the peptide was in the +5 charge state), which is only 2 ppm away from the predicted monoisotopic mass of the linked peptides, i.e., 9441.37 daltons. FIG. 22, panel A. Under reducing conditions, two peaks were observed at retention times of 39.65 and 113.05 minutes (labeled Chain A and Chain B, respectively), which were not present under non-reducing conditions. FIG. 21, panel C. These two peaks had real monoisotopic masses of 7321.48 daltons (1831.12×4−3=7321.48) and 2126.90 daltons (1063.95×2−1=2126.90) (FIG. 22, panels B and C), which exactly matched the theoretical monoisotopic masses of chains A and B (of FIG. 21, panel A), respectively.

In addition, mass analyses of NEM-treated unaltered anti-CTLA4 versus the engineered anti-CTLA4 antibody discussed immediately above showed that both had about the same percentage of free cysteine residues, i.e., cysteine residues that are not part of a disulfide bridge. Data not shown. Taken together, these data indicated that the two newly introduced cysteine pairs at F170C (HC)-S162C (LC) and V173C (HC)-Q160C (LC) do form disulfide bonds.

Example 7: Characterization of IgG2/IgG4 MabPairs where One Antibody Contains No Partner-Directing Alterations The following experiment was done to determine whether MabPairs like those described in Example 6, but containing IgG2 and IgG4 antibodies rather than IgG1 and IgG4 antibodies, could be successfully made in a single host cell line.

DNA gBlocks® (double-stranded DNAs suitable for assembly by Gibson reaction, among other uses; Integrated DNA Technologies (IDT), Coralville, Iowa) encoding the HC and LC of an IgG2 antibody with human constant regions were synthesized by IDT. These were assembled and inserted into a mammalian expression vector using Gibson reactions. The HC had the following substitutions: C131S, K147D, F170C, V173C, D399R, and K409E. The first four of these were used to enhance cognate HC/LC pairing and discourage non-cognate HC/LC pairing, and the last two were alterations disfavoring HC1/HC2 heterodimer formation. The amino acid sequence of the CH1, hinge, CH2, and CH3 domains of this engineered HC are provided in SEQ ID NO:42. The LC had the substitutions S131K, Q160C, S162C and C214S, which were used to enhance cognate HC/LC pairing and discourage non-cognate HC/LC pairing. The amino acid sequence of this engineered CL kappa domain is provided in SEQ ID NO:44.

This engineered IgG2 antibody, either alone or in combination with an unaltered IgG4 anti-PD1 102 antibody (described in Example 2), was expressed by transiently transfecting EXPI293™ cells with the plasmid DNAs described above and culturing the transfected cells. Expressed antibodies were recovered from the cell supernatants and purified using a Protein A column. Mass spectrometry of antibodies purified from cells transfected with DNAs encoding both the IgG2 and IgG4 antibodies was carried out after deglycosylation by PNGase F. In Table 24 below the calculated masses of full-length deglycosylated IgG antibodies lacking the C-terminal lysine of the HC (which is mostly removed by carboxyl peptidase in mammalian cells) resulting from all possible cognate and non-cognate HC/LC pairings of the IgG2 (comprising HC2 and LC2) and IgG4 (comprising HC1 and LC1) antibodies described above are shown.

TABLE 24

Calculated masses of IgG antibodies

| Chain Components* | Predicted Mass |
|---|---|
| HC1-LC1 and HC1-LC1 | 146,424.20 |
| HC2-LC2 and HC2-LC2 | 143,659.64 |
| HC2-LC1 and HC2-LC1 | 145,116.62 |
| HC1-LC2 and HC1-LC2 | 144,967.22 |
| HC1-LC2 and HC2-LC1 | 145,041.92 |
| HC1-LC1 and HC2-LC2 | 145,041.92 |
| HC1-LC1 and HC1-LC2 | 145,696.71 |
| HC2-LC1 and HC2-LC2 | 144,389.13 |
| HC1-LC1 and HC2-LC1 | 145,771.41 |
| HC1-LC2 and HC2-LC2 | 144,314.43 |

*HC1 and LC1 are the HC and LC from the IgG4 antibody, and HC2 and LC2 are the HC and LC from the IgG2 antibody.

Actual mass spectrometry results are shown in FIG. 23, panel A. Two main peaks were detected. The smaller of the two was at 143,666.77 daltons, which matches the calculated mass of the IgG2 antibody (143,659.64 daltons) with an error of 50 ppm. The larger of the two peaks was at 146,426.81 daltons, which matches the predicted mass of the IgG4 antibody (146,424.20 daltons) with an error of 18 ppm. Each of the two main peaks was accompanied by a shoulder peak at a slightly larger mass, which is believed to be due to incomplete removal of the HC C-terminal lysine by carboxyl peptidase in the mammalian cells that produced the antibodies. See FIG. 23, panel A. Calculated masses of antibodies resulting from heterodimeric HC/HC pairings and/or non-cognate HC/LC pairing ranged from 144,314.43 to 145,771.41 daltons. Table 24. No substantial peaks were observed in this size range (FIG. 23, panel A), indicating that only two major species of antibodies were present.

To confirm that only cognate HC/LC pairs were present, the purified antibodies were also treated with IdeS Protease, 2-MEA, and EDTA to generate Fab' fragments and subsequently analyzed by mass spectrometry analysis as described in Example 6. Table 25 below shows the calculated masses of Fab' fragments resulting from the four possible Fd/LC pairings, including cognate and non-cognate pairs.

TABLE 25

Calculated masses of Fab' fragments

| Fd/LC combination* | Calculated mass of Fab' (daltons) |
|---|---|
| Fd1/LC1 | 49,458.32 |
| Fd2/LC2 | 48,015.87 |
| Fd1/LC2 | 48,730.83 |
| Fd2/LC1 | 48,745.36 |

*Fd1 and LC1 are from the IgG4 antibody, and Fc2 and LC2 are from the IgG2 antibody.

Actual results from the mass spectrometry are shown in FIG. 23 panel B. Major peaks were detected at 48,017.74 and 48015.87 daltons, which matched the calculated masses for the Fd2/LC2 (with as error of 39 ppm) and Fd1/LC1 (with an error of 36 ppm) Fab' fragments. No other peaks at or near the predicted masses of the Fab' fragments resulting from non-cognate HC/LC pairings, i.e., 48,730.83 or 48,745.36 daltons, were detected.

The mass spectrometry results described above indicate that only two major species of antibodies, both having homodimeric HC/HC and cognate HC/LC pairings, were produced in cells transfected with DNAs encoding the engineered IgG2 antibody and the unaltered IgG4 antibody described above. Thus, these results strongly suggest that the alterations in the IgG2 antibody were sufficient to create a situation where only two major species of antibodies were produced in cells transfected DNAs encoding an engineered IgG2 antibody and an unaltered IgG4 antibody.

Example 8: ELISA-Based Assay to Assess Binding Activity of an Anti-PD1 and Anti-CTLA4 MabPair Antibody Mixture Produced in a Host Cell The following assay was performed to assess antigen binding of an anti-PD1, anti-CTLA4 MabPair mixture produced in a single host cell. Microtiter plates (96 well) were coated with biotinylated human PD1 (extracellular domain having a hexa-histidine (His-6) tag) or biotinylated human CTLA4 (extracellular domain having a glutathione S-transferase (GST) tag) using 100 μl at 1 μg/mL in phosphate buffered saline (PBS). The plates were washed three times with 1×PBST, and blocked with 250 μl/well of Block Buffer (3% non-fat milk in 1×PBST), with shaking at RT for 1 hr. The plates were washed three more times, and standard antibody control samples or test samples containing antibody mixtures in Dilution Buffer (PBST plus 0.1% bovine serum albumin (BSA)) were added at 100 μl/well with shaking at room temperature (RT) for 2 hours. After 3 washes, 100 μl of HRP-conjugated donkey-anti-human IgG at a dilution of 1:5000 in Dilution Buffer was added at to each well, and plates were shaken for 2 hours at RT. After three washes, 100 μl of substrate was added to each well, and the plates were incubated with shaking for 20 minutes. The reaction was stopped by adding 0.16 M sulfuric acid, and the plates were read in an ENVISION® (PerkinElmer, Waltham, Mass., USA) plate reader at 450 nm.

The concentration of anti-PD1 and anti-CTLA4 antibodies in the tested MabPair mixtures was deduced from standard curves made using control anti-PD1 and anti-CTLA4 antibodies, respectively. The results indicated that MabPair variant mixtures 17B, 17C, 18B, 18C, 19C comprised 18.0%, 11.8%, 27.2%, 23.4%, 27.2% anti-PD1 antibody, respectively, and 82.0%, 88.2%, 72.8%, 76.6%, 72.8% anti-CTLA4 antibody, respectively. Hence, these data indicated that the host cells producing these variant mixtures produced more anti-CTLA4 antibody than anti-PD1 antibody.

Example 9: Luciferase Reporter Assay to Assess the Potency of Anti-PD1 Antibody in Anti-PD1 and Anti-CTLA4 MabPair Antibody Mixture The following experiment tests the ability of an anti-PD1 antibody in a MabPair mixture containing anti-PD1 and anti-CTLA4 antibodies to inhibit the interaction of PDL1 and PD1 where the PD1 is expressed on a cell surface.

Jurkat cells stably expressing PD1 and luciferase (from Promega Corporation, Madison, Wis., USA) were seeded into 48 wells of 96-well plates (to avoid edge effects) at $4 \times 10^4$ cells/well in a volume of 20 μl. Following one day of incubation, $5 \times 10^4$ CHO cells stably expressing PDL1 in 20 μl were added to each well, along with 20 μl of a control antibody or a MabPair mixture. The PDL1 expressed on the CHO cells can engage with the PD1 on the Jurkat cells, activating an intracellular signaling pathway that inhibits expression of luciferase. If an antibody prevents PD1/PDL1 engagement by binding to PD1, luciferase expression will increase. A 1:3 dilution series of the antibodies or mixtures was done so that different wells had different concentrations of the antibody or the mixture. The plates were incubated at 37° C. in 5% $CO_2$ for 6 hours. BIO-GLO™ luciferase reagent (Promega, cat. no. G7941) was added at 40 µl per well to lyse the cells, and plates were read in ENVISION® plate reader (PerkinElmer). The results are shown in FIG. 24 and Table 26 below. These data indicate that the anti-PD1 and anti-CTLA4 MabPair antibody mixtures 17B, 17C, 18B, 18C and 19C blocked the PDL1-PD1 interaction with comparable potency compared to the unaltered anti-PD1 antibody alone (indicated as "anti-PD1").

TABLE 26

Potency of anti-PD1 antibody in MabPair mixtures

| Percent Anti-PD1 | Antibody | $IC_{50}$ (nM)* |
|---|---|---|
| 100.0 | anti-PD1 | 1.31 |
| 18.0 | 17B mixture | 2.6 |
| 11.8 | 17C mixture | 1.47 |
| 27.2 | 18B mixture | 2.09 |
| 23.4 | 18C mixture | 1.88 |
| 27.2 | 19C mixture | 2.44 |

*Based on the concentration of anti-PD1 antibody in each mixture as determined in Example 8.

Example 10: Luciferase Reporter Assay to Assess the Potency of Anti-CTLA4 Antibody in an Anti-PD1 and Anti-CTLA4 MabPair Antibody Mixture The following experiment tests the ability of an anti-CTLA4 antibody in a MabPair mixture containing anti-PD1 and anti-CTLA4 antibodies to inhibit the interaction of CD80 and/or CD86 with CTLA4 where the CTLA4 is expressed on a cell surface.

Jurkat cells stably expressing CTLA4 and luciferase (from Promega Corporation, Madison, Wis., USA) were seeded into 48 wells of 96-well microtiter plates at $5\times10^4$ cells/well in a volume of 15 µl. Following one day of incubation, $5\times10^4$ Raji cells expressing CD80 and CD86 in 15 µl were added to each well, along with 15 µl of a control anti-CTLA4 antibody or a MabPair mixture. The CD80 and CD86 expressed on the Raji cells can engage with the CTLA4 on the Jurkat cells, activating an intracellular signaling pathway that inhibits expression of luciferase. If an antibody prevents CTLA4 engagement with CD80 and/or CD86 by binding to CTLA4, luciferase expression will increase. A 1:3 dilution series of the antibody or the mixtures was done so that different wells had different concentrations of the antibody or a mixture. The plates were incubated at 37° C. in 5% $CO_2$ for 16 hours. BIO-GLO™ luciferase reagent (Promega, Cat no. G7941) was added at 40 µl per well to lyse the cells, and plates were read in an ENVISION® plate reader (PerkinElmer). Results are shown in FIG. 25 and Table 27 below.

TABLE 27

Potency of anti-CTLA4 antibody in MabPair mixtures.

| Percent anti-CTLA4 | Antibody | $IC_{50}$ (nM)* |
|---|---|---|
| 100.0 | anti-CTLA4 | 4.594 |
| 82.0 | 17B mixture | 23.18 |

TABLE 27-continued

Potency of anti-CTLA4 antibody in MabPair mixtures.

| Percent anti-CTLA4 | Antibody | $IC_{50}$ (nM)* |
|---|---|---|
| 88.2 | 17C mixture | 16.56 |
| 72.8 | 18B mixture | 23.56 |
| 76.6 | 18C mixture | 8.001 |
| 72.8 | 19C mixture | 10.89 |

*Based on the concentration of anti-CTLA4 antibody in each mixture as determined in Example 8.

These data indicate that the anti-CTLA4 antibody in the anti-PD1 and anti-CTLA4 MabPair mixtures 17B, 17C, 18B, 18C and 19C blocked the CTLA4-CD80/86 interaction, albeit with less potency than the unaltered anti-CTLA4 antibody alone. The 18C mixture was the most potent among the MabPair antibody mixtures. Thus, although these data indicate that the anti-CTLA4 antibodies in the variant mixtures had decreased activity (about 2-6 fold less) compared to the unaltered anti-CTLA4 antibody alone, the MabPair mixtures containing altered anti-CTLA4 antibodies still did exhibit anti-CTLA activity. These results may suggest that the alterations in these anti-CTLA4 antibodies affected their potency, whereas little change in the potency of the anti-PD1 antibodies was observed.

Example 11: Luciferase Assay to Assess the Potency of an Anti-CTLA4 Antibody Comprising Partner-Directing Alterations that is Part of a MabPair Also Including an Anti-PD1 Antibody Lacking Such Alterations This experiment tested the potency of the engineered IgG1 anti-CTLA4 111 antibody, described in Example 6, which comprised both alterations disfavoring heterodimers and partner-directing alterations, in the context of a MabPair including the unaltered anti-PD1 102 antibody described in Example 6. The assay was performed essentially as described in Example 10. As controls, the unaltered anti-CTLA4 111 antibody (not as part of a MabPair) and another unaltered anti-CTLA4 antibody (anti-CTLA4 110 antibody) with a very closely related sequence were also tested. The amino acid sequences of the constant domains of the anti-CTLA4 110 antibody are the same as those of the anti-CTLA4 antibody 1E1, which are provided in amino acids 119-448 of SEQ ID NO:38 (HC) and 108-214 SEQ ID NO:40 (LC). The amino acid sequences of the framework regions of the variable domains of the anti-CTLA4 antibody 110 are the same as those of the anti-CTLA4 antibody 1E1 except for a single substitution in a framework region. Results are shown in FIG. 26 and summarized in Table 28 below.

TABLE 28

Potency of anti-CTLA4 antibody in the context of MabPair

| Percent anti-CTLA4 | Antibody | $IC_{50}$ (nM) |
|---|---|---|
| 100.0 | Unaltered anti-CTLA4 110 antibody | 8.42 |
| 100.0 | Unaltered anti-CTLA4 111 antibody | 9.13 |
| 100.0 | Engineered anti-CTLA4 111 antibody | 2.79 |
| 35.3 | MabPair containing an anti-PD1 antibody and the engineered anti-CTLA4 111 antibody | 3.88* |

*Based on the concentration of anti-CTLA4 antibody in the MabPair mixture, which was determined as described in Example 8.

These data indicate that the engineered anti-CTLA4 111 antibody in the MabPair blocked the CTLA4-CD80/86 interaction with potency comparable to that of the altered anti-CTLA4 111 antibody alone and slightly higher than that of the unaltered anti-CTLA4 111 or anti-CTLA4 110 antibodies alone. Thus, the presence of the anti-PD1 antibody in the MabPair did not substantially affect the potency of the altered anti-CTLA4 111 antibody in this cell-based assay.

Example 12: Comparison of 3-in-1 Anti-HER2 Antibody Mixtures Versus a Combination of Two Anti-HER2 Antibodies in Ability to Kill Human Breast Cancer Cells The following experiments were done to determine the relative abilities of various 3-in-1 antibody mixtures to kill cancer cells as compared to a combination of the two antibodies that were the starting place for the creation of the mixtures, either singly or in combination.

Human HER2-expressing breast cancer cell lines BT-474 and SK-BR-3 were seeded at $1.0 \times 10^4$ cells/mL in 96-well, flat bottom plates at 100 µL/well. Cells were incubated at 37° C. at 5% $CO_2$ for 4 hours. The anti-HER2 antibodies 4D5-8 and 2C4 served as a starting point for making the variant antibody mixtures 1A-16D. Example 3 and Tables 17-20. Antibody 4D5-8, antibody 2C4, a combination of these two antibodies, or one of the 3-in-1 antibody mixtures 14D, 15C, 13D, 14C, or 15D (see Table 20) was added to each well in a volume of 100 µL. A series of 1:4 dilutions starting from 136 nM was done. As a negative control, two duplicate wells containing a human IgG1/K antibody believed to be irrelevant to growth of the cancer cells were included at the highest antibody concentration tested (136 nM). After 96 hrs of incubation, 100 µL of supernatant was removed from each well, and 100 µL of CELL TITER GLO® reagent (Promega, cat. no. G7572) was added. The contents were mixed for 2 minutes on an orbital shaker to induce cell lysis. The plates were incubated at room temperature for 10 minutes to stabilize the luminescent signal. The luminescence signals were recorded at 1 sec per well in an ENVISION® plate reader (PerkinElmer, Waltham, Mass., USA). The intensity of the luminescent signal is proportional to the quantity of ATP present in the cells, which is a reflection of cell viability. Results are shown in FIG. 27 and in Table 29 below.

TABLE 29

$IC_{50}$'s for inhibiting cancer cell viability of anti-HER2 antibodies or mixtures thereof

| Antibody or mixture | $IC_{50}$ in BT-474 cells (nM) | $IC_{50}$ in SK-BR-3 cells (nM) |
| --- | --- | --- |
| 14D mixture | 0.35 | 0.12 |
| 15C mixture | 0.22 | 0.17 |
| 13D mixture | 0.50 | 0.42 |
| 14C mixture | 0.48 | 0.42 |
| 15D mixture | 0.46 | 0.20 |
| 4D5-8 + 2C4 mixture | 0.93 | 0.47 |
| 4D5-8 | 0.67 | 0.02 |
| 2C4 | >68.0 | 3.72 |

The IgG1/κLC control antibody (labeled "IgG1" in FIG. 27) did not affect viability of BT-474 cells. The anti-HER2 antibody 2C4 had a slight negative effect on the viability of BT-474 cells. The anti-HER2 antibody 4D5-8 had a significant negative effect on BT-474 cell viability, and the combination of 4D5-8 and 2C4 also had a negative effect. The anti-HER2 3-in-1 antibody mixtures 14D, 15C, 13D, 14C, and 15D all had a more negative effect on BT-474 cell viability than the 4D5-8+2C4 antibody mixture, suggesting that all 3 antibody components (4D5-8, 2C4, and a bispecific antibody that comprises half of each of these antibodies) inhibit the BT-474 tumor cell growth more than a combination of only 4D5-8 and 2C4. The 3-in-1 antibody cocktail sample 15C was the most potent inhibitor in BT-474 cells with $IC_{50}$ of 0.22 nM.

In SK-BR-3 cells, IgG1/κLC control antibody did not affect cell viability. The antibody 2C4 had a small effect SK-BR-3 cell viability, while 4D5-8 had a much larger effect. The combination of 4D5-8 and 2C4 had a greater effect on viability than 2C4 and a lesser effect than 4D5-8. The anti-HER2 3-in-1 antibody mixtures 14D, 15C, 13D, 14C, and 15D all had slightly greater effects on cell viability than the mixture of 2C4+4D5-8. These data suggest that the antibody species in the 3-in-1 mixtures work together to inhibit growth of tumor cells.

These data suggest that a 3-in-1 mixture containing two different monospecific anti-HER2 antibodies plus a bispecific antibody comprising half of each antibody can effectively inhibit growth of HER2-expressing cancer cells.

What is claimed is:

1. A mixture of antibodies comprising two and not more than three different major antibody species, which comprises
   (a) a first antibody comprising two chains of a first heavy chain (HC1), each having the same first amino acid sequence, and two chains of a first light chain (LC1), each having the same second amino acid sequence, and
   (b) a second antibody comprising two chains of a second heavy chain (HC2), each having the same third amino acid sequence, and two chains of a second light chain (LC2), each having the same fourth amino acid sequence,
   wherein:
   (1) the first and second antibodies are each full-length human and/or humanized IgG antibodies comprising IgG1, IgG2, and/or IgG4 constant domains;
   (2) the HC1 and the HC2 have different amino acid sequences, and the LC1 and the LC2 have different amino acid sequences;
   (3) the first heavy chain constant domain (CH1) and the light chain constant domain (CL) of the first antibody and/or the second antibody comprise one or more partner-directing alteration(s) that create(s) two pairs of contacting cysteine residues and one charge pair bridging the HC and LC of the first antibody and/or the second antibody, wherein
      (A) the one or more partner-directing alteration(s) is (are) in the CH1 domain and the CL domain of the first and/or second antibody or antibodies,
      (B) if the first and/or second antibody or antibodies comprise(s) the pairs of contacting cysteine residues and comprise(s) an IgG1 CH1, then the pairs of HC and LC positions, respectively, of the contacting cysteine residues are selected from the group consisting of: positions 170 and 162; positions 170 and 176; positions 173 and 160; and positions 183 and 176,
      (C) if the first and/or second antibody comprise(s) the pairs of contacting cysteine residues and comprise(s) an IgG2 CH1, then the pairs of HC and LC positions, respectively, of the contacting cysteine residues are selected from the group consisting of: positions 170 and 162; and positions 173 and 160,
      (D) if the first and/or second antibody comprise(s) the pairs of contacting cysteine residues and comprise(s) an IgG4 CH1, then the pairs of HC and LC positions, respectively, of the contacting cysteine residues in the IgG4 antibody or antibodies are selected from the group consisting of: positions 170 and 162; positions 183 and 176; and positions 173 and 162,
      (E) if both the first and second antibodies comprise a pair of contacting cysteine residues, then the first and second antibodies do not comprise contacting cysteine residues at the same pairs of positions,
      (F) the charge pair is selected from the group consisting of: 147R/K in the CH1 and 131D/E in the CL; 147D/E in the CH1 and 131R/K in the CL; 168D/E in the CH1 and 174R/K in the CL; 168R/K in the CH1 and 174D/E in the CL, and
      (G) if both the first and second antibodies comprise a charge pair comprising charged amino acids at the same positions, then: if the first antibody comprises 147R/K in the CH1 and 131D/E in the CL, then the second antibody comprises 147D/E in the CH1 and 131R/K in the CL and vice versa; and if the first antibody comprises 168D/E in the CH1 and 174R/K in the CL, then the second antibody comprises 168R/K in the CH1 and 174D/E in the CL and vice versa,
   wherein the numbering system of Kabat et al., is used for the VH and VL domains, and the EU system of Edelman et al. is used for the CL, CH1, hinge, CH2, and CH3 domains.

2. The mixture of claim 1, wherein
   (a) the first antibody is an IgG1 antibody and comprises the pairs of contacting cysteine residues, wherein the first antibody comprises C220G/A/S in the HC and C214S/A/G in the LC; or
   (b) the first antibody is an IgG2 or IgG4 antibody and comprises the pairs of contacting cysteine residues, wherein the first antibody comprises the alterations 0131SING in the HC and C214S/A/G in the LC.

3. The mixture of claim 1, wherein the mixture comprises a third major IgG antibody species comprising the HC1, the LC1, the HC2, and the LC2.

4. The mixture of claim 1, wherein the mixture comprises not more than two major antibody species.

5. The mixture of claim 4, wherein one of the HC1 or the HC2 comprises the alterations 399R and 409E in its HC, and the other comprises 409R in its HC.

6. The mixture of claim 1, wherein the first antibody comprises the one or more partner-directing alteration(s) of claim 1(b)(3) and the second does not.

7. The mixture of claim 6, wherein
   (a) the first antibody is an IgG2 antibody and comprises 131S/A/G, 147D/E, 170C, and 173C in its HC and 131K/R, 160C, 162C, and 214S/A/G in its LC, or
   (b) the first antibody is an IgG1 antibody and comprises 147D/E, 170C, 173C, 220S/A/G in its HC and 131K/R, 160C, 162C, and 214S/A/G in its LC.

8. The mixture of claim 7(a), wherein the first antibody comprises 131S, 147D, 170C, and 173C in its HC and 131K, 160C, 162C, and 214S in its LC.

9. The mixture of claim 8, wherein one of either the first or the second antibody comprises 399R and 409E in its HC, and the other comprises 409R in its HC.

10. The mixture of claim 9, wherein the first antibody comprises 399R and 409E in its HC, and the second antibody comprises 409R in its HC.

11. The mixture of claim 7(b), wherein the first antibody comprises 147D, 170C, 173C, 220G in its HC and 131K, 160C, 162C, and 214S in its LC.

12. The mixture of claim 11, wherein one of either the first or the second antibody comprises 399R and 409E in its HC, and the other comprises 409R in its HC.

13. The mixture of claim 12, wherein the first antibody comprises 399R and 409E in its HC, and the second antibody comprises 409R in its HC.

14. The mixture of claim 13, wherein the HC2 is an IgG4 HC and comprises 228P.

15. The mixture of claim 14, wherein the first antibody binds to human Cytotoxic T Lymphocyte-Associated 4 (CTLA4) and comprises 255K, and the second antibody binds to human Programmed Cell Death 1 (PD1).

16. The mixture of claim 12, wherein the first antibody comprises 409R in its HC, and the second antibody comprises 399R and 409E in its HC.

17. The mixture of claim 16, wherein the first antibody binds to human CD37 and the second antibody binds to human CD20.

18. The mixture of claim 1, wherein
(a) both the first and second antibodies comprise the one or more partner-directing alteration(s),
(b) the HC1 and the HC2 comprise a charged amino acid at an HC residue at the same position in both the HC1 and the HC2,
(c) the charged amino acid at the HC residue in the HC1 is opposite in charge to the charged amino acid at the HC residue at the same position in the HC2,
(d) the LC1 and the LC2 comprise a charged amino acid at an LC residue at the same position in both the LC1 and the LC2,
(e) the LC residue contacts the HC residue,
(f) the charged amino acid at the LC residue in the LC1 is opposite in charge to the charged amino acid at the LC residue in the LC2, and
(g) the charged amino acid at the LC residue in the LC1 is opposite in charge to the amino acid at the HC residue in the HC1.

19. The mixture of claim 18, wherein:
both the HC1 and the HC2 comprise charged amino acids at positions 44, 105, 147, and 168; and
both the LC1 and the LC2 comprise charged amino acids at positions 43, 100, 131, and 174.

20. The mixture of claim 18, wherein one of HC1 or HC2 comprises 399R and 409E, and the other comprises 409R.

21. The mixture of claim 1, wherein
(a) one of the first and second antibodies binds to human CTLA4 and the other binds to human PD1,
(b) both the first and second antibodies bind to human HER2, but they do not compete for binding to HER2,
(c) one of the first and second antibodies binds to human LAG3 and the other binds to human PD1,
(d) one of the first and second antibodies binds to human GITR and the other binds to human PD1,
(d) one of the first and second antibodies binds to human VEGF and the other binds to human PD1,
(f) one of the first and second antibodies binds to human CSFR1a and the other binds to human PD1,
(g) one of the first and second antibodies binds to human OX40 and the other binds to human PD1,
(h) one of the first and second antibodies binds to human TIGIT and the other binds to human PD1,
(i) one of the first and second antibodies binds to human CTLA4 and the other binds to human PDL1,
(j) one of the first and second antibodies binds to human VEGF and the other binds to human PDL1,
(k) one of the first and second antibodies binds to human OX40 and the other binds to human PDL1,
(l) one of the first and second antibodies binds to human CSFR1a and the other binds to human PDL1,
(m) one of the first and second antibodies binds to human TIGIT and the other binds to human PDL1,
(n) one of the first and second antibodies binds to human Tim3 and the other binds to human PDL1,
(o) one of the first and second antibodies binds to human CTLA4 and the other binds to human VEGF,
(p) one of the first and second antibodies binds to human CTLA4 and the other binds to human 41BB,
(q) one of the first and second antibodies binds to human CD20 and the other binds to human CD37,
(r) one of the first and second antibodies binds to human ANG2 and the other binds to human VEGF,
(s) one of the first and second antibodies binds to human TNF and the other binds to human IL17a,
(t) one of the first and second antibodies binds to human CD38 and the other binds to human CD138,
(u) one of the first and second antibodies binds to human EGFR and the other binds to human HER2,
(v) one of the first and second antibodies binds to human EGFR and the other binds to human HER3,
(w) one of the first and second antibodies binds to human MET and the other binds to human VEGF
(x) one of the first and second antibodies binds to human MET and the other binds to human EGFR,
(y) one of the first and second antibodies binds to human TSLP and the other binds to human IL33,
(z) one of the first and second antibodies binds to human IL4 and the other binds to human IL13,
(aa) one of the first and second antibodies binds to human CSF1R protein and the other binds to a human SIRP-alpha protein,
(bb) one of the first and second antibodies binds to human PD1 protein and the other binds to a human SIRP-alpha protein, or
(cc) one of the first and second antibodies binds to human PD1 and the other binds to human CCR8.

* * * * *